US012649798B2

(12) United States Patent
Oostindie et al.

(10) Patent No.: US 12,649,798 B2
(45) Date of Patent: Jun. 9, 2026

(54) POLYPEPTIDE VARIANTS AND USES THEREOF

(71) Applicant: GENMAB B.V., Utrecht (NL)

(72) Inventors: Simone Oostindie, Utrecht (NL);
Andreas Hollenstein, Utrecht (NL);
Frank Beurskens, Utrecht (NL);
Kristin Strumane, Werkhoven (NL);
Janine Schuurman, Diemen (NL); Rob De Jong, Utrecht (NL)

(73) Assignee: GENMAB B.V., Utrecht (NL)

( * ) Notice: Subject to any disclaimer, the term of this patent is extended or adjusted under 35 U.S.C. 154(b) by 543 days.

(21) Appl. No.: 16/963,701

(22) PCT Filed: Jan. 24, 2019

(86) PCT No.: PCT/EP2019/051809

§ 371 (c)(1),
(2) Date: Jul. 21, 2020

(87) PCT Pub. No.: WO2019/145455

PCT Pub. Date: Aug. 1, 2019

(65) Prior Publication Data

US 2021/0107988 A1     Apr. 15, 2021

(30) Foreign Application Priority Data

Jan. 24, 2018     (DK) ................................. 2018 00041

(51) Int. Cl.
*C07K 16/28*     (2006.01)
*A61P 35/00*     (2006.01)

(52) U.S. Cl.
CPC .......... *C07K 16/2893* (2013.01); *A61P 35/00* (2018.01); *C07K 16/2887* (2013.01); *C07K 16/2896* (2013.01); *C07K 2317/24* (2013.01); *C07K 2317/31* (2013.01); *C07K 2317/72* (2013.01); *C07K 2317/734* (2013.01)

(58) Field of Classification Search
None
See application file for complete search history.

(56) References Cited

U.S. PATENT DOCUMENTS

| | | | |
|---|---|---|---|
| 4,179,337 A | 12/1979 | Davis et al. | |
| 4,495,285 A | 1/1985 | Shimizu et al. | |
| 4,609,546 A | 9/1986 | Hiratani | |
| 4,681,581 A | 7/1987 | Coates | |
| 4,735,210 A | 4/1988 | Goldenberg | |
| 4,766,106 A | 8/1988 | Katre et al. | |
| 5,101,827 A | 4/1992 | Goldenberg | |
| 5,102,990 A | 4/1992 | Rhodes | |
| 5,648,471 A | 7/1997 | Buttram et al. | |
| 5,697,902 A | 12/1997 | Goldenberg | |
| 6,214,345 B1 | 4/2001 | Firestone et al. | |

| | | | |
|---|---|---|---|
| 7,740,847 B2 * | 6/2010 | Allan | A61P 35/00 |
| | | | 435/69.6 |
| 10,759,867 B2 | 9/2020 | Parren et al. | |
| 11,180,572 B2 | 11/2021 | De Jong et al. | |
| 12,049,512 B2 | 7/2024 | Parren et al. | |
| 12,173,076 B2 | 12/2024 | Beurskens et al. | |
| 12,338,289 B2 | 6/2025 | De Jong et al. | |
| 2014/0242075 A1 | 8/2014 | Parren et al. | |
| 2014/0271617 A1 * | 9/2014 | Igawa | A61P 37/04 |
| | | | 506/17 |
| 2015/0010550 A1 * | 1/2015 | Lazar | C07K 16/32 |
| | | | 424/139.1 |
| 2015/0175707 A1 | 6/2015 | De Jong et al. | |
| 2015/0353636 A1 | 12/2015 | Parren et al. | |
| 2019/0276549 A1 | 9/2019 | De Jong et al. | |
| 2020/0181277 A1 | 6/2020 | Beurskens et al. | |
| 2020/0247897 A1 | 8/2020 | Jensen et al. | |
| 2021/0163619 A1 | 6/2021 | Parren et al. | |
| 2021/0230301 A1 | 7/2021 | De Jong et al. | |
| 2021/0238296 A1 | 8/2021 | De Jong et al. | |
| 2022/0411529 A1 * | 12/2022 | De Jong | C07K 16/2896 |
| 2023/0107363 A1 | 4/2023 | De Jong et al. | |

(Continued)

FOREIGN PATENT DOCUMENTS

| | | |
|---|---|---|
| EP | 2233500 A1 | 9/2010 |
| WO | 02083180 A1 | 10/2002 |
| WO | 2004035607 A2 | 4/2004 |

(Continued)

OTHER PUBLICATIONS

Diebolder, C. et al. "Complement Is Activated by IgG Hexamers Assembled at the Cell Surface," Science, vol. 343:1260-1263 (2014).
U.S. Appl. No. 16/921,154, filed Jul. 6, 2020, Paul Parren, US 20210163619.
U.S. Appl. No. 14/130,543, filed May 5, 2014, Paul Parren, U.S. Pat. No. 10,759,867.
U.S. Appl. No. 17/012,102, filed Sep. 4, 2020, Rob N. DeJong, US 20210230301.
U.S. Appl. No. 14/413,178, filed Mar. 17, 2015, Rob N. DeJong, U.S. Pat. No. 11,180,572.
U.S. Appl. No. 17/896,916, filed Aug. 26, 2022, Paul Parren.

(Continued)

*Primary Examiner* — Daniel E Kolker
*Assistant Examiner* — Cheom-Gil Cheong
(74) *Attorney, Agent, or Firm* — Nelson Mullins Riley & Scarborough LLP; Jane E. Remillard, Esq.; Christopher L. Frank

(57) ABSTRACT

The present invention relates to combination therapy involving two or more Fc region-containing antigen-binding polypeptides, such as antibodies, wherein the polypeptides have been modified such that hetero-oligomerization between the polypeptides is strongly favored over homo-oligomerization when the polypeptides are bound to their corresponding target antigens. The invention also relates to polypeptides, compositions, kits and devices suitable for use in the combination therapy of the invention.

28 Claims, 37 Drawing Sheets

Specification includes a Sequence Listing.

(56) References Cited

U.S. PATENT DOCUMENTS

| | | | |
|---|---|---|---|
| 2025/0223374 A1 | 7/2025 | Parren et al. | |
| 2025/0326854 A1 | 10/2025 | Beurskens et al. | |

FOREIGN PATENT DOCUMENTS

| | | | | |
|---|---|---|---|---|
| WO | 2004043493 A1 | 5/2004 | | |
| WO | 2007089149 A2 | 8/2007 | | |
| WO | 2009017394 A1 | 2/2009 | | |
| WO | 2010062171 A2 | 6/2010 | | |
| WO | 2011112978 A1 | 9/2011 | | |
| WO | 2012/130831 A1 | 10/2012 | | |
| WO | WO-2013004842 A2 * | 1/2013 | .............. | A61P 29/00 |
| WO | 2014009358 A1 | 1/2014 | | |
| WO | 2014/108198 A1 | 7/2014 | | |
| WO | 2016/071377 A1 | 5/2016 | | |
| WO | 2016/164480 A1 | 10/2016 | | |
| WO | 2017/093447 A1 | 6/2017 | | |
| WO | WO-2017093448 A1 * | 6/2017 | .............. | A61P 35/00 |
| WO | 2019145455 A1 | 8/2019 | | |

OTHER PUBLICATIONS

U.S. Appl. No. 14/760,135, filed Jul. 9, 2015, Paul Parren, US 20150353636.

U.S. Appl. No. 17/972,356, filed Oct. 24, 2022, Mette Hamborg Jensen.

U.S. Appl. No. 16/618,722, filed Dec. 2, 2019, Mette Hamborg Jensen, US 20200247897.

U.S. Appl. No. 17/745,667, filed May 16, 2022, Rob N. DeJong, US 20230107363.

U.S. Appl. No. 16/345,044, filed Apr. 25, 2019, Rob N. DeJong, US 20190276549.

U.S. Appl. No. 16/482,747, filed Aug. 1, 2019, Frank Beurskens, US 20200181277.

U.S. Appl. No. 17/051,205, filed Oct. 28, 2020, Rob N. DeJong, US 20210238296.

U.S. Appl. No. 18/475,055, filed Sep. 26, 2023, Paul Parren.

U.S. Appl. No. 18/475,842, filed Sep. 27, 2023, Mette Hamborg Jensen.

U.S. Appl. No. 18/741,587, filed Jun. 12, 2024, Paul Parren, US 20250043018.

U.S. Appl. No. 18/816,860, filed Aug. 27, 2024, Paul Parren.

U.S. Appl. No. 18/744,540, filed Jun. 14, 2024, Paul Parren.

U.S. Appl. No. 18/938,588, filed Nov. 6, 2024, Frank Beurskens.

Barbas, C. et al., "Molecular Profile of an Antibody Response to HIV-1 as Probed by Combinatorial Libraries," Academic Press, vol. 230(3): 812-823 (1993).

Cox et al., "Glycan optimization of a human monoclonal antibody in the aquatic plant Lemna minor," Nature Biotechnology, vol. 24 (12):1591-1597 (2006).

Crowe, J et al., "Humanized monoclonal antibody CAMPATH-1H: myeloma cell expression of genomic constructs, nucleotide sequence of cDNA constructs and comparison of effector mechanisms of myeloma and Chinese hamster ovary cell-derived material," Clinical Exp. Immunol., vol. 87(1): 105-110 (1992).

David, G. et al, "Protein iodination with solid state lactoperoxidase," Biochemistry, vol. 13, 1014, 1 page (1974).

Dubowchik, G. M. et al., "Receptor-mediated and enzyme-dependent targeting of cytotoxic anticancer drugs," Pharm. Therapeutics, vol. 83(2):67-123 (1999).

Edelman, GM. et al., "The Covalent Structure of an Entire $\gamma$G Immunoglobulin Molecule," PNAS, vol. 63(1): 78-85 (1969).

Goldenberg, D., "New Developments in Monoclonal Antibodies For Cancer Detection and Therapy," A Cancer Journal for Clinicians, Journal of Immunological Methods, vol. 44:43-64 (1994).

Hamilton, S. R., et al., "Production of complex human glycoproteins in yeast," Science, vol. 301: 1244-1246 (2003).

Hunter et al, "Preparation of Iodine-III Labelled Human Growth Hormone of High Specific Activity," Nature, vol. 4827: 495-496 (1962).

International Search Report and Written Opinion ,PCT/EP2019/051809, May 20, 2019, 9 pages.

Junghans, Cancer Chemotherapy and Biotherapy, 2 Edition, Lippincott Raven, 4 pages (1996).

Li. et al., "Crystallizable Fragment Glycoengineering for Therapeutic Antibodies Development," Front. Immunol., vol. 8 (1554) 1-15 pages (2017).

Liu, H., et al., "Heterogeneity of monoclonal antibodies," Journal of Pharm Seciences, vol. 97: 2426-2447 (2008).

Nygren, H., "Conjugation of horseradish peroxidase to Fab fragments with different homo-bifunctional and heterobifunctional cross-linking reagents," The Journal of Histochemistry and Cytochemistry, vol. 30: 407-412 (1982).

Pain, D. et al., "Preparation of protein A-peroxidase monoconjugate using a heterobifunction-al reagent, and its use in enzyme immunoassays," Journal of Immunological Affairs, vol. 40: 219-30 (1981).

Pastan et al., "Immunotoxins," Cell, vol. 47: 641-648 (1986).

Potgieter, T. et al., "Production of Monoclonal Antibodies by Glycoengineered Pichia pastoris," Journal of Biotechnology, vol. 139: 318-325 (2009).

Rowe et al., "Handbook of Pharmaceutical Excipients," Pharmaceutical Press, 7th Edition (2012).

Saphire et al., "Crystal Structure of a Neutralizing Human IgG Against HIV-1: A Template for Vaccine Design," Science, vol. 293(5532): 1155-1159 (2001).

Vink, et al., "A simple, robust and highly efficient transient expression system for producing antibodies," Elsevier, vol. 65 (1): 5-10 (2014).

* cited by examiner

FIG. 1

```
EU              216    220     228
                 |      |       |
IgG1m(a)-Fc     EPK---SCDKTHTCPP-------------------------------------------------
IgG1m(f)-Fc     EPK---SCDKTHTCPP-------------------------------------------------
IgG2-Fc         ERK---CC-V-E-CPP-------------------------------------------------
IgG3-Fc         ELKTP-LGDTTHTCPRCPEPKSCDTPPPCPRCPEPKSCDTPPPCPRCPEPKSCDTPPPCP
IgG4-Fc         ESKYG------PPCPS-------------------------------------------------

EU               229    237                                              287
                  |      |                                                |
IgG1m(a)-Fc     -CPAPELLGGPSVFLFPPKPKDTLMISRTPEVTCVVVDVSHEDPEVKFNWYVDGVEVHNA
IgG1m(f)-Fc     -CPAPELLGGPSVFLFPPKPKDTLMISRTPEVTCVVVDVSHEDPEVKFNWYVDGVEVHNA
IgG2-Fc         -CPAPPVA-GPSVFLFPPKPKDTLMISRTPEVTCVVVDVSHEDPEVQFNWYVDGVEVHNA
IgG3-Fc         RCPAPELLGGPSVFLFPPKPKDTLMISRTPEVTCVVVDVSHEDPEVQFKWYVDGVEVHNA
IgG4-Fc         -CPAPEFLGGPSVFLFPPKPKDTLMISRTPEVTCVVVDVSQEDPEVQFNWYVDGVEVHNA

EU               288                                                     347
                  |                                                       |
IgG1m(a)-Fc     KTKPREEQYNSTYRVVSVLTVLHQDWLNGKEYKCKVSNKALPAPIEKTISKAKGQPREPQ
IgG1m(f)-Fc     KTKPREEQYNSTYRVVSVLTVLHQDWLNGKEYKCKVSNKALPAPIEKTISKAKGQPREPQ
IgG2-Fc         KTKPREEQFNSTFRVVSVLTVVHQDWLNGKEYKCKVSNKGLPAPIEKTISKTKGQPREPQ
IgG3-Fc         KTKPREEQYNSTFRVVSVLTVLHQDWLNGKEYKCKVSNKALPAPIEKTISKTKGQPREPQ
IgG4-Fc         KTKPREEQFNSTYRVVSVLTVLHQDWLNGKEYKCKVSNKGLPSSIEKTISKAKGQPREPQ

EU               348                                                     407
                  |                                                       |
IgG1m(a)-Fc     VYTLPPSRDELTKNQVSLTCLVKGFYPSDIAVEWESNGQPENNYKTTPPVLDSDGSFFLY
IgG1m(f)-Fc     VYTLPPSREEMTKNQVSLTCLVKGFYPSDIAVEWESNGQPENNYKTTPPVLDSDGSFFLY
IgG2-Fc         VYTLPPSREEMTKNQVSLTCLVKGFYPSDIAVEWESNGQPENNYKTTPPMLDSDGSFFLY
IgG3-Fc         VYTLPPSREEMTKNQVSLTCLVKGFYPSDIAVEWESSGQPENNYNTTPPMLDSDGSFFLY
IgG4-Fc         VYTLPPSQEEMTKNQVSLTCLVKGFYPSDIAVEWESNGQPENNYKTTPPVLDSDGSFFLY

EU               408                                     447
                  |                                       |
IgG1m(a)-Fc     SKLTVDKSRWQQGNVFSCSVMHEALHNHYTQKSLSLSPGK
IgG1m(f)-Fc     SKLTVDKSRWQQGNVFSCSVMHEALHNHYTQKSLSLSPGK
IgG2-Fc         SKLTVDKSRWQQGNVFSCSVMHEALHNHYTQKSLSLSPGK
IgG3-Fc         SKLTVDKSRWQQGNIFSCSVMHEALHNRFTQKSLSLSPGK
IgG4-Fc         SRLTVDKSRWQEGNVFSCSVMHEALHNHYTQKSLSLSLGK
```

| EC50 ng/mL | Single ↓/→ | I253A | I253D | I253E | I253F | I253G | I253H | I253K | I253L | I253M | I253N | I253Q | I253R | I253S | I253T | I253V | I253W | I253Y |
|---|---|---|---|---|---|---|---|---|---|---|---|---|---|---|---|---|---|---|
| | | 26 | 267 | 372 | 183 | 104 | 522 | 248 | 144 | 304 | 362 | 249 | 162 | 70 | 32 | <15 | 21 | 197 |
| H310A | 73 | 40 | 119 | 119 | 115 | 91 | 107 | 104 | 55 | 74 | 117 | 84 | 98 | 39 | 17 | <15 | 56 | 79 |
| H310D | 1107 | 69 | 665 | 675 | 251 | 244 | 233 | 48 | 313 | 174 | 397 | 389 | 57 | 153 | 76 | 25 | 100 | 279 |
| H310E | 150 | 43 | 227 | 249 | 177 | 145 | 192 | 55 | 113 | 83 | 157 | 153 | 46 | 53 | 30 | <15 | 115 | 178 |
| H310F | 51 | 26 | 85 | 89 | 62 | 64 | 82 | 66 | 54 | 50 | 74 | 57 | 49 | 16 | <15 | <15 | 49 | 45 |
| H310G | 160 | 31 | 278 | 276 | 110 | 101 | 169 | 153 | 122 | 83 | 151 | 144 | 141 | 42 | 56 | 17 | 36 | 61 |
| H310I | 112 | 16 | 111 | 118 | 66 | 31 | 80 | 89 | flat | 70 | 75 | 91 | 52 | 27 | 39 | <15 | 19 | 59 |
| H310K | 556 | <15 | 308 | 377 | 150 | 83 | 333 | 422 | 185 | 222 | 146 | 285 | 286 | 34 | 47 | 54 | 39 | 189 |
| H310L | 785 | 26 | 435 | 420 | 180 | 107 | 366 | 269 | 138 | 193 | 322 | 311 | 221 | 81 | 63 | 27 | 90 | 247 |
| H310M | 641 | 19 | 404 | 522 | 140 | 67 | 293 | 258 | 186 | 228 | 296 | 364 | 203 | 42 | 47 | <15 | 39 | 167 |
| H310N | 92 | <15 | 114 | 140 | 81 | 62 | 110 | 83 | 61 | 65 | 95 | 91 | 76 | 51 | 49 | 22 | 66 | 101 |
| H310Q | 212 | 52 | 268 | 316 | 217 | 190 | 253 | 223 | 197 | 209 | 250 | 292 | 252 | 105 | 80 | <15 | 137 | 247 |
| H310R | 497 | <15 | 475 | 429 | 179 | <15 | 245 | 487 | 260 | 195 | 180 | 345 | 339 | 35 | 65 | <15 | <15 | 127 |
| H310S | 175 | <15 | 251 | 270 | 143 | 67 | 159 | 91 | 74 | 118 | 178 | 151 | 153 | 47 | 37 | <15 | 79 | 170 |
| H310T | 162 | <15 | 238 | 234 | 189 | 80 | 148 | 84 | 106 | 75 | 158 | 154 | 81 | 41 | <15 | <15 | 120 | 182 |
| H310V | 73 | 38 | 115 | 114 | 94 | 73 | 77 | 87 | 80 | 92 | 118 | 111 | 84 | 52 | 54 | 26 | 81 | 99 |
| H310W | 190 | 94 | 335 | 366 | 241 | 276 | 230 | 267 | 227 | 263 | 327 | 324 | 212 | 183 | 121 | 32 | 241 | 229 |
| H310Y | 31 | 28 | 85 | 82 | 75 | 83 | 75 | 83 | 69 | 54 | 70 | 83 | 66 | 30 | <15 | <15 | 62 | 61 |

FIG. 2

| EC50 ng/mL | Single | Q438A | Q438D | Q438E | Q438F | Q438G | Q438H | Q438I | Q438K | Q438L | Q438M | Q438N | Q438R | Q438S | Q438T | Q438V | Q438W | Q438Y |
|---|---|---|---|---|---|---|---|---|---|---|---|---|---|---|---|---|---|---|
| Single ↓/→ | | 109 | 845 | 58 | 38 | 205 | 191 | 56 | 216 | <15 | <15 | 170 | 416 | 55 | 80 | 78 | 117 | 38 |
| Y436A | 133 | 133 | 527 | 67 | 185 | 212 | 180 | 75 | 185 | 39 | <15 | 109 | 101 | 52 | 74 | 57 | 115 | 67 |
| Y436D | 552 | 424 | 1044 | 279 | 211 | 858 | 507 | 185 | 573 | 58 | <15 | 301 | 446 | 119 | 157 | 190 | 198 | 73 |
| Y436E | 594 | 415 | 876 | 276 | 203 | 597 | 467 | 188 | 623 | 50 | 67 | 320 | 491 | 126 | 157 | 138 | 190 | 76 |
| Y436F | 35 | 106 | 119 | 85 | 117 | 206 | 108 | 48 | 98 | 27 | 35 | 71 | 71 | 24 | 51 | 48 | 68 | 48 |
| Y436G | 646 | 325 | 908 | 237 | 152 | 212 | 102 | 109 | 294 | 49 | 57 | 201 | 344 | 105 | 106 | 74 | 143 | 79 |
| Y436H | 72 | 90 | 227 | 56 | 93 | 65 | 53 | 67 | 158 | <15 | 26 | 65 | 82 | 27 | 35 | 37 | 120 | 45 |
| Y436I | <15 | 47 | 70 | <15 | 70 | <15 | <15 | <15 | <15 | <15 | <15 | <15 | <15 | <15 | <15 | <15 | 43 | 28 |
| Y436K | 592 | 91 | 669 | 53 | 148 | 101 | 90 | 70 | 131 | <15 | 19 | 89 | 137 | 40 | 58 | 44 | 177 | 71 |
| Y436L | 191 | 198 | 625 | 114 | 178 | 139 | 98 | 146 | 211 | 44 | 46 | 148 | 208 | 62 | 89 | 76 | 153 | 82 |
| Y436M | 60 | 82 | 206 | 43 | 140 | 42 | 41 | 46 | 75 | <15 | 27 | 46 | 40 | <15 | 19 | <15 | 85 | 48 |
| Y436N | 382 | 73 | 589 | 45 | 145 | 91 | 77 | 88 | 138 | <15 | <15 | 87 | 83 | 41 | 48 | 40 | 161 | 70 |
| Y436Q | 274 | 65 | 285 | 37 | 136 | 63 | 51 | 45 | 70 | <15 | <15 | 44 | 52 | 33 | 39 | 16 | 133 | 80 |
| Y436R | 242 | 39 | 265 | 21 | 93 | 52 | 38 | 30 | 108 | <15 | <15 | 48 | 55 | 26 | 24 | 25 | 80 | 52 |
| Y436S | 585 | 203 | 984 | 155 | 206 | 260 | 114 | 152 | 412 | 37 | <15 | 167 | 278 | 98 | 113 | 85 | 163 | 69 |
| Y436T | 494 | 131 | 777 | 81 | 168 | 137 | 110 | 126 | 394 | 37 | <15 | 126 | 176 | 70 | 75 | 73 | 178 | 69 |
| Y436V | 199 | 66 | 445 | 52 | 131 | 108 | 185 | 65 | 166 | <15 | <15 | 56 | 61 | 39 | 38 | 85 | 109 | 71 |
| Y436W | 110 | 145 | 412 | 199 | 137 | 115 | 155 | 124 | 143 | 34 | <15 | 109 | 74 | 69 | 71 | 87 | 102 | 66 |

FIG. 3

| EC50 ng/mL | Single ↓/→ | K439A | K439D | K439E | K439F | K439H | K439I | K439L | K439M | K439N | K439Q | K439R | K439S | K439T | K439V | K439W | K439Y |
|---|---|---|---|---|---|---|---|---|---|---|---|---|---|---|---|---|---|
| | | 87 | 111 | 864 | 353 | 147 | 298 | 167 | 92 | 58 | 87 | 55 | 53 | 303 | 711 | 225 | 926 |
| S440A | <15 | 16 | 33 | 32 | 41 | <15 | 51 | 26 | 35 | 35 | 30 | <15 | <15 | <15 | <15 | 38 | 30 |
| S440D | <15 | 21 | <15 | 17 | 55 | 45 | 61 | 48 | 38 | 38 | 42 | <15 | <15 | <15 | <15 | 30 | 54 |
| S440E | 59 | 38 | 28 | 48 | 79 | 55 | 89 | 75 | 62 | 54 | 69 | <15 | <15 | 56 | 78 | 46 | 97 |
| S440F | 62 | 59 | 49 | 58 | 97 | 57 | 94 | 73 | 72 | 71 | 76 | <15 | 47 | 71 | 71 | 49 | 91 |
| S440G | 32 | 33 | 51 | 39 | 47 | 53 | 50 | 64 | 51 | 32 | 52 | <15 | <15 | 23 | 30 | <15 | 65 |
| S440H | <15 | 24 | 25 | 26 | 24 | 28 | 43 | 59 | 23 | 21 | 48 | <15 | <15 | 24 | 34 | <15 | 43 |
| S440I | 79 | 50 | 56 | 32 | 78 | 70 | 103 | 96 | 63 | 51 | 77 | <15 | <15 | 60 | 65 | 33 | 93 |
| S440K | 431 | 29 | <15 | <15 | 52 | 49 | 71 | 82 | 39 | 35 | 49 | <15 | 29 | 51 | 94 | 58 | 81 |
| S440L | 167 | 68 | 92 | 147 | 158 | 106 | 160 | 162 | 91 | 84 | 125 | <15 | <15 | 116 | 144 | 36 | 290 |
| S440M | 45 | 33 | 46 | 58 | 47 | 64 | 56 | 69 | 51 | 44 | 65 | <15 | <15 | 31 | 44 | 157 | 83 |
| S440N | 31 | 24 | 27 | 35 | 46 | 45 | 52 | 68 | 21 | 28 | 56 | <15 | <15 | 36 | 36 | <15 | 67 |
| S440Q | <15 | 41 | <15 | 31 | 41 | 33 | 39 | 31 | 50 | 28 | 51 | <15 | <15 | <15 | 18 | 54 | <15 |
| S440R | <15 | 43 | <15 | <15 | 34 | 26 | 22 | <15 | 30 | <15 | 42 | <15 | <15 | <15 | <15 | 40 | 44 |
| S440T | <15 | 46 | <15 | 25 | 31 | 49 | 45 | 51 | 53 | 19 | <15 | <15 | <15 | 55 | 39 | <15 | 65 |
| S440V | 44 | 37 | 38 | 67 | 64 | 61 | 68 | 58 | 67 | 48 | 30 | <15 | <15 | <15 | 57 | <15 | 94 |
| S440W | <15 | 39 | <15 | 30 | 29 | 23 | 21 | 40 | 31 | 0 | <15 | <15 | <15 | <15 | <15 | 51 | 35 |
| S440Y | <15 | 30 | 20 | 27 | 23 | 33 | 30 | 26 | 44 | 23 | <15 | <15 | <15 | <15 | <15 | 32 | 25 |

FIG. 4

CDC on Wien 133
I253G + H310R

IgG1-Campath
- ● E430G (single mAb)
- △ E430G/I253G (single mAb)
- ▽ E430G/H310R (single mAb)
- ☐ E430G/I253G + E430G/H310R (mAb mixture)
- ✕ IgG1-b12

CDC on Wien 133
I253K + H310D

IgG1-Campath
- ● E430G (single mAb)
- △ E430G/I253K (single mAb)
- ▽ E430G/H310D (single mAb)
- ☐ E430G/I253K + E430G/H310D (mAb mixture)
- ✕ IgG1-b12

CDC on Wien 133
I253R + H310D

FIG. 6A

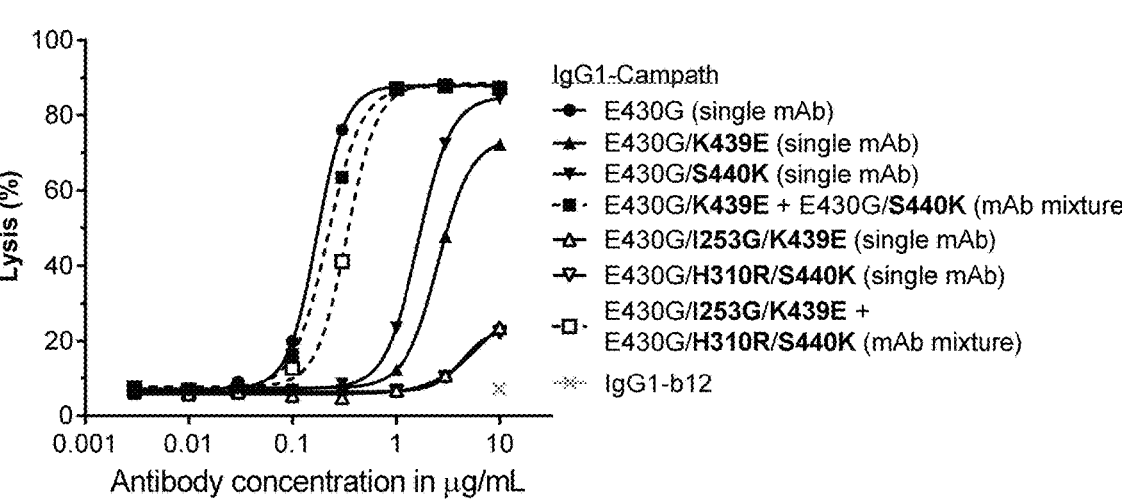

CDC on Wien 133
I253G/K439E + H310R/S440K

IgG1-Campath
- E430G (single mAb)
- E430G/K439E (single mAb)
- E430G/S440K (single mAb)
- E430G/K439E + E430G/S440K (mAb mixture)
- E430G/I253G/K439E (single mAb)
- E430G/H310R/S440K (single mAb)
- E430G/I253G/K439E + E430G/H310R/S440K (mAb mixture)
- IgG1-b12

FIG. 6B

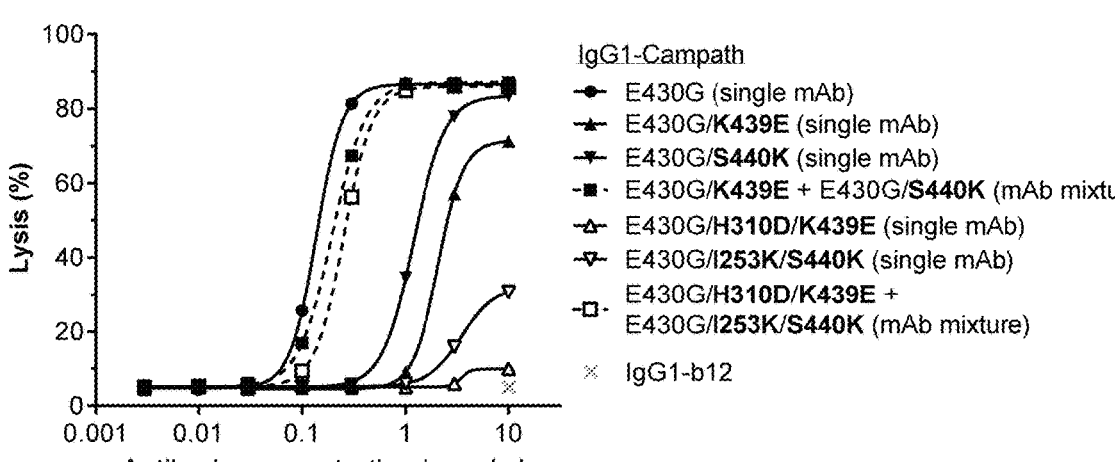

CDC on Wien 133
H310D/K439E + I253K/S440K

IgG1-Campath
- E430G (single mAb)
- E430G/K439E (single mAb)
- E430G/S440K (single mAb)
- E430G/K439E + E430G/S440K (mAb mixture)
- E430G/H310D/K439E (single mAb)
- E430G/I253K/S440K (single mAb)
- E430G/H310D/K439E + E430G/I253K/S440K (mAb mixture)
- IgG1-b12

FIG. 6C

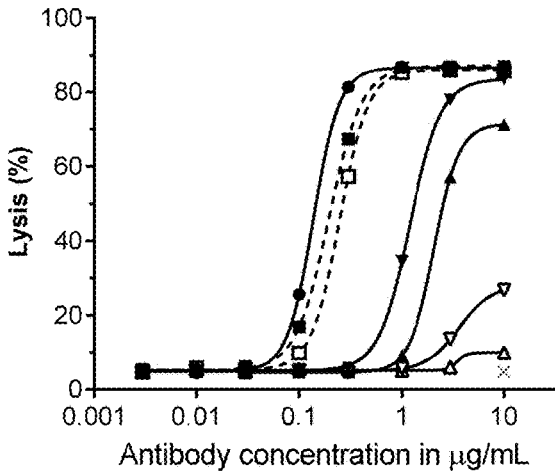

CDC on Wien 133
H310D/K439E + I253R/S440K

IgG1-Campath
- ● E430G (single mAb)
- ▲ E430G/K439E (single mAb)
- ▼ E430G/S440K (single mAb)
- ■ E430G/K439E + E430G/S440K (mAb mixture)
- △ E430G/H310D/K439E (single mAb)
- ▽ E430G/I253R/S440K (single mAb)
- □ E430G/H310D/K439E + E430G/I253R/S440K (mAb mixture)
- ✕ IgG1-b12

FIG. 6D

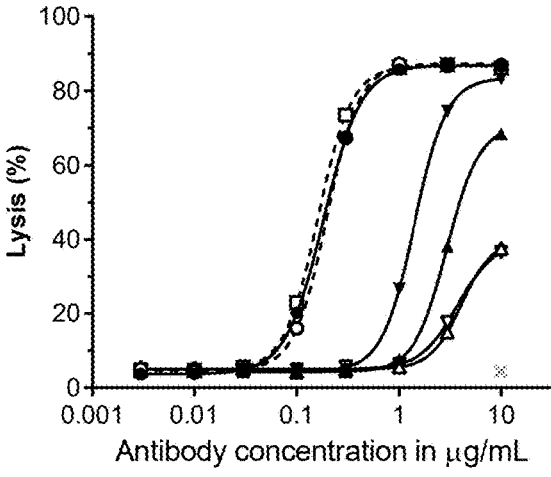

CDC on Wien 133
K439E-Y436N + S440K-Q438R

IgG1-Campath
- ● E430G (single mAb)
- ▲ E430G-K439E (single mAb)
- ▼ E430G-S440K (single mAb)
- ○ E430G-K439E + E430G-S440K (mAb mixture)
- △ E430G-K439E-Y436N (single mAb)
- ▽ E430G-S440K-Q438R (single mAb)
- □ E430G-K439E-Y436N + E430G-S440K-Q438R (mAb mixture)
- ✕ IgG1-b12

CDC on Wien 133
K439E-Q438N + S440K-Y436K

IgG1-Campath
- ● E430G (single mAb)
- ▲ E430G-K439E (single mAb)
- ▼ E430G-S440K (single mAb)
- ■ E430G-K439E + E430G-S440K (mAb mixture)
- △ E430G-K439E-Q438N (single mAb)
- ▽ E430G-S440K-Y436K (single mAb)
- □ E430G-K439E-Q438N + E430G-S440K-Y436K (mAb mixture)
- ✕ IgG1-b12

CDC on Wien 133
K439E-Q438N + S440K-Q438R

IgG1-Campath
- ● E430G (single mAb)
- ▲ E430G-K439E (single mAb)
- ▼ E430G-S440K (single mAb)
- ■ E430G-K439E + E430G-S440K (mAb mixture)
- △ E430G-K439E-Q438N (single mAb)
- ▽ E430G-S440K-Q438R (single mAb)
- □ E430G-K439E-Q438N + E430G-S440K-Q438R (mAb mixture)
- ✕ IgG1-b12

CDC on Wien 133
K439E-Y436N + S440K-Y436K

IgG1-Campath
- E430G (single mAb)
- E430G-K439E (single mAb)
- E430G-S440K (single mAb)
- E430G-K439E + E430G-S440K (mAb mixture)
- E430G-K439E-Y436N (single mAb)
- E430G-S440K-Y436K (single mAb)
- E430G-K439E-Y436N + E430G-S440K-Y436K (mAb mixture)
- IgG1-b12

FcRn binding IgG1-CAMPATH-1H variants (pH 6; Ab conc. 40 μg/ml)

Absorbance (405 nm)

FIG. 8D
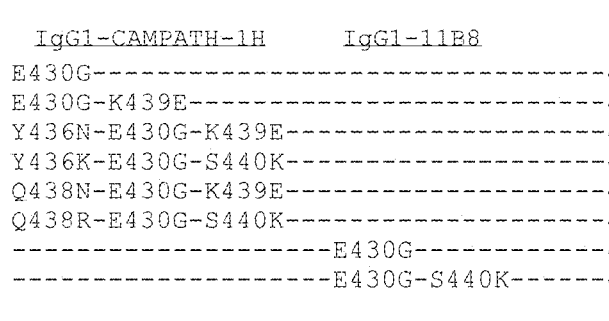
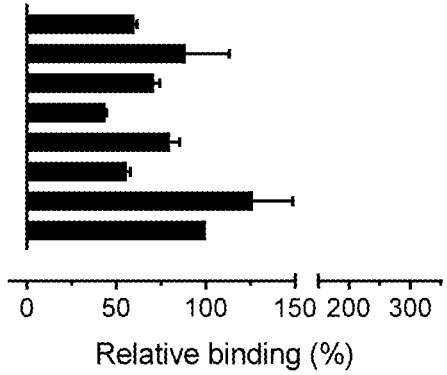
FCGR3AV - 20 ug/mL IgG
FIG. 8E
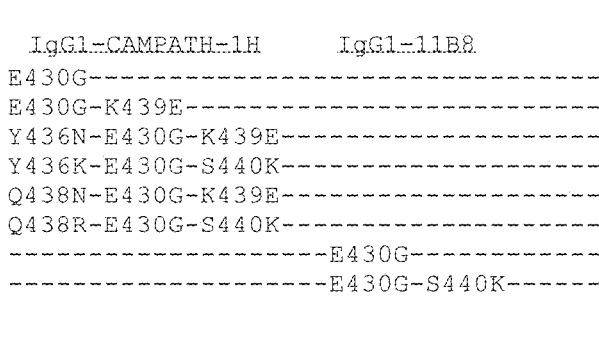
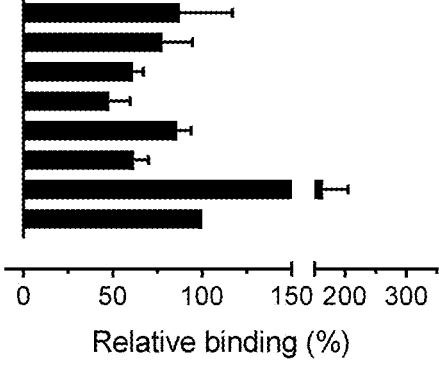
FCGR3AF - 20 ug/mL IgG Fc-Fc interaction enhancing mutations
E345K; E345R; E430G

FcGammaR 2B binding

FcGammaR 3AF binding

Q438N+Y436K at different ratio's

Antibody 1------------------------Antibody 2----------------------

●— CAMP-E430G-K439E-Q438N-titrated--11B8-E430G-S440K-Y436K-titrated--

▲— CAMP-E430G-K439E-Q438N-titrated--11B8-E430G-S440K-Y436K-20 ug/mL--

△— CAMP-E430G-K439E-Q438N-titrated--b12-E430G-S440K-Y436K---20 ug/mL--

✕— CAMP-E430G-K439E-Q438N-titrated--b12------------------------20 ug/mL---

▽— CAMP-E430G-K439E-Q438N-2 ug/mL---11B8-E430G-S440K-Y436K-titrated--

■  b12-E430G-K439E-Q438N--20 ug/mL--11B8-E430G-S440K-Y436K-20 ug/mL--

□  b12------------------20 ug/mL--11B8-E430G-S440K-Y436K-20 ug/mL--

○  b12------------------20 ug/mL--b12--------------------20 ug/mL--

Q438N + Q438R at different ratio's

Antibody 1------------------------Antibody 2------------------------

●— CAMP-E430G-K439E-Q438N-titrated--11B8-E430G-S440K-Q438R-titrated--

▲— CAMP-E430G-K439E-Q438N-titrated--11B8-E430G-S440K-Q438R-20 ug/mL--

△— CAMP-E430G-K439E-Q438N-titrated--b12-E430G-S440K-Q438R---20 ug/mL--

✳— CAMP-E430G-K439E-Q438N-titrated--b12-------------------20 ug/mL--

▽— CAMP-E430G-K439E-Q438N-2 ug/mL----11B8-E430G-S440K-Q438R-titrated--

■  b12-E430G-K439E-Q438N---20 ug/mL--11B8-E430G-S440K-Q438R-20 ug/mL--

□  b12-------------------20 ug/mL--11B8-E430G-S440K-Q438R-20 ug/mL--

○  b12-------------------20 ug/mL--b12-------------------20 ug/mL--

Relative AUC (%)

POLYPEPTIDE VARIANTS AND USES THEREOF

CROSS-REFERENCE TO RELATED APPLICATIONS

This application is a 35 U.S.C. 371 national stage filing of International Application No. PCT/EP2019/051809, filed Jan. 24, 2019, which claims priority to Danish Patent Application No. PA 2018 00041, filed Jan. 24, 2018. The contents of the aforementioned applications are hereby incorporated by reference.

SEQUENCE LISTING

The instant application contains a Sequence Listing which has been submitted electronically in ASCII format and is hereby incorporated by reference in its entirety. Said ASCII copy, created on Jul. 21, 2020, is named GMI_193US_Sequence_Listing.txt and is 221,622 bytes in size.

FIELD OF THE INVENTION

The present invention relates to combination therapy involving two or more Fc region-containing antigen-binding polypeptides, such as antibodies, wherein the polypeptides have been modified such that hetero-oligomerization between the polypeptides is strongly favored over homo-oligomerization when the polypeptides are bound to their corresponding target antigens. The invention also relates to polypeptides, use of such polypeptides, compositions, kits and devices suitable for use in the combination therapy of the invention.

BACKGROUND OF THE INVENTION

Antibodies are highly effective molecules which can have effects on target cells via various mechanisms. In some instances, the mere binding of an antibody to a target antigen on a cell surface can have an antagonistic or agonistic effect on the target antigen and thus on the target cell. Alternatively, or in addition, the effect of an antibody on a target cell is achieved through the ability of antibodies to induce effector functions, typically Fc-mediated effector functions, such as complement-dependent cytotoxicity (CDC), antibody-dependent cell-mediated cytotoxicity (ADCC) and antibody-dependent cell-mediated phagocytosis (ADCP).

ADCC and ADCP are initiated by binding of the IgG Fc region to Fcγ receptors on effector cells. WO2012/130831 discloses Fc region-containing polypeptides that have altered ADCC function as a consequence of one or more amino acid substitutions in the Fc region of the polypeptide.

CDC is initiated by binding of C1q to the Fc regions of antibodies. C1q is a multimeric protein consisting of six globular binding heads attached to a stalk. The individual globular binding heads have low affinity for IgG, and C1q must gain avidity by binding multiple IgG1 molecules on a cell surface to trigger the classical complement pathway. IgG hexamerization upon target binding on the cell surface has been shown to support avid C1q binding. The hexamerization is mediated through intermolecular non-covalent Fc-Fc interactions. Fc-Fc interactions can be enhanced by point mutations in the CH3 domain, including E345R and E430G (see, e.g. WO2013/004842 and WO2014/108198). WO2017/093447 is directed to antibodies that bind a death receptor comprising an intracellular death domain. The application discloses that a K439E mutation in the Fc region of an antibody results in Fc-Fc repulsion, and thus weak Fc-Fc interactions between two antibody molecules having said mutation. This effect could be neutralized by introducing a S440K mutation in the other antibody molecule, leading to a restoration of the Fc-Fc interactions, see also Diebolder et al. (2014) Science 343:126.

While antibody therapy is often highly efficacious, antibody target antigens are often not uniquely expressed in diseased cells or tissue, but are also found in other, healthy, cells or tissue. Thus, antibody therapy may lack selectivity for the target tissue and non-diseased tissue may be affected by the antibody treatment resulting in toxicity.

There is therefore a need for improved antibody treatment, in particular treatment with improved selectivity. Accordingly, it is an object of the present invention to provide for a method of treating a disease by increasing the selectivity of polypeptides or antibodies. It is yet a further object of the present invention to provide for a method of treating a disease by providing for a first and a second polypeptide which have no single agent activity, but only show activity when bound together on the same target cell or tissue. Thus, it is an object of the present invention to provide for a method of treating a disease by administering a first polypeptide capable of binding to a first antigen and a second polypeptide capable of binding to a second antigen, wherein the first and second polypeptide has no effect, or only little effect, on tissues or target organs expressing either the first or second antigen, while providing effective treatment on tissues or target organs expressing both the first and second antigen. It is a further object of the present invention to provide for a method of treating a disease by administering to a subject a first polypeptide and a second polypeptide which have been modified to prevent homo-oligomerization (self-oligomerization) while favoring hetero-oligomerization. It is another object of the present invention to provide for polypeptides, which may be used in such method of treatment, i.e. polypeptides having at least one self-oligomerization inhibiting mutation. It is yet another object of the present invention to provide for a first polypeptide having a self-oligomerization inhibiting mutation and a second polypeptide having a self-oligomerization inhibiting mutation, where the self-oligomerization inhibiting mutations in the first and second polypeptide are complementary, thereby allowing for hetero-oligomerization of the first and second polypeptide when bound to a target cell.

SUMMARY OF THE INVENTION

The present invention provides methods, polypeptides and compositions which can be used to improve the selectivity of an antibody treatment for desired target cell populations.

The methods or uses of the invention relate to a treatment with two antibodies (or antibody-like polypeptides), wherein the two antibodies bind two different target antigens and wherein the Fc regions of the antibodies have been modified such that hetero-oligomerization of the two antibodies is strongly favored over homo-oligomerization. As a result of these modifications, more antibody oligomerization will occur on cells that express both antigen targets (allowing efficient (hetero)oligomerization of the two antibodies), than on cells that only express one of the targets (resulting in inefficient or no (homo)oligomerization). As oligomerization generally enhances the efficacy of antibodies, the antibody combination treatment will be more efficacious against cells that co-express the targets than against cells that only express one of the targets. Thus, the antibody combination treatment has an improved selectivity for cells or tissue expressing both target antigens. Accordingly, by selecting two antigens that are co-expressed in a desired target cell population, but not, or less, co-expressed in cell populations that should not be targeted, a combined antibody treatment can be designed which will have a selective effect against the desired target cell populations.

It is contemplated that the increased efficacy will not only be obtained when the two target antigens are co-expressed on the same cell, but also in other situations where the target cells are in close proximity. Furthermore, besides classical antibodies, also antibody-like polypeptides can be used provided that they comprise an Fc region and an antigen-binding region.

Accordingly, in a first aspect, the invention relates to a method of treating a disease or disorder comprising administering to a subject in need thereof: a first polypeptide comprising a first Fc region of a human IgG and a first antigen-binding region capable of binding to a first antigen, in combination with a second polypeptide comprising a second Fc region of a human IgG and a second antigen-binding region capable of binding to a second antigen, wherein a) said first polypeptide comprises an I253G mutation of an amino acid position corresponding to I253 in human IgG1 and said second polypeptide comprises an H310R mutation of an amino acid position corresponding to H310 in human IgG1, or vice versa,
    or
    said first polypeptide comprises an I253K or I253R mutation of an amino acid position corresponding to I253 in human IgG1 and said second polypeptide comprises an H310D mutation of an amino acid position corresponding to H310 in human IgG1, or vice versa,
  and/or
  b) said first polypeptide comprises a Y436N, Y436K, Y436Q or Y436R mutation of an amino acid position corresponding to Y436 in human IgG1 and said second polypeptide comprises a Q438R, Q438K, Q438H, Q438G or Q438N mutation of an amino acid position corresponding to Q438 in human IgG1, or vice versa,
    or
    said first polypeptide comprises a Y436N or Y436Q mutation of an amino acid position corresponding to Y436 in human IgG1 and said second polypeptide comprises a Y436K or Y436R mutation of an amino acid position corresponding to Y436 in human IgG1, or vice versa,
    or
    said first polypeptide comprises a Q438R, Q438K or Q438H mutation of an amino acid position corresponding to Q438 in human IgG1 and said second polypeptide comprises a Q438N or Q438G mutation of an amino acid position corresponding to Q438 in human IgG1, or vice versa,
  and/or
  c) said first polypeptide comprises a K439F, K439I, K439Y, K439T, K439V, K439W mutation of an amino acid position corresponding to K439 in human IgG1 and said second polypeptide comprises an S440K mutation of an amino acid position corresponding to S440 in human IgG1, or vice versa,
wherein the amino acid positions correspond to human IgG1 according to EU numbering.

In one embodiment of the method of the invention, said first polypeptide comprises a Y436N or Y436K mutation of an amino acid position corresponding to Q436 in human IgG1 and said second polypeptide comprises a Q438N or Q438R mutation of an amino acid position corresponding to Q438 in human IgG1, or vice versa.

In one aspect of the invention said first polypeptide comprises a F436N, F436K, F436Q or F436R mutation of an amino acid position corresponding to F436 in human IgG3 and said second polypeptide comprises a Q438R, Q438K, Q438H, Q438G or Q438N mutation of an amino acid position corresponding to Q438 in human IgG1, or vice versa,
  or
  said first polypeptide comprises a F436N or F436Q mutation of an amino acid position corresponding to F436 in human IgG3 and said second polypeptide comprises a F436K or F436R mutation of an amino acid position corresponding to F436 in human IgG3, or vice versa.

In a further aspect, the invention relates to a first polypeptide, comprising a first Fc region of a human IgG and a first antigen-binding region capable of binding to a first antigen, for use as a medicament in combination with a second polypeptide, comprising a second Fc region of a human IgG and a second antigen-binding region capable of binding to a second antigen, wherein a) said first polypeptide comprises an I253G mutation of an amino acid position corresponding to I253 in human IgG1 and said second polypeptide comprises an H310R mutation of an amino acid position corresponding to H310 in human IgG1, or vice versa,
    or
    said first polypeptide comprises an I253K or I253R mutation of an amino acid position corresponding to I253 in human IgG1 and said second polypeptide comprises an H310D mutation of an amino acid position corresponding to H310 in human IgG1, or vice versa,
  and/or
  b) said first polypeptide comprises a Y436N, Y436K, Y436Q or Y436R mutation of an amino acid position corresponding to Y436 in human IgG1 and said second polypeptide comprises a Q438R, Q438K, Q438H, Q438G or Q438N mutation of an amino acid position corresponding to Q438 in human IgG1, or vice versa,
    or
    said first polypeptide comprises a Y436N or Y436Q mutation of an amino acid position corresponding to Y436 in human IgG1 and said second polypeptide comprises a Y436K or Y436R mutation of an amino acid position corresponding to Y436 in human IgG1, or vice versa,
    or
    said first polypeptide comprises a Q438R, Q438K or Q438H mutation of an amino acid position corresponding to Q438 in human IgG1 and said second polypeptide comprises a Q438N or Q438G mutation of an amino acid position corresponding to Q438 in human IgG1, or vice versa,
  and/or
  c) said first polypeptide comprises a K439F, K439I, K439Y, K439T, K439V, K439W mutation of an amino acid position corresponding to K439 in human IgG1 and said second polypeptide comprises an S440K mutation of an amino acid position corresponding to S440 in human IgG1, or vice versa, wherein the amino acid positions correspond to human IgG1 according to EU numbering.

In a further aspect, the invention relates to a polypeptide comprising an Fc region of a human IgG and an antigen-binding region capable of binding to an antigen, wherein said polypeptide comprises a) a I253G, I253K or I253R mutation of an amino acid position corresponding to I253 in human IgG1,
    or
       a H310R or H310D or mutation of an amino acid position corresponding to H310 in human IgG1,
    and/or
    b) a Y436N, Y436K, Y436Q or Y436R mutation of an amino acid position corresponding to Y436 in human IgG1,
    or
       a Q438R, Q438K, Q438H, Q438G or Q438N mutation of an amino acid position corresponding to Q438 in human IgG1,
    and/or
    c) a K439F, K439I, K439Y, K439T, K439V, K439W mutation of an amino acid position corresponding to K439 in human IgG1,
    or
       an S440K mutation of an amino acid position corresponding to S440 in human IgG1, wherein the amino acid positions correspond to human IgG1 according to EU numbering, with the proviso that if the polypeptide comprises said S440K mutation, then at least one of the other mutations specified in options a) and b) is also present.

In another aspect, the invention relates to compositions comprising one or more polypeptides of the invention as defined herein.

In further aspects, the invention relates to pharmaceutical compositions comprising one or more polypeptides of the invention as defined herein.

In a further aspect, the invention relates to a kit comprising a first container comprising a first polypeptide suitable for use in the invention as defined herein and a second container comprising a second polypeptide suitable for use in the invention as defined herein.

In an even further aspect, the invention relates to a device, such as a dual chamber syringe, comprising a first compartment comprising a first polypeptide suitable for use in the invention as defined herein and a second compartment comprising a second polypeptide suitable for use in the invention as defined herein.

These and other aspects of the invention, particularly various uses and therapeutic applications for the polypeptide or antibody, are described in further detail below.

BRIEF DESCRIPTION OF THE DRAWINGS

FIG. 1 shows the amino acid sequence alignment of the human IgG1m(a) (corresponding to amino acids 99-330 of SEQ ID NO: 24), IgG1m(f) (corresponding to amino acids 99-330 of SEQ ID NO: 22), IgG2 (corresponding to amino acids 99-326 of SEQ ID NO: 31), IgG3 (corresponding to amino acids 99-377 of SEQ ID NO: 32) and IgG4 (corresponding to amino acids 99-327 of SEQ ID NO: 33) Fc backbones with the EU based (IgG1-specific) numbering scheme (Edelman et al. 1969 Proc Natl Acad Sci USA 63, 78-85).

FIG. 2 shows the results of a CDC assay testing IgG1-Campath-E430G antibody variants with the indicated I253 or H310 mutations for the effect of manipulating Fc-Fc interactions and CDC efficacy on Wien 133 cells. Wien 133 cells were incubated with concentration series of the single antibody variants and all possible antibody combinations of I253+H310 mutant pairs in the presence of 5% pooled normal human serum (NHS). CDC efficacy is presented as the half maximal effective antibody concentration (EC50) in ng/mL, as determined by the percentage of TO-PRO-3 iodide-positive cells. Maximal cell lysis with an undefinable low EC50 value is indicated as <15 ng/mL.

FIG. 3 shows the results of a CDC assay testing IgG1-Campath-E430G antibody variants with the indicated Y436 or Q438 mutations for the effect of manipulating Fc-Fc interactions and CDC efficacy on Wien 133 cells. Wien 133 cells were incubated with concentration series of the single antibody variants and all possible antibody combinations of Y436+Q438 mutant pairs in the presence of 5% pooled NHS. CDC efficacy is presented as the half maximal effective antibody concentration (EC50) in ng/mL, as determined by the percentage of TO-PRO-3 iodide-positive cells. Maximal cell lysis with an undefinable low EC50 value is indicated as <15 ng/mL.

FIG. 4 shows the results of a CDC assay testing IgG1-Campath-E430G antibody variants with the indicated K439 or S440 mutations for the effect of manipulating Fc-Fc interactions and CDC efficacy on Wien 133 cells. Wien 133 cells were incubated with concentration series of the single antibody variants and all possible antibody combinations of K439+S440 mutant pairs in the presence of 5% pooled NHS. CDC efficacy is presented as the half maximal effective antibody concentration (EC50) in ng/mL, as determined by the percentage of TO-PRO-3 iodide-positive cells. Maximal cell lysis with an undefinable low EC50 value is indicated as <15 ng/mL.

FIGS. 6A-6G show the effect of combining Fc-Fc inhibiting mutations on the CDC efficacy of IgG1-Campath-E430G. Wien 133 cells were incubated with concentration series of the indicated IgG1-Campath-E430G antibody variants containing one or two Fc-Fc inhibition mutations in single antibodies (single mAb) and in combinations thereof (mAb mixture) in the presence of 20% pooled NHS. CDC efficacy is presented as the percentage lysis determined by the percentage PI-positive cells. The IgG-b12 antibody against HIV gp120 was used as a non-binding control antibody.

FIGS. 8A-8E show FcγR binding of IgG1-CAMPATH-1H variants with Fc-Fc enhancing mutation E430G and self-oligomerization inhibiting substitutions. Binding of immobilized IgG1-CAMPATH-1H-E430G variants with self-oligomerization inhibiting substitutions K439E, S440K, Y436K, Y436N, Q438N and Q438R to dimeric His-tagged biotinylated ECDs of (FIG. 8A) FcγRIIA allotype 131H, (FIG. 8B) FcγRIIA allotype 131R, (FIG. 8C) FcγRIIB, (FIG. 8D) FcγRIIIA allotype 158V and (FIG. 8E) FcγRIIIA allotype 158F as tested in ELISA assays. Binding is presented for 20 μg/mL antibody samples relative to no antibody control (background) and binding to IgG1-CAMPATH-1H-E430G (100%). Detection was performed using Streptavidin-polyHRP and ABTS.

(FIG. 12A, FIG. 12B) Wien 133 cells were incubated with antibody concentration series in the presence of 20% NHS. CDC efficacy is presented as the AUC normalized to non-binding control antibody IgG1-b12 (0%) and the mixture of IgG1-CAMPATH-1H-E430G+IgG1-11B8-E430G (100%).

(FIG. 14F, FIG. 14G) Wien 133 cells were incubated with antibody concentration series in the presence of 20% NHS. CDC efficacy is presented as the normalized AUC of the percentage PI-positive cells. Normalization was performed to non-binding control antibody IgG1-b12 (0%) and IgG1-CAMPATH-1H-E430G (100%; FIG. 14F) or to non-binding control antibody IgG1-b12 (0%) and a mixture of IgG1-CAMPATH-1H-E430G+IgG1-11B8-E430G (100%; FIG. 14G).

(FIG. 21A) CDC efficacy of single agents IgG1-CAMPATH-1H-E430G-K439E-Q438N and IgG1-11B8-E430G-S440K-Y436K and mixtures thereof. (FIG. 21B) CDC efficacy of single agents IgG1-CAMPATH-1H-E430G-K439E-Q438N and IgG1-11B8-E430G-S440K-Q438R and mixtures thereof.

(FIG. 22A) CDC and (FIG. 22B) maximal cell lysis induced by single agent antibody variants harboring mutation E430G in combination with either mutation K439E or S440K and mixtures thereof. (FIG. 22C) CDC and (FIG. 22D) maximal cell lysis induced by antibody variants harboring the E430G, K439E, and Y436N mutations mixed with IgG1-CAMPATH-1H or IgG1-b12 antibody variants harboring complementary mutations, compared to their single agent control reactions. (FIG. 22E) CDC and (FIG. 22F) maximal cell lysis induced by antibody variants harboring the E430G, K439E, and Q438N mutations mixed with IgG1-CAMPATH-1H or IgG1-b12 antibody variants harboring complementary mutations, compared to their single agent control reactions.

DETAILED DESCRIPTION OF THE INVENTION

Definitions

Figure 5A:
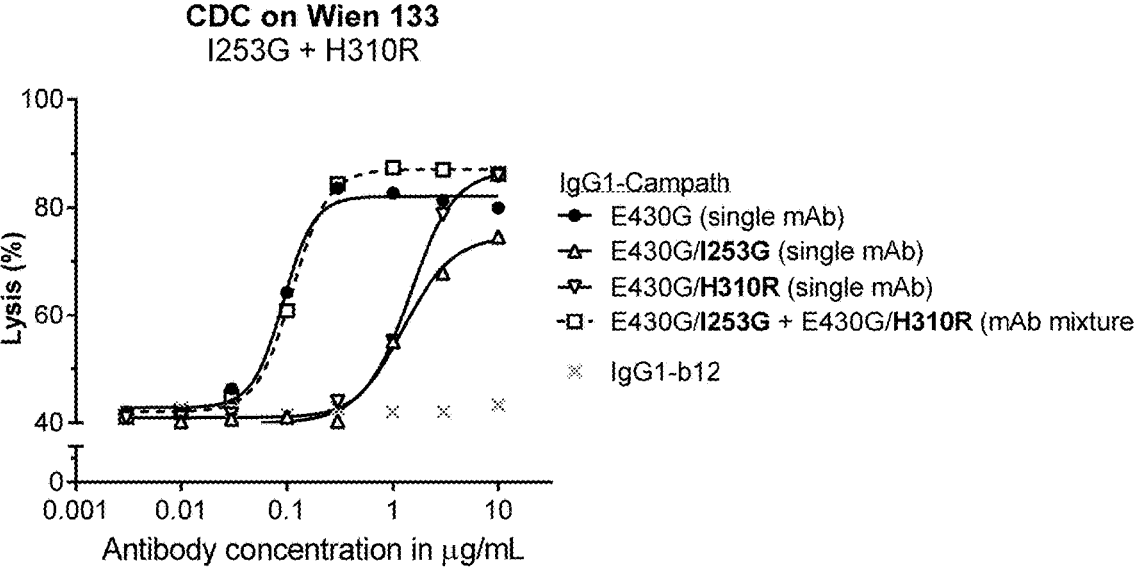
FIGS. 5A-5C show the effect of Fc-Fc inhibiting mutations I253G and H310R (FIG. 5A), I253K and H310D (FIG. 5B), and I253R and H310D (FIG. 5C) on the CDC efficacy of IgG1-Campath-E430G. Wien 133 cells were incubated with concentration series of the indicated IgG1-Campath-E430G antibody variants containing a single Fc-Fc inhibiting mutation (single mAb) and the combinations thereof (mAb mixture) in the presence of 20% pooled NHS. CDC efficacy is presented as the percentage lysis determined by the percentage PI-positive cells. The IgG-b12 antibody against HIV gp120 was used as a non-binding control antibody.

The term "polypeptide comprising an Fc-region of an IgG and an antigen-binding region" refers in the context of the present invention to a polypeptide which comprises an Fc-region of an immunoglobulin of the IgG isotype and a binding region which is a capable of binding to an antigen, which can be any type of molecule, such as a polypeptide, e.g. present on a cell, bacterium, or virion. The Fc-region of an immunoglobulin is defined as the fragment of an antibody which would be typically generated after digestion of an antibody with papain (which is known for someone skilled in the art) which includes the two CH2-CH3 regions of an immunoglobulin and a connecting region, e.g. a hinge region. Thus, the term "Fc-region of an IgG" means in the context of the present invention that a connecting region, e.g. hinge region, and the CH2 and CH3 region of an immunoglobulin are present. The constant domain of an antibody heavy chain defines the antibody isotype, which can e.g. be IgG1, IgG2, IgG3 or IgG4. The Fc-region mediates the effector functions of antibodies with cell surface receptors called Fc receptors and proteins of the complement system. The polypeptide comprising an Fc-domain of an IgG and an antigen-binding region may be an antibody, like a chimeric, humanized, or human antibody or a heavy chain only antibody or a ScFv-Fc-fusion, or an Fc-fusion-protein. The polypeptide is not limited to human origin but can be of any origin, such as e.g. mouse, rat, rabbit or cynomolgus origin.

The term "immunoglobulin" or "Ig" refers to a class of structurally related glycoproteins consisting of two pairs of polypeptide chains, one pair of light (L) low molecular weight chains and one pair of heavy (H) high molecular weight chains, all four potentially inter-connected by disulfide bonds. "IgG" refers to an immunoglobulin G. The structure of immunoglobulins has been well characterized. See for instance Fundamental Immunology Ch. 7 (Paul, W., ed., 2nd ed. Raven Press, N.Y. (1989)). Briefly, each heavy chain typically is comprised of a heavy chain variable region (abbreviated herein as VH) and a heavy chain constant region. The heavy chain constant region typically is comprised of three domains, CH1, CH2, and CH3. The heavy chains are inter-connected via disulfide bonds in the so-called "hinge region". Each light chain typically is comprised of a light chain variable region (abbreviated herein as VL) and a light chain constant region. The light chain constant region typically is comprised of one domain, CL. The VH and VL regions may be further subdivided into regions of hypervariability (or hypervariable regions which may be hypervariable in sequence and/or form of structurally defined loops), also termed complementarity determining regions (CDRs), interspersed with regions that are more conserved, termed framework regions (FRs). Each VH and VL is typically composed of three CDRs and four FRs, arranged from amino-terminus to carboxy-terminus in the following order: FR1, CDR1, FR2, CDR2, FR3, CDR3, FR4 (see also Chothia and Lesk J. Mol. Biol. 196, 901 917 (1987)). Unless otherwise stated or contradicted by context, CDR sequences herein are identified according to IMGT rules using DomainGapAlign (Lefranc M P., Nucleic Acids Research 1999; 27:209-212 and Ehrenmann F., Kaas Q. and Lefranc M.-P. Nucleic Acids Res., 38, D301-307 (2010); see also internet http address www.imgt.org/. Unless otherwise stated or contradicted by context, reference to amino acid positions in the present invention is according to the EU-numbering (Edelman et al., Proc Natl Acad Sci USA. 1969 May; 63(1):78-85; Kabat et al., Sequences of proteins of immunological interest. 5th Edition—1991 NIH Publication No. 91-3242).

The term "amino acid corresponding to position . . . " as used herein refers to an amino acid position number in a human IgG1 heavy chain. Corresponding amino acid positions in other immunoglobulins may be found by alignment with human IgG1. FIG. 1 gives an alignment of IgG1, IgG2, IgG3 and IgG4 sequences showing which positions in IgG2, IgG3 and IgG4 correspond to which positions in IgG1. Thus, an amino acid or segment in one sequence that "corresponds to" an amino acid or segment in another sequence is one that aligns with the other amino acid or segment using a standard sequence alignment program such as ALIGN, ClustalW or similar, typically at default settings and has at least 50%, at least 80%, at least 90%, or at least 95% identity to a human IgG1 heavy chain. It is considered well-known in the art how to align a sequence or segment in a sequence and thereby determine the corresponding position in a sequence to an amino acid position according to the present invention.

The term "hinge region" as used herein is intended to refer to the hinge region of an immunoglobulin heavy chain. Thus, for example the hinge region of a human IgG1 antibody corresponds to amino acids 216-230 according to the EU numbering.

The term "CH2 region" or "CH2 domain" as used herein is intended to refer the CH2 region of an immunoglobulin heavy chain. Thus, for example the CH2 region of a human IgG1 antibody corresponds to amino acids 231-340 according to the EU numbering. However, the CH2 region may also be any of the other isotypes as described herein.

The term "CH3 region" or "CH3 domain" as used herein is intended to refer the CH3 region of an immunoglobulin heavy chain. Thus, for example the CH3 region of a human IgG1 antibody corresponds to amino acids 341-447 according to the EU numbering. However, the CH3 region may also be any of the other isotypes as described herein.

The term "Fc region" or "Fc domain", which may be used interchangeably herein, refers to an antibody region comprising, arranged from amino-terminus to carboxy-terminus, at least a hinge region, a CH2 domain and a CH3 domain. An Fc region of an IgG1 antibody can, for example, be generated by digestion of an IgG1 antibody with papain.

The term "antibody" (Ab) in the context of the present invention refers to an immunoglobulin molecule, a fragment of an immunoglobulin molecule, or a derivative of either thereof, which has the ability to specifically bind to an antigen. An antibody used in the present invention comprises an Fc-domain of an immunoglobulin and an antigen-binding region. An antibody generally contains a CH2-CH3 region and a connecting region, e.g. a hinge region, e.g. at least an Fc-domain. The variable regions of the heavy and light chains of the immunoglobulin molecule contain a binding domain that interacts with an antigen. An antibody may also be a monospecific or a multispecific antibody, such as a bispecific antibody or similar molecule. The term "bispecific antibody" refers to an antibody having specificities for at least two different, typically non-overlapping, epitopes. Such epitopes may be on the same or different targets. If the epitopes are on different targets, such targets may be on the same cell or different cells or cell types. As indicated above, unless otherwise stated or clearly contradicted by the context, the term antibody herein includes fragments of an antibody which comprise at least a portion of an Fc-region and which retain the ability to specifically bind to the antigen. Such fragments may be provided by any known technique, such as enzymatic cleavage, peptide synthesis and recombinant expression techniques. It has been shown that the antigen-binding function of an antibody may be performed by fragments of a full-length antibody. Examples of binding fragments encompassed within the term "Ab" or "antibody" include, without limitation, monovalent antibodies (described in WO2007059782 by Genmab); heavy-chain antibodies, consisting only of two heavy chains and naturally occurring in e.g. camelids (e.g., Hamers-Casterman (1993) Nature 363:446); ThioMabs (Roche, WO2011069104); strand-exchange engineered domain (SEED or Seed-body) which are asymmetric and bispecific antibody-like molecules (Merck, WO2007110205); Triomab (Pharma/Fresenius Biotech, Lindhofer et al. 1995 J Immunol 155:219; WO2002020039); FcΔAdp (Regeneron, WO2010151792), Azymetric Scaffold (Zymeworks/Merck, WO2012/058768); mAb-Fv (Xencor, WO2011/028952), Xmab (Xencor); Dual variable domain immunoglobulin (Abbott, DVD-Ig, U.S. Pat. No. 7,612, 181); Dual domain double head antibodies (Unilever; Sanofi Aventis, WO20100226923); Di-diabody (ImClone/Eli Lilly); Knobs-into-holes antibody formats (Genentech, WO9850431); DuoBody (Genmab, WO 2011/131746); Bispecific IgG1 and IgG2 (Pfizer/Rinat, WO11143545); Duet-Mab (MedImmune, US2014/0348839); Electrostatic steering antibody formats (Amgen, EP1870459 and WO 2009089004; Chugai, US201000155133; Oncomed, WO2010129304A2); CrossMAbs (Roche, WO2011117329); LUZ-Y (Genentech), Biclonic (Merus, WO2013157953); Dual Targeting domain antibodies (GSK/Domantis); Two-in-one Antibodies or Dual action Fabs recognizing two targets (Genentech, NovImmune, Adimab); Cross-linked Mabs (Karmanos Cancer Center); covalently fused mAbs (AIMM), CovX-body (CovX/Pfizer); FynomAbs (Covagen/Janssen cilag); DutaMab (Dutalys/Roche); iMab (MedImmune); IgG-like Bispecific (ImClone/Eli Lilly, Shen, J., et al. J Immunol Methods, 2007. 318(1-2): p. 65-74); TIG-body, DIG-body and PIG-body (Pharmabcine); Dual-affinity retargeting molecules (Fc-DART or Ig-DART, by Macrogenics, WO/2008/157379, WO/2010/080538); BEAT (Glenmark); Zybodies (Zyngenia); approaches with common light chain (Crucell/Merus, U.S. Pat. No. 7,262,028) or common heavy chains (κλBodies by NovImmune, WO2012023053), as well as fusion proteins comprising a polypeptide sequence fused to an antibody fragment containing an Fc-domain like scFv-fusions, like BsAb by ZymoGenetics/BMS, HERCULES by Biogen Idec (US007951918), SCORPIONS by Emergent BioSolutions/Trubion and Zymogenetics/BMS, Ts2Ab (MedImmune/AZ (Dimasi, N., et al. J Mol Biol, 2009. 393(3): p. 672-92), scFv fusion by Genentech/Roche, scFv fusion by Novartis, scFv fusion by Immunomedics, scFv fusion by Changzhou Adam Biotech Inc (CN 102250246), TvAb by Roche (WO 2012025525, WO 2012025530), mAb$^2$ by f-Star (WO2008/003116), and dual scFv-fusions. It also should be understood that the term antibody, unless specified otherwise, also includes polyclonal antibodies, monoclonal antibodies (such as human monoclonal antibodies), antibody mixtures (recombinant polyclonals) for instance generated by technologies exploited by Symphogen and Merus (Oligoclonics), multimeric Fc proteins as described in WO2015/158867, fusion proteins as described in WO2014/031646 and antibody-like polypeptides, such as chimeric antibodies and humanized antibodies. An antibody as generated can potentially be of any isotype.

The terms "antigen-binding region", "antigen-binding site" or "antigen-binding domain", as used herein, refer to a region of a polypeptide, such as an antibody, which is capable of binding to an antigen. This binding region is typically defined by the VH and VL domains of an antibody which may be further subdivided into regions of hypervariability (or hypervariable regions which may be hypervariable in sequence and/or form of structurally defined loops), also termed complementarity determining regions (CDRs), interspersed with regions that are more conserved, termed framework regions (FRs). The antigen can be any molecule, such as a polypeptide, e.g. present on a cell, bacterium, or virion.

The term "cell-associated antigen", when used herein, refers to an antigen which is associated to a cell rather than soluble in circulation. In one embodiment, the cell-associated antigen is a cell-surface-located antigen, e.g. an antigen exposed on the cell surface. In another embodiment, the cell-associated antigen is an integral membrane protein.

The term "full-length antibody" when used herein, refers to an antibody which contains all heavy and light chain constant and variable domains corresponding to those that are normally found in a wild-type antibody of that isotype.

The term "human antibody", as used herein, is intended to include antibodies having variable and constant regions derived from human germline immunoglobulin sequences. The human antibodies of the invention may include amino acid residues not encoded by human germline immunoglobulin sequences (e.g., mutations, insertions or deletions introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

The term "chimeric antibody", as used herein, refers to an antibody in which both chain types are chimeric as a result of antibody engineering. A chimeric chain is a chain that contains a foreign variable domain (originating from a non-human species, or synthetic or engineered from any species including human) linked to a constant region of human origin. The variable domain of a chimeric chain has a V region amino acid sequence which, analyzed as a whole, is closer to non-human species than to human.

The term "humanized antibody", as used herein, refers to an antibody in which both chain types are humanized as a result of antibody engineering. A humanized chain is typically a chain in which the complementarity determining regions (CDR) of the variable domains are foreign (originating from one species other than human, or synthetic) whereas the remainder of the chain is of human origin. Humanization assessment is based on the resulting amino acid sequence, and not on the methodology per se, which allows protocols other than grafting to be used. The variable domain of a humanized chain has a V region amino acid sequence which, analyzed as a whole, is closer to human than to other species.

The terms "monoclonal antibody", "monoclonal Ab", "monoclonal antibody composition", "mAb", or the like, as used herein refer to a preparation of Ab molecules of single molecular composition. A monoclonal antibody composition displays a single binding specificity and affinity for a particular epitope. Accordingly, the term "human monoclonal antibody" refers to Abs displaying a single binding specificity which have variable and constant regions derived from human germline immunoglobulin sequences. The human mAbs may be generated by a hybridoma which includes a B cell obtained from a transgenic or trans-chromosomal non-human animal, such as a transgenic mouse, having a genome comprising a human heavy chain transgene repertoire and a light chain transgene repertoire, rearranged to produce a functional human antibody and fused to an immortalized cell.

The term "isotype" as used herein, refers to the immunoglobulin class (for instance IgG1, IgG2, IgG3, IgG4, IgD, IgA1, IgGA2, IgE, or IgM or any allotypes thereof such as IgG1m(za) and IgG1m(f)) that is encoded by heavy chain constant region genes. Further, each heavy chain isotype can be combined with either a kappa (κ) or lambda (λ) light chain.

The term "mixed isotype" used herein refers to Fc region of an immunoglobulin generated by combining structural features of one isotype with the analogous region from another isotype thereby generating a hybrid isotype. A mixed isotype may comprise an Fc region having a sequence comprised of two or more isotypes selected from the following IgG1, IgG2, IgG3, IgG4, IgD, IgA1, IgGA2, IgE, or IgM thereby generating combinations such as e.g. IgG1/IgG3, IgG1/IgG4, IgG2/IgG3 or IgG2/IgG4.

The terms "antigen", "target antigen" or "antigen target" as used herein, refers to a molecule, such as a protein, to which the antigen-binding region of the polypeptide binds. An antigen molecule can contain one or more epitopes.

The term "epitope" means a protein determinant capable of specific binding to an antibody variable domain. Epitopes usually consist of surface groupings of molecules such as amino acids, sugar side chains or a combination thereof and usually have specific three-dimensional structural characteristics, as well as specific charge characteristics. Conformational and non-conformational epitopes are distinguished in that the binding to the former but not the latter is lost in the presence of denaturing solvents. The epitope may comprise amino acid residues directly involved in the binding (also called immunodominant component of the epitope) and other amino acid residues, which are not directly involved in the binding.

As used herein, the term "affinity" is the strength of binding of one molecule, e.g. an antibody, to another, e.g. a target or antigen, at a single site, such as the monovalent binding of an individual antigen binding site of an antibody to an antigen.

As used herein, the term "avidity" refers to the combined strength of multiple binding sites between two structures, such as between multiple antigen-binding sites of antibodies simultaneously interacting with a target or e.g. between antibody and C1q. When more than one binding interactions are present, the two structures will only dissociate when all binding sites dissociate, and thus, the dissociation rate will be slower than for the individual binding sites, and thereby providing a greater effective total binding strength (avidity) compared to the strength of binding of the individual binding sites (affinity).

A "variant" or "polypeptide variant" or "antibody variant" in the present invention is a polypeptide or antibody molecule which comprises one or more mutations as compared to a reference antibody. Exemplary reference antibody formats include, without limitation, a wild-type antibody, such as a wild-type IgG1 antibody, a full-length antibody or Fc-containing antibody fragment, a bispecific antibody, a human antibody, humanized antibody, chimeric antibody or any combination thereof. Exemplary mutations include amino acid deletions, insertions, and substitutions of amino acids in the parent amino acid sequence. Amino acid substitutions may exchange a native amino acid for another naturally-occurring amino acid, or for a non-naturally-occurring amino acid derivative. The amino acid substitution may be conservative or non-conservative. In the context of the present invention, conservative substitutions may be defined by substitutions within the classes of amino acids reflected in one or more of the following three tables:

| Amino acid residue classes for conservative substitutions | |
| --- | --- |
| Acidic Residues | Asp (D) and Glu (E) |
| Basic Residues | Lys (K), Arg (R), and His (H) |
| Hydrophilic Uncharged Residues | Ser (S), Thr (T), Asn (N), and Gln (Q) |
| Aliphatic Uncharged Residues | Gly (G), Ala (A), Val (V), Leu (L), and Ile (I) |
| Non-polar Uncharged Residues | Cys (C), Met (M), and Pro (P) |
| Aromatic Residues | Phe (F), Tyr (Y), and Trp (W) |

| Alternative conservative amino acid residue substitution classes | | | |
|---|---|---|---|
| 1 | A | S | T |
| 2 | D | E | |
| 3 | N | Q | |
| 4 | R | K | |
| 5 | I | L | M |
| 6 | F | Y | W |

| Alternative Physical and Functional Classifications of Amino Acid Residues | |
|---|---|
| Alcohol group-containing residues | S and T |
| Aliphatic residues | I, L, V, and M |
| Cycloalkenyl-associated residues | F, H, W, and Y |
| Hydrophobic residues | A, C, F, G, H, I, L, M, R, T, V, W, and Y |
| Negatively charged residues | D and E |
| Polar residues | C, D, E, H, K, N, Q, R, S, and T |
| Positively charged residues | H, K, and R |
| Small residues | A, C, D, G, N, P, S, T, and V |
| Very small residues | A, G, and S |
| Residues involved in turn formation | A, C, D, E, G, H, K, N, Q, R, S, P, and T |
| Flexible residues | Q, T, K, S, G, N, D, E, and R |

In the context of the present invention, a substitution in a variant is indicated as:

Original amino acid—position—substituted amino acid;

The three letter code, or one letter code, are used, including the codes Xaa and X to indicate amino acid residue. Accordingly, the notation "I253G" or "Ile253Gly" means that the variant comprises a substitution of Isoleucine with Glycine in the variant amino acid position corresponding to the amino acid in position 253 in the reference antibody.

Where a position as such is not present in an antibody, but the variant comprises an insertion of an amino acid, for example:

Position—inserted amino acid; the notation, e.g., "253G" is used.

Such notation is particularly relevant in connection with modification(s) in a series of homologous polypeptides or antibodies.

Similarly, when the identity of the substitution amino acid residue(s) is immaterial:

Original amino acid—position; or "I253".

For a modification where the original amino acid(s) and/or substituted amino acid(s) may comprise more than one, but not all amino acid(s), the substitution of Isoleucine for Glycine, Lysine or Arginine in position 253: "Ile253Gly, Lys, Arg" or "I253G,K,R" or "I253G/K/R" or "I253 to G, K or R" may be used interchangeably in the context of the invention.

Furthermore, the term "a substitution" embraces a substitution into any one of the other nineteen natural amino acids, or into other amino acids, such as non-natural amino acids. For example, a substitution of amino acid E in position 345 includes each of the following substitutions: 345A, 345C, 345D, 345G, 345H, 345F, 345I, 345K, 345L, 345M, 345N, 345P, 345Q, 345R, 345S, 345T, 345V, 345W, and 345Y. This is equivalent to the designation 345X, wherein the X designates any amino acid. These substitutions can also be designated E345A, E345C, etc., or E345A, C, etc, or E345A/C/etc. The same applies to analogy to each and every position mentioned herein, to specifically include herein any one of such substitutions.

When used herein, the term "and/or" between options or embodiments is intended to cover all possible alternatives and combinations. E.g. "A and/or B and/or C" would be intended to cover all of the following embodiments:

A

B

C

A and B

A and C

B and C

A and B and C

As used herein, the term "effector cell" refers to an immune cell which is involved in the effector phase of an immune response, as opposed to the recognition and activation phases of an immune response. Exemplary immune cells include a cell of a myeloid or lymphoid origin, for instance lymphocytes (such as B cells and T cells including cytolytic T cells (CTLs)), killer cells, natural killer cells, macrophages, monocytes, eosinophils, polymorphonuclear cells, such as neutrophils, granulocytes, mast cells, and basophils. Some effector cells express Fc receptors (FcRs) or complement receptors and carry out specific immune functions. In some embodiments, an effector cell such as, e.g., a natural killer cell, is capable of inducing ADCC. For example, monocytes, macrophages, neutrophils, dendritic cells and Kupffer cells which express FcRs, are involved in specific killing of target cells and presenting antigens to other components of the immune system, or binding to cells that present antigens. In some embodiments, the ADCC can be further enhanced by antibody driven classical complement activation resulting in the deposition of activated C3 fragments on the target cell. C3 cleavage products are ligands to complement receptors (CRs), such as CR3, expressed on myeloid cells. The recognition of complement fragments by CRs on effector cells may promote enhanced Fc receptor-mediated ADCC. In some embodiments antibody driven classical complement activation leads to C3 fragments on the target cell. These C3 cleavage products may promote direct complement-dependent cellular cytotoxicity (CDCC). In some embodiments, an effector cell may phagocytose a target antigen, target particle or target cell. The expression of a particular FcR or complement receptor on an effector cell may be regulated by humoral factors such as cytokines. For example, expression of FcγRI has been found to be up-regulated by interferon γ (IFNγ) and/or G-CSF. This enhanced expression increases the cytotoxic activity of FcγRI-bearing cells against targets. An effector cell can phagocytose a target antigen or phagocytose or lyse a target cell. In some embodiments antibody driven classical complement activation leads to C3 fragments on the target cell. These C3 cleavage products may promote direct phagocytosis by effector cells or indirectly by enhancing antibody mediated phagocytosis.

The term "Fc-mediated effector functions," as used herein, is intended to refer to functions that are a consequence of binding a polypeptide or antibody to its target, such as an antigen, on a cell membrane wherein the Fc effector function is attributable to the Fc region of the polypeptide or antibody. Examples of Fc effector functions include (i) C1q-binding, (ii) complement activation, (iii) complement-dependent cytotoxicity (CDC), (iv) antibody-dependent cell-mediated cytotoxicity (ADCC), (v) Fc-gamma receptor-binding, (vi) antibody-dependent cellular phagocytosis (ADCP), (vii) complement-dependent cellular cytotoxicity (CDCC), (viii) complement-enhanced cytotoxicity, (ix) binding to complement receptor of a complement opsonized antibody mediated by the antibody, (x) opsonisation, and (xi) a combination of any of (i) to (x).

The term "vector," as used herein, refers to a nucleic acid molecule capable of inducing transcription of a nucleic acid segment ligated into the vector. One type of vector is a "plasmid", which is in the form of a circular double stranded DNA loop. Another type of vector is a viral vector, wherein the nucleic acid segment may be ligated into the viral genome.

The term "host cell" refers to a cell into which an expression vector has been introduced, as by transfection. It should be understood that such terms are intended to refer not only to the particular subject cell, but also to the progeny of such a cell. Host cells include, for example, CHO cells, HEK-293 cells, PER.C6, NS0 cells, and lymphocytic cells, and prokaryotic cells such as E. coli and other eukaryotic hosts such as plant cells and fungi.

As used herein, the term "oligomer" refers to a molecule that consists of more than one but a limited number of monomer units (e.g. antibodies) in contrast to a polymer that, at least in principle, consists of an unlimited number of monomers. Exemplary oligomers are dimers, trimers, tetramers, pentamers and hexamers. Greek prefixes are often used to designate the number of monomer units in the oligomer, for example a tetramer being composed of four units and a hexamer of six units.

The term "oligomerization", as used herein, is intended to refer to a process that converts monomers to a finite degree of polymerization. Herein, it is observed, that, antibodies comprising target-binding regions according to the invention can form oligomers, such as hexamers, via non-covalent association of Fc-regions after target binding, e.g., at a cell surface. In the context of the present application, the terms "self-oligomerization", "auto-oligomerization" or "homo-oligomerization" may be used interchangeably and is intended to refer to a process of oligomerization between antibody molecules that have identical protein sequences disregarding post-translational modifications. The term "hetero-oligomerization", as used herein, is intended to refer to a process of oligomerization between antibody molecules that have different protein sequences disregarding post-translational modifications. Different antibodies participating in hetero-oligomerization could for instance bind different antigens, such as different target proteins, glycoproteins, glycans, or glycolipids.

The term "self-oligomerization inhibiting substitution" is intended to refer to a substitution in a polypeptide comprising an Fc region of an immunoglobulin and an antigen-binding region that inhibits the process of oligomerization between antibody molecules that have identical protein sequences disregarding post-translational modifications. Inhibition of self-oligomerization can be illustrated as an increase in EC50 of CDC activity or a reduction in maximal CDC lysis activity of the antibody, when measured according to the methods described in examples 5 and 9.

The term "clustering", as used herein, is intended to refer to oligomerization of antibodies, polypeptides, antigens or other proteins through non-covalent interactions.

The term "co-dependent", as used herein, is intended to refer to a functional effect that is dependent on the simultaneous binding of two or more different polypeptides with self-oligomerization inhibiting substitutions to a target on the same cell. In the context of the present invention, functional effects, such as CDC activity, can be dependent on the simultaneous binding of a first and second polypeptide i.e. the effect is said to be co-dependent. Thus, the effector function e.g. CDC activity of a first polypeptide having a self-oligomerization inhibiting substitution is dependent on the binding of a second polypeptide having a self-oligomerization inhibiting substitution, where the co-dependent effector function is present if said self-oligomerization substitutions are complementary.

When used herein, in the context of two antigens, the term "co-located" or grammatical variations thereof, is intended to refer, on one hand, to situations where the two antigens are co-expressed on the same cell. The antigens may already be adjacent to each other on the cell or the antigens may be brought together via oligomerization of the binding polypeptides, e.g. antibodies, of the invention. Furthermore, the term "co-located" is also intended to refer to situations wherein the two antigens are expressed on different cells, but wherein such cells are located in close proximity to each other.

As used herein, the term "complement activation" refers to the activation of the classical complement pathway, which is initiated by a large macromolecular complex called C1 binding to antibody-antigen complexes on a surface. C1 is a complex, which consists of the recognition protein C1q that is composed of 6 heterotrimeric subunits, and a hetero-tetramer of serine proteases, C1r2C1s2. C1 is the first protein complex in the early events of the classical complement cascade that involves a series of cleavage reactions that starts with the cleavage of C4 into C4a and C4b and C2 into C2a and C2b. C4b is deposited and forms together with C2a an enzymatic active convertase called C3 convertase, which cleaves complement component C3 into C3b and C3a, which forms a C5 convertase. This C5 convertase splits C5 in C5a and C5b and the last component is deposited on the membrane and that in turn triggers the late events of complement activation in which terminal complement components C5b, C6, C7, C8 and C9 assemble into the membrane attack complex (MAC). The complement cascade results in the creation of pores due to which causes cell lysis, also known as complement-dependent cytotoxicity (CDC). Complement activation can be evaluated by using C1q efficacy or CDC kinetics CDC assays (as described in WO2013/004842, WO2014/108198) or by the method Cellular deposition of C3b and C4b described in Beurskens et al Apr. 1, 2012 vol. 188 no. 7 3532-3541.

The term "complement-dependent cytotoxicity" ("CDC"), as used herein, is intended to refer to the process of antibody-mediated complement activation leading to lysis of a cell or virion when antibody is bound to its target on the cell or virion as a result of pores in the membrane that are created by MAC assembly. CDC can be evaluated by in vitro assay such as a CDC assay in which normal human serum is used as a complement source with an antibody concentration series, as described in Example 2, 3, 4, 5 and 6 or in a C1q concentration series.

The term "antibody-dependent cell-mediated cytotoxicity" ("ADCC") as used herein, is intended to refer to a mechanism of killing of antibody-coated target cells or virions by cells expressing Fc receptors that recognize the Fc region of the bound antibody. ADCC can be determined using in vitro methods such as a chromium-release ADCC assay or a Luminescent ADCC Reporter BioAssay.

The term "antibody-drug conjugate", as used herein refers to an antibody or Fc-containing polypeptide having specificity for at least one type of malignant cell, a drug, and a linker coupling the drug to e.g. the antibody. The linker is cleavable or non-cleavable in the presence of the malignant cell; wherein the antibody-drug conjugate kills the malignant cell.

The term "antibody-drug conjugate uptake", as used herein refers to the process in which antibody-drug conjugates are bound to a target on a cell followed by uptake/engulfment by the cell membrane and thereby are drawn into the cell. Antibody-drug conjugate uptake may be evaluated as "antibody-mediated internalization and cell killing by anti-TF ADC in an in vitro killing assay" as described in WO 2011/157741.

The term "death receptor", as used herein refers to a member of the tumor necrosis factor receptor superfamily (TNFR-SF) comprising an intracellular death domain, including DR1, DR2 (also known as FAS), DR3, DR4, DR5, DR6, EDAR and NGFR. In humans, the DR1 protein is encoded by a nucleic acid sequence encoding the amino acid sequence UniprotKB/Swissprot P19438, the DR2 protein is encoded by a nucleic acid sequence encoding the amino acid sequence UniprotKB/Swissprot P25445, the DR3 protein is encoded by a nucleic acid sequence encoding the amino acid sequence UniprotKB/Swissprot Q93038, the DR4 protein is encoded by a nucleic acid sequence encoding the amino acid sequence UniprotKB/Swissprot O00220, the DR5 protein is encoded by a nucleic acid sequence encoding the amino acid sequence UniprotKB/Swissprot O14763), the DR6 protein is encoded by a nucleic acid sequence encoding the amino acid sequence UniprotKB/Swissprot O75509, the EDAR protein is encoded by a nucleic acid sequence encoding the amino acid sequence UniprotKB/Swissprot Q9UNE0, and the NGFR protein is encoded by a nucleic acid sequence encoding the amino acid sequence UniprotKB/Swissprot P08138. The death domains (DDs) are well-known protein interaction modules that belong to the death domain superfamily (Park Apoptosis. 2011 March; 16(3):209-20).

Further Aspects and Embodiments of the Invention

As explained above, the invention is directed to a combination treatment involving two variant Fc-region-containing polypeptides, a first variant polypeptide and a second variant polypeptide, typically variant antibodies, which have been modified in their Fc regions so that hetero-oligomerization is favored over homo-oligomerization. That is, oligomerization between first variant molecules and second variant molecules is favored over oligomerization between first variant molecules and first variant molecules or oligomerization between second variant molecules and second variant molecules. This can be achieved by introducing modifications of positions corresponding to 253, 310, 436, 438, 439 and/or 440 in the Fc region of human IgG1, as described in further details herein.

Accordingly, the invention relates to a method of treating a disease or disorder comprising administering to a subject in need thereof: a first polypeptide comprising a first Fc region of a human IgG and a first antigen-binding region capable of binding to a first antigen, in combination with a second polypeptide comprising a second Fc region of a human IgG and a second antigen-binding region capable of binding to a second antigen, wherein a) said first polypeptide comprises an I253G mutation of an amino acid position corresponding to I253 in human IgG1 and said second polypeptide comprises an H310R mutation of an amino acid position corresponding to H310 in human IgG1, or vice versa, or said first polypeptide comprises an I253K or I253R mutation of an amino acid position corresponding to I253 in human IgG1 and said second polypeptide comprises an H310D mutation of an amino acid position corresponding to H310 in human IgG1, or vice versa, and/or b) said first polypeptide comprises a Y436N, Y436K, Y436Q or Y436R mutation of an amino acid position corresponding to Y436 in human IgG1 and said second polypeptide comprises a Q438R, Q438K, Q438H, Q438G or Q438N mutation of an amino acid position corresponding to Q438 in human IgG1, or vice versa, or said first polypeptide comprises a Y436N or Y436Q mutation of an amino acid position corresponding to Y436 in human IgG1 and said second polypeptide comprises a Y436K or Y436R mutation of an amino acid position corresponding to Y436 in human IgG1, or vice versa, or said first polypeptide comprises a Q438R, Q438K or Q438H mutation of an amino acid position corresponding to Q438 in human IgG1 and said second polypeptide comprises a Q438N or Q438G mutation of an amino acid position corresponding to Q438 in human IgG1, or vice versa, and/or c) said first polypeptide comprises a K439F, K439I, K439Y, K439T, K439V, K439W mutation of an amino acid position corresponding to K439 in human IgG1 and said second polypeptide comprises an S440K mutation of an amino acid position corresponding to S440 in human IgG1, or vice versa, wherein the amino acid positions correspond to human IgG1 according to EU numbering.

In one aspect of the invention said first polypeptide comprises a F436N, F436K, F436Q or F436R mutation of an amino acid position corresponding to F436 in human IgG3 and said second polypeptide comprises a Q438R, Q438K, Q438H, Q438G or Q438N mutation of an amino acid position corresponding to Q438 in human IgG1, or vice versa, or said first polypeptide comprises a F436N or F436Q mutation of an amino acid position corresponding to F436 in human IgG3 and said second polypeptide comprises a F436K or F436R mutation of an amino acid position corresponding to F436 in human IgG3, or vice versa.

The amino acid in position 436 according to EU numbering is not conserved between IgG1 and IgG3. Thus, amino acid position 436 in IgG1 is a Tyrosine (Y) whereas the amino acid position 436 in IgG3 is a Phenylalanine (F).

In one embodiment of the method of invention, said first polypeptide comprises a Y436N, Y436K, Y436Q or Y436R mutation of an amino acid position corresponding to Y436 in human IgG1 and said second polypeptide comprises a Q438R, Q438K, Q438H, Q438G or Q438N mutation of an amino acid position corresponding to Q438 in human IgG1, or vice versa, or said first polypeptide comprises a Y436N or Y436Q mutation of an amino acid position corresponding to Y436 in human IgG1 and said second polypeptide comprises a Y436K or Y436R mutation of an amino acid position corresponding to Y436 in human IgG1, or vice versa, or said first polypeptide comprises a Q438R, Q438K or Q438H mutation of an amino acid position corresponding to Q438 in human IgG1 and said second polypeptide comprises a Q438N or Q438G mutation of an amino acid position corresponding to Q438 in human IgG1, or vice versa, wherein the amino acid positions correspond to human IgG1 according to EU numbering.

In one embodiment of the method of invention, said first polypeptide comprises a Y436N, Y436K, Y436Q or Y436R mutation of an amino acid position corresponding to Y436 in human IgG1 and said second polypeptide comprises a Q438R, Q438K, Q438H, Q438G or Q438N mutation of an amino acid position corresponding to Q438 in human IgG1, or vice versa, wherein the amino acid positions correspond to human IgG1 according to EU numbering.

In one embodiment of the method of invention, said first polypeptide comprises a Y436N or Y436K, mutation of an amino acid position corresponding to Y436 in human IgG1 and said second polypeptide comprises a Q438R or Q438N mutation of an amino acid position corresponding to Q438 in human IgG1, or vice versa, or said first polypeptide comprises a Q438R mutation of an amino acid position corresponding to Q438 in human IgG1 and said second polypeptide comprises a Q438N mutation of an amino acid position corresponding to Q438 in human IgG1, or vice versa, wherein the amino acid positions correspond to human IgG1 according to EU numbering.

As explained above, the Fc regions can be of a human IgG1, but also of a different human IgG, such as IgG2, IgG3 or IgG4. FIG. 1 shows which positions in human IgG2, IgG3 and IgG4 correspond to which positions in IgG1.

An Fc region of a polypeptide used in the present invention is, like that of an antibody, comprised of two heavy chains. It is to be understood that when certain mutations in the Fc region are specified, said mutations are present in both chains of the Fc region.

In one embodiment of the method of the invention, a) said first polypeptide comprises an I253G mutation of an amino acid position corresponding to I253 in human IgG1 and said second polypeptide comprises an H310R mutation of an amino acid position corresponding to H310 in human IgG1, or vice versa, or said first polypeptide comprises an I253K or I253R mutation of an amino acid position corresponding to I253 in human IgG1 and said second polypeptide comprises an H310D mutation of an amino acid position corresponding to H310 in human IgG1, or vice versa, and/or b) said first polypeptide comprises a Y436N mutation of an amino acid position corresponding to Y436 in human IgG1 and said second polypeptide comprises a Q438R mutation of an amino acid position corresponding to Q438 in human IgG1, or vice versa, or said first polypeptide comprises a Y436N mutation of an amino acid position corresponding to Y436 in human IgG1 and said second polypeptide comprises a Y436K mutation of an amino acid position corresponding to Y436 in human IgG1, or vice versa, or said first polypeptide comprises a Q438R mutation of an amino acid position corresponding to Q438 in human IgG1 and said second polypeptide comprises a Q438N mutation of an amino acid position corresponding to Q438 in human IgG1, or vice versa, and/or c) said first polypeptide comprises a K439F, K439I, K439Y, K439T, K439V, K439W mutation of an amino acid position corresponding to K439 in human IgG1 and said second polypeptide comprises an S440K mutation of an amino acid position corresponding to S440 in human IgG1, or vice versa.

In one embodiment of the method of the invention, said first polypeptide comprises a Y436N or Y436K mutation of an amino acid position corresponding to Q436 in human IgG1 and said second polypeptide comprises a Q438N or Q438R mutation of an amino acid position corresponding to Q438 in human IgG1, or vice versa.

In one embodiment of the method of the invention, said first polypeptide comprises a Y436N mutation of an amino acid position corresponding to Q436 in human IgG1 and said second polypeptide comprises a Q438N or Q438R mutation of an amino acid position corresponding to Q438 in human IgG1, or vice versa.

In one embodiment of the method of the invention, said first polypeptide comprises a Y436N mutation of an amino acid position corresponding to Q436 in human IgG1 and said second polypeptide comprises a Q438R mutation of an amino acid position corresponding to Q438 in human IgG1, or vice versa.

In one embodiment of the method of the invention, said first polypeptide comprises a Y436N mutation of an amino acid position corresponding to Q436 in human IgG1 and said second polypeptide comprises a Q436K mutation of an amino acid position corresponding to Q436 in human IgG1, or vice versa.

In one embodiment of the method of the invention, said first polypeptide comprises a Y436K mutation of an amino acid position corresponding to Q436 in human IgG1 and said second polypeptide comprises a Q438N or Q438R mutation of an amino acid position corresponding to Q438 in human IgG1, or vice versa.

In one embodiment of the method of the invention, said first polypeptide comprises a Y436K mutation of an amino acid position corresponding to Q436 in human IgG1 and said second polypeptide comprises a Q438N mutation of an amino acid position corresponding to Q438 in human IgG1, or vice versa.

In one embodiment of the method of the invention, said first polypeptide comprises a Y436K mutation of an amino acid position corresponding to Q436 in human IgG1 and said second polypeptide comprises a Q438R mutation of an amino acid position corresponding to Q438 in human IgG1, or vice versa.

In one embodiment of the method of the invention, said first polypeptide comprises a Y438N mutation of an amino acid position corresponding to Q438 in human IgG1 and said second polypeptide comprises a Q438R mutation of an amino acid position corresponding to Q438 in human IgG1, or vice versa.

In another embodiment of the method of the invention, a) said first polypeptide comprises an I253G mutation of an amino acid position corresponding to I253 in human IgG1 and said second polypeptide comprises an H310R mutation of an amino acid position corresponding to H310 in human IgG1, or vice versa, or said first polypeptide comprises an I253K or I253R mutation of an amino acid position corresponding to I253 in human IgG1 and said second polypeptide comprises an H310D mutation of an amino acid position corresponding to H310 in human IgG1, or vice versa, and b) said first polypeptide comprises a Y436N, Y436K, Y436Q or Y436R mutation of an amino acid position corresponding to Y436 in human IgG1 and said second polypeptide comprises a Q438R, Q438K, Q438H, Q438G or Q438N mutation of an amino acid position corresponding to Q438 in human IgG1, or vice versa, wherein preferably said first polypeptide comprises a Y436N mutation of an amino acid position corresponding to Y436 in human IgG1 and said second polypeptide comprises a Q438R mutation of an amino acid position corresponding to Q438 in human IgG1, or vice versa, or said first polypeptide comprises a Y436N or Y436Q mutation of an amino acid position corresponding to Y436 in human IgG1 and said second polypeptide comprises a Y436K or Y436R mutation of an amino acid position corresponding to Y436 in human IgG1, or vice versa, wherein preferably said first polypeptide comprises a Y436N mutation of an amino acid position corresponding to Y436 in human IgG1 and said second polypeptide comprises a Y436K mutation of an amino acid position corresponding to Y436 in human IgG1, or vice versa, or said first polypeptide comprises a Q438R, Q438K or Q438H mutation of an amino acid position corresponding to Q438 in human IgG1 and said second polypeptide comprises a Q438N or Q438G mutation of an amino acid position corresponding to Q438 in human IgG1, or vice versa, wherein preferably said first polypeptide comprises a Q438R mutation of an amino acid position corresponding to Q438 in human IgG1 and said second polypeptide comprises a Q438N mutation of an amino acid position corresponding to Q438 in human IgG1, or vice versa.

In another embodiment of the method of the invention, a) said first polypeptide comprises an I253G mutation of an amino acid position corresponding to I253 in human IgG1 and said second polypeptide comprises an H310R mutation of an amino acid position corresponding to H310 in human IgG1, or vice versa, or said first polypeptide comprises an I253K or I253R mutation of an amino acid position corresponding to I253 in human IgG1 and said second polypeptide comprises an H310D mutation of an amino acid position corresponding to H310 in human IgG1, or vice versa, and c) said first polypeptide comprises a K439F, K439I, K439Y, K439T, K439V, K439W mutation of an amino acid position corresponding to K439 in human IgG1 and said second polypeptide comprises an S440K mutation of an amino acid position corresponding to S440 in human IgG1, or vice versa.

In another embodiment of the method of the invention, b) said first polypeptide comprises a Y436N, Y436K, Y436Q or Y436R mutation of an amino acid position corresponding to Y436 in human IgG1 and said second polypeptide comprises a Q438R, Q438K, Q438H, Q438G or Q438N mutation of an amino acid position corresponding to Q438 in human IgG1, or vice versa, wherein preferably said first polypeptide comprises a Y436N mutation of an amino acid position corresponding to Y436 in human IgG1 and said second polypeptide comprises a Q438R mutation of an amino acid position corresponding to Q438 in human IgG1, or vice versa, or said first polypeptide comprises a Y436N or Y436Q mutation of an amino acid position corresponding to Y436 in human IgG1 and said second polypeptide comprises a Y436K or Y436R mutation of an amino acid position corresponding to Y436 in human IgG1, or vice versa, wherein preferably said first polypeptide comprises a Y436N mutation of an amino acid position corresponding to Y436 in human IgG1 and said second polypeptide comprises a Y436K mutation of an amino acid position corresponding to Y436 in human IgG1, or vice versa, or said first polypeptide comprises a Q438R, Q438K or Q438H mutation of an amino acid position corresponding to Q438 in human IgG1 and said second polypeptide comprises a Q438N or Q438G mutation of an amino acid position corresponding to Q438 in human IgG1, or vice versa, wherein preferably said first polypeptide comprises a Q438R mutation of an amino acid position corresponding to Q438 in human IgG1 and said second polypeptide comprises a Q438N mutation of an amino acid position corresponding to Q438 in human IgG1, or vice versa and c) said first polypeptide comprises a K439F, K439I, K439Y, K439T, K439V, K439W mutation of an amino acid position corresponding to K439 in human IgG1 and said second polypeptide comprises an S440K mutation of an amino acid position corresponding to S440 in human IgG1, or vice versa.

In another embodiment of the method of the invention, a) said first polypeptide comprises an I253G mutation of an amino acid position corresponding to I253 in human IgG1 and said second polypeptide comprises an H310R mutation of an amino acid position corresponding to H310 in human IgG1, or vice versa, or said first polypeptide comprises an I253K or I253R mutation of an amino acid position corresponding to I253 in human IgG1 and said second polypeptide comprises an H310D mutation of an amino acid position corresponding to H310 in human IgG1, or vice versa, and b) said first polypeptide comprises a Y436N, Y436K, Y436Q or Y436R mutation of an amino acid position corresponding to Y436 in human IgG1 and said second polypeptide comprises a Q438R, Q438K, Q438H, Q438G or Q438N mutation of an amino acid position corresponding to Q438 in human IgG1, or vice versa, wherein preferably said first polypeptide comprises a Y436N mutation of an amino acid position corresponding to Y436 in human IgG1 and said second polypeptide comprises a Q438R mutation of an amino acid position corresponding to Q438 in human IgG1, or vice versa, or said first polypeptide comprises a Y436N or Y436Q mutation of an amino acid position corresponding to Y436 in human IgG1 and said second polypeptide comprises a Y436K or Y436R mutation of an amino acid position corresponding to Y436 in human IgG1, or vice versa, wherein preferably said first polypeptide comprises a Y436N mutation of an amino acid position corresponding to Y436 in human IgG1 and said second polypeptide comprises a Y436K mutation of an amino acid position corresponding to Y436 in human IgG1, or vice versa, or said first polypeptide comprises a Q438R, Q438K or Q438H mutation of an amino acid position corresponding to Q438 in human IgG1 and said second polypeptide comprises a Q438N or Q438G mutation of an amino acid position corresponding to Q438 in human IgG1, or vice versa, wherein preferably said first polypeptide comprises a Q438R mutation of an amino acid position corresponding to Q438 in human IgG1 and said second polypeptide comprises a Q438N mutation of an amino acid position corresponding to Q438 in human IgG1, or vice versa, and c) said first polypeptide comprises a K439F, K439I, K439Y, K439T, K439V, K439W mutation of an amino acid position corresponding to K439 in human IgG1 and said second polypeptide comprises an S440K mutation of an amino acid position corresponding to S440 in human IgG1, or vice versa.

In a further embodiment of the method of the invention, the first and second polypeptides do not comprise the mutations specified in option c), but said first polypeptide further comprises a K439E mutation of an amino acid position corresponding to K439 in human IgG1 and said second polypeptide further comprises an S440K mutation of an amino acid position corresponding to S440 in human IgG1, or vice versa.

In another embodiments of the method of the invention, i) said first polypeptide comprises an I253G mutation of an amino acid position corresponding to I253 in human IgG1 and said second polypeptide comprises an H310R mutation of an amino acid position corresponding to H310 in human IgG1, or vice versa, or ii) said first polypeptide comprises an I253R mutation of an amino acid position corresponding to I253 in human IgG1 and said second polypeptide comprises an H310D mutation of an amino acid position corresponding to H310 in human IgG1, or vice versa, or iii) said first polypeptide comprises an I253G mutation of an amino acid position corresponding to I253 in human IgG1 and said second polypeptide comprises an H310R mutation of an amino acid position corresponding to H310 in human IgG1, or vice versa, and said first polypeptide comprises a K439E mutation of an amino acid position corresponding to K439 in human IgG1 and said second polypeptide comprises an S440K mutation of an amino acid position corresponding to S440 in human IgG1, or vice versa, or iv) said first polypeptide comprises an I253R mutation of an amino acid position corresponding to I253 in human IgG1 and said second polypeptide comprises an H310D mutation of an amino acid position corresponding to H310 in human IgG1, or vice versa, and said first polypeptide comprises a K439E mutation of an amino acid position corresponding to K439 in human IgG1 and said second polypeptide comprises an S440K mutation of an amino acid position corresponding to S440 in human IgG1, or vice versa, or v) said first polypeptide comprises a Y436N mutation of an amino acid position corresponding to Y436 in human IgG1 and said second polypeptide comprises a Q438R mutation of an amino acid position corresponding to Q438 in human IgG1, or vice versa, or vi) said first polypeptide comprises a Y436N mutation of an amino acid position corresponding to Y436 in human IgG1 and said second polypeptide comprises a Y436K mutation of an amino acid position corresponding to Y436 in human IgG1, or vice versa, or vii) said first polypeptide comprises a Q438R mutation of an amino acid position corresponding to Q438 in human IgG1 and said second polypeptide comprises a Q438N mutation of an amino acid position corresponding to Q438 in human IgG1, or vice versa, or viii) said first polypeptide comprises a Y436N mutation of an amino acid position corresponding to Y436 in human IgG1 and said second polypeptide comprises a Q438R mutation of an amino acid position corresponding to Q438 in human IgG1, or vice versa, and said first polypeptide comprises an I253G mutation of an amino acid position corresponding to I253 in human IgG1 and said second polypeptide comprises an H310R mutation of an amino acid position corresponding to H310 in human IgG1, or vice versa, or ix) said first polypeptide comprises a Y436N mutation of an amino acid position corresponding to Y436 in human IgG1 and said second polypeptide comprises a Q438R mutation of an amino acid position corresponding to Q438 in human IgG1, or vice versa, said first polypeptide comprises an I253R mutation of an amino acid position corresponding to I253 in human IgG1 and said second polypeptide comprises an H310D mutation of an amino acid position corresponding to H310 in human IgG1, or vice versa, or x) said first polypeptide comprises a Y436N mutation of an amino acid position corresponding to Y436 in human IgG1 and said second polypeptide comprises a Q438R mutation of an amino acid position corresponding to Q438 in human IgG1, or vice versa, and said first polypeptide comprises an I253G mutation of an amino acid position corresponding to I253 in human IgG1 and said second polypeptide comprises an H310R mutation of an amino acid position corresponding to H310 in human IgG1, or vice versa, and said first polypeptide comprises a K439E mutation of an amino acid position corresponding to K439 in human IgG1 and said second polypeptide comprises an S440K mutation of an amino acid position corresponding to S440 in human IgG1, or vice versa, or xi) said first polypeptide comprises a Y436N mutation of an amino acid position corresponding to Y436 in human IgG1 and said second polypeptide comprises a Q438R mutation of an amino acid position corresponding to Q438 in human IgG1, or vice versa, and said first polypeptide comprises an I253R mutation of an amino acid position corresponding to I253 in human IgG1 and said second polypeptide comprises an H310D mutation of an amino acid position corresponding to H310 in human IgG1, or vice versa, and said first polypeptide comprises a K439E mutation of an amino acid position corresponding to K439 in human IgG1 and said second polypeptide comprises an S440K mutation of an amino acid position corresponding to S440 in human IgG1, or vice versa, or xii) said first polypeptide comprises a Y436N mutation of an amino acid position corresponding to Y436 in human IgG1 and said second polypeptide comprises a Y436K mutation of an amino acid position corresponding to Y436 in human IgG1, or vice versa, said first polypeptide comprises an I253G mutation of an amino acid position corresponding to I253 in human IgG1 and said second polypeptide comprises an H310R mutation of an amino acid position corresponding to H310 in human IgG1, or vice versa, or xiii) said first polypeptide comprises a Y436N mutation of an amino acid position corresponding to Y436 in human IgG1 and said second polypeptide comprises a Y436K mutation of an amino acid position corresponding to Y436 in human IgG1, or vice versa, said first polypeptide comprises an I253R mutation of an amino acid position corresponding to I253 in human IgG1 and said second polypeptide comprises an H310D mutation of an amino acid position corresponding to H310 in human IgG1, or vice versa, or xiv) said first polypeptide comprises a Y436N mutation of an amino acid position corresponding to Y436 in human IgG1 and said second polypeptide comprises a Y436K mutation of an amino acid position corresponding to Y436 in human IgG1, or vice versa, said first polypeptide comprises an I253G mutation of an amino acid position corresponding to I253 in human IgG1 and said second polypeptide comprises an H310R mutation of an amino acid position corresponding to H310 in human IgG1, or vice versa, and said first polypeptide comprises a K439E mutation of an amino acid position corresponding to K439 in human IgG1 and said second polypeptide comprises an S440K mutation of an amino acid position corresponding to S440 in human IgG1, or vice versa, or xv) said first polypeptide comprises a Y436N mutation of an amino acid position corresponding to Y436 in human IgG1 and said second polypeptide comprises a Y436K mutation of an amino acid position corresponding to Y436 in human IgG1, or vice versa, said first polypeptide comprises an I253R mutation of an amino acid position corresponding to I253 in human IgG1 and said second polypeptide comprises an H310D mutation of an amino acid position corresponding to H310 in human IgG1, or vice versa, and said first polypeptide comprises a K439E mutation of an amino acid position corresponding to K439 in human IgG1 and said second polypeptide comprises an S440K mutation of an amino acid position corresponding to S440 in human IgG1, or vice versa, or xvi) said first polypeptide comprises a Q438R mutation of an amino acid position corresponding to Q438 in human IgG1 and said second polypeptide comprises a Q438N mutation of an amino acid position corresponding to Q438 in human IgG1, or vice versa, said first polypeptide comprises an I253G mutation of an amino acid position corresponding to I253 in human IgG1 and said second polypeptide comprises an H310R mutation of an amino acid position corresponding to H310 in human IgG1, or vice versa, or xvii) said first polypeptide comprises a Q438R mutation of an amino acid position corresponding to Q438 in human IgG1 and said second polypeptide comprises a Q438N mutation of an amino acid position corresponding to Q438 in human IgG1, or vice versa, said first polypeptide comprises an I253R mutation of an amino acid position corresponding to I253 in human IgG1 and said second polypeptide comprises an H310D mutation of an amino acid position corresponding to H310 in human IgG1, or vice versa, or xviii) said first polypeptide comprises a Q438R mutation of an amino acid position corresponding to Q438 in human IgG1 and said second polypeptide comprises a Q438N mutation of an amino acid position corresponding to Q438 in human IgG1, or vice versa, said first polypeptide comprises an I253G mutation of an amino acid position corresponding to I253 in human IgG1 and said second polypeptide comprises an H310R mutation of an amino acid position corresponding to H310 in human IgG1, or vice versa, and said first polypeptide comprises a K439E mutation of an amino acid position corresponding to K439 in human IgG1 and said second polypeptide comprises an S440K mutation of an amino acid position corresponding to S440 in human IgG1, or vice versa, or xix) said first polypeptide comprises a Q438R mutation of an amino acid position corresponding to Q438 in human IgG1 and said second polypeptide comprises a Q438N mutation of an amino acid position corresponding to Q438 in human IgG1, or vice versa, said first polypeptide comprises an I253R mutation of an amino acid position corresponding to I253 in human IgG1 and said second polypeptide comprises an H310D mutation of an amino acid position corresponding to H310 in human IgG1, or vice versa, and said first polypeptide comprises a K439E mutation of an amino acid position corresponding to K439 in human IgG1 and said second polypeptide comprises an S440K mutation of an amino acid position corresponding to S440 in human IgG1, or vice versa, or xx) said first polypeptide comprises a Y436N mutation of an amino acid position corresponding to Y436 in human IgG1 and said second polypeptide comprises a Q438R mutation of an amino acid position corresponding to Q438 in human IgG1, or vice versa, and said first polypeptide comprises a K439E mutation of an amino acid position corresponding to K439 in human IgG1 and said second polypeptide comprises an S440K mutation of an amino acid position corresponding to S440 in human IgG1, or vice versa, or xxi) said first polypeptide comprises a Y436N mutation of an amino acid position corresponding to Y436 in human IgG1 and said second polypeptide comprises a Y436K mutation of an amino acid position corresponding to Y436 in human IgG1, or vice versa, and said first polypeptide comprises a K439E mutation of an amino acid position corresponding to K439 in human IgG1 and said second polypeptide comprises an S440K mutation of an amino acid position corresponding to S440 in human IgG1, or vice versa, or xxii) said first polypeptide comprises a Q438R mutation of an amino acid position corresponding to Q438 in human IgG1 and said second polypeptide comprises a Q438N mutation of an amino acid position corresponding to Q438 in human IgG1, or vice versa, and said first polypeptide comprises a K439E mutation of an amino acid position corresponding to K439 in human IgG1 and said second polypeptide comprises an S440K mutation of an amino acid position corresponding to S440 in human IgG1, or vice versa.

In preferred embodiments of the method of the invention, i) said first polypeptide comprises a Y436N mutation of an amino acid position corresponding to Y436 in human IgG1 and said second polypeptide comprises a Q438R mutation of an amino acid position corresponding to Q438 in human IgG1, or vice versa, or ii) said first polypeptide comprises a Y436N mutation of an amino acid position corresponding to Y436 in human IgG1 and said second polypeptide comprises a Q438N mutation of an amino acid position corresponding to Q438 in human IgG1, or vice versa, or iii) said first polypeptide comprises a Y436N mutation of an amino acid position corresponding to Y436 in human IgG1 and said second polypeptide comprises a Y436K mutation of an amino acid position corresponding to Y436 in human IgG1, or vice versa, or iv) said first polypeptide comprises a Y436K mutation of an amino acid position corresponding to Y436 in human IgG1 and said second polypeptide comprises a Q438R mutation of an amino acid position corresponding to Q438 in human IgG1, or vice versa, or v) said first polypeptide comprises a Y436K mutation of an amino acid position corresponding to Y436 in human IgG1 and said second polypeptide comprises a Q438N mutation of an amino acid position corresponding to Q438 in human IgG1, or vice versa, or vi) said first polypeptide comprises a Q438R mutation of an amino acid position corresponding to Q438 in human IgG1 and said second polypeptide comprises a Q438N mutation of an amino acid position corresponding to Q438 in human IgG1, or vice versa, and vii) said first polypeptide comprises a K439E mutation of an amino acid position corresponding to K439 in human IgG1 and said second polypeptide comprises an S440K mutation of an amino acid position corresponding to S440 in human IgG1, or vice versa.

In one embodiment of the method of the invention, i) said first polypeptide comprises a Y436N or Y436K mutation of an amino acid position corresponding to Q436 in human IgG1 and said second polypeptide comprises a Q438N or Q438R mutation of an amino acid position corresponding to Q438 in human IgG1, or vice versa, and ii) said first polypeptide comprises a K439E mutation of an amino acid position corresponding to K439 in human IgG1 and said second polypeptide comprises an S440K mutation of an amino acid position corresponding to S440 in human IgG1, or vice versa.

In one embodiment of the method of the invention, i) said first polypeptide comprises a Y436N mutation of an amino acid position corresponding to Q436 in human IgG1 and said second polypeptide comprises a Q438R mutation of an amino acid position corresponding to Q438 in human IgG1, or vice versa, and ii) said first polypeptide comprises a K439E mutation of an amino acid position corresponding to K439 in human IgG1 and said second polypeptide comprises an S440K mutation of an amino acid position corresponding to S440 in human IgG1, or vice versa.

In one embodiment of the method of the invention, i) said first polypeptide comprises a Y438N mutation of an amino acid position corresponding to Q438 in human IgG1 and said second polypeptide comprises a Q438R mutation of an amino acid position corresponding to Q438 in human IgG1, or vice versa, and ii) said first polypeptide comprises a K439E mutation of an amino acid position corresponding to K439 in human IgG and said second polypeptide comprises an S440K mutation of an amino acid position corresponding to S440 in human IgG, or vice versa.

The following Table provides a non-limiting list of embodiments of the method of the invention, describing combinations of a first polypeptide and a second polypeptide with specific mutations, Thus, for example, embodiment 1 of the Table below is a combination of a first polypeptide comprising 253G and K439E mutations at positions corresponding to I253 and K439, respectively, in human IgG, with a second polypeptide comprising H310R and S440K mutations at positions corresponding to H310 and S440, respectively, in human IgG. As described herein, the first and second polypeptides of all of the embodiments 1 to 288 can optionally comprise further mutations, such as oligomerization-enhancing mutations, e.g. E430G.

| Embodiment | First polypeptide mutations | Second polypeptide mutations |
|---|---|---|
| 1 | I253G K439E | H310R S440K |
| 2 | I253G Y436N K439E | H310R Q438R S440K |
| 3 | I253G Y436N K439E | H310R Q438K S440K |
| 4 | I253G Y436N K439E | H310R Q438H S440K |
| 5 | I253G Y436N K439E | H310R Q438G S440K |
| 6 | I253G Y436N K439E | H310R Q438N S440K |
| 7 | H310R Y436N K439E | I253G Q438R S440K |
| 8 | H310R Y436N K439E | I253G Q438K S440K |
| 9 | H310R Y436N K439E | I253G Q438H S440K |
| 10 | H310R Y436N K439E | I253G Q438G S440K |
| 11 | H310R Y436N K439E | I253G Q438N S440K |
| 12 | I253G Y436K K439E | H310R Q438R S440K |
| 13 | I253G Y436K K439E | H310R Q438K S440K |
| 14 | I253G Y436K K439E | H310R Q438H S440K |
| 15 | I253G Y436K K439E | H310R Q438G S440K |
| 16 | I253G Y436K K439E | H310R Q438N S440K |
| 17 | H310R Y436K K439E | I253G Q438R S440K |
| 18 | H310R Y436K K439E | I253G Q438K S440K |
| 19 | H310R Y436K K439E | I253G Q438H S440K |
| 20 | H310R Y436K K439E | I253G Q438G S440K |
| 21 | H310R Y436K K439E | I253G Q438N S440K |
| 22 | I253G Y436Q K439E | H310R Q438R S440K |
| 23 | I253G Y436Q K439E | H310R Q438K S440K |
| 24 | I253G Y436Q K439E | H310R Q438H S440K |
| 25 | I253G Y436Q K439E | H310R Q438G S440K |
| 26 | I253G Y436Q K439E | H310R Q438N S440K |
| 27 | H310R Y436Q K439E | I253G Q438R S440K |
| 28 | H310R Y436Q K439E | I253G Q438K S440K |
| 29 | H310R Y436Q K439E | I253G Q438H S440K |
| 30 | H310R Y436Q K439E | I253G Q438G S440K |
| 31 | H310R Y436Q K439E | I253G Q438N S440K |

-continued

| Embodiment | First polypeptide mutations | Second polypeptide mutations |
| --- | --- | --- |
| 32 | I253G Y436R K439E | H310R Q438R S440K |
| 33 | I253G Y436R K439E | H310R Q438K S440K |
| 34 | I253G Y436R K439E | H310R Q438H S440K |
| 35 | I253G Y436R K439E | H310R Q438G S440K |
| 36 | I253G Y436R K439E | H310R Q438N S440K |
| 37 | H310R Y436R K439E | I253G Q438R S440K |
| 38 | H310R Y436R K439E | I253G Q438K S440K |
| 39 | H310R Y436R K439E | I253G Q438H S440K |
| 40 | H310R Y436R K439E | I253G Q438G S440K |
| 41 | H310R Y436R K439E | I253G Q438N S440K |
| 42 | I253G S440K | H310R K439E |
| 43 | I253G Y436N S440K | H310R Q438R K439E |
| 44 | I253G Y436N S440K | H310R Q438K K439E |
| 45 | I253G Y436N S440K | H310R Q438H K439E |
| 46 | I253G Y436N S440K | H310R Q438G K439E |
| 47 | I253G Y436N S440K | H310R Q438N K439E |
| 48 | H310R Y436N S440K | I253G Q438R K439E |
| 49 | H310R Y436N S440K | I253G Q438K K439E |
| 50 | H310R Y436N S440K | I253G Q438H K439E |
| 51 | H310R Y436N S440K | I253G Q438G K439E |
| 52 | H310R Y436N S440K | I253G Q438N K439E |
| 53 | I253G Y436K S440K | H310R Q438R K439E |
| 54 | I253G Y436K S440K | H310R Q438K K439E |
| 55 | I253G Y436K S440K | H310R Q438H K439E |
| 56 | I253G Y436K S440K | H310R Q438G K439E |
| 57 | I253G Y436K S440K | H310R Q438N K439E |
| 58 | H310R Y436K S440K | I253G Q438R K439E |
| 59 | H310R Y436K S440K | I253G Q438K K439E |
| 60 | H310R Y436K S440K | I253G Q438H K439E |
| 61 | H310R Y436K S440K | I253G Q438G K439E |
| 62 | H310R Y436K S440K | I253G Q438N K439E |
| 63 | I253G Y436Q S440K | H310R Q438R K439E |
| 64 | I253G Y436Q S440K | H310R Q438K K439E |
| 65 | I253G Y436Q S440K | H310R Q438H K439E |
| 66 | I253G Y436Q S440K | H310R Q438G K439E |
| 67 | I253G Y436Q S440K | H310R Q438N K439E |
| 68 | H310R Y436Q S440K | I253G Q438R K439E |
| 69 | H310R Y436Q S440K | I253G Q438K K439E |
| 70 | H310R Y436Q S440K | I253G Q438H K439E |
| 71 | H310R Y436Q S440K | I253G Q438G K439E |
| 72 | H310R Y436Q S440K | I253G Q438N K439E |
| 73 | I253G Y436R S440K | H310R Q438R K439E |
| 74 | I253G Y436R S440K | H310R Q438K K439E |
| 75 | I253G Y436R S440K | H310R Q438H K439E |
| 76 | I253G Y436R S440K | H310R Q438G K439E |
| 77 | I253G Y436R S440K | H310R Q438N K439E |
| 78 | H310R Y436R S440K | I253G Q438R K439E |
| 79 | H310R Y436R S440K | I253G Q438K K439E |
| 80 | H310R Y436R S440K | I253G Q438H K439E |
| 81 | H310R Y436R S440K | I253G Q438G K439E |
| 82 | H310R Y436R S440K | I253G Q438N K439E |
| 83 | I253R K439E | H310D S440K |
| 84 | I253R Y436N K439E | H310D Q438R S440K |
| 85 | I253R Y436N K439E | H310D Q438K S440K |
| 86 | I253R Y436N K439E | H310D Q438H S440K |
| 87 | I253R Y436N K439E | H310D Q438G S440K |
| 88 | I253R Y436N K439E | H310D Q438N S440K |
| 89 | H310D Y436N K439E | I253R Q438R S440K |
| 90 | H310D Y436N K439E | I253R Q438K S440K |
| 91 | H310D Y436N K439E | I253R Q438H S440K |
| 92 | H310D Y436N K439E | I253R Q438G S440K |
| 93 | H310D Y436N K439E | I253R Q438N S440K |
| 94 | I253R Y436K K439E | H310D Q438R S440K |
| 95 | I253R Y436K K439E | H310D Q438K S440K |
| 96 | I253R Y436K K439E | H310D Q438H S440K |
| 97 | I253R Y436K K439E | H310D Q438G S440K |
| 98 | I253R Y436K K439E | H310D Q438N S440K |
| 99 | H310D Y436K K439E | I253R Q438R S440K |
| 100 | H310D Y436K K439E | I253R Q438K S440K |
| 101 | H310D Y436K K439E | I253R Q438H S440K |
| 102 | H310D Y436K K439E | I253R Q438G S440K |
| 103 | H310D Y436K K439E | I253R Q438N S440K |
| 104 | I253R Y436Q K439E | H310D Q438R S440K |
| 105 | I253R Y436Q K439E | H310D Q438K S440K |
| 106 | I253R Y436Q K439E | H310D Q438H S440K |
| 107 | I253R Y436Q K439E | H310D Q438G S440K |
| 108 | I253R Y436Q K439E | H310D Q438N S440K |
| 109 | H310D Y436Q K439E | I253R Q438R S440K |
| 110 | H310D Y436Q K439E | I253R Q438K S440K |
| 111 | H310D Y436Q K439E | I253R Q438H S440K |
| 112 | H310D Y436Q K439E | I253R Q438G S440K |
| 113 | H310D Y436Q K439E | I253R Q438N S440K |
| 114 | I253R Y436R K439E | H310D Q438R S440K |
| 115 | I253R Y436R K439E | H310D Q438K S440K |
| 116 | I253R Y436R K439E | H310D Q438H S440K |
| 117 | I253R Y436R K439E | H310D Q438G S440K |
| 118 | I253R Y436R K439E | H310D Q438N S440K |
| 119 | H310D Y436R K439E | I253R Q438R S440K |
| 120 | H310D Y436R K439E | I253R Q438K S440K |
| 121 | H310D Y436R K439E | I253R Q438H S440K |
| 122 | H310D Y436R K439E | I253R Q438G S440K |
| 123 | H310D Y436R K439E | I253R Q438N S440K |
| 124 | I253R S440K | H310D K439E |
| 125 | I253R Y436N S440K | H310D Q438R K439E |
| 126 | I253R Y436N S440K | H310D Q438K K439E |
| 127 | I253R Y436N S440K | H310D Q438H K439E |
| 128 | I253R Y436N S440K | H310D Q438G K439E |
| 129 | I253R Y436N S440K | H310D Q438N K439E |
| 130 | H310D Y436N S440K | I253R Q438R K439E |
| 131 | H310D Y436N S440K | I253R Q438K K439E |
| 132 | H310D Y436N S440K | I253R Q438H K439E |
| 133 | H310D Y436N S440K | I253R Q438G K439E |
| 134 | H310D Y436N S440K | I253R Q438N K439E |
| 135 | I253R Y436K S440K | H310D Q438R K439E |
| 136 | I253R Y436K S440K | H310D Q438K K439E |
| 137 | I253R Y436K S440K | H310D Q438H K439E |
| 138 | I253R Y436K S440K | H310D Q438G K439E |
| 139 | I253R Y436K S440K | H310D Q438N K439E |
| 140 | H310D Y436K S440K | I253R Q438R K439E |
| 141 | H310D Y436K S440K | I253R Q438K K439E |
| 142 | H310D Y436K S440K | I253R Q438H K439E |
| 143 | H310D Y436K S440K | I253R Q438G K439E |
| 144 | H310D Y436K S440K | I253R Q438N K439E |
| 145 | I253R Y436Q S440K | H310D Q438R K439E |
| 146 | I253R Y436Q S440K | H310D Q438K K439E |
| 147 | I253R Y436Q S440K | H310D Q438H K439E |
| 148 | I253R Y436Q S440K | H310D Q438G K439E |
| 149 | I253R Y436Q S440K | H310D Q438N K439E |
| 150 | H310D Y436Q S440K | I253R Q438R K439E |
| 151 | H310D Y436Q S440K | I253R Q438K K439E |
| 152 | H310D Y436Q S440K | I253R Q438H K439E |
| 153 | H310D Y436Q S440K | I253R Q438G K439E |
| 154 | H310D Y436Q S440K | I253R Q438N K439E |
| 155 | I253R Y436R S440K | H310D Q438R K439E |
| 156 | I253R Y436R S440K | H310D Q438K K439E |
| 157 | I253R Y436R S440K | H310D Q438H K439E |
| 158 | I253R Y436R S440K | H310D Q438G K439E |
| 159 | I253R Y436R S440K | H310D Q438N K439E |
| 160 | H310D Y436R S440K | I253R Q438R K439E |
| 161 | H310D Y436R S440K | I253R Q438K K439E |
| 162 | H310D Y436R S440K | I253R Q438H K439E |
| 163 | H310D Y436R S440K | I253R Q438G K439E |
| 164 | H310D Y436R S440K | I253R Q438N K439E |
| 165 | I253K K439E | H310D S440K |
| 166 | I253K Y436N K439E | H310D Q438R S440K |
| 167 | I253K Y436N K439E | H310D Q438K S440K |
| 168 | I253K Y436N K439E | H310D Q438H S440K |
| 169 | I253K Y436N K439E | H310D Q438G S440K |
| 170 | I253K Y436N K439E | H310D Q438N S440K |
| 171 | H310D Y436N K439E | I253K Q438R S440K |
| 172 | H310D Y436N K439E | I253K Q438K S440K |
| 173 | H310D Y436N K439E | I253K Q438H S440K |
| 174 | H310D Y436N K439E | I253K Q438G S440K |
| 175 | H310D Y436N K439E | I253K Q438N S440K |
| 176 | I253K Y436K K439E | H310D Q438R S440K |
| 177 | I253K Y436K K439E | H310D Q438K S440K |
| 178 | I253K Y436K K439E | H310D Q438H S440K |
| 179 | I253K Y436K K439E | H310D Q438G S440K |
| 180 | I253K Y436K K439E | H310D Q438N S440K |
| 181 | H310D Y436K K439E | I253K Q438R S440K |
| 182 | H310D Y436K K439E | I253K Q438K S440K |
| 183 | H310D Y436K K439E | I253K Q438H S440K |
| 184 | H310D Y436K K439E | I253K Q438G S440K |
| 185 | H310D Y436K K439E | I253K Q438N S440K |

-continued

-continued

| Embodiment | First polypeptide mutations | Second polypeptide mutations |
|---|---|---|
| 186 | I253K Y436Q K439E | H310D Q438R S440K |
| 187 | I253K Y436Q K439E | H310D Q438K S440K |
| 188 | I253K Y436Q K439E | H310D Q438H S440K |
| 189 | I253K Y436Q K439E | H310D Q438G S440K |
| 190 | I253K Y436Q K439E | H310D Q438N S440K |
| 191 | H310D Y436Q K439E | I253K Q438R S440K |
| 192 | H310D Y436Q K439E | I253K Q438K S440K |
| 193 | H310D Y436Q K439E | I253K Q438H S440K |
| 194 | H310D Y436Q K439E | I253K Q438G S440K |
| 195 | H310D Y436Q K439E | I253K Q438N S440K |
| 196 | I253K Y436R K439E | H310D Q438R S440K |
| 197 | I253K Y436R K439E | H310D Q438K S440K |
| 198 | I253K Y436R K439E | H310D Q438H S440K |
| 199 | I253K Y436R K439E | H310D Q438G S440K |
| 200 | I253K Y436R K439E | H310D Q438N S440K |
| 201 | H310D Y436R K439E | I253K Q438R S440K |
| 202 | H310D Y436R K439E | I253K Q438K S440K |
| 203 | H310D Y436R K439E | I253K Q438H S440K |
| 204 | H310D Y436R K439E | I253K Q438G S440K |
| 205 | H310D Y436R K439E | I253K Q438N S440K |
| 206 | I253K S440K | H310D K439E |
| 207 | I253K Y436N S440K | H310D Q438R K439E |
| 208 | I253K Y436N S440K | H310D Q438K K439E |
| 209 | I253K Y436N S440K | H310D Q438H K439E |
| 210 | I253K Y436N S440K | H310D Q438G K439E |
| 211 | I253K Y436N S440K | H310D Q438N K439E |
| 212 | H310D Y436N S440K | I253K Q438R K439E |
| 213 | H310D Y436N S440K | I253K Q438K K439E |
| 214 | H310D Y436N S440K | I253K Q438H K439E |
| 215 | H310D Y436N S440K | I253K Q438G K439E |
| 216 | H310D Y436N S440K | I253K Q438N K439E |
| 217 | I253K Y436K S440K | H310D Q438R K439E |
| 218 | I253K Y436K S440K | H310D Q438K K439E |
| 219 | I253K Y436K S440K | H310D Q438H K439E |
| 220 | I253K Y436K S440K | H310D Q438G K439E |
| 221 | I253K Y436K S440K | H310D Q438N K439E |
| 222 | H310D Y436K S440K | I253K Q438R K439E |
| 223 | H310D Y436K S440K | I253K Q438K K439E |
| 224 | H310D Y436K S440K | I253K Q438H K439E |
| 225 | H310D Y436K S440K | I253K Q438G K439E |
| 226 | H310D Y436K S440K | I253K Q438N K439E |
| 227 | I253K Y436Q S440K | H310D Q438R K439E |
| 228 | I253K Y436Q S440K | H310D Q438K K439E |
| 229 | I253K Y436Q S440K | H310D Q438H K439E |
| 230 | I253K Y436Q S440K | H310D Q438G K439E |
| 231 | I253K Y436Q S440K | H310D Q438N K439E |
| 232 | H310D Y436Q S440K | I253K Q438R K439E |
| 233 | H310D Y436Q S440K | I253K Q438K K439E |
| 234 | H310D Y436Q S440K | I253K Q438H K439E |
| 235 | H310D Y436Q S440K | I253K Q438G K439E |
| 236 | H310D Y436Q S440K | I253K Q438N K439E |
| 237 | I253K Y436R S440K | H310D Q438R K439E |
| 238 | I253K Y436R S440K | H310D Q438K K439E |
| 239 | I253K Y436R S440K | H310D Q438H K439E |
| 240 | I253K Y436R S440K | H310D Q438G K439E |
| 241 | I253K Y436R S440K | H310D Q438N K439E |
| 242 | H310D Y436R S440K | I253K Q438R K439E |
| 243 | H310D Y436R S440K | I253K Q438K K439E |
| 244 | H310D Y436R S440K | I253K Q438H K439E |
| 245 | H310D Y436R S440K | I253K Q438G K439E |
| 246 | H310D Y436R S440K | I253K Q438N K439E |
| 247 | Y436N K439E | Q438R S440K |
| 248 | Y436N K439E | Q438K S440K |
| 249 | Y436N K439E | Q438H S440K |
| 250 | Y436N K439E | Q438G S440K |
| 251 | Y436N K439E | Q438N S440K |
| 252 | Y436K K439E | Q438R S440K |
| 253 | Y436K K439E | Q438K S440K |
| 254 | Y436K K439E | Q438H S440K |
| 255 | Y436K K439E | Q438G S440K |
| 256 | Y436K K439E | Q438N S440K |
| 257 | Y436Q K439E | Q438R S440K |
| 258 | Y436Q K439E | Q438K S440K |
| 259 | Y436Q K439E | Q438H S440K |
| 260 | Y436Q K439E | Q438G S440K |
| 261 | Y436Q K439E | Q438N S440K |
| 262 | Y436R K439E | Q438R S440K |

| Embodiment | First polypeptide mutations | Second polypeptide mutations |
|---|---|---|
| 263 | Y436R K439E | Q438K S440K |
| 264 | Y436R K439E | Q438H S440K |
| 265 | Y436R K439E | Q438G S440K |
| 266 | Y436R K439E | Q438N S440K |
| 267 | Y436N S440K | Q438R K439E |
| 268 | Y436N S440K | Q438K K439E |
| 269 | Y436N S440K | Q438H K439E |
| 270 | Y436N S440K | Q438G K439E |
| 271 | Y436N S440K | Q438N K439E |
| 272 | Y436K S440K | Q438R K439E |
| 273 | Y436K S440K | Q438K K439E |
| 274 | Y436K S440K | Q438H K439E |
| 275 | Y436K S440K | Q438G K439E |
| 276 | Y436K S440K | Q438N K439E |
| 277 | Y436Q S440K | Q438R K439E |
| 278 | Y436Q S440K | Q438K K439E |
| 279 | Y436Q S440K | Q438H K439E |
| 280 | Y436Q S440K | Q438G K439E |
| 281 | Y436Q S440K | Q438N K439E |
| 282 | Y436R S440K | Q438R K439E |
| 283 | Y436R S440K | Q438K K439E |
| 284 | Y436R S440K | Q438H K439E |
| 285 | Y436R S440K | Q438G K439E |
| 286 | Y436R S440K | Q438N K439E |
| 287 | Q438N S440K | Q438R K439E |
| 288 | Q438R S440K | Q438N K439E |

Optional Further Modifications

In some embodiments, one or both polypeptides used in the invention comprise further mutations that enhance oligomerization, such as hexamerization. Such mutations have e.g. been described in WO2013/004842 and WO2014/108198. By including such further mutations, the propensity of the first and second polypeptides to form hetero-oligomers, such as hetero-hexamers, will be even further enhanced. Examples of amino acid mutations that enhance Fc-Fc interaction between polypeptides and thereby oligomer formation are E430G, E345K, E430S, E430F, E430T, E345Q, E345R, E345Y, S440W, S440Y, T437R and K248E. Thus, such mutations promote or enhance oligomer formation, such as hexamer formation, and may also be described as Fc-Fc interaction enhancing mutations, hexmerization enhancing mutations or self-oligomerization enhancing mutations.

Thus, in some embodiments, said first polypeptide further comprises a mutation of an amino acid position corresponding to E430, E345, S440, T437 or K248 in human IgG1, and/or said second polypeptide further comprises a mutation of an amino acid position corresponding to E430, E345, S440, T437 or K248 in human IgG1, or vice versa, with the proviso that if said first or second polypeptide comprises a K439E, K439D, S440K, S440R or S440H mutation, said further mutation in said polypeptide is not at position S440.

In some of these embodiments, said further mutation in said first polypeptide is selected from the group consisting of: E430G, E345K, E430S, E430F, E430T, E345Q, E345R, E345Y, S440W and S440Y.

In some of these embodiments, said further mutation in said second polypeptide is selected from the group consisting of: E430G, E345K, E430S, E430F, E430T, E345Q, E345R, E345Y, S440W and S440Y.

In some of these embodiments, said further mutation in said first polypeptide is selected from the group consisting of: E430G, E345K, E430S, E430F, E430T, E345Q, E345R, E345Y, S440W and S440Y, and said further mutation in said second polypeptide is selected from the group consisting of: E430G, E345K, E430S, E430F, E430T, E345Q, E345R, E345Y, S440W and S440Y, and/or said first polypeptide comprises a T437R and a K248E mutation, and/or said second polypeptide comprises a T437R and a K248E mutation.

In some embodiments, said further mutation in said first polypeptide is selected from the group consisting of: E430G, E345K and E345R, and said further mutation in said second polypeptide is selected from the group consisting of: E430G, E345K and E345K. The further mutation may be independently selected from the group for said first and second polypeptide.

In some embodiments, said further mutation in said first polypeptide is selected from the group consisting of: E430G and E345K, and said further mutation in said second polypeptide is selected from the group consisting of: E430G and E345K. In a preferred embodiment, said further mutation in said first polypeptide is E430G and said further mutation in said second polypeptide E430G. In one embodiment, said further mutation in said first polypeptide is E345K and said further mutation in said second polypeptide E345K. In one embodiment, said further mutation in said first polypeptide is E345R and said further mutation in said second polypeptide E345R.

In one embodiment, said first polypeptide comprises a T437R and a K248E mutation, and said second polypeptide comprises a T437R and a K248E mutation.

In one embodiment of the invention, said first polypeptide comprises an E430G mutation and said second polypeptide comprises an E430G mutation.

In another embodiment of the invention, i) said first polypeptide comprises a Y436N mutation of an amino acid position corresponding to Y436 in human IgG1 and said second polypeptide comprises a Q438R mutation of an amino acid position corresponding to Q438 in human IgG1, or vice versa, or ii) said first polypeptide comprises a Y436N mutation of an amino acid position corresponding to Y436 in human IgG1 and said second polypeptide comprises a Q438N mutation of an amino acid position corresponding to Q438 in human IgG1, or vice versa, or iii) said first polypeptide comprises a Y436N mutation of an amino acid position corresponding to Y436 in human IgG1 and said second polypeptide comprises a Y436K mutation of an amino acid position corresponding to Y436 in human IgG1, or vice versa, or iv) said first polypeptide comprises a Y436K mutation of an amino acid position corresponding to Y436 in human IgG1 and said second polypeptide comprises a Q438R mutation of an amino acid position corresponding to Q438 in human IgG1, or vice versa, or v) said first polypeptide comprises a Y436K mutation of an amino acid position corresponding to Y436 in human IgG1 and said second polypeptide comprises a Q438N mutation of an amino acid position corresponding to Q438 in human IgG1, or vice versa, or vi) said first polypeptide comprises a Q438R mutation of an amino acid position corresponding to Q438 in human IgG1 and said second polypeptide comprises a Q438N mutation of an amino acid position corresponding to Q438 in human IgG1, or vice versa, and vii) said first polypeptide comprises a K439E mutation of an amino acid position corresponding to K439 in human IgG1 and said second polypeptide comprises an S440K mutation of an amino acid position corresponding to S440 in human IgG1, or vice versa, and viii) said first polypeptide comprises a E430G, E345K or E345R mutation of an amino acid position corresponding to K430 or E345 in human IgG1 and said second polypeptide comprises an E430G, E345K or E345R mutation of an amino acid position corresponding to K430 or E345 in human IgG1, or vice versa.

The E430G, E345K or E345R mutations may be independently selected for said first and second polypeptide. Thus, said first and second polypeptide may have the same mutation or a different mutation selected from the group consisting of: E430G, E345K or E345R.

In another embodiment of the invention, i) said first polypeptide comprises a Y436N or Y436K mutation of an amino acid position corresponding to Q436 in human IgG1 and said second polypeptide comprises a Q438N or Q438R mutation of an amino acid position corresponding to Q438 in human IgG1, or vice versa, and ii) said first polypeptide comprises a K439E mutation of an amino acid position corresponding to K439 in human IgG1 and said second polypeptide comprises an S440K mutation of an amino acid position corresponding to S440 in human IgG1, or vice versa and iii) said first polypeptide comprises a E430G or E345K mutation of an amino acid position corresponding to K430 or E345 in human IgG1 and said second polypeptide comprises an E430G or E345R mutation of an amino acid position corresponding to K430 or E345 in human IgG1, or vice versa.

In another embodiment of the invention, i) said first polypeptide comprises a Y436N or Y436K mutation of an amino acid position corresponding to Q436 in human IgG1 and said second polypeptide comprises a Q438N or Q438R mutation of an amino acid position corresponding to Q438 in human IgG1, or vice versa, and ii) said first polypeptide comprises a K439E mutation of an amino acid position corresponding to K439 in human IgG1 and said second polypeptide comprises an S440K mutation of an amino acid position corresponding to S440 in human IgG1, or vice versa and iii) said first and second polypeptide comprises a E430G mutation of an amino acid position corresponding to K430 in human IgG1.

In another embodiment of the invention, said first polypeptide comprises a Y436N, K439E and E430G mutation wherein the amino acid positions correspond to Y436, K439 and E430 respectively in human IgG1 and said second polypeptide comprises a Q438R, S440K and E430G mutation wherein the amino acid positions correspond to Q438, S440 and E430 in human IgG1, or vice versa.

In another embodiment of the invention, said first polypeptide comprises a Y436K, K439E and E430G mutation wherein the amino acid positions correspond to Y436, K439 and E430 respectively in human IgG1 and said second polypeptide comprises a Q438N, S440K and E430G mutation wherein the amino acid positions correspond to Q438, S440 and E430 in human IgG1, or vice versa.

In another embodiment of the invention, said first polypeptide comprises a Y436K, K439E and E430G mutation wherein the amino acid positions correspond to Y436, K439 and E430 respectively in human IgG1 and said second polypeptide comprises a Q438R, S440K and E430G mutation wherein the amino acid positions correspond to Q438, S440 and E430 in human IgG1, or vice versa.

In some embodiments, one or both polypeptides used in the invention comprise(s) further mutations that alter the ability of the polypeptide induce or mediate effector functions, such as Fc-mediated effector functions, e.g. CDC or ADCC. Such an altered ability can be an increased ability to induce effector functions or a decreased ability to induce effector functions. In some embodiments, one or both polypeptides used in the invention comprise further mutations that alter the ability of the polypeptide to bind Fc gamma receptors. Mutations that alter the ability of an antibody to induce effector functions and/or bind Fc gamma receptors have been described in the art. By including such further mutations, the propensity of the first and second variant polypeptides to induce effector functions will be increased or decreased and thus may be modulated according to what is desired in the given situation. For example, it can be desirable to introduce mutations that increase the ability of the polypeptides to induce CDC to even further promote the efficacy of hetero-oligomers. In some other situations, it may e.g. be a priority to further reduce toxicity of homo-oligomers by introducing mutations that reduce the ability to induce CDC.

Accordingly, in some embodiments of the invention, said first polypeptide and/or said second polypeptide has been further modified so that the polypeptide has an altered ability to induce effector functions, such as Fc-mediated effector functions, compared to a polypeptide which is identical except for said further modification.

In some embodiments, said first polypeptide and/or said second polypeptide has been further modified so that the polypeptide has an altered ability to induce antibody-dependent cell-mediated cytotoxicity compared to a polypeptide which is identical except for said further modification.

In other embodiments, said first polypeptide and/or said second polypeptide has been further modified so that the polypeptide has an altered ability to induce complement-dependent cytotoxicity compared to a polypeptide which is identical except for said modification.

Polypeptide Formats

As described above, in a preferred embodiment of the method of the invention, said first polypeptide is an antibody. In another preferred embodiment of the invention, said second polypeptide is an antibody. In a more preferred embodiment, said first polypeptide is an antibody and said second polypeptide is an antibody.

In a further embodiment, said first polypeptide is a full-length antibody and/or said second polypeptide is a full-length antibody.

The Fc region or antibody may be of any IgG isotype, e.g. IgG1, IgG2, IgG3 or IgG4. In one embodiment of the invention the polypeptide or antibody has an Fc region that is a human IgG1, IgG2, IgG3 or IgG4 isotype. In one embodiment of the invention the Fc region is a mixed isotype, such as a mixed isotype selected from the group consisting of: IgG1/IgG2, IgG1/IgG3, IgG1/IgG4, IgG2/

IgG3, IgG2/IgG4 and IgG3/IgG4. In a mixed isotype, the Fc region is comprised of an amino acid sequence from more than one isotype.

In preferred embodiments, said first polypeptide is an IgG1 antibody and/or said second polypeptide is an IgG1 antibody.

In one embodiment of the invention, the first and/or second polypeptide comprises a first and/or second Fc region comprising the sequence as set forth in SEQ ID NO: 22, 23, 24, 25, 31, 32, and 33, wherein at least one mutation according to the invention has been introduced into said sequence. The first and second Fc region may be independently selected from the sequences as set forth in SEQ ID NO: 22, 23, 24, 25, 31, 32, and 33. Thus, the first and second Fc region may be of the same parent sequence or of a different parent sequence.

In one embodiment of the invention, the first and/or second polypeptide comprises a first and/or second Fc region comprising the sequence as set forth in SEQ ID NO: 22, 23, 24 and 25, wherein at least one mutation according to the invention has been introduced into said sequence.

In one embodiment of the invention, the first polypeptide comprises a first Fc region comprising a sequence selected from the group consisting of SEQ ID NO: 22, 23, 24, 25, 26, 27, 28, 29, 30, 31, 32, and 33, wherein at least one mutation according to the invention has been introduced. In one embodiment of the invention the second polypeptide comprises a second Fc region comprising a sequence selected from the group consisting of SEQ ID NO: 22, 23, 24, 25, 26, 27, 28, 29, 30, 31, 32, and 33, wherein at least one mutation according to the invention has been introduced.

In one embodiment of the invention, the first polypeptide comprises a first Fc region comprising a sequence selected from the group consisting of SEQ ID NO: 22, 23, 24, 25, 26, 27, 28, 29, 30, 31, 32, and 33, wherein at least two mutations, or at least three mutations, according to the invention has been introduced. In one embodiment of the invention the second polypeptide comprises a second Fc region comprising a sequence selected from the group consisting of SEQ ID NO: 22, 23, 24, 25, 26, 27, 28, 29, 30, 31, 32, and 33 wherein at least two mutations, or at least three mutations, according to the invention has been introduced.

In one embodiment of the invention, the first polypeptide comprises a first Fc region comprising a sequence selected from the group consisting of: SEQ ID NO 63, 64, 65, 66, 67, 68, 69, 70, 71, 72, 74, 75, 76, 77, 79, 80, 81, 82, 83, 84, 85, 86, 87, 88, 89, 90, 91, 92, 93, 94, 95, 96, 98, 99, 100, 101, 102, 103, 104, 105, 106, 107, 108, 109, 110. In one embodiment of the invention the second polypeptide comprises a second Fc region comprising a sequence selected from the group consisting of: SEQ ID NO 63, 64, 65, 66, 67, 68, 69, 70, 71, 72, 74, 75, 76, 77, 79, 80, 81, 82, 83, 84, 85, 86, 87, 88, 89, 90, 91, 92, 93, 94, 95, 96, 98, 99, 100, 101, 102, 103, 104, 105, 106, 107, 108, 109, 110.

In one embodiment of the invention the
i) first polypeptide comprises a first Fc region comprising a sequence selected from the group consisting of: 74, 76, 79 and 81, and
ii) the second polypeptide comprises a second Fc region comprising a sequence selected from the group consisting of: 75, 77, 80 and 82, or vice versa, wherein the first and second Fc region has at most 5 further mutation (s), such as at most 4, such as at most 3 such as at most 2 such as at most one.

In one embodiment of the invention, the second polypeptide comprises a second Fc region comprising a sequence as set forth in SEQ ID NO: 63. In one embodiment of the invention the second polypeptide comprises a first Fc region comprising a sequence as set forth in SEQ ID NO: 64. In one embodiment of the invention the first polypeptide comprises a first Fc region comprising a sequence as set forth in SEQ ID NO: 65. In one embodiment of the invention the first polypeptide comprises a first Fc region comprising a sequence as set forth in SEQ ID NO: 66. In one embodiment of the invention the first polypeptide comprises a first Fc region comprising a sequence as set forth in SEQ ID NO: 67. In one embodiment of the invention the first polypeptide comprises a first Fc region comprising a sequence as set forth in SEQ ID NO: 68. In one embodiment of the invention the first polypeptide comprises a first Fc region comprising a sequence as set forth in SEQ ID NO: 69. In one embodiment of the invention the first polypeptide comprises a first Fc region comprising a sequence as set forth in SEQ ID NO: 70. In one embodiment of the invention the first polypeptide comprises a first Fc region comprising a sequence as set forth in SEQ ID NO: 71. In one embodiment of the invention the first polypeptide comprises a first Fc region comprising a sequence as set forth in SEQ ID NO: 72. In one embodiment of the invention the first polypeptide comprises a first Fc region comprising a sequence as set forth in SEQ ID NO: 74. In one embodiment of the invention the first polypeptide comprises a first Fc region comprising a sequence as set forth in SEQ ID NO: 75. In one embodiment of the invention the first polypeptide comprises a first Fc region comprising a sequence as set forth in SEQ ID NO: 76. In one embodiment of the invention the first polypeptide comprises a first Fc region comprising a sequence as set forth in SEQ ID NO: 77. In one embodiment of the invention the first polypeptide comprises a first Fc region comprising a sequence as set forth in SEQ ID NO: 79. In one embodiment of the invention the first polypeptide comprises a first Fc region comprising a sequence as set forth in SEQ ID NO: 80. In one embodiment of the invention the first polypeptide comprises a first Fc region comprising a sequence as set forth in SEQ ID NO: 81. In one embodiment of the invention the first polypeptide comprises a first Fc region comprising a sequence as set forth in SEQ ID NO: 82. In one embodiment of the invention the first polypeptide comprises a first Fc region comprising a sequence as set forth in SEQ ID NO: 83. In one embodiment of the invention the first polypeptide comprises a first Fc region comprising a sequence as set forth in SEQ ID NO: 84. In one embodiment of the invention the first polypeptide comprises a first Fc region comprising a sequence as set forth in SEQ ID NO: 85. In one embodiment of the invention the first polypeptide comprises a first Fc region comprising a sequence as set forth in SEQ ID NO: 86. In one embodiment of the invention the first polypeptide comprises a first Fc region comprising a sequence as set forth in SEQ ID NO: 87. In one embodiment of the invention the first polypeptide comprises a first Fc region comprising a sequence as set forth in SEQ ID NO: 88. In one embodiment of the invention the first polypeptide comprises a first Fc region comprising a sequence as set forth in SEQ ID NO: 89. In one embodiment of the invention the first polypeptide comprises a first Fc region comprising a sequence as set forth in SEQ ID NO: 90. In one embodiment of the invention the first polypeptide comprises a first Fc region comprising a sequence as set forth in SEQ ID NO: 91. In one embodiment of the invention the first polypeptide comprises a first Fc region comprising a sequence as set forth in SEQ ID NO: 92. In one embodiment of the invention the first polypeptide comprises a first Fc region comprising a sequence as set forth in SEQ ID NO: 93. In one embodiment of the invention the first polypeptide comprises a first Fc region comprising a sequence as set forth in SEQ ID NO: 94. In one embodiment of the invention the first polypeptide comprises a first Fc region comprising a sequence as set forth in SEQ ID NO: 95. In one embodiment of the invention the first polypeptide comprises a first Fc region comprising a sequence as set forth in SEQ ID NO: 96. In one embodiment of the invention the first polypeptide comprises a first Fc region comprising a sequence as set forth in SEQ ID NO: 97. In one embodiment of the invention the first polypeptide comprises a first Fc region comprising a sequence as set forth in SEQ ID NO: 98. In one embodiment of the invention the first polypeptide comprises a first Fc region comprising a sequence as set forth in SEQ ID NO: 99. In one embodiment of the invention the first polypeptide comprises a first Fc region comprising a sequence as set forth in SEQ ID NO: 100. In one embodiment of the invention the first polypeptide comprises a first Fc region comprising a sequence as set forth in SEQ ID NO: 101. In one embodiment of the invention the first polypeptide comprises a first Fc region comprising a sequence as set forth in SEQ ID NO: 102. In one embodiment of the invention the first polypeptide comprises a first Fc region comprising a sequence as set forth in SEQ ID NO: 103. In one embodiment of the invention the first polypeptide comprises a first Fc region comprising a sequence as set forth in SEQ ID NO: 104. In one embodiment of the invention the first polypeptide comprises a first Fc region comprising a sequence as set forth in SEQ ID NO: 105. In one embodiment of the invention the first polypeptide comprises a first Fc region comprising a sequence as set forth in SEQ ID NO: 106. In one embodiment of the invention the first polypeptide comprises a first Fc region comprising a sequence as set forth in SEQ ID NO: 107. In one embodiment of the invention the first polypeptide comprises a first Fc region comprising a sequence as set forth in SEQ ID NO: 108. In one embodiment of the invention the first polypeptide comprises a first Fc region comprising a sequence as set forth in SEQ ID NO: 109. In one embodiment of the invention the first polypeptide comprises a first Fc region comprising a sequence as set forth in SEQ ID NO: 110.

In one embodiment of the invention, the second polypeptide comprises a second Fc region comprising a sequence as set forth in SEQ ID NO: 63. In one embodiment of the invention the second polypeptide comprises a second Fc region comprising a sequence as set forth in SEQ ID NO: 64. In one embodiment of the invention the second polypeptide comprises a second Fc region comprising a sequence as set forth in SEQ ID NO: 65. In one embodiment of the invention the second polypeptide comprises a second Fc region comprising a sequence as set forth in SEQ ID NO: 66. In one embodiment of the invention the second polypeptide comprises a second Fc region comprising a sequence as set forth in SEQ ID NO: 67. In one embodiment of the invention the second polypeptide comprises a second Fc region comprising a sequence as set forth in SEQ ID NO: 68. In one embodiment of the invention the second polypeptide comprises a second Fc region comprising a sequence as set forth in SEQ ID NO: 69. In one embodiment of the invention the second polypeptide comprises a second Fc region comprising a sequence as set forth in SEQ ID NO: 70. In one embodiment of the invention the second polypeptide comprises a second Fc region comprising a sequence as set forth in SEQ ID NO: 71. In one embodiment of the invention the second polypeptide comprises a second Fc region comprising a sequence as set forth in SEQ ID NO: 72. In one embodiment of the invention the second polypeptide comprises a second Fc region comprising a sequence as set forth in SEQ ID NO: 74. In one embodiment of the invention the second polypeptide comprises a second Fc region comprising a sequence as set forth in SEQ ID NO: 75. In one embodiment of the invention the second polypeptide comprises a second Fc region comprising a sequence as set forth in SEQ ID NO: 76. In one embodiment of the invention the second polypeptide comprises a second Fc region comprising a sequence as set forth in SEQ ID NO: 77. In one embodiment of the invention the second polypeptide comprises a second Fc region comprising a sequence as set forth in SEQ ID NO: 79. In one embodiment of the invention the second polypeptide comprises a second Fc region comprising a sequence as set forth in SEQ ID NO: 80. In one embodiment of the invention the second polypeptide comprises a second Fc region comprising a sequence as set forth in SEQ ID NO: 81. In one embodiment of the invention the second polypeptide comprises a second Fc region comprising a sequence as set forth in SEQ ID NO: 82. In one embodiment of the invention the second polypeptide comprises a second Fc region comprising a sequence as set forth in SEQ ID NO: 83. In one embodiment of the invention the second polypeptide comprises a second Fc region comprising a sequence as set forth in SEQ ID NO: 84. In one embodiment of the invention the second polypeptide comprises a second Fc region comprising a sequence as set forth in SEQ ID NO: 85. In one embodiment of the invention the second polypeptide comprises a second Fc region comprising a sequence as set forth in SEQ ID NO: 86. In one embodiment of the invention the second polypeptide comprises a second Fc region comprising a sequence as set forth in SEQ ID NO: 87. In one embodiment of the invention the second polypeptide comprises a second Fc region comprising a sequence as set forth in SEQ ID NO: 88. In one embodiment of the invention the second polypeptide comprises a second Fc region comprising a sequence as set forth in SEQ ID NO: 89. In one embodiment of the invention the second polypeptide comprises a second Fc region comprising a sequence as set forth in SEQ ID NO: 90. In one embodiment of the invention the second polypeptide comprises a second Fc region comprising a sequence as set forth in SEQ ID NO: 91. In one embodiment of the invention the second polypeptide comprises a second Fc region comprising a sequence as set forth in SEQ ID NO: 92. In one embodiment of the invention the second polypeptide comprises a second Fc region comprising a sequence as set forth in SEQ ID NO: 93. In one embodiment of the invention the second polypeptide comprises a second Fc region comprising a sequence as set forth in SEQ ID NO: 94. In one embodiment of the invention the second polypeptide comprises a second Fc region comprising a sequence as set forth in SEQ ID NO: 95. In one embodiment of the invention the second polypeptide comprises a second Fc region comprising a sequence as set forth in SEQ ID NO: 96. In one embodiment of the invention the second polypeptide comprises a second Fc region comprising a sequence as set forth in SEQ ID NO: 97. In one embodiment of the invention the second polypeptide comprises a second Fc region comprising a sequence as set forth in SEQ ID NO: 98. In one embodiment of the invention the second polypeptide comprises a second Fc region comprising a sequence as set forth in SEQ ID NO: 99. In one embodiment of the invention the second polypeptide comprises a second Fc region comprising a sequence as set forth in SEQ ID NO: 100. In one embodiment of the invention the second polypeptide comprises a second Fc region comprising a sequence as set forth in SEQ ID NO: 101. In one embodiment of the invention the second polypeptide comprises a second Fc region comprising a sequence as set forth in SEQ ID NO: 102. In one embodiment of the invention the second polypeptide comprises a second Fc region comprising a sequence as set forth in SEQ ID NO: 103. In one embodiment of the invention the second polypeptide comprises a second Fc region comprising a sequence as set forth in SEQ ID NO: 104. In one embodiment of the invention the second polypeptide comprises a second Fc region comprising a sequence as set forth in SEQ ID NO: 105. In one embodiment of the invention the second polypeptide comprises a second Fc region comprising a sequence as set forth in SEQ ID NO: 106. In one embodiment of the invention the second polypeptide comprises a second Fc region comprising a sequence as set forth in SEQ ID NO: 107. In one embodiment of the invention the second polypeptide comprises a second Fc region comprising a sequence as set forth in SEQ ID NO: 108. In one embodiment of the invention the second polypeptide comprises a second Fc region comprising a sequence as set forth in SEQ ID NO: 109. In one embodiment of the invention the second polypeptide comprises a second Fc region comprising a sequence as set forth in SEQ ID NO: 110.

As described above, in some embodiments of the invention further mutations may be introduced into the Fc region that alters the ability of the polypeptide or antibody to induce/mediate effector functions or other properties of the polypeptide or antibody. Such other properties may be plasma clearance and mutations relevant for such modifications are well known to persons skilled in the art.

In one embodiment of the invention, the first polypeptide comprises a first Fc region comprising a sequence selected from the group consisting of: SEQ ID NO 22, 23, 24, 25, 31, 32, and 33, wherein at most 10 mutations has been introduced. In one embodiment of the invention the second polypeptide comprises a second Fc region comprising a sequence selected from the group consisting of: SEQ ID NO 22, 23, 24, 25, 31, 32, and 33, wherein at most 10 mutations has been introduced. The at most 10 mutations introduced into said sequence may include the amino acid mutations introduced according to the present invention.

In one embodiment of the invention, the first polypeptide comprises a first Fc region comprising a sequence as set forth in: SEQ ID NO 22, wherein at most 10 mutations have been introduced. In one embodiment of the invention the first polypeptide comprises a first Fc region comprising a sequence as set forth in: SEQ ID NO 23, wherein at most 10 mutations have been introduced. In one embodiment of the invention the first polypeptide comprises a first Fc region comprising a sequence as set forth in: SEQ ID NO 24, wherein at most 10 mutations have been introduced. In one embodiment of the invention the first polypeptide comprises a first Fc region comprising a sequence as set forth in: SEQ ID NO 25, wherein at most 10 mutations have been introduced. In one embodiment of the invention the first polypeptide comprises a first Fc region comprising a sequence as set forth in: SEQ ID NO 31, wherein at most 10 mutations have been introduced. In one embodiment of the invention the first polypeptide comprises a first Fc region comprising a sequence as set forth in: SEQ ID NO 32, wherein at most 10 mutations have been introduced. In one embodiment of the invention the first polypeptide comprises a first Fc region comprising a sequence as set forth in: SEQ ID NO 32, wherein at most 10 mutations have been introduced.

In one embodiment of the invention, the second polypeptide comprises a second Fc region comprising a sequence as set forth in: SEQ ID NO 22, wherein at most 10 mutations have been introduced. In one embodiment of the invention the second polypeptide comprises a second Fc region comprising a sequence as set forth in: SEQ ID NO 23, wherein at most 10 mutations have been introduced. In one embodiment of the invention the second polypeptide comprises a second Fc region comprising a sequence as set forth in: SEQ ID NO 24, wherein at most 10 mutations have been introduced. In one embodiment of the invention the second polypeptide comprises a second Fc region comprising a sequence as set forth in: SEQ ID NO 25, wherein at most 10 mutations have been introduced. In one embodiment of the invention the second polypeptide comprises a second Fc region comprising a sequence as set forth in: SEQ ID NO 31, wherein at most 10 mutations have been introduced. In one embodiment of the invention the second polypeptide comprises a second Fc region comprising a sequence as set forth in: SEQ ID NO 32, wherein at most 10 mutations have been introduced. In one embodiment of the invention the second polypeptide comprises a second Fc region comprising a sequence as set forth in: SEQ ID NO 32, wherein at most 10 mutations have been introduced.

In one embodiment of the invention at most 10 mutations has been introduced, such as at most 9 mutations, such as at most 8 mutations, such as at most 7 mutations, such as at most 6 mutations, such as at most 5 mutations, such as at most 4 mutations, or such as at most 3 mutations.

In one embodiment of the invention the first and second polypeptide comprises a first and second Fc region comprising a sequence selected from the group consisting of: SEQ ID NO 22, 23, 24, 25, 31, 32, and 33, wherein at most 10 mutations has been introduced, such as at most 9 mutations, such as at most 8 mutations, such as at most 7 mutations, such as at most 6 mutations, such as at most 5 mutations, such as at most 4 mutations, or such as at most 3 mutations.

In one embodiment of the invention the first and second polypeptide comprises a first and second Fc region comprising the sequence as set forth in SEQ ID NO 22, wherein at most 10 mutations has been introduced, such as at most 9 mutations, such as at most 8 mutations, such as at most 7 mutations, such as at most 6 mutations, such as at most 5 mutations, such as at most 4 mutations, or such as at most 3 mutations.

In further embodiments, said first antibody is human, humanized or chimeric and/or said second antibody is human, humanized or chimeric.

The polypeptide of the invention is not limited to polypeptides, such as antibodies, which have a natural, e.g. a human Fc domain but it may also be a polypeptide having other mutations than those of the present invention, such as e.g. mutations that affect glycosylation or enable the antibody to be a bispecific antibody. By the term "natural antibody" is meant any antibody which does not comprise any genetically introduced mutations that are not naturally occurring. An antibody which comprises naturally occurring modifications, e.g. different allotypes, is thus to be understood as a "natural antibody" in the sense of the present invention, and can thereby be understood as a parent antibody. Such antibodies may serve as a template for the one or more mutations according to the present invention, and thereby providing the variant antibodies of the invention.

The polypeptide or antibody used in the invention has the specified mutations, but may also have additional mutations to introduce additional functions into the polypeptide or antibody. In one embodiment, the Fc region comprises at most ten mutations, such as nine mutations, such as eight mutations, such as seven mutations, such as six mutations, such as five mutations, such as four mutations, such as three mutations or such as two mutations. The additional mutations also allow for a variation in the Fc region at positions which are not involved in Fc-Fc interaction, as well as in positions not involved in Fc effector functions. Further, as mentioned, additional mutations may also be due to allelic variations.

Thus, in one embodiment of the invention the polypeptide or antibody has an Fc region that is an IgG1m(f), IgG1m(a), IgG1m(z), IgG1m(x) allotype or mixed allotype.

The polypeptides or antibodies used in the invention may be monospecific or multispecific, such as bispecific. Thus, in one embodiment, said first antibody is bispecific and/or said second polypeptide is bispecific.

Target Antigens, Target Cells and Diseases to be Treated

As explained above, the present invention provides methods which can be used to improve the selectivity of an antibody treatment for desired target cell populations.

The methods relate to a treatment with a first and second antigen-binding polypeptide, wherein the two antibodies bind two different target antigens (a first antigen and a second antigen) and wherein the Fc regions of the antibodies have been modified such that hetero-oligomerization of the two antibodies is strongly favored over homo-oligomerization. As a result of these modifications, more antibody oligomerization will occur on cells that express both antigen targets (allowing efficient (hetero)oligomerization of the two antibodies), than on cells that only express one of the targets (resulting in inefficient or no (homo)oligomerization). As oligomerization generally enhances the efficacy of antibodies, the antibody combination treatment will be more efficacious against cells that co-express the targets than against cells that only express one of the targets. Thus, the antibody combination treatment has an improved selectivity for cells or tissues expressing both target antigens. Accordingly, by selecting two antigens that are co-expressed in a desired target cell population, but not, or less, co-expressed in cell populations that should not be targeted, a combined antibody treatment can be designed which will have a selective effect against the desired target cell populations.

Accordingly, in a preferred embodiment of the method of the invention, said first and second antigens are both cell surface-exposed molecules and ligands. Target antigens which activate, inhibit, modulate and or regulate signal transduction pathways may be particularly suitable as targets according to the present invention.

The following protein classes may also be particular suitable as antigen-binding target for the first and/or second polypeptide according to the invention, tumor necrosis receptor super family, GPI-anchored proteins, hematopoietic factor receptor family, cytokine receptor family, serine/threonine kinase receptor family, Hydrolases and regulators superfamily, hormone receptor family, B7 family-related protein, immunoglobulin superfamily, interleukin receptor family, Integrin, Ig-like cell adhesion molecule family, Protein tyrosine phosphatases, receptor type, C-type lectin, Tetraspanins, Membrane spanning 4-domains, Interleukin receptors, Activating leukocyte immunoglobulin like receptors, C-C motif chemokine receptors, G protein-coupled receptors, Toll like receptors, Receptor Tyrosine Kinases. In one embodiment of the invention the first and second antigen binding regions is capable of binding to a target antigen form the same protein class. In one embodiment of the invention the first and second antigen-binding regions is capable of binding to a target antigen from different protein classes.

In one embodiment of the invention the first antigen-binding region is capable of binding to a target antigen from the protein class of GPI-anchored proteins and the second antigen-binding region is capable of binding to a target antigen from the protein class of Tetraspanins. In one embodiment of the invention the first antigen-binding region is capable of binding to a target antigen from the protein class of Tetraspanins and the second antigen-binding region is capable of binding to a target antigen from the protein class of GPI-anchored proteins.

In one embodiment of the invention the first antigen-binding region is capable of binding to a target antigen from the protein class of GPI-anchored proteins and the second antigen-binding region is capable of binding to a target antigen from the protein class of Membrane spanning 4-domains. In one embodiment of the invention the first antigen-binding region is capable of binding to a target antigen from the protein class of Membrane spanning 4-domains and the second antigen-binding region is capable of binding to a target antigen from the protein class of GPI-anchored proteins.

In one embodiment of the invention the first antigen-binding region is capable of binding to a target antigen from the protein class of Membrane spanning 4-domains and the second antigen-binding region is capable of binding to a target antigen from the protein class of Tetraspanins.

CD20 is an example of the protein class of Membrane spanning 4-domains. Example illustrates the use of the present invention on the protein class of Membrane spanning 4-domains.

CD37 is an example of the protein class of protein class of Tetraspanins. Example illustrates the use of the present invention on the protein class of Tetraspanins.

In one embodiment of the invention the first antigen-binding region is capable of binding to a target antigen from the protein class of tumor necrosis receptor super family and the second antigen-binding region is capable of binding to a target antigen from the protein class of tumor necrosis receptor super family.

In one embodiment of the invention the first antigen-binding region is capable of binding to a target antigen from the protein class of tumor necrosis receptor super family and the second antigen-binding region is capable of binding to a target antigen from the protein class of immunoglobulin superfamily.

In one embodiment of the invention the first and/or second polypeptide comprises a first antigen-binding region and/or second antigen-binding region, wherein the antigen binding region binds to a member of the tumor necrosis factor receptor super family (TNFR-SF), G-protein Coupled Receptor (GPCR) superfamily, a membrane spanning-4 domain or a membrane Tetraspanin.

Some TNFRSF are involved in apoptosis and contains an intracellular death domain such as FAS, DR4, DR5, TNFR1, DR6, DR3, EDAR and NGFR. Other TNFRSF are involved in other signal transduction pathways, such as proliferation, survival, and differentiation such as DcR1, DcR2, DcR3, OPG, TROY, XEDAR, LTbR, HVEM, TWEAKR, CD120b, OX40, CD40, CD27, CD30, 4-1BB, RANK, TACI, BLySR, BCMA, GITR, RELT. TNF receptors are expressed in a wide variety of tissues in mammals, especially in leukocytes.

DR5 is an example of the TNFRSF class of receptors. Example 19 illustrates the use of the present invention on the TNFRSF class of receptors.

In one embodiment of the invention the first and/or second antigen-binding region binds to a member of the TNFR-SF selected form the group consisting of: FAS, DR4, DR5, TNFR1, DR6, DR3, EDAR, NGFR, OX40, CD40, CD30, CD27, 4-1BB, RANK, TACI, BLySR, BCMA, RELT and GITR.

In one embodiment of the invention the first antigen-binding region binds to DR5. In one embodiment of the invention the second antigen-binding region binds to DR5.

In one embodiment of the invention the first and/or second antigen-binding region binds to a member of the TNFR-SF which does not comprise an intracellular death domain. In one embodiment of the invention the TNFR-SF is selected from the group of: OX40, CD40, CD30, CD27, 4-1BB, RANK, TACI, BLySR, BCMA, RELT and GITR. In one embodiment of the invention the TNFR-SF is selected form the group of: FAS, DR4, DR4, TNFR1, DR6, DR3, EDAR, and NGFR.

Polypeptides according to the invention may bind any target, examples of such targets or antigens according to the invention may be, directed against are: TNFR1, FAS, DR3, DR4, DR5, DR6, NGFR, EDAR, DcR1, DcR2, DcR3, OPG, TROY, XEDAR, LTbR, HVEM, TWEAKR, CD120b, OX40, CD40, CD27, CD30, 4-1BB, RANK, TACI, BLySR, BCMA, GITR, RELT.

In one embodiment of the invention the first antigen-binding region binds to CAMPATH-1. In one embodiment of the invention the second antigen-binding region binds to CAMPATH-1.

In one embodiment of the invention the first antigen-binding region binds to CD20. In one embodiment of the invention the second antigen-binding region binds to CD20.

In one embodiment of the invention the first antigen-binding region binds to CD37. In one embodiment of the invention the second antigen-binding region binds to CD37.

In one embodiment of the invention the first antigen-binding region binds to CAMPATH-1 and the second antigen-binding region binds to CD20, or vice versa.

In one embodiment of the invention the first antigen-binding region binds to CD37 and the second antigen-binding region binds to CD20, or vice versa.

In a preferred embodiment of the method of the invention, said first and second antigens are co-located in cells or tissue that are target cells or target tissue for the disease or disorder to be treated. A preferred disease to be treated is cancer.

In a further preferred embodiment, a) said first and second antigens are not co-located in cells or tissue that are not target cells or target tissue for the disease or disorder to be treated, or b) said first and second antigens are co-located to a lesser extent in cells or tissue that are not target cells or target tissue for the disease or disorder to be treated than in cells or tissue that are target cells or target tissue for the disease or disorder to be treated.

In one embodiment of the method of the invention, said first and second antigens are not identical and are not both death receptors comprising an intracellular death domain. In another embodiment, neither the first antigen nor the second antigen is a death receptor.

It is contemplated that the increased efficacy will not only be obtained when the two target antigens are co-expressed on the same cell, but also in other situations where the target cells are in close proximity.

Dosages, Modes of Administration and Combination Therapies

The invention provides methods of treating a disease or disorder comprising administering polypeptides as defined herein to a subject in need thereof. In one embodiment, the subject is human. The method of the invention involves administering an effective amount of the polypeptides.

"Treatment" or "treating" refers to the administration of an effective amount of a therapeutically active polypeptide according to the present invention with the purpose of easing, ameliorating, arresting or eradicating (curing) symptoms or disease states.

An "effective amount" or "therapeutically effective amount" refers to an amount effective, at dosages and for periods of time necessary, to achieve a desired therapeutic result. A therapeutically effective amount of a polypeptide, such as an antibody, may vary according to factors such as the disease stage, age, sex, and weight of the individual, and the ability of the antibody to elicit a desired response in the individual. A therapeutically effective amount is also one in which any toxic or detrimental effects of the antibody or antibody portion are outweighed by the therapeutically beneficial effects.

Preferably, said first polypeptide and said second polypeptide are administered sequentially within a certain time interval, such as within 5 days, within 2 days, within 1 day, within 12 hours, within 6 hours, within 2 hours, within 1 hour or simultaneously. One polypeptide may be administered more frequently than the other.

Administration may be carried out by any suitable route, but will typically be parenteral, such as intravenous, intramuscular or subcutaneous.

Effective dosages and the dosage regimens for the polypeptide, e.g. an antibody, depend on the disease or condition to be treated and may be determined by the persons skilled in the art. An exemplary, non-limiting range for a therapeutically effective amount of an antibody of the present invention is about 0.1 to 100 mg/kg, such as about 0.1 to 50 mg/kg, for example about 0.1 to 20 mg/kg, such as about 0.1 to 10 mg/kg, for instance about 0.5, about 0.3, about 1, about 3, about 5, or about 8 mg/kg.

The molar ratio at which the first polypeptide and second polypeptide are administered in the method of the invention may vary depending on the target antigens to which they bind and the extent to which they are selective for the target cell population. In one embodiment of the method of the invention, said first polypeptide and said second polypeptide are administered at a 1:50 to 50:1 molar ratio, such as a 1:1 molar ratio, a 1:2 molar ratio, a 1:3 molar ratio, a 1:4 molar ratio, a 1:5 molar ratio, a 1:6 molar ratio, a 1:7 molar ratio, a 1:8 molar ratio, a 1:9 molar ratio, a 1:10 molar ratio, a 1:15 molar ratio, a 1:20 molar ratio, a 1:25 molar ratio, a 1:30 molar ratio, a 1:35 molar ratio, a 1:40 molar ratio, a 1:45 molar ratio, a 1:50 molar ratio, a 50:1 molar ratio, a 45:1 molar ratio, a 40:1 molar ratio, a 35:1 molar ratio, a 30:1 molar ratio, a 25:1 molar ratio, a 20:1 molar ratio, a 15:1 molar ratio, a 10:1 molar ratio, a 9:1 molar ratio, a 8:1 molar ratio, a 7:1 molar ratio, a 6:1 molar ratio, a 5:1 molar ratio, a 4:1 molar ratio, a 3:1 molar ratio, a 2:1 molar ratio, or an equimolar ratio.

In a preferred embodiment, said first polypeptide and said second polypeptide are administered at a 1:50 to 50:1 molar ratio, such as 1:1 molar ratio, a 1:2 molar ratio, a 1:3 molar ratio, a 1:4 molar ratio, a 1:5 molar ratio, a 1:6 molar ratio, a 1:7 molar ratio, a 1:8 molar ratio, a 1:9 molar ratio, a 1:5 molar ratio, a 1:5 molar ratio, a 1:5 molar ratio, a 1:10 molar ratio, a 1:15 molar ratio, a 1:20 molar ratio, a 1:25 molar ratio, a 1:30 molar ratio, a 1:35 molar ratio, a 1:40 molar ratio, a 1:45 molar ratio a 1:50 molar ratio, a 50:1 molar ratio, a 45:1 molar ratio, a 40:1 molar ratio, a 35:1 molar ratio, a 30:1 molar ratio a 25:1 molar ratio, a 20:1 molar ratio, a 15:1 molar ratio, a 10:1 molar ratio, a 9:1 molar ratio, a 8:1 molar ratio, a 7:1 molar ratio, a 6:1 molar ratio, a 5:1 molar ratio, a 4:1 molar ratio, a 3:1 molar ratio, a 2:1 molar ratio.

In one embodiment of the present invention the first polypeptide and the second polypeptide are administered at molar ratio of about a 1:50 to 50:1, such as a molar ratio of about 1:40 to 40:1, such as a molar ratio of about 1:30 to 30:1, such as a molar ratio of about 1:20 to 20:1, such as a molar ratio of about 1:10 to 10:1, such as a molar ratio of about 1:9 to 9:1, such as a molar ratio of about 1:5 to 5:1.

Polypeptides or antibodies of the present invention may also be administered in combination therapy, i.e., combined with other therapeutic agents relevant for the disease or condition to be treated. Accordingly, in one embodiment, the antibody-containing medicament is for combination with one or more further therapeutic agents, such as cytotoxic, chemotherapeutic or anti-angiogenic agents. Such combined administration may be simultaneous, separate or sequential.

In a further embodiment, the present invention provides a method for treating or preventing disease, such as cancer, which method comprises administration to a subject in need thereof of a therapeutically effective amount of a variant or pharmaceutical composition of the present invention, in combination with radiotherapy and/or surgery.

In one embodiment of the invention the method according to any aspect or embodiment disclosed herein relates to further administering an additional therapeutic agent. In one embodiment of the invention the additional therapeutic agent is one or more anti-cancer agent(s) selected from the group consisting of chemotherapeutics (including but not limited to paclitaxel, temozolomide, cisplatin, carboplatin, oxaliplatin, irinotecan, doxorubicin, gemcitabine, 5-fluorouracil, pemetrexed), kinase inhibitors (including but not limited to sorafenib, sunitinib or everolimus), apoptosis-modulating agents (including but not limited to recombinant human TRAIL or birinapant), RAS inhibitors, proteasome inhibitors (including but not limited to bortezomib), histon deacetylase inhibitors (including but not limited to vorinostat), nutraceuticals, cytokines (including but not limited to IFN-γ), antibodies or antibody mimetics (including but not limited to anti-EGFR, anti-IGF-1R, anti-VEGF, anti-CD20, anti-CD38, anti-HER2, anti-PD-1, anti-PD-L1, anti-CTLA4, anti-CD40, anti-CD137, anti-GITR antibodies and antibody mimetics), antibody-drug conjugates.

Polypeptides

As explained above, in a further aspect, the invention relates to polypeptides that can be used in the method of the invention, in combination with a suitable "counterpart" polypeptide, so that the combination favors hetero-oligomerization over homo-oligomerization.

Accordingly, the invention also relates to a polypeptide comprising a Fc region of a human IgG and an antigen-binding region capable of binding to an antigen, wherein said polypeptide comprises a) a I253G, I253K or I253R mutation of an amino acid position corresponding to I253 in human IgG1,
   or
   a H310R or H310D or mutation of an amino acid position corresponding to H310 in human IgG1,
and/or
b) a Y436N, Y436K, Y436Q or Y436R mutation of an amino acid position corresponding to Y436 in human IgG1,
   or
   a Q438R, Q438K, Q438H, Q438G or Q438N mutation of an amino acid position corresponding to Q438 in human IgG1, and/or c) a K439F, K439I, K439Y, K439T, K439V, K439W mutation of an amino acid position corresponding to K439 in human IgG1, or an S440K mutation of an amino acid position corresponding to S440 in human IgG1, wherein the amino acid positions correspond to human IgG1 according to EU numbering, with the proviso that if the polypeptide comprises said S440K mutation, then at least one of the other mutations specified in options a) and b) is also present In one embodiment, said polypeptide comprises a) a I253G, I253K or I253R mutation of an amino acid position corresponding to I253 in human IgG1, or a H310R or H310D or mutation of an amino acid position corresponding to H310 in human IgG1, and b) a Y436N, Y436K, Y436Q or Y436R mutation of an amino acid position corresponding to Y436 in human IgG1, or a Q438R, Q438K, Q438H, Q438G or Q438N mutation of an amino acid position corresponding to Q438 in human IgG1.

In another embodiment, said polypeptide comprises a) a I253G, I253K or I253R mutation of an amino acid position corresponding to I253 in human IgG1, or a H310R or H310D or mutation of an amino acid position corresponding to H310 in human IgG1, and c) a K439F, K439I, K439Y, K439T, K439V, K439W mutation of an amino acid position corresponding to K439 in human IgG1, or an S440K mutation of an amino acid position corresponding to S440 in human IgG1.

In another embodiment, said polypeptide comprises b) a Y436N, Y436K, Y436Q or Y436R mutation of an amino acid position corresponding to Y436 in human IgG1, or a Q438R, Q438K, Q438H, Q438G or Q438N mutation of an amino acid position corresponding to Q438 in human IgG1, and c) a K439F, K439I, K439Y, K439T, K439V, K439W mutation of an amino acid position corresponding to K439 in human IgG1, or an S440K mutation of an amino acid position corresponding to S440 in human IgG1.

In another embodiment, wherein said polypeptide comprises a) a I253G, I253K or I253R mutation of an amino acid position corresponding to I253 in human IgG1, or a H310R or H310D or mutation of an amino acid position corresponding to H310 in human IgG1, and b) a Y436N, Y436K, Y436Q or Y436R mutation of an amino acid position corresponding to Y436 in human IgG1, or a Q438R, Q438K, Q438H, Q438G or Q438N mutation of an amino acid position corresponding to Q438 in human IgG1, and c) a K439F, K439I, K439Y, K439T, K439V, K439W mutation of an amino acid position corresponding to K439 in human IgG1, or an S440K mutation of an amino acid position corresponding to S440 in human IgG1.

In another embodiment, the polypeptide does not comprise the mutations specified in option c) and said polypeptide further comprises a K439E mutation of an amino acid position corresponding to K439 in human IgG1 or a S440K mutation of an amino acid position corresponding to S440 in human IgG1.

In another embodiment, i) said polypeptide comprises an I253G mutation of an amino acid position corresponding to I253 in human IgG1 and a K439E mutation of an amino acid position corresponding to K439 in human IgG1 or a S440K mutation of an amino acid position corresponding to S440 in human IgG1, or ii) said polypeptide comprises an I253R mutation of an amino acid position corresponding to I253 in human IgG1 and a K439E mutation of an amino acid position corresponding to K439 in human IgG1 or a S440K mutation of an amino acid position corresponding to S440 in human IgG1, or iii) said polypeptide comprises an H310R mutation of an amino acid position corresponding to H310 in human IgG1 and a K439E mutation of an amino acid position corresponding to K439 in human IgG1 or a S440K mutation of an amino acid position corresponding to S440 in human IgG1, or iv) said polypeptide comprises an H310D mutation of an amino acid position corresponding to H310 in human IgG1 and a K439E mutation of an amino acid position corresponding to K439 in human IgG1 or a S440K mutation of an amino acid position corresponding to S440 in human IgG1, or v) said polypeptide comprises a Y436N mutation of an amino acid position corresponding to Y436 in human IgG1, and a K439E mutation of an amino acid position corresponding to K439 in human IgG1 or a S440K mutation of an amino acid position corresponding to S440 in human IgG1, or vi) said polypeptide comprises a Y436K mutation of an amino acid position corresponding to Y436 in human IgG1, and
    a K439E mutation of an amino acid position corre-
        sponding to K439 in human IgG1 or a S440K
        mutation of an amino acid position corresponding to
        S440 in human IgG1,
or
vii) said polypeptide comprises a Q438R mutation of an
    amino acid position corresponding to Q438 in human
    IgG1,
    and
    a K439E mutation of an amino acid position corre-
        sponding to K439 in human IgG1 or a S440K
        mutation of an amino acid position corresponding to
        S440 in human IgG1,
or
viii) said polypeptide comprises a Q438N mutation of an
    amino acid position corresponding to Q438 in human
    IgG1,
    and
    a K439E mutation of an amino acid position corre-
        sponding to K439 in human IgG1 or a S440K
        mutation of an amino acid position corresponding to
        S440 in human IgG1,
or
ix) said polypeptide comprises a Y436N mutation of an
    amino acid position corresponding to Y436 in human
    IgG1,
    and
    a I253G mutation of an amino acid position corre-
        sponding to I253 in human IgG1 or a H310R muta-
        tion of an amino acid position corresponding to
        H310 in human IgG1,
or
x) said polypeptide comprises a Y436K mutation of an
    amino acid position corresponding to Y436 in human
    IgG1,
    and
    a I253G mutation of an amino acid position corre-
        sponding to I253 in human IgG1 or a H310R muta-
        tion of an amino acid position corresponding to
        H310 in human IgG1,
or
xi) said polypeptide comprises a Q438R mutation of an
    amino acid position corresponding to Q438 in human
    IgG1,
    and
    a I253G mutation of an amino acid position corre-
        sponding to I253 in human IgG1 or a H310R muta-
        tion of an amino acid position corresponding to
        H310 in human IgG1,
or
xii) said polypeptide comprises a Q438N mutation of an
    amino acid position corresponding to Q438 in human
    IgG1,
    and
    a I253G mutation of an amino acid position corre-
        sponding to I253 in human IgG1 or a H310R muta-
        tion of an amino acid position corresponding to
        H310 in human IgG1,
or
xiii) said polypeptide comprises a Y436N mutation of an
    amino acid position corresponding to Y436 in human
    IgG1, and
    a I253R mutation of an amino acid position corre-
        sponding to I253 in human IgG1 or a H310D muta-
        tion of an amino acid position corresponding to
        H310 in human IgG1,
or
xiv) said polypeptide comprises a Y436K mutation of an
    amino acid position corresponding to Y436 in human
    IgG1,
    and
    a I253R mutation of an amino acid position corre-
        sponding to I253 in human IgG1 or a H310D muta-
        tion of an amino acid position corresponding to
        H310 in human IgG1,
or
xv) said polypeptide comprises a Q438R mutation of an
    amino acid position corresponding to Q438 in human
    IgG1,
    and
    a I253R mutation of an amino acid position corre-
        sponding to I253 in human IgG1 or a H310D muta-
        tion of an amino acid position corresponding to
        H310 in human IgG1,
or
xvi) said polypeptide comprises a Q438N mutation of an
    amino acid position corresponding to Q438 in human
    IgG1,
    and
    a I253R mutation of an amino acid position corre-
        sponding to I253 in human IgG1 or a H310D muta-
        tion of an amino acid position corresponding to
        H310 in human IgG1.
    In a further embodiment, said polypeptide further com-
prises a mutation of an amino acid position corresponding to
E430, E345, S440, T437 or K248 in human IgG1, with the
proviso that if said polypeptide comprises a K439E, K439D,
S440K, S440R or S440H mutation, said further mutation in
said polypeptide is not at position S440.
    In another embodiment, said polypeptide comprises one
or more mutations selected from the group consisting of:
E430G, E345K, E430S, E430F, E430T, E345Q, E345R,
E345Y, S440W and S440Y and/or said polypeptide com-
prises a T437R and a K248E mutation.
    In another embodiment, said polypeptide comprises one
or both mutations selected from the group consisting of:
E430G and E345K.
    In another embodiment, said polypeptide comprises an
E430G mutation.
    In another embodiment, said polypeptide has been further
modified so that the polypeptide has an altered ability to
induce effector functions, such as Fc-mediated effector func-
tions, compared to a polypeptide which is identical except
for said further modification.
    In one such embodiment, said polypeptide has been
further modified so that the polypeptide has an altered ability
to induce antibody-dependent cell-mediated cytotoxicity
(ADCC) compared to a polypeptide which is identical
except for said further modification. An example of an
amino acid mutation which alters the ability of a polypeptide
or antibody to induce ADCC is G237A. A G237A mutation
will decrease a polypeptides ability to bind to Fc gamma
receptors and thereby decrease the polypeptides ability to
induce ADCC. A polypeptide with a decrease ability to
induce ADCC may be of particular interest when enhanced
control of the effector functions induced by the polypeptide
is of interest e.g. when the target to which the antibody binds
is ubiquitously expressed. Thus, in one embodiment of the present invention said polypeptide has been modified by introducing a further G237A mutation.

In one embodiment said polypeptide comprises a G237A mutation.

In another such embodiment, said polypeptide has been further modified so that the polypeptide has an altered ability to induce complement-dependent cytotoxicity (CDC) compared to a polypeptide which is identical except for said modification.

An example of an amino acid mutations which alters the ability of a polypeptide or antibody to induce CDC are E430G, E345K, E430S, E430F, E430T, E345Q, E345R, E345Y, S440W, S440Y T437R, K248E, E333S and K326W. A polypeptide with an increased ability to induce CDC may be of particular interest when eradicating or depleting a specific cell type or tissue is of interest. Thus, in one embodiment of the present invention said polypeptide has been modified by introducing one or more amino acid mutations from the group consisting of E430G, E345K, E430S, E430F, E430T, E345Q, E345R, E345Y, S440W, S440Y T437R, K248E, E333S and K326W.

In one embodiment said polypeptide comprises an E333S and/or K326W mutation.

In one embodiment said polypeptide comprises an E333S.

In one embodiment said polypeptide comprises an E333S and K326W mutation.

In one embodiment, the polypeptide is an antibody, such as a full-length antibody. In one embodiment, said polypeptide is an IgG1 antibody. In one embodiment, said antibody is human, humanized or chimeric. In one embodiment, said antibody is bispecific.

In one embodiment of the polypeptide of the invention, said antigen is a cell surface-exposed molecule. In one embodiment, said antigen is not a death receptor.

The invention further relates to a pharmaceutical composition comprising a polypeptide of the invention as defined herein and a pharmaceutically-acceptable carrier.

Further Aspects and Embodiments of the Invention

As described above, in a further aspect, the invention relates to a first polypeptide, comprising a first Fc region of a human IgG and a first antigen-binding region capable of binding to a first antigen, for use as a medicament in combination with a second polypeptide, comprising a second Fc region of a human IgG and a second antigen-binding region capable of binding to a second antigen, wherein a) said first polypeptide comprises an I253G mutation of an amino acid position corresponding to I253 in human IgG1 and said second polypeptide comprises an H310R mutation of an amino acid position corresponding to H310 in human IgG1, or vice versa,
    or
    said first polypeptide comprises an I253K or I253R mutation of an amino acid position corresponding to I253 in human IgG1 and said second polypeptide comprises an H310D mutation of an amino acid position corresponding to H310 in human IgG1, or vice versa,
  and/or
  b) said first polypeptide comprises a Y436N, Y436K, Y436Q or Y436R mutation of an amino acid position corresponding to Y436 in human IgG1 and said second polypeptide comprises a Q438R, Q438K, Q438H, Q438G or Q438N mutation of an amino acid position corresponding to Q438 in human IgG1, or vice versa,
    or
    said first polypeptide comprises a Y436N or Y436Q mutation of an amino acid position corresponding to Y436 in human IgG1 and said second polypeptide comprises a Y436K or Y436R mutation of an amino acid position corresponding to Y436 in human IgG1, or vice versa,
    or
    said first polypeptide comprises a Q438R, Q438K or Q438H mutation of an amino acid position corresponding to Q438 in human IgG1 and said second polypeptide comprises a Q438N or Q438G mutation of an amino acid position corresponding to Q438 in human IgG1, or vice versa,
  and/or
  c) said first polypeptide comprises a K439F, K439I, K439Y, K439T, K439V, K439W mutation of an amino acid position corresponding to K439 in human IgG1 and said second polypeptide comprises an S440K mutation of an amino acid position corresponding to S440 in human IgG1, or vice versa,
wherein the amino acid positions correspond to human IgG1 according to EU numbering.

In one embodiment,
  a) said first polypeptide comprises an I253G mutation of an amino acid position corresponding to I253 in human IgG1 and said second polypeptide comprises an H310R mutation of an amino acid position corresponding to H310 in human IgG1, or vice versa,
    or
    said first polypeptide comprises an I253K or I253R mutation of an amino acid position corresponding to I253 in human IgG1 and said second polypeptide comprises an H310D mutation of an amino acid position corresponding to H310 in human IgG1, or vice versa,
  and/or
  b) said first polypeptide comprises a Y436N mutation of an amino acid position corresponding to Y436 in human IgG1 and said second polypeptide comprises a Q438R mutation of an amino acid position corresponding to Q438 in human IgG1, or vice versa,
    or
    said first polypeptide comprises a Y436N mutation of an amino acid position corresponding to Y436 in human IgG1 and said second polypeptide comprises a Y436K mutation of an amino acid position corresponding to Y436 in human IgG1, or vice versa,
    or
    said first polypeptide comprises a Q438R mutation of an amino acid position corresponding to Q438 in human IgG1 and said second polypeptide comprises a Q438N mutation of an amino acid position corresponding to Q438 in human IgG1, or vice versa,
  and/or
  c) said first polypeptide comprises a K439F, K439I, K439Y, K439T, K439V, K439W mutation of an amino acid position corresponding to K439 in human IgG1 and said second polypeptide comprises an S440K mutation of an amino acid position corresponding to S440 in human IgG1, or vice versa.

In another embodiment,
  a) said first polypeptide comprises an I253G mutation of an amino acid position corresponding to I253 in human IgG1 and said second polypeptide comprises an H310R mutation of an amino acid position corresponding to H310 in human IgG1, or vice versa, or said first polypeptide comprises an I253K or I253R mutation of an amino acid position corresponding to I253 in human IgG1 and said second polypeptide comprises an H310D mutation of an amino acid position corresponding to H310 in human IgG1, or vice versa, and b) said first polypeptide comprises a Y436N, Y436K, Y436Q or Y436R mutation of an amino acid position corresponding to Y436 in human IgG1 and said second polypeptide comprises a Q438R, Q438K, Q438H, Q438G or Q438N mutation of an amino acid position corresponding to Q438 in human IgG1, or vice versa, wherein preferably said first polypeptide comprises a Y436N mutation of an amino acid position corresponding to Y436 in human IgG1 and said second polypeptide comprises a Q438R mutation of an amino acid position corresponding to Q438 in human IgG1, or vice versa, or said first polypeptide comprises a Y436N or Y436Q mutation of an amino acid position corresponding to Y436 in human IgG1 and said second polypeptide comprises a Y436K or Y436R mutation of an amino acid position corresponding to Y436 in human IgG1, or vice versa, wherein preferably said first polypeptide comprises a Y436N mutation of an amino acid position corresponding to Y436 in human IgG1 and said second polypeptide comprises a Y436K mutation of an amino acid position corresponding to Y436 in human IgG1, or vice versa, or said first polypeptide comprises a Q438R, Q438K or Q438H mutation of an amino acid position corresponding to Q438 in human IgG1 and said second polypeptide comprises a Q438N or Q438G mutation of an amino acid position corresponding to Q438 in human IgG1, or vice versa, wherein preferably said first polypeptide comprises a Q438R mutation of an amino acid position corresponding to Q438 in human IgG1 and said second polypeptide comprises a Q438N mutation of an amino acid position corresponding to Q438 in human IgG1, or vice versa.

In another embodiment, a) said first polypeptide comprises an I253G mutation of an amino acid position corresponding to I253 in human IgG1 and said second polypeptide comprises an H310R mutation of an amino acid position corresponding to H310 in human IgG1, or vice versa, or said first polypeptide comprises an I253K or I253R mutation of an amino acid position corresponding to I253 in human IgG1 and said second polypeptide comprises an H310D mutation of an amino acid position corresponding to H310 in human IgG1, or vice versa, and c) said first polypeptide comprises a K439F, K439I, K439Y, K439T, K439V, K439W mutation of an amino acid position corresponding to K439 in human IgG1 and said second polypeptide comprises an S440K mutation of an amino acid position corresponding to S440 in human IgG1, or vice versa.

In another embodiment, b) said first polypeptide comprises a Y436N, Y436K, Y436Q or Y436R mutation of an amino acid position corresponding to Y436 in human IgG1 and said second polypeptide comprises a Q438R, Q438K, Q438H, Q438G or Q438N mutation of an amino acid position corresponding to Q438 in human IgG1, or vice versa, wherein preferably said first polypeptide comprises a Y436N mutation of an amino acid position corresponding to Y436 in human IgG1 and said second polypeptide comprises a Q438R mutation of an amino acid position corresponding to Q438 in human IgG1, or vice versa, or said first polypeptide comprises a Y436N or Y436Q mutation of an amino acid position corresponding to Y436 in human IgG1 and said second polypeptide comprises a Y436K or Y436R mutation of an amino acid position corresponding to Y436 in human IgG1, or vice versa, wherein preferably said first polypeptide comprises a Y436N mutation of an amino acid position corresponding to Y436 in human IgG1 and said second polypeptide comprises a Y436K mutation of an amino acid position corresponding to Y436 in human IgG1, or vice versa, or said first polypeptide comprises a Q438R, Q438K or Q438H mutation of an amino acid position corresponding to Q438 in human IgG1 and said second polypeptide comprises a Q438N or Q438G mutation of an amino acid position corresponding to Q438 in human IgG1, or vice versa, wherein preferably said first polypeptide comprises a Q438R mutation of an amino acid position corresponding to Q438 in human IgG1 and said second polypeptide comprises a Q438N mutation of an amino acid position corresponding to Q438 in human IgG1, or vice versa and c) said first polypeptide comprises a K439F, K439I, K439Y, K439T, K439V, K439W mutation of an amino acid position corresponding to K439 in human IgG1 and said second polypeptide comprises an S440K mutation of an amino acid position corresponding to S440 in human IgG1, or vice versa.

In another embodiment, a) said first polypeptide comprises an I253G mutation of an amino acid position corresponding to I253 in human IgG1 and said second polypeptide comprises an H310R mutation of an amino acid position corresponding to H310 in human IgG1, or vice versa, or said first polypeptide comprises an I253K or I253R mutation of an amino acid position corresponding to I253 in human IgG1 and said second polypeptide comprises an H310D mutation of an amino acid position corresponding to H310 in human IgG1, or vice versa, and b) said first polypeptide comprises a Y436N, Y436K, Y436Q or Y436R mutation of an amino acid position corresponding to Y436 in human IgG1 and said second polypeptide comprises a Q438R, Q438K, Q438H, Q438G or Q438N mutation of an amino acid position corresponding to Q438 in human IgG1, or vice versa, wherein preferably said first polypeptide comprises a Y436N mutation of an amino acid position corresponding to Y436 in human IgG1 and said second polypeptide comprises a Q438R mutation of an amino acid position corresponding to Q438 in human IgG1, or vice versa, or said first polypeptide comprises a Y436N or Y436Q mutation of an amino acid position corresponding to Y436 in human IgG1 and said second polypeptide comprises a Y436K or Y436R mutation of an amino acid position corresponding to Y436 in human IgG1, or vice versa, wherein preferably said first polypeptide comprises a Y436N mutation of an amino acid position corresponding to Y436 in human IgG1 and said second polypeptide comprises a Y436K mutation of an amino acid position corresponding to Y436 in human IgG1, or vice versa, or said first polypeptide comprises a Q438R, Q438K or Q438H mutation of an amino acid position corresponding to Q438 in human IgG1 and said second polypeptide comprises a Q438N or Q438G mutation of an amino acid position corresponding to Q438 in human IgG1, or vice versa, wherein preferably said first polypeptide comprises a Q438R mutation of an amino acid position corresponding to Q438 in human IgG1 and said second polypeptide comprises a Q438N mutation of an amino acid position corresponding to Q438 in human IgG1, or vice versa, and c) said first polypeptide comprises a K439F, K439I, K439Y, K439T, K439V, K439W mutation of an amino acid position corresponding to K439 in human IgG1 and said second polypeptide comprises an S440K mutation of an amino acid position corresponding to S440 in human IgG1, or vice versa.

In a further embodiment, the first and second polypeptides do not comprise the mutations specified in option c) and said first polypeptide further comprises a K439E mutation of an amino acid position corresponding to K439 in human IgG1 and said second polypeptide further comprises an S440K mutation of an amino acid position corresponding to S440 in human IgG1, or vice versa.

In a further embodiment, i) said first polypeptide comprises an I253G mutation of an amino acid position corresponding to I253 in human IgG1 and said second polypeptide comprises an H310R mutation of an amino acid position corresponding to H310 in human IgG1, or vice versa, or ii) said first polypeptide comprises an I253R mutation of an amino acid position corresponding to I253 in human IgG1 and said second polypeptide comprises an H310D mutation of an amino acid position corresponding to H310 in human IgG1, or vice versa, or iii) said first polypeptide comprises an I253G mutation of an amino acid position corresponding to I253 in human IgG1 and said second polypeptide comprises an H310R mutation of an amino acid position corresponding to H310 in human IgG1, or vice versa, and said first polypeptide comprises a K439E mutation of an amino acid position corresponding to K439 in human IgG1 and said second polypeptide comprises an S440K mutation of an amino acid position corresponding to S440 in human IgG1, or vice versa, or iv) said first polypeptide comprises an I253R mutation of an amino acid position corresponding to I253 in human IgG1 and said second polypeptide comprises an H310D mutation of an amino acid position corresponding to H310 in human IgG1, or vice versa, and said first polypeptide comprises a K439E mutation of an amino acid position corresponding to K439 in human IgG1 and said second polypeptide comprises an S440K mutation of an amino acid position corresponding to S440 in human IgG1, or vice versa, or v) said first polypeptide comprises a Y436N mutation of an amino acid position corresponding to Y436 in human IgG1 and said second polypeptide comprises a Q438R mutation of an amino acid position corresponding to Q438 in human IgG1, or vice versa, or vi) said first polypeptide comprises a Y436N mutation of an amino acid position corresponding to Y436 in human IgG1 and said second polypeptide comprises a Y436K mutation of an amino acid position corresponding to Y436 in human IgG1, or vice versa, or vii) said first polypeptide comprises a Q438R mutation of an amino acid position corresponding to Q438 in human IgG1 and said second polypeptide comprises a Q438N mutation of an amino acid position corresponding to Q438 in human IgG1, or vice versa, or viii) said first polypeptide comprises a Y436N mutation of an amino acid position corresponding to Y436 in human IgG1 and said second polypeptide comprises a Q438R mutation of an amino acid position corresponding to Q438 in human IgG1, or vice versa, and said first polypeptide comprises an I253G mutation of an amino acid position corresponding to I253 in human IgG1 and said second polypeptide comprises an H310R mutation of an amino acid position corresponding to H310 in human IgG1, or vice versa, or ix) said first polypeptide comprises a Y436N mutation of an amino acid position corresponding to Y436 in human IgG1 and said second polypeptide comprises a Q438R mutation of an amino acid position corresponding to Q438 in human IgG1, or vice versa, said first polypeptide comprises an I253R mutation of an amino acid position corresponding to I253 in human IgG1 and said second polypeptide comprises an H310D mutation of an amino acid position corresponding to H310 in human IgG1, or vice versa, or x) said first polypeptide comprises a Y436N mutation of an amino acid position corresponding to Y436 in human IgG1 and said second polypeptide comprises a Q438R mutation of an amino acid position corresponding to Q438 in human IgG1, or vice versa, and said first polypeptide comprises an I253G mutation of an amino acid position corresponding to I253 in human IgG1 and said second polypeptide comprises an H310R mutation of an amino acid position corresponding to H310 in human IgG1, or vice versa, and said first polypeptide comprises a K439E mutation of an amino acid position corresponding to K439 in human IgG1 and said second polypeptide comprises an S440K mutation of an amino acid position corresponding to S440 in human IgG1, or vice versa, or xi) said first polypeptide comprises a Y436N mutation of an amino acid position corresponding to Y436 in human IgG1 and said second polypeptide comprises a Q438R mutation of an amino acid position corresponding to Q438 in human IgG1, or vice versa, and said first polypeptide comprises an I253R mutation of an amino acid position corresponding to I253 in human IgG1 and said second polypeptide comprises an H310D mutation of an amino acid position corresponding to H310 in human IgG1, or vice versa, and said first polypeptide comprises a K439E mutation of an amino acid position corresponding to K439 in human IgG1 and said second polypeptide comprises an S440K mutation of an amino acid position corresponding to S440 in human IgG1, or vice versa, or xii) said first polypeptide comprises a Y436N mutation of an amino acid position corresponding to Y436 in human IgG1 and said second polypeptide comprises a Y436K mutation of an amino acid position corresponding to Y436 in human IgG1, or vice versa, said first polypeptide comprises an I253G mutation of an amino acid position corresponding to I253 in human IgG1 and said second polypeptide comprises an H310R mutation of an amino acid position corresponding to H310 in human IgG1, or vice versa, or xiii) said first polypeptide comprises a Y436N mutation of an amino acid position corresponding to Y436 in human IgG1 and said second polypeptide comprises a Y436K mutation of an amino acid position corresponding to Y436 in human IgG1, or vice versa, said first polypeptide comprises an I253R mutation of an amino acid position corresponding to I253 in human IgG1 and said second polypeptide comprises an H310D mutation of an amino acid position corresponding to H310 in human IgG1, or vice versa, or xiv) said first polypeptide comprises a Y436N mutation of an amino acid position corresponding to Y436 in human IgG1 and said second polypeptide comprises a Y436K mutation of an amino acid position corresponding to Y436 in human IgG1, or vice versa, said first polypeptide comprises an I253G mutation of an amino acid position corresponding to I253 in human IgG1 and said second polypeptide comprises an H310R mutation of an amino acid position corresponding to H310 in human IgG1, or vice versa, and said first polypeptide comprises a K439E mutation of an amino acid position corresponding to K439 in human IgG1 and said second polypeptide comprises an S440K mutation of an amino acid position corresponding to S440 in human IgG1, or vice versa, or xv) said first polypeptide comprises a Y436N mutation of an amino acid position corresponding to Y436 in human IgG1 and said second polypeptide comprises a Y436K mutation of an amino acid position corresponding to Y436 in human IgG1, or vice versa, said first polypeptide comprises an I253R mutation of an amino acid position corresponding to I253 in human IgG1 and said second polypeptide comprises an H310D mutation of an amino acid position corresponding to H310 in human IgG1, or vice versa, and said first polypeptide comprises a K439E mutation of an amino acid position corresponding to K439 in human IgG1 and said second polypeptide comprises an S440K mutation of an amino acid position corresponding to S440 in human IgG1, or vice versa, or xvi) said first polypeptide comprises a Q438R mutation of an amino acid position corresponding to Q438 in human IgG1 and said second polypeptide comprises a Q438N mutation of an amino acid position corresponding to Q438 in human IgG1, or vice versa, said first polypeptide comprises an I253G mutation of an amino acid position corresponding to I253 in human IgG1 and said second polypeptide comprises an H310R mutation of an amino acid position corresponding to H310 in human IgG1, or vice versa, or xvii) said first polypeptide comprises a Q438R mutation of an amino acid position corresponding to Q438 in human IgG1 and said second polypeptide comprises a Q438N mutation of an amino acid position corresponding to Q438 in human IgG1, or vice versa, said first polypeptide comprises an I253R mutation of an amino acid position corresponding to I253 in human IgG1 and said second polypeptide comprises an H310D mutation of an amino acid position corresponding to H310 in human IgG1, or vice versa, or xviii) said first polypeptide comprises a Q438R mutation of an amino acid position corresponding to Q438 in human IgG1 and said second polypeptide comprises a Q438N mutation of an amino acid position corresponding to Q438 in human IgG1, or vice versa, said first polypeptide comprises an I253G mutation of an amino acid position corresponding to I253 in human IgG1 and said second polypeptide comprises an H310R mutation of an amino acid position corresponding to H310 in human IgG1, or vice versa, and said first polypeptide comprises a K439E mutation of an amino acid position corresponding to K439 in human IgG1 and said second polypeptide comprises an S440K mutation of an amino acid position corresponding to S440 in human IgG1, or vice versa, or xix) said first polypeptide comprises a Q438R mutation of an amino acid position corresponding to Q438 in human IgG1 and said second polypeptide comprises a Q438N mutation of an amino acid position corresponding to Q438 in human IgG1, or vice versa, said first polypeptide comprises an I253R mutation of an amino acid position corresponding to I253 in human IgG1 and said second polypeptide comprises an H310D mutation of an amino acid position corresponding to H310 in human IgG1, or vice versa, and said first polypeptide comprises a K439E mutation of an amino acid position corresponding to K439 in human IgG1 and said second polypeptide comprises an S440K mutation of an amino acid position corresponding to S440 in human IgG1, or vice versa, or xx) said first polypeptide comprises a Y436N mutation of an amino acid position corresponding to Y436 in human IgG1 and said second polypeptide comprises a Q438R mutation of an amino acid position corresponding to Q438 in human IgG1, or vice versa, and said first polypeptide comprises a K439E mutation of an amino acid position corresponding to K439 in human IgG1 and said second polypeptide comprises an S440K mutation of an amino acid position corresponding to S440 in human IgG1, or vice versa, or xxi) said first polypeptide comprises a Y436N mutation of an amino acid position corresponding to Y436 in human IgG1 and said second polypeptide comprises a Y436K mutation of an amino acid position corresponding to Y436 in human IgG1, or vice versa, and said first polypeptide comprises a K439E mutation of an amino acid position corresponding to K439 in human IgG1 and said second polypeptide comprises an S440K mutation of an amino acid position corresponding to S440 in human IgG1, or vice versa, or xxii) said first polypeptide comprises a Q438R mutation of an amino acid position corresponding to Q438 in human IgG1 and said second polypeptide comprises a Q438N mutation of an amino acid position corresponding to Q438 in human IgG1, or vice versa, and said first polypeptide comprises a K439E mutation of an amino acid position corresponding to K439 in human IgG1 and said second polypeptide comprises an S440K mutation of an amino acid position corresponding to S440 in human IgG1, or vice versa.

In a further embodiment, said first polypeptide further comprises a mutation of an amino acid position corresponding to E430, E345, S440, T437 or K248 in human IgG1, and/or said second polypeptide further comprises a mutation of an amino acid position corresponding to E430, E345, S440, T437 or K248 in human IgG1, or vice versa, with the proviso that if said first or second polypeptide comprises a K439E, K439D, S440K, S440R or S440H mutation, said further mutation in said polypeptide is not at position S440.

In a further embodiment hereof, said first polypeptide comprises one or more mutations selected from the group consisting of: E430G, E345K, E430S, E430F, E430T, E345Q, E345R, E345Y, S440W and S440Y, and/or said second polypeptide comprises one or more mutations selected from the group consisting of: E430G, E345K, E430S, E430F, E430T, E345Q, E345R, E345Y, S440W and S440Y, and/or said first polypeptide comprises a T437R and a K248E mutation, and/or said second polypeptide comprises a T437R and a K248E mutation.

In an even further embodiment hereof, said first polypeptide comprises one or both mutations selected from the group consisting of: E430G and E345K, and/or said polypeptide comprises one or both mutations selected from the group consisting of: E430G and E345K.

In a yet even further embodiment hereof, said first polypeptide comprises E430G and said second polypeptide comprises E430G.

In another embodiment, said first polypeptide and/or said second polypeptide has been further modified so that the polypeptide has an altered ability to induce effector functions, such as Fc-mediated effector functions, compared to a polypeptide which is identical except for said further modification.

In one embodiment, said first polypeptide and/or said second polypeptide has been further modified so that the polypeptide has an altered ability to induce antibody-dependent cell-mediated cytotoxicity compared to a polypeptide which is identical except for said further modification.

In another embodiment, said first polypeptide and/or said second polypeptide has been further modified so that the polypeptide has an altered ability to induce complement-dependent cytotoxicity compared to a polypeptide which is identical except for said modification.

In one embodiment, said first polypeptide is an antibody, such as a full-length antibody and/or said second polypeptide is an antibody, such as a full-length antibody.

In one embodiment, said first polypeptide is an IgG1 antibody and/or said second polypeptide is an IgG1 antibody.

In one embodiment, said first antibody is human, humanized or chimeric and/or said second antibody is human, humanized or chimeric.

In one embodiment, said first antibody is bispecific and/or said second polypeptide is bispecific.

In one embodiment, said first and second antigens are both cell surface-exposed molecules.

In one embodiment, said first and second antigens are co-located in cells or tissues that are target cells or target tissue for the disease or disorder to be treated.

In a further embodiment, a) said first and second antigens are not co-located in cells or tissue that are not target cells or target tissue for the disease or disorder to be treated, or b) said first and second antigens are co-located to a lesser extent in cells or tissue that are not target cells or target tissue for the disease or disorder to be treated than in cells or tissue that are target cells or target tissue for the disease or disorder to be treated.

In one embodiment, said first and second antigens are not identical and are not both death receptors comprising an intracellular death domain. In a further embodiment, neither the first antigen nor the second antigen is a death receptor.

In one embodiment, said first polypeptide and said second polypeptide are administered at a 1:50 to 50:1 molar ratio, such as 1:1 molar ratio, a 1:2 molar ratio, a 1:3 molar ratio, a 1:4 molar ratio, a 1:5 molar ratio, a 1:6 molar ratio, a 1:7 molar ratio, a 1:8 molar ratio, a 1:9 molar ratio, a 1:5 molar ratio, a 1:5 molar ratio, a 1:5 molar ratio, a 1:10 molar ratio, a 1:15 molar ratio, a 1:20 molar ratio, a 1:25 molar ratio, a 1:30 molar ratio, a 1:35 molar ratio, a 1:40 molar ratio, a 1:45 molar ratio a 1:50 molar ratio, a 50:1 molar ratio, a 45:1 molar ratio, a 40:1 molar ratio, a 35:1 molar ratio, a 30:1 molar ratio a 25:1 molar ratio, a 20:1 molar ratio, a 15:1 molar ratio, a 10:1 molar ratio, a 9:1 molar ratio, a 8:1 molar ratio, a 7:1 molar ratio, a 6:1 molar ratio, a 5:1 molar ratio, a 4:1 molar ratio, a 3:1 molar ratio, a 2:1 molar ratio.

In one embodiment of the present invention said first polypeptide and said second polypeptide are administered at molar ratio of about a 1:50 to 50:1, such as a molar ratio of about 1:40 to 40:1, such as a molar ratio of about 1:30 to 30:1, such as a molar ratio of about 1:20 to 20:1, such as a molar ratio of about 1:10 to 10:1, such as a molar ratio of about 1:9 to 9:1, such as a molar ratio of about 1:5 to 5:1.

In one embodiment, said first polypeptide and said second polypeptide are administered simultaneously.

In one embodiment of the invention, said first polypeptide and said second polypeptide are administered simultaneously.

In one embodiment, the use is for the treatment of cancer.

In an even further aspect, the invention relates to the use of a first polypeptide, comprising a first Fc region of a human IgG and a first antigen-binding region capable of binding to a first antigen, in combination with a second polypeptide, comprising a second Fc region of a human IgG and a second antigen-binding region capable of binding to a second antigen, for the manufacture of a medicament for the treatment of cancer, wherein a) said first polypeptide comprises an I253G mutation of an amino acid position corresponding to I253 in human IgG1 and said second polypeptide comprises an H310R mutation of an amino acid position corresponding to H310 in human IgG1, or vice versa,
or
said first polypeptide comprises an I253K or I253R mutation of an amino acid position corresponding to I253 in human IgG1 and said second polypeptide comprises an H310D mutation of an amino acid position corresponding to H310 in human IgG1, or vice versa,
and/or
b) said first polypeptide comprises a Y436N, Y436K, Y436Q or Y436R mutation of an amino acid position corresponding to Y436 in human IgG1 and said second polypeptide comprises a Q438R, Q438K, Q438H, Q438G or Q438N mutation of an amino acid position corresponding to Q438 in human IgG1, or vice versa,
or
said first polypeptide comprises a Y436N or Y436Q mutation of an amino acid position corresponding to Y436 in human IgG1 and said second polypeptide comprises a Y436K or Y436R mutation of an amino acid position corresponding to Y436 in human IgG1, or vice versa,
or
said first polypeptide comprises a Q438R, Q438K or Q438H mutation of an amino acid position corresponding to Q438 in human IgG1 and said second polypeptide comprises a Q438N or Q438G mutation of an amino acid position corresponding to Q438 in human IgG1, or vice versa,
and/or
c) said first polypeptide comprises a K439F, K439I, K439Y, K439T, K439V, K439W mutation of an amino acid position corresponding to K439 in human IgG1 and said second polypeptide comprises an S440K mutation of an amino acid position corresponding to S440 in human IgG1, or vice versa,
wherein the amino acid positions correspond to human IgG1 according to EU numbering.

Compositions

As described above, in some embodiments of the method of the invention, the first and second polypeptides are administered separately. In other embodiments, however, the polypeptides may be formulated together in one pharmaceutical composition.

In a main aspect, the invention relates to a composition comprising a first polypeptide and a second polypeptide as defined herein.

Accordingly, the invention relates to a composition comprising a first polypeptide comprising a first Fc region of a human IgG and a first antigen-binding region capable of binding to a first antigen, in combination with a second polypeptide comprising a second Fc region of a human IgG and a second antigen-binding region capable of binding to a second antigen, wherein d) said first polypeptide comprises an I253G mutation of an amino acid position corresponding to I253 in human IgG1 and said second polypeptide comprises an H310R mutation of an amino acid position corresponding to H310 in human IgG1, or vice versa,
or
said first polypeptide comprises an I253K or I253R mutation of an amino acid position corresponding to I253 in human IgG1 and said second polypeptide comprises an H310D mutation of an amino acid position corresponding to H310 in human IgG1, or vice versa,
and/or
e) said first polypeptide comprises a Y436N, Y436K, Y436Q or Y436R mutation of an amino acid position corresponding to Y436 in human IgG1 and said second polypeptide comprises a Q438R, Q438K, Q438H, Q438G or Q438N mutation of an amino acid position corresponding to Q438 in human IgG1, or vice versa,
or
said first polypeptide comprises a Y436N or Y436Q mutation of an amino acid position corresponding to Y436 in human IgG1 and said second polypeptide comprises a Y436K or Y436R mutation of an amino acid position corresponding to Y436 in human IgG1, or vice versa,
or
said first polypeptide comprises a Q438R, Q438K or Q438H mutation of an amino acid position corresponding to Q438 in human IgG1 and said second polypeptide comprises a Q438N or Q438G mutation of an amino acid position corresponding to Q438 in human IgG1, or vice versa,
and/or
f) said first polypeptide comprises a K439F, K439I, K439Y, K439T, K439V, K439W mutation of an amino acid position corresponding to K439 in human IgG1 and said second polypeptide comprises an S440K mutation of an amino acid position corresponding to S440 in human IgG1, or vice versa,
wherein the amino acid positions correspond to human IgG1 according to EU numbering.

In one embodiment of the invention, said first polypeptide comprises a Y436N, Y436K, Y436Q or Y436R mutation of an amino acid position corresponding to Y436 in human IgG1 and said second polypeptide comprises a Q438R, Q438K, Q438H, Q438G or Q438N mutation of an amino acid position corresponding to Q438 in human IgG1, or vice versa,
or
said first polypeptide comprises a Y436N or Y436Q mutation of an amino acid position corresponding to Y436 in human IgG1 and said second polypeptide comprises a Y436K or Y436R mutation of an amino acid position corresponding to Y436 in human IgG1, or vice versa,
or
said first polypeptide comprises a Q438R, Q438K or Q438H mutation of an amino acid position corresponding to Q438 in human IgG1 and said second polypeptide comprises a Q438N or Q438G mutation of an amino acid position corresponding to Q438 in human IgG1, or vice versa,
wherein the amino acid positions correspond to human IgG1 according to EU numbering.

In one embodiment of the invention, said first polypeptide comprises a Y436N, Y436K, Y436Q or Y436R mutation of an amino acid position corresponding to Y436 in human IgG1 and said second polypeptide comprises a Q438R, Q438K, Q438H, Q438G or Q438N mutation of an amino acid position corresponding to Q438 in human IgG1, or vice versa,
wherein the amino acid positions correspond to human IgG1 according to EU numbering.

In one embodiment of the invention, said first polypeptide comprises a Y436N or Y436K, mutation of an amino acid position corresponding to Y436 in human IgG1 and said second polypeptide comprises a Q438R or Q438N mutation of an amino acid position corresponding to Q438 in human IgG1, or vice versa, or said first polypeptide comprises a Q438R mutation of an amino acid position corresponding to Q438 in human IgG1 and said second polypeptide comprises a Q438N mutation of an amino acid position corresponding to Q438 in human IgG1, or vice versa, wherein the amino acid positions correspond to human IgG1 according to EU numbering.

In one embodiment of the invention, said first polypeptide comprises a Y436N or Y436K mutation of an amino acid position corresponding to Q436 in human IgG1 and said second polypeptide comprises a Q438N or Q438R mutation of an amino acid position corresponding to Q438 in human IgG1, or vice versa.

In one embodiment of the invention, said first polypeptide comprises a Y436N mutation of an amino acid position corresponding to Q436 in human IgG1 and said second polypeptide comprises a Q438R mutation of an amino acid position corresponding to Q438 in human IgG1, or vice versa.

Thus, in a further main aspect, the invention relates to a pharmaceutical composition comprising a first polypeptide and a second polypeptide as defined herein and a pharmaceutically-acceptable carrier.

In one embodiment, said first polypeptide and said second polypeptide are present in the composition at a 1:50 to 50:1 molar ratio, such as a 1:1 molar ratio, a 1:2 molar ratio, a 1:3 molar ratio, a 1:4 molar ratio, a 1:5 molar ratio, a 1:6 molar ratio, a 1:7 molar ratio, a 1:8 molar ratio, a 1:9 molar ratio, a 1:10 molar ratio, a 1:15 molar ratio, a 1:20 molar ratio, a 1:25 molar ratio, a 1:30 molar ratio, a 1:35 molar ratio, a 1:40 molar ratio, a 1:45 molar ratio, a 1:50 molar ratio, a 50:1 molar ratio, a 45:1 molar ratio, a 40:1 molar ratio, a 35:1 molar ratio, a 30:1 molar ratio, a 25:1 molar ratio, a 20:1 molar ratio, a 15:1 molar ratio, a 10:1 molar ratio, a 9:1 molar ratio, a 8:1 molar ratio, a 7:1 molar ratio, a 6:1 molar ratio, a 5:1 molar ratio, a 4:1 molar ratio, a 3:1 molar ratio, a 2:1 molar ratio, or an equimolar ratio.

In one embodiment of the present invention said first polypeptide and said second polypeptide are present in the composition at molar ratio of about a 1:50 to 50:1, such as a molar ratio of about 1:40 to 40:1, such as a molar ratio of about 1:30 to 30:1, such as a molar ratio of about 1:20 to 20:1, such as a molar ratio of about 1:10 to 10:1, such as a molar ratio of about 1:9 to 9:1, such as a molar ratio of about 1:5 to 5:1.

In one embodiment of the present invention said first polypeptide and said second polypeptide are present in the composition at molar ratio of about a 1:1.

Polypeptides for use according to the invention may be formulated with pharmaceutically acceptable carriers or diluents as well as any other known adjuvants and excipients in accordance with conventional techniques such as those disclosed in (Rowe et al., Handbook of Pharmaceutical Excipients, 2012 June, ISBN 9780857110275). The pharmaceutically acceptable carriers or diluents as well as any other known adjuvants and excipients should be suitable for the polypeptides or antibodies and the chosen mode of administration. Suitability for carriers and other components of pharmaceutical compositions is determined based on the lack of significant negative impact on the desired biological properties of the chosen compound or pharmaceutical composition of the present invention (e.g., less than a substantial impact (10% or less relative inhibition, 5% or less relative inhibition, etc.) upon antigen binding).

A pharmaceutical composition may also include diluents, fillers, salts, buffers, detergents (e.g., a nonionic detergent, such as Tween-20 or Tween-80), stabilizers (e.g., sugars or protein-free amino acids), preservatives, tissue fixatives, solubilizers, and/or other materials suitable for inclusion in a pharmaceutical composition.

In one embodiment of the present invention the pharmaceutical composition comprises polypeptides together with a pharmaceutical carrier. Pharmaceutically acceptable carriers include any and all suitable solvents, dispersion media, coatings, antibacterial and antifungal agents, isotonicity agents, antioxidants and absorption-delaying agents, and the like that are physiologically compatible with a compound of the present invention.

Examples of suitable aqueous and non-aqueous carriers which may be employed in the pharmaceutical compositions of the present invention include water, saline, phosphate-buffered saline, ethanol, dextrose, polyols (such as glycerol, propylene glycol, polyethylene glycol, and the like), and suitable mixtures thereof, vegetable oils, such as olive oil, corn oil, peanut oil, cottonseed oil, and sesame oil, carboxymethyl cellulose colloidal solutions, tragacanth gum and injectable organic esters, such as ethyl oleate, and/or various buffers. Other carriers are well known in the pharmaceutical arts.

Pharmaceutical compositions of the present invention may also comprise pharmaceutically acceptable antioxidants for instance (1) water-soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like.

Pharmaceutical compositions of the present invention may also comprise isotonicity agents, such as sugars, poly-alcohols, such as mannitol, sorbitol, glycerol or sodium chloride in the compositions.

The pharmaceutical compositions of the present invention may also contain one or more adjuvants appropriate for the chosen route of administration such as preservatives, wetting agents, emulsifying agents, dispersing agents, preservatives or buffers, which may enhance the shelf life or effectiveness of the pharmaceutical composition. The compounds of the present invention may be prepared with carriers that will protect the compound against rapid release, such as a controlled release formulation, including implants, transdermal patches, and micro-encapsulated delivery systems. Such carriers may include gelatin, glyceryl monostearate, glyceryl distearate, biodegradable, biocompatible polymers such as ethylene vinyl acetate, polyanhydrides, polyglycolic acid, collagen, poly-ortho-esters, and polylactic acid alone or with a wax, or other materials well known in the art. Methods for the preparation of such formulations are generally known to those skilled in the art.

The actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

Kit-of-Parts

The invention also relates to kit-of-parts for simultaneous, separate or sequential use in therapy comprising polypeptides or antibodies described herein.

Thus, in a further aspect, the invention relates to a kit, i.e. a kit-of-parts, comprising a first container comprising a first polypeptide of the invention as defined herein and a second container comprising a second polypeptide of the invention as defined herein.

In a further aspect, the invention relates to a device, such as a dual chamber syringe, comprising a first compartment comprising a first polypeptide according to the invention as defined herein and a second compartment comprising a second polypeptide of the invention as defined herein. In one embodiment, the device is an administration device, such as a dual chamber syringe, i.e. a syringe comprising two compartments, one compartment comprising the first polypeptide and a second compartment comprising the second polypeptide.

Conjugates

In one embodiment, the first and/or second polypeptide or antibody used in the invention is conjugated, optionally via a linker, to one or more therapeutic moieties, such as a cytotoxin, a chemotherapeutic drug, a cytokine, an immunosuppressant, and/or a radioisotope. Such conjugates are referred to herein as "immunoconjugates" or "drug conjugates". Immunoconjugates which include one or more cytotoxins are referred to as "immunotoxins".

A cytotoxin or cytotoxic agent includes any agent that is detrimental to (e.g., kills) cells. Suitable therapeutic agents for forming immunoconjugates of the present invention include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, maytansine or an analog or derivative thereof, enediyene antitumor antibiotics including neocarzinostatin, calicheamycins, esperamicins, dynemicins, lidamycin, kedarcidin or analogs or derivatives thereof, anthracyclins, mitoxantrone, mithramycin, actinomycin D, 1-dehydrotestosterone, glucocorticoids, procaine, tetracaine, lidocaine, propranolol, and puromycin, antimetabolites (such as methotrexate, 6-mercaptopurine, 6-thioguanine, cytarabine, fludarabin, 5-fluorouracil, decarbazine, hydroxyurea, asparaginase, gemcitabine, cladribine), alkylating agents (such as mechlorethamine, thioepa, chlorambucil, melphalan, carmustine (BSNU), lomustine (CCNU), cyclophosphamide, busulfan, dibromomannitol, streptozotocin, dacarbazine (DTIC), procarbazine, mitomycin C, cisplatin and other platinum derivatives, such as carboplatin; as well as duocarmycin A, duocarmycin SA, CC-1065 (a.k.a. rachelmycin), or analogs or derivatives of CC-1065), dolastatin, pyrrolo[2,1-c][1,4]benzodiazepins (PDBs) or analogues thereof, antibiotics (such as dactinomycin (formerly actinomycin), bleomycin, daunorubicin (formerly daunomycin), doxorubicin, idarubicin, mithramycin, mitomycin, mitoxantrone, plicamycin, anthramycin (AMC)), anti-mitotic agents (e.g., tubulin-inhibitors) such as monomethyl auristatin E, monomethyl auristatin F, or other analogs or derivatives of dolastatin 10; Histone deacetylase inhibitors such as the hydroxamic acids trichostatin A, vorinostat (SAHA), belinostat, LAQ824, and panobinostat as well as the benzamides, entinostat, CI994, mocetinostat and aliphatic acid compounds such as phenylbutyrate and valproic acid, proteasome inhibitors such as Danoprevir, bortezomib, amatoxins such as alpha-amantin, diphtheria toxin and related molecules (such as diphtheria A chain and active fragments thereof and hybrid molecules); ricin toxin (such as ricin A or a deglycosylated ricin A chain toxin), cholera toxin, a Shiga-like toxin (SLT-I, SLT-II, SLT-IIV), LT toxin, C3 toxin, Shiga toxin, pertussis toxin, tetanus toxin, soybean Bowman-Birk protease inhibitor, *Pseudomonas* exotoxin, alorin, saporin, modeccin, gelanin, abrin A chain, modeccin A chain, alpha-sarcin, *Aleurites fordii* proteins, dianthin proteins, *Phytolacca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, and enomycin toxins. Other suitable conjugated molecules include antimicrobial/lytic peptides such as CLIP, Magainin 2, mellitin, Cecropin, and P18; ribonuclease (RNase), DNase I, Staphylococcal enterotoxin-A, pokeweed antiviral protein, diphtherin toxin, and *Pseudomonas* endotoxin. See, for example, Pastan et al., Cell 47, 641 (1986) and Goldenberg, Calif. A Cancer Journal for Clinicians 44, 43 (1994). Therapeutic agents that may be administered in combination with an antibody of the present invention as described elsewhere herein, such as, e.g., anti-cancer cytokines or chemokines, are also candidates for therapeutic moieties useful for conjugation to an antibody of the present invention.

In one embodiment, a polypeptide used in the present invention comprises a conjugated nucleic acid or nucleic acid-associated molecule. In one such embodiment, the conjugated nucleic acid is a cytotoxic ribonuclease, an antisense nucleic acid, an inhibitory RNA molecule (e.g., a siRNA molecule) or an immunostimulatory nucleic acid (e.g., an immunostimulatory CpG motif-containing DNA molecule). In another embodiment, a polypeptide used in the present invention is conjugated to an aptamer or a ribozyme.

In one embodiment, polypeptides comprising one or more radiolabeled amino acids are provided. Non-limiting examples of labels for polypeptides include $^3$H, $^{14}$C, $^{15}$N, $^{35}$S, $^{90}$Y, $^{99}$Tc, $^{125}$I, $^{131}$I, and $^{186}$Re. Methods for preparing radiolabeled amino acids and related peptide derivatives are known in the art, (see, for instance Junghans et al., in Cancer Chemotherapy and Biotherapy 655-686 (2$^{nd}$ Ed., Chafner and Longo, eds., Lippincott Raven (1996)) and U.S. Pat. Nos. 4,681,581, 4,735,210, 5,101,827, 5,102,990 (U.S. RE35,500), U.S. Pat. Nos. 5,648,471 and 5,697,902. For example, a radioisotope may be conjugated by the chloramine-T method.

In one embodiment, a polypeptide or antibody used in the present invention is conjugated to a radioisotope or to a radioisotope-containing chelate. For example, the polypeptide can be conjugated to a chelator linker, e.g. DOTA, DTPA or tiuxetan, which allows for the polypeptide to be complexed with a radioisotope. Non-limiting examples of radioisotopes include $^3$H, $^{14}$C, $^{15}$N, $^{35}$S, $^{90}$Y, $^{99}$Tc, $^{125}$I, $^{111}$In, $^{131}$I, $^{186}$Re, $^{213}$Bs, $^{225}$Ac and $^{227}$Th.

In one embodiment, a polypeptide or antibody used in the present invention may be conjugated to a cytokine selected from the group consisting of IL-2, IL-4, IL-6, IL-7, IL-10, IL-12, IL-13, IL-15, IL-18, IL-23, IL-24, IL-27, IL-28a, IL-28b, IL-29, KGF, IFNα, IFNβ, IFNγ, GM-CSF, CD40L, Flt3 ligand, stem cell factor, ancestim, and TNFα.

Polypeptides or antibodies used in the present invention may also be chemically modified by covalent conjugation to a polymer to for instance increase their circulating half-life. Exemplary polymers, and methods to attach them to peptides, are illustrated in for instance U.S. Pat. Nos. 4,766,106, 4,179,337, 4,495,285 and 4,609,546. Additional polymers include polyoxyethylated polyols and polyethylene glycol (PEG) (e.g., a PEG with a molecular weight of between about 1,000 and about 40,000, such as between about 2,000 and about 20,000).

Conjugation to a therapeutic moiety may take place at the C-terminus of the polypeptide or at another site, typically at a site which does not interfere with oligomer formation.

Any method known in the art for conjugating the polypeptide or antibody used in the present invention to the conjugated molecule(s), such as those described above, may be employed, including the methods described by Hunter et al., Nature 144, 945 (1962), David et al., Biochemistry 13, 1014 (1974), Pain et al., J. Immunol. Meth. 40, 219 (1981) and Nygren, J. Histochem. and Cytochem. 30, 407 (1982). Such variants may be produced by chemically conjugating the other moiety to the N-terminal side or C-terminal side of the variant or fragment thereof (e.g., an antibody H or L chain) (see, e.g., Antibody Engineering Handbook, edited by Osamu Kanemitsu, published by Chijin Shokan (1994)). Such conjugated variant derivatives may also be generated by conjugation at internal residues or sugars, where appropriate.

The agents may be coupled either directly or indirectly to a polypeptide or antibody used in the present invention. One example of indirect coupling of a second agent is coupling via a spacer or linker moiety to cysteine or lysine residues in an antibody. In one embodiment, a polypeptide or antibody is conjugated to a prodrug molecule that can be activated in vivo to a therapeutic drug. In some embodiments, the linker is cleavable under intracellular conditions, such that the cleavage of the linker releases the drug unit from the antibody in the intracellular environment. In some embodiments, the linker is cleavable by a cleavable agent that is present in the intracellular environment (e.g. within a lysosome or endosome or caveola). For example, the spacers or linkers may be cleavable by tumor-cell associated enzymes or other tumor-specific conditions, by which the active drug is formed. Examples of such prodrug technologies and linkers are described in WO02083180, WO2004043493, WO2007018431, WO2007089149, WO2009017394 and WO201062171 by Syntarga B V, et al. Suitable antibody-prodrug technology and duocarmycin analogs can also be found in U.S. Pat. No. 6,989,452 (Medarex). The linker can also or alternatively be, e.g. a peptidyl linker that is cleaved by an intracellular peptidase or protease enzyme, including but not limited to, a lysosomal or endosomal protease. In some embodiments, the peptidyl linker is at least two amino acids long or at least three amino acids long. Cleaving agents can include cathepsins B and D and plasmin, all of which are known to hydrolyze dipeptide drug derivatives resulting in the release of active drug inside the target cells (see e.g. Dubowchik and Walker, 1999, Pharm. Therapeutics 83:67-123). In a specific embodiment, the peptidyl linker cleavable by an intracellular protease is a Val-Cit (valine-citrulline) linker or a Phe-Lys (phenylalanine-lysine) linker (see e.g. U.S. Pat. No.

6,214,345, which describes the synthesis of doxorubicin with the Val-Cit linker and different examples of Phe-Lys linkers). Examples of the structures of a Val-Cit and a Phe-Lys linker include but are not limited to MC-vc-PAB described below, MC-vc-GABA, MC-Phe-Lys-PAB or MC-Phe-Lys-GABA, wherein MC is an abbreviation for maleimido caproyl, vc is an abbreviation for Val-Cit, PAB is an abbreviation for p-aminobenzylcarbamate and GABA is an abbreviation for γ-aminobutyric acid.

Methods of Preparing Polypeptides of the Invention, Such as Antibodies

Polypeptides of the invention, such as antibodies, are typically produced recombinantly, i.e. by expression of nucleic acid constructs encoding the polypeptides in suitable host cells, followed by purification of the produced recombinant polypeptide from the cell culture. Nucleic acid constructs can be produced by standard molecular biological techniques well-known in the art. The constructs are typically introduced into the host cell using a vector.

Suitable nucleic acid constructs, vectors are known in the art, and described in the Examples. In most embodiments, the polypeptide comprises not only a heavy chain (or Fc-containing fragment thereof) but also a light chain. In such embodiments, the nucleotide sequences encoding the heavy and light chain portions will typically be expressed in the same cells and may be present on the same or different nucleic acids or vectors.

Host cells suitable for the recombinant expression of antibodies are well-known in the art, and include CHO, HEK-293, Expi293F, PER-C6, NS/0 and Sp2/0 cells.

In one embodiment, said host cell is a cell which is capable of Asn-linked glycosylation of proteins, e.g. a eukaryotic cell, such as a mammalian cell, e.g. a human cell. In a further embodiment, said host cell is a non-human cell which is genetically engineered to produce glycoproteins having human-like or human glycosylation. Examples of such cells are genetically-modified *Pichia pastoris* (Hamilton et al., Science 301 (2003) 1244-1246; Potgieter et al., J. Biotechnology 139 (2009) 318-325) and genetically-modified *Lemna minor* (Cox et al., Nature Biotechnology 12 (2006) 1591-1597).

In one embodiment, said host cell is a mammalian or non-mammalian cell which produces homogenous glycoforms. In a further embodiment, said host cell is genetically engineered to produce glycoengineered antibodies, such as e.g. antibodies without core fucose. Examples of CHO cells producing defucosylated antibodies include Lec13 cells and genetically-modified CHO cells, such as GDP-mannose-4, 6-dehydratase (GMD) knockout cells; GDP-fucose transporter knockout cells; FUT8 knockout cells; RNAi of FUT8 and/or GMD; or cells overexpressing GlcNAc transferase III or RMD (GDP-6-deoxy-d-lyxo-4-hexulose reductase) (reviewed in Li et al. 2017 Front Immunol 13; 8:1554).

In one embodiment, said host cell is a host cell which is not capable of efficiently removing C-terminal lysine K447 residues from antibody heavy chains. For example, Table 2 in Liu et al. (2008) J Pharm Sci 97: 2426 (incorporated herein by reference) lists a number of such antibody production systems, e.g. Sp2/0, NS/0 or transgenic mammary gland (goat), wherein only partial removal of C-terminal lysines is obtained.

The present invention is further illustrated by the following examples which should not be construed as further limiting.

TABLE 1

<div style="text-align: center;">SEQUENCE LIST</div>

| SEQ ID NO | Name | Sequence |
|---|---|---|
| SEQ ID NO 1 | VH CAMPATH-1H | QVQLQESGPGLVRPSQTLSLTCTVSGFTFTDFYMNWVRQPPG RGLEWIGFIRDKAKGYTTEYNPSVKGRVTMLVDTSKNQFSLRL SSVTAADTAVYYCAREGHTAAPFDYWGQGSLVTVSS |
| SEQ ID NO 2 | VH CAMPATH-1H CDR1 | GFTFTDFY |
| SEQ ID NO 3 | VH CAMPATH-1H CDR2 | IRDKAKGYTT |
| SEQ ID NO 4 | VH CAMPATH-1H CDR3 | AREGHTAAPFDY |
| SEQ ID NO 5 | VL CAMPATH-1H | DIQMTQSPSSLSASVGDRVTITCKASQNIDKYLNWYQQKPGKA PKLLIYNTNNLQTGVPSRFSGSGSGTDFTFTISSLQPEDIATYY CLQHISRPRTFGQGTKVEIK |
| SEQ ID NO 6 | VL CAMPATH-1H CDR1 | QNIDKY |
|  | VL CAMPATH-1H CDR2 | NTN |
| SEQ ID NO 7 | VL CAMPATH-1H CDR3 | LQHISRPRT |
| SEQ ID NO 8 | VH CD20-11B8 | EVQLVQSGGGLVHPGGSLRLSCTGSGFTFSYHAMHWVRQAP GKGLEWVSIIGTGGVTYYADSVKGRFTISRDNVKNSLYLQMNS LRAEDMAVYYCARDYYGAGSFYDGLYGMDVWGQGTTVTVSS |
| SEQ ID NO 9 | VH CD20-11B8 CDR1 | GFTFSYHA |
| SEQ ID NO 10 | VH CD20-11B8 CDR2 | IGTGGVT |
| SEQ ID NO 11 | VH CD20-11B8 CDR3 | ARDYYGAGSFYDGLYGMDV |
| SEQ ID NO 12 | VL CD20-11B8 | EIVLTQSPATLSLSPGERATLSCRASQSVSSYLAWYQQKPGQA PRLLIYDASNRATGIPARFSGSGSGTDFTLTISSLEPEDFAVYY CQQRSDWPLTFGGGTKVEIK |
| SEQ ID NO 13 | VL CD20-11B8 CDR1 | QSVSSY |
|  | VL CD20-11B8 CDR2 | DAS |
| SEQ ID NO 14 | VL CD20-11B8 CDR3 | QQRSDWPLT |
| SEQ ID NO 15 | VH gp120-b12 | QVQLVQSGAEVKKPGASVKVSCQASGYRFSNFVIHWVRQAP GQRFEWMGWINPYNGNKEFSAKFQDRVTFTADTSANTAYME LRSLRSADTAVYYCARVGPYSWDDSPQDNYYMDVWGKGTTV IVSS |
| SEQ ID NO 16 | VH gp120-b12 CDR1 | GYRFSNFV |
| SEQ ID NO 17 | VH gp120-b12 CDR2 | INPYNGNK |
| SEQ ID NO 18 | VH gp120-b12 CDR3 | ARVGPYSWDDSPQDNYYMDV |
| SEQ ID NO 19 | VL gp120-b12 | EIVLTQSPGTLSLSPGERATFSCRSSHSIRSRRVAWYQHKPGQ APRLVIHGVSNRASGISDRFSGSGSGTDFTLTITRVEPEDFALY YCQVYGASSYTFGQGTKLERK |
| SEQ ID NO 20 | VL gp120-b12 CDR1 | HSIRSRR |
|  | VL gp120-b12 CDR2 | GVS |

TABLE 1-continued

| SEQUENCE LIST |
| --- |

| SEQ ID NO | Name | Sequence |
| --- | --- | --- |
| SEQ ID NO 21 | VL gp120-b12-CDR3 | QVYGASSYT |
| SEQ ID NO 22 | constant region human HC IgG1m(f) | ASTKGPSVFPLAPSSKSTSGGTAALGCLVKDYFPEPVTVSWNS GALTSGVHTFPAVLQSSGLYSLSSVVTVPSSSLGTQTYICNVN HKPSNTKVDKRVEPKSCDKTHTCPPCPAPELLGGPSVFLFPPK PKDTLMISRTPEVTCVVVDVSHEDPEVKFNWYVDGVEVHNAK TKPREEQYNSTYRVVSVLTVLHQDWLNGKEYKCKVSNKALPA PIEKTISKAKGQPREPQVYTLPPSREEMTKNQVSLTCLVKGFYP SDIAVEWESNGQPENNYKTTPPVLDSDGSFFLYSKLTVDKSR WQQGNVFSCSVMHEALHNHYTQKSLSLSPGK |
| SEQ ID NO 23 | constant region human HC IgG1m(z) | ASTKGPSVFPLAPSSKSTSGGTAALGCLVKDYFPEPVTVSWNS GALTSGVHTFPAVLQSSGLYSLSSVVTVPSSSLGTQTYICNVN HKPSNTKVDKKVEPKSCDKTHTCPPCPAPELLGGPSVFLFPPK PKDTLMISRTPEVTCVVVDVSHEDPEVKFNWYVDGVEVHNAK TKPREEQYNSTYRVVSVLTVLHQDWLNGKEYKCKVSNKALPA PIEKTISKAKGQPREPQVYTLPPSREEMTKNQVSLTCLVKGFYP SDIAVEWESNGQPENNYKTTPPVLDSDGSFFLYSKLTVDKSR WQQGNVFSCSVMHEALHNHYTQKSLSLSPGK |
| SEQ ID NO 24 | constant region human HC IgG1m(a) | ASTKGPSVFPLAPSSKSTSGGTAALGCLVKDYFPEPVTVSWNS GALTSGVHTFPAVLQSSGLYSLSSVVTVPSSSLGTQTYICNVN HKPSNTKVDKPVEPKSCDKTHTCPPCPAPELLGGPSVFLFPPK PKDTLMISRTPEVTCVVVDVSHEDPEVKFNWYVDGVEVHNAK TKPREEQYNSTYRVVSVLTVLHQDWLNGKEYKCKVSNKALPA PIEKTISKAKGQPREPQVYTLPPSRDELTKNQVSLTCLVKGFYP SDIAVEWESNGQPENNYKTTPPVLDSDGSFFLYSKLTVDKSR WQQGNVFSCSVMHEALHNHYTQKSLSLSPGK |
| SEQ ID NO 25 | constant region human HC IgG1m(x) | ASTKGPSVFPLAPSSKSTSGGTAALGCLVKDYFPEPVTVSWNS GALTSGVHTFPAVLQSSGLYSLSSVVTVPSSSLGTQTYICNVN HKPSNTKVDKPVEPKSCDKTHTCPPCPAPELLGGPSVFLFPPK PKDTLMISRTPEVTCVVVDVSHEDPEVKFNWYVDGVEVHNAK TKPREEQYNSTYRVVSVLTVLHQDWLNGKEYKCKVSNKALPA PIEKTISKAKGQPREPQVYTLPPSREEMTKNQVSLTCLVKGFYP SDIAVEWESNGQPENNYKTTPPVLDSDGSFFLYSKLTVDKSR WQQGNVFSCSVMHEGLHNHYTQKSLSLSPGK |
| SEQ ID NO 26 | constant region human IgG1m(f)-E430G | ASTKGPSVFPLAPSSKSTSGGTAALGCLVKDYFPEPVTVSWNS HCGALTSGVHTFPAVLQSSGLYSLSSVVTVPSSSLGTQTYICNVN HKPSNTKVDKRVEPKSCDKTHTCPPCPAPELLGGPSVFLFPPK PKDTLMISRTPEVTCVVVDVSHEDPEVKFNWYVDGVEVHNAK TKPREEQYNSTYRVVSVLTVLHQDWLNGKEYKCKVSNKALPA PIEKTISKAKGQPREPQVYTLPPSREEMTKNQVSLTCLVKGFYP SDIAVEWESNGQPENNYKTTPPVLDSDGSFFLYSKLTVDKSR WQQGNVFSCSVMHGALHNHYTQKSLSLSPGK |
| SEQ ID NO 27 | constant region human HC IgG1m(f)-E345K | ASTKGPSVFPLAPSSKSTSGGTAALGCLVKDYFPEPVTVSWNS GALTSGVHTFPAVLQSSGLYSLSSVVTVPSSSLGTQTYICNVN HKPSNTKVDKRVEPKSCDKTHTCPPCPAPELLGGPSVFLFPPK PKDTLMISRTPEVTCVVVDVSHEDPEVKFNWYVDGVEVHNAK TKPREEQYNSTYRVVSVLTVLHQDWLNGKEYKCKVSNKALPA PIEKTISKAKGQPRKPQVYTLPPSREEMTKNQVSLTCLVKGFY PSDIAVEWESNGQPENNYKTTPPVLDSDGSFFLYSKLTVDKSR WQQGNVFSCSVMHEALHNHYTQKSLSLSPGK |
| SEQ ID NO 28 | constant region human HC IgG1m(f)-E345R | ASTKGPSVFPLAPSSKSTSGGTAALGCLVKDYFPEPVTVSWNS GALTSGVHTFPAVLQSSGLYSLSSVVTVPSSSLGTQTYICNVN HKPSNTKVDKRVEPKSCDKTHTCPPCPAPELLGGPSVFLFPPK PKDTLMISRTPEVTCVVVDVSHEDPEVKFNWYVDGVEVHNAK TKPREEQYNSTYRVVSVLTVLHQDWLNGKEYKCKVSNKALPA PIEKTISKAKGQPRRPQVYTLPPSREEMTKNQVSLTCLVKGFY PSDIAVEWESNGQPENNYKTTPPVLDSDGSFFLYSKLTVDKSR WQQGNVFSCSVMHEALHNHYTQKSLSLSPGK |
| SEQ ID NO 29 | constant region human HC IgG1m(f)-K439E | ASTKGPSVFPLAPSSKSTSGGTAALGCLVKDYFPEPVTVSWNS GALTSGVHTFPAVLQSSGLYSLSSVVTVPSSSLGTQTYICNVN HKPSNTKVDKRVEPKSCDKTHTCPPCPAPELLGGPSVFLFPPK PKDTLMISRTPEVTCVVVDVSHEDPEVKFNWYVDGVEVHNAK TKPREEQYNSTYRVVSVLTVLHQDWLNGKEYKCKVSNKALPA PIEKTISKAKGQPREPQVYTLPPSREEMTKNQVSLTCLVKGFYP SDIAVEWESNGQPENNYKTTPPVLDSDGSFFLYSKLTVDKSR WQQGNVFSCSVMHEALHNHYTQESLSLSPGK |

TABLE 1-continued

SEQUENCE LIST

| SEQ ID NO | Name | Sequence |
|---|---|---|
| SEQ ID NO 30 | constant region human HC IgG1m(f)-S440K | ASTKGPSVFPLAPSSKSTSGGTAALGCLVKDYFPEPVTVSWNS GALTSGVHTFPAVLQSSGLYSLSSVVTVPSSSLGTQTYICNVN HKPSNTKVDKRVEPKSCDKTHTCPPCPAPELLGGPSVFLFPPK PKDTLMISRTPEVTCVVVDVSHEDPEVKFNWYVDGVEVHNAK TKPREEQYNSTYRVVSVLTVLHQDWLNGKEYKCKVSNKALPA PIEKTISKAKGQPREPQVYTLPPSREEMTKNQVSLTCLVKGFYP SDIAVEWESNGQPENNYKTTPPVLDSDGSFFLYSKLTVDKSR WQQGNVFSCSVMHEALHNHYTQKKLSLSPGK |
| SEQ ID NO 31 | constant region human HC IgG2 | ASTKGPSVFPLAPCSRSTSESTAALGCLVKDYFPEPVTVSWNS GALTSGVHTFPAVLQSSGLYSLSSVVTVPSSNFGTQTYTCNVD HKPSNTKVDKTVERKCCVECPPCPAPPVAGPSVFLFPPKPKDT LMISRTPEVTCVVVDVSHEDPEVQFNWYVDGVEVHNAKTKPR EEQFNSTFRVVSVLTVVHQDWLNGKEYKCKVSNKGLPAPIEKT ISKTKGQPREPQVYTLPPSREEMTKNQVSLTCLVKGFYPSDIA VEWESNGQPENNYKTTPPMLDSDGSFFLYSKLTVDKSRWQQ GNVFSCSVMHEALHNHYTQKSLSLSPGK |
| SEQ ID NO 32 | constant region human HC IgG3 | ASTKGPSVFPLAPCSRSTSGGTAALGCLVKDYFPEPVTVSWN SGALTSGVHTFPAVLQSSGLYSLSSVVTVPSSSLGTQTYTCNV NHKPSNTKVDKRVELKTPLGDTTHTCPRCPEPKSCDTPPPCP RCPEPKSCDTPPPCPRCPEPKSCDTPPPCPRCPAPELLGGPS VFLFPPKPKDTLMISRTPEVTCVVVDVSHEDPEVQFKWYVDGV EVHNAKTKPREEQYNSTFRVVSVLTVLHQDWLNGKEYKCKVS NKALPAPIEKTISKTKGQPREPQVYTLPPSREEMTKNQVSLTCL VKGFYPSDIAVEWESSGQPENNYNTTPPMLDSDGSFFLYSKLT VDKSRWQQGNIFSCSVMHEALHNRFTQKSLSLSPGK |
| SEQ ID NO 33 | constant region human HC IgG4 | ASTKGPSVFPLAPCSRSTSESTAALGCLVKDYFPEPVTVSWNS GALTSGVHTFPAVLQSSGLYSLSSVVTVPSSSLGTKTYTCNVD HKPSNTKVDKRVESKYGPPCPSCPAPEFLGGPSVFLFPPKPK DTLMISRTPEVTCVVVDVSQEDPEVQFNWYVDGVEVHNAKTK PREEQFNSTYRVVSVLTVLHQDWLNGKEYKCKVSNKGLPSSIE KTISKAKGQPREPQVYTLPPSQEEMTKNQVSLTCLVKGFYPSD IAVEWESNGQPENNYKTIPPVLDSDGSFFLYSRLTVDKSRWQ EGNVFSCSVMHEALHNHYTQKSLSLSLGK |
| SEQ ID NO 34 | Constant region human kappa LC | RTVAAPSVFIFPPSDEQLKSGTASVVCLLNNFYPREAKVQWKV DNALQSGNSQESVTEQDSKDSTYSLSSTLTLSKADYEKHKVYA CEVTHQGLSSPVTKSFNRGEC |
| SEQ ID NO 35 | VH CD20-7D8 | EVQLVESGGGLVQPDRSLRLSCAASGFTFHDYAMHWVRQAP GKGLEWVSTISWNSGTIGYADSVKGRFTISRDNAKNSLYLQMN SLRAEDTALYYCAKDIQYGNYYYGMDVWGQGTTVTVSS |
| SEQ ID NO 36 | VH CD20-7D8 CDR1 | GFTFHDYA |
| SEQ ID NO 37 | VH CD20-7D8 CDR2 | ISWNSGTI |
| SEQ ID NO 38 | VH CD20-7D8 CDR3 | AKDIQYGNYYYGMDV |
| SEQ ID NO 39 | VL CD20-7D8 | EIVLTQSPATLSLSPGERATLSCRASQSVSSYLAWYQQKPGQA PRLLIYDASNRATGIPARFSGSGSGTDFTLTISSLEPEDFAVYY CQQRSNWPITFGQGTRLEIK |
| SEQ ID NO 40 | VL CD20-7D8 CDR1 | QSVSSY |
| | VL CD20-7D8 CDR2 | DAS |
| SEQ ID NO 41 | VL CD20-7D8 CDR3 | QQRSNWPIT |
| SEQ ID NO 42 | VH CD37-37-3 | QVQVKESGPGLVAPSQSLSITCTVSGFSLTTSGVSWVRQPPG KGLEWLGVIWGDGSTNYHSALKSRLSIKKDHSKSQVFLKLNSL QTDDTATYYCAKGGYSLAHWGQGTLVTVSA |
| SEQ ID NO 43 | VH CD37-37-3 CDR1 | GFSLTTSG |

TABLE 1-continued

| SEQUENCE LIST | | |
|---|---|---|
| SEQ ID NO | Name | Sequence |
| SEQ ID NO 44 | VH CD37-37-3 CDR2 | IWGDGST |
| SEQ ID NO 45 | VH CD37-37-3 CDR3 | AKGGYSLAH |
| SEQ ID NO 46 | VL CD37-37-3 | DIQMTQSPASLSVSVGETVTITCRASENIRSNLAWYQQKQGKS PQLLVNVATNLADGVPSRFSGSGSGTQYSLKINSLQSEDFGTY YCQHYWGTTWTFGGGTKLEIK |
| SEQ ID NO 47 | VL CD37-37-3 CDR1 | ENIRSN |
| | VL CD37-37-3 CDR2 | VAT |
| SEQ ID NO 48 | VL CD37-37-3 CDR3 | QHYWGTTWT |
| SEQ ID NO 49 | VH hDR5-01-G56T | EVQLQQSGAEVVKPGASVKLSCKASGFNIKDTFIHWVKQAPG QGLEWIGRIDPANTNTKYDPKFQGKATITTDTSSNTAYMELSSL RSEDTAVYYCVRGLYTYYFDYWGQGTLVTVSS |
| SEQ ID NO 50 | VH hDR5-01-G56T CDR1 | GFNIKDTF |
| SEQ ID NO 51 | VH hDR5-01-G56T CDR2 | IDPANTNT |
| SEQ ID NO 52 | VH hDR5-01-G56T CDR3 | VRGLYTYYFDY |
| SEQ ID NO 53 | VL hDR5-01-G56T | EIVMTQSPATLSVSPGERATLSCRASQSISNNLHWYQQKPGQ APRLLIKFASQSITGIPARFSGSGSGTEFTLTISSLQSEDFAVYY CQQGNSWPYTFGQGTKLEIK |
| SEQ ID NO 54 | VL hDR5-01-G56T CDR1 | QSISNN |
| | VL hDR5-01-G56T CDR2 | FAS |
| SEQ ID NO 55 | VL hDR5-01-G56T CDR3 | QQGNSWPYT |
| SEQ ID NO 56 | VH hDR5-05 | QVQLVQSGAEVKKPGASVKVSCKASGFNIKDTHMHWVRQAP GQRLEWIGRIDPANGNTEYDQKFQGRVTITVDTSASTAYMELS SLRSEDTAVYYCARWGTNVYFAYWGQGTLVTVSS |
| SEQ ID NO 57 | VH hDR5-05 CDR1 | GFNIKDTH |
| SEQ ID NO 58 | VH hDR5-05 CDR2 | IDPANGNT |
| SEQ ID NO 59 | VH hDR5-05 CDR3 | ARWGTNVYFAY |
| SEQ ID NO 60 | VL hDR5-05 | DIQLTQSPSSLSASVGDRVTITCSASSSVSYMYWYQQKPGKAP KPWIYRTSNLASGVPSRFSGSGSGTDFTLTISSLQPEDFATYY CQQYHSYPPTFGGGTKVEIK |
| SEQ ID NO 61 | VL hDR5-05 CDR1 | SSVSY |
| | VL hDR5-05 CDR2 | RTS |
| SEQ ID NO 62 | VL hD R5-05 CDR3 | QQYHSYPPT |

TABLE 1-continued

| | SEQUENCE LIST | |
|---|---|---|
| SEQ ID NO | Name | Sequence |
| SEQ ID NO 63 | constant region human HC IgG1m(f)- E430G-S440K- Q438R-E333S | ASTKGPSVFPLAPSSKSTSGGTAALGCLVKDYFPEPVTVSWNS GALTSGVHTFPAVLQSSGLYSLSSVVTVPSSSLGTQTYICNVN HKPSNTKVDKRVEPKSCDKTHTCPPCPAPELLGGPSVFLFPPK PKDTLMISRTPEVTCVVVDVSHEDPEVKFNWYVDGVEVHNAK TKPREEQYNSTYRVVSVLTVLHQDWLNGKEYKCKVSNKALPA PISKTISKAKGQPREPQVYTLPPSREEMTKNQVSLTCLVKGFYP SDIAVEWESNGQPENNYKTTPPVLDSDGSFFLYSKLTVDKSR WQQGNVFSCSVMHGALHNHYTRKKLSLSPGK |
| SEQ ID NO 64 | constant region human HC IgG1m(f)- E430G-S440K- Y436K-E333S | ASTKGPSVFPLAPSSKSTSGGTAALGCLVKDYFPEPVTVSWNS GALTSGVHTFPAVLQSSGLYSLSSVVTVPSSSLGTQTYICNVN HKPSNTKVDKRVEPKSCDKTHTCPPCPAPELLGGPSVFLFPPK PKDTLMISRTPEVTCVVVDVSHEDPEVKFNWYVDGVEVHNAK TKPREEQYNSTYRVVSVLTVLHQDWLNGKEYKCKVSNKALPA PISKTISKAKGQPREPQVYTLPPSREEMTKNQVSLTCLVKGFYP SDIAVEWESNGQPENNYKTTPPVLDSDGSFFLYSKLTVDKSR WQQGNVFSCSVMHGALHNHKTQKKLSLSPGK |
| SEQ ID NO 65 | constant region human HC IgG1 m(f)- E345K-K439E- Q438N | ASTKGPSVFPLAPSSKSTSGGTAALGCLVKDYFPEPVTVSWNS GALTSGVHTFPAVLQSSGLYSLSSVVTVPSSSLGTQTYICNVN HKPSNTKVDKRVEPKSCDKTHTCPPCPAPELLGGPSVFLFPPK PKDTLMISRTPEVTCVVVDVSHEDPEVKFNWYVDGVEVHNAK TKPREEQYNSTYRVVSVLTVLHQDWLNGKEYKCKVSNKALPA PIEKTISKAKGQPRKPQVYTLPPSREEMTKNQVSLTCLVKGFY PSDIAVEWESNGQPENNYKTTPPVLDSDGSFFLYSKLTVDKSR WQQGNVFSCSVMHEALHNHYTNESLSLSPGK |
| SEQ ID NO 66 | constant region human HC IgG1 m(f)- E345K-S440K- Q438R | ASTKGPSVFPLAPSSKSTSGGTAALGCLVKDYFPEPVTVSWNS GALTSGVHTFPAVLQSSGLYSLSSVVTVPSSSLGTQTYICNVN HKPSNTKVDKRVEPKSCDKTHTCPPCPAPELLGGPSVFLFPPK PKDTLMISRTPEVTCVVVDVSHEDPEVKFNWYVDGVEVHNAK TKPREEQYNSTYRVVSVLTVLHQDWLNGKEYKCKVSNKALPA PIEKTISKAKGQPRKPQVYTLPPSREEMTKNQVSLTCLVKGFY PSDIAVEWESNGQPENNYKTTPPVLDSDGSFFLYSKLTVDKSR WQQGNVFSCSVMHEALHNHYTRKKLSLSPGK |
| SEQ ID NO 67 | constant region human HC IgG1m(f)- E345K-S440K- Y436K | ASTKGPSVFPLAPSSKSTSGGTAALGCLVKDYFPEPVTVSWNS GALTSGVHTFPAVLQSSGLYSLSSVVTVPSSSLGTQTYICNVN HKPSNTKVDKRVEPKSCDKTHTCPPCPAPELLGGPSVFLFPPK PKDTLMISRTPEVTCVVVDVSHEDPEVKFNWYVDGVEVHNAK TKPREEQYNSTYRVVSVLTVLHQDWLNGKEYKCKVSNKALPA PIEKTISKAKGQPRKPQVYTLPPSREEMTKNQVSLTCLVKGFY PSDIAVEWESNGQPENNYKTTPPVLDSDGSFFLYSKLTVDKSR WQQGNVFSCSVMHEALHNHKTQKKLSLSPGK |
| SEQ ID NO 68 | constant region human HC IgG1m(f)- E345K-K439E- Y436N | ASTKGPSVFPLAPSSKSTSGGTAALGCLVKDYFPEPVTVSWNS GALTSGVHTFPAVLQSSGLYSLSSVVTVPSSSLGTQTYICNVN HKPSNTKVDKRVEPKSCDKTHTCPPCPAPELLGGPSVFLFPPK PKDTLMISRTPEVTCVVVDVSHEDPEVKFNWYVDGVEVHNAK TKPREEQYNSTYRVVSVLTVLHQDWLNGKEYKCKVSNKALPA PIEKTISKAKGQPRKPQVYTLPPSREEMTKNQVSLTCLVKGFY PSDIAVEWESNGQPENNYKTTPPVLDSDGSFFLYSKLTVDKSR WQQGNVFSCSVMHEALHNHNTQESLSLSPGK |
| SEQ ID NO 69 | constant region human HC IgG1m(f)- E345R-K439E- Q438N | ASTKGPSVFPLAPSSKSTSGGTAALGCLVKDYFPEPVTVSWNS GALTSGVHTFPAVLQSSGLYSLSSVVTVPSSSLGTQTYICNVN HKPSNTKVDKRVEPKSCDKTHTCPPCPAPELLGGPSVFLFPPK PKDTLMISRTPEVTCVVVDVSHEDPEVKFNWYVDGVEVHNAK TKPREEQYNSTYRVVSVLTVLHQDWLNGKEYKCKVSNKALPA PIEKTISKAKGQPRRPQVYTLPPSREEMTKNQVSLTCLVKGFY PSDIAVEWESNGQPENNYKTTPPVLDSDGSFFLYSKLTVDKSR WQQGNVFSCSVMHEALHNHYTNESLSLSPGK |
| SEQ ID NO 70 | constant region human HC IgG1m(f)- E345R-S440K- Q438R | ASTKGPSVFPLAPSSKSTSGGTAALGCLVKDYFPEPVTVSWNS GALTSGVHTFPAVLQSSGLYSLSSVVTVPSSSLGTQTYICNVN HKPSNTKVDKRVEPKSCDKTHTCPPCPAPELLGGPSVFLFPPK PKDTLMISRTPEVTCVVVDVSHEDPEVKFNWYVDGVEVHNAK TKPREEQYNSTYRVVSVLTVLHQDWLNGKEYKCKVSNKALPA PIEKTISKAKGQPRRPQVYTLPPSREEMTKNQVSLTCLVKGFY PSDIAVEWESNGQPENNYKTTPPVLDSDGSFFLYSKLTVDKSR WQQGNVFSCSVMHEALHNHYTRKKLSLSPGK |

TABLE 1-continued

| SEQ ID NO | Name | Sequence |
|---|---|---|

SEQUENCE LIST

SEQ ID NO 71    constant region human HC IgG1m(f)- E345R-S440K- Y436K

ASTKGPSVFPLAPSSKSTSGGTAALGCLVKDYFPEPVTVSWNS
GALTSGVHTFPAVLQSSGLYSLSSVVTVPSSSLGTQTYICNVN
HKPSNTKVDKRVEPKSCDKTHTCPPCPAPELLGGPSVFLFPPK
PKDTLMISRTPEVTCVVVDVSHEDPEVKFNWYVDGVEVHNAK
TKPREEQYNSTYRVVSVLTVLHQDWLNGKEYKCKVSNKALPA
PIEKTISKAKGQPRRPQVYTLPPSREEMTKNQVSLTCLVKGFY
PSDIAVEWESNGQPENNYKTTPPVLDSDGSFFLYSKLTVDKSR
WQQGNVFSCSVMHEALHNHKTQKKLSLSPGK

SEQ ID NO 72    constant region human HC IgG1m(f)- E345R-K439E- Y436N

ASTKGPSVFPLAPSSKSTSGGTAALGCLVKDYFPEPVTVSWNS
GALTSGVHTFPAVLQSSGLYSLSSVVTVPSSSLGTQTYICNVN
HKPSNTKVDKRVEPKSCDKTHTCPPCPAPELLGGPSVFLFPPK
PKDTLMISRTPEVTCVVVDVSHEDPEVKFNWYVDGVEVHNAK
TKPREEQYNSTYRVVSVLTVLHQDWLNGKEYKCKVSNKALPA
PIEKTISKAKGQPRRPQVYTLPPSREEMTKNQVSLTCLVKGFY
PSDIAVEWESNGQPENNYKTTPPVLDSDGSFFLYSKLTVDKSR
WQQGNVFSCSVMHEALHNHNTQESLSLSPGK

SEQ ID NO 73    constant region human HC IgG1m(f)- E430G-K439E

ASTKGPSVFPLAPSSKSTSGGTAALGCLVKDYFPEPVTVSWNS
GALTSGVHTFPAVLQSSGLYSLSSVVTVPSSSLGTQTYICNVN
HKPSNTKVDKRVEPKSCDKTHTCPPCPAPELLGGPSVFLFPPK
PKDTLMISRTPEVTCVVVDVSHEDPEVKFNWYVDGVEVHNAK
TKPREEQYNSTYRVVSVLTVLHQDWLNGKEYKCKVSNKALPA
PIEKTISKAKGQPREPQVYTLPPSREEMTKNQVSLTCLVKGFYP
SDIAVEWESNGQPENNYKTTPPVLDSDGSFFLYSKLTVDKSR
WQQGNVFSCSVMHGALHNHYTQESLSLSPGK

SEQ ID NO 74    constant region human HC IgG1m(f)- E430G-K439E- Q438N

ASTKGPSVFPLAPSSKSTSGGTAALGCLVKDYFPEPVTVSWNS
GALTSGVHTFPAVLQSSGLYSLSSVVTVPSSSLGTQTYICNVN
HKPSNTKVDKRVEPKSCDKTHTCPPCPAPELLGGPSVFLFPPK
PKDTLMISRTPEVTCVVVDVSHEDPEVKFNWYVDGVEVHNAK
TKPREEQYNSTYRVVSVLTVLHQDWLNGKEYKCKVSNKALPA
PIEKTISKAKGQPREPQVYTLPPSREEMTKNQVSLTCLVKGFYP
SDIAVEWESNGQPENNYKTTPPVLDSDGSFFLYSKLTVDKSR
WQQGNVFSCSVMHGALHNHYTNESLSLSPGK

SEQ ID NO 75    constant region human HC IgG1m(f)- E430G-S440K- Q438N

ASTKGPSVFPLAPSSKSTSGGTAALGCLVKDYFPEPVTVSWNS
GALTSGVHTFPAVLQSSGLYSLSSVVTVPSSSLGTQTYICNVN
HKPSNTKVDKRVEPKSCDKTHTCPPCPAPELLGGPSVFLFPPK
PKDTLMISRTPEVTCVVVDVSHEDPEVKFNWYVDGVEVHNAK
TKPREEQYNSTYRVVSVLTVLHQDWLNGKEYKCKVSNKALPA
PIEKTISKAKGQPREPQVYTLPPSREEMTKNQVSLTCLVKGFYP
SDIAVEWESNGQPENNYKTTPPVLDSDGSFFLYSKLTVDKSR
WQQGNVFSCSVMHGALHNHYTNKKLSLSPGK

SEQ ID NO 76    constant region human HC IgG1m(f)- E430G-K439E- Q438R

ASTKGPSVFPLAPSSKSTSGGTAALGCLVKDYFPEPVTVSWNS
GALTSGVHTFPAVLQSSGLYSLSSVVTVPSSSLGTQTYICNVN
HKPSNTKVDKRVEPKSCDKTHTCPPCPAPELLGGPSVFLFPPK
PKDTLMISRTPEVTCVVVDVSHEDPEVKFNWYVDGVEVHNAK
TKPREEQYNSTYRVVSVLTVLHQDWLNGKEYKCKVSNKALPA
PIEKTISKAKGQPREPQVYTLPPSREEMTKNQVSLTCLVKGFYP
SDIAVEWESNGQPENNYKTTPPVLDSDGSFFLYSKLTVDKSR
WQQGNVFSCSVMHGALHNHYTRESLSLSPGK

SEQ ID NO 77    constant region human HC IgG1m(f)- E430G-S440K- Q438R

ASTKGPSVFPLAPSSKSTSGGTAALGCLVKDYFPEPVTVSWNS
GALTSGVHTFPAVLQSSGLYSLSSVVTVPSSSLGTQTYICNVN
HKPSNTKVDKRVEPKSCDKTHTCPPCPAPELLGGPSVFLFPPK
PKDTLMISRTPEVTCVVVDVSHEDPEVKFNWYVDGVEVHNAK
TKPREEQYNSTYRVVSVLTVLHQDWLNGKEYKCKVSNKALPA
PIEKTISKAKGQPREPQVYTLPPSREEMTKNQVSLTCLVKGFYP
SDIAVEWESNGQPENNYKTTPPVLDSDGSFFLYSKLTVDKSR
WQQGNVFSCSVMHGALHNHYTRKKLSLSPGK

SEQ ID NO 78    constant region human HC IgG1m(f)- E430G-S440K

ASTKGPSVFPLAPSSKSTSGGTAALGCLVKDYFPEPVTVSWNS
GALTSGVHTFPAVLQSSGLYSLSSVVTVPSSSLGTQTYICNVN
HKPSNTKVDKRVEPKSCDKTHTCPPCPAPELLGGPSVFLFPPK
PKDTLMISRTPEVTCVVVDVSHEDPEVKFNWYVDGVEVHNAK
TKPREEQYNSTYRVVSVLTVLHQDWLNGKEYKCKVSNKALPA
PIEKTISKAKGQPREPQVYTLPPSREEMTKNQVSLTCLVKGFYP
SDIAVEWESNGQPENNYKTTPPVLDSDGSFFLYSKLTVDKSR
WQQGNVFSCSVMHGALHNHYTQKKLSLSPGK

TABLE 1-continued

| | | |
|---|---|---|
| SEQ ID<br>NO | Name | Sequence |

| SEQ ID<br>NO 79 | constant region<br>human HC<br>IgG1m(f)-<br>E430G-K439E-<br>Y436K | ASTKGPSVFPLAPSSKSTSGGTAALGCLVKDYFPEPVTVSWNS<br>GALTSGVHTFPAVLQSSGLYSLSSVVTVPSSSLGTQTYICNVN<br>HKPSNTKVDKRVEPKSCDKTHTCPPCPAPELLGGPSVFLFPPK<br>PKDTLMISRTPEVTCVVVDVSHEDPEVKFNWYVDGVEVHNAK<br>TKPREEQYNSTYRVVSVLTVLHQDWLNGKEYKCKVSNKALPA<br>PIEKTISKAKGQPREPQVYTLPPSREEMTKNQVSLTCLVKGFYP<br>SDIAVEWESNGQPENNYKTTPPVLDSDGSFFLYSKLTVDKSR<br>WQQGNVFSCSVMHGALHNHKTQESLSLSPGK |
| SEQ ID<br>NO 80 | constant region<br>human HC<br>IgG1m(f)-<br>E430G-S440K-<br>Y436K | ASTKGPSVFPLAPSSKSTSGGTAALGCLVKDYFPEPVTVSWNS<br>GALTSGVHTFPAVLQSSGLYSLSSVVTVPSSSLGTQTYICNVN<br>HKPSNTKVDKRVEPKSCDKTHTCPPCPAPELLGGPSVFLFPPK<br>PKDTLMISRTPEVTCVVVDVSHEDPEVKFNWYVDGVEVHNAK<br>TKPREEQYNSTYRVVSVLTVLHQDWLNGKEYKCKVSNKALPA<br>PIEKTISKAKGQPREPQVYTLPPSREEMTKNQVSLTCLVKGFYP<br>SDIAVEWESNGQPENNYKTTPPVLDSDGSFFLYSKLTVDKSR<br>WQQGNVFSCSVMHGALHNHKTQKKLSLSPGK |
| SEQ ID<br>NO 81 | constant region<br>human HC<br>IgG1m(f)-<br>E430G-K439E-<br>Y436N | ASTKGPSVFPLAPSSKSTSGGTAALGCLVKDYFPEPVTVSWNS<br>GALTSGVHTFPAVLQSSGLYSLSSVVTVPSSSLGTQTYICNVN<br>HKPSNTKVDKRVEPKSCDKTHTCPPCPAPELLGGPSVFLFPPK<br>PKDTLMISRTPEVTCVVVDVSHEDPEVKFNWYVDGVEVHNAK<br>TKPREEQYNSTYRVVSVLTVLHQDWLNGKEYKCKVSNKALPA<br>PIEKTISKAKGQPREPQVYTLPPSREEMTKNQVSLTCLVKGFYP<br>SDIAVEWESNGQPENNYKTTPPVLDSDGSFFLYSKLTVDKSR<br>WQQGNVFSCSVMHGALHNHNTQESLSLSPGK |
| SEQ ID<br>NO 82 | constant region<br>human HC<br>IgG1m(f)-<br>E430G-S440K-<br>Y436N | ASTKGPSVFPLAPSSKSTSGGTAALGCLVKDYFPEPVTVSWNS<br>GALTSGVHTFPAVLQSSGLYSLSSVVTVPSSSLGTQTYICNVN<br>HKPSNTKVDKRVEPKSCDKTHTCPPCPAPELLGGPSVFLFPPK<br>PKDTLMISRTPEVTCVVVDVSHEDPEVKFNWYVDGVEVHNAK<br>TKPREEQYNSTYRVVSVLTVLHQDWLNGKEYKCKVSNKALPA<br>PIEKTISKAKGQPREPQVYTLPPSREEMTKNQVSLTCLVKGFYP<br>SDIAVEWESNGQPENNYKTTPPVLDSDGSFFLYSKLTVDKSR<br>WQQGNVFSCSVMHGALHNHNTQKKLSLSPGK |
| SEQ ID<br>NO 83 | constant region<br>human HC<br>IgG1m(f)-<br>E430G-K439E-<br>Q438N-G237A | ASTKGPSVFPLAPSSKSTSGGTAALGCLVKDYFPEPVTVSWNS<br>GALTSGVHTFPAVLQSSGLYSLSSVVTVPSSSLGTQTYICNVN<br>HKPSNTKVDKRVEPKSCDKTHTCPPCPAPELLGAPSVFLFPPK<br>PKDTLMISRTPEVTCVVVDVSHEDPEVKFNWYVDGVEVHNAK<br>TKPREEQYNSTYRVVSVLTVLHQDWLNGKEYKCKVSNKALPA<br>PIEKTISKAKGQPREPQVYTLPPSREEMTKNQVSLTCLVKGFYP<br>SDIAVEWESNGQPENNYKTTPPVLDSDGSFFLYSKLTVDKSR<br>WQQGNVFSCSVMHGALHNHYTNESLSLSPGK |
| SEQ ID<br>NO 84 | constant region<br>human HC<br>IgG1m(f)-<br>E430G-S440K-<br>Q438R-G237A | ASTKGPSVFPLAPSSKSTSGGTAALGCLVKDYFPEPVTVSWNS<br>GALTSGVHTFPAVLQSSGLYSLSSVVTVPSSSLGTQTYICNVN<br>HKPSNTKVDKRVEPKSCDKTHTCPPCPAPELLGAPSVFLFPPK<br>PKDTLMISRTPEVTCVVVDVSHEDPEVKFNWYVDGVEVHNAK<br>TKPREEQYNSTYRVVSVLTVLHQDWLNGKEYKCKVSNKALPA<br>PIEKTISKAKGQPREPQVYTLPPSREEMTKNQVSLTCLVKGFYP<br>SDIAVEWESNGQPENNYKTTPPVLDSDGSFFLYSKLTVDKSR<br>WQQGNVFSCSVMHGALHNHYTRKKLSLSPGK |
| SEQ ID<br>NO 85 | constant region<br>human HC<br>IgG1m(f)-<br>E430G-S440K-<br>Y436K-G237A | ASTKGPSVFPLAPSSKSTSGGTAALGCLVKDYFPEPVTVSWNS<br>GALTSGVHTFPAVLQSSGLYSLSSVVTVPSSSLGTQTYICNVN<br>HKPSNTKVDKRVEPKSCDKTHTCPPCPAPELLGAPSVFLFPPK<br>PKDTLMISRTPEVTCVVVDVSHEDPEVKFNWYVDGVEVHNAK<br>TKPREEQYNSTYRVVSVLTVLHQDWLNGKEYKCKVSNKALPA<br>PIEKTISKAKGQPREPQVYTLPPSREEMTKNQVSLTCLVKGFYP<br>SDIAVEWESNGQPENNYKTTPPVLDSDGSFFLYSKLTVDKSR<br>WQQGNVFSCSVMHGALHNHKTQKKLSLSPGK |
| SEQ ID<br>NO 86 | constant region<br>human HC<br>IgG1m(f)-<br>E430G-K439E-<br>Y436N-G237A | ASTKGPSVFPLAPSSKSTSGGTAALGCLVKDYFPEPVTVSWNS<br>GALTSGVHTFPAVLQSSGLYSLSSVVTVPSSSLGTQTYICNVN<br>HKPSNTKVDKRVEPKSCDKTHTCPPCPAPELLGAPSVFLFPPK<br>PKDTLMISRTPEVTCVVVDVSHEDPEVKFNWYVDGVEVHNAK<br>TKPREEQYNSTYRVVSVLTVLHQDWLNGKEYKCKVSNKALPA<br>PIEKTISKAKGQPREPQVYTLPPSREEMTKNQVSLTCLVKGFYP<br>SDIAVEWESNGQPENNYKTTPPVLDSDGSFFLYSKLTVDKSR<br>WQQGNVFSCSVMHGALHNHNTQESLSLSPGK |

TABLE 1-continued

| SEQ ID NO | Name | Sequence |
|---|---|---|
| SEQ ID NO 87 | constant region human HC IgG1m(f)- E430G-S440K- Q438R-K326W- E333S | ASTKGPSVFPLAPSSKSTSGGTAALGCLVKDYFPEPVTVSWNS GALTSGVHTFPAVLQSSGLYSLSSVVTVPSSSLGTQTYICNVN HKPSNTKVDKRVEPKSCDKTHTCPPCPAPELLGGPSVFLFPPK PKDTLMISRTPEVTCVVVDVSHEDPEVKFNWYVDGVEVHNAK TKPREEQYNSTYRVVSVLTVLHQDWLNGKEYKCKVSNWALPA PISKTISKAKGQPREPQVYTLPPSREEMTKNQVSLTCLVKGFYP SDIAVEWESNGQPENNYKTTPPVLDSDGSFFLYSKLTVDKSR WQQGNVFSCSVMHGALHNHYTRKKLSLSPGK |
| SEQ ID NO 88 | constant region human HC IgG1m(f)- E430G-S440K- Y436K-K326W- E333S | ASTKGPSVFPLAPSSKSTSGGTAALGCLVKDYFPEPVTVSWNS GALTSGVHTFPAVLQSSGLYSLSSVVTVPSSSLGTQTYICNVN HKPSNTKVDKRVEPKSCDKTHTCPPCPAPELLGGPSVFLFPPK PKDTLMISRTPEVTCVVVDVSHEDPEVKFNWYVDGVEVHNAK TKPREEQYNSTYRVVSVLTVLHQDWLNGKEYKCKVSNWALPA PISKTISKAKGQPREPQVYTLPPSREEMTKNQVSLTCLVKGFYP SDIAVEWESNGQPENNYKTTPPVLDSDGSFFLYSKLTVDKSR WQQGNVFSCSVMHGALHNHKTQKKLSLSPGK |
| SEQ ID NO 89 | constant region human HC IgG2-E430G- K439E-Q438N | ASTKGPSVFPLAPCSRSTSESTAALGCLVKDYFPEPVTVSWNS GALTSGVHTFPAVLQSSGLYSLSSVVTVPSSNFGTQTYTCNVD HKPSNTKVDKTVERKCCVECPPCPAPPVAGPSVFLFPPKPKDT LMISRTPEVTCVVVDVSHEDPEVQFNWYVDGVEVHNAKTKPR EEQFNSTFRVVSVLTVVHQDWLNGKEYKCKVSNKGLPAPIEKT ISKTKGQPREPQVYTLPPSREEMTKNQVSLTCLVKGFYPSDIA VEWESNGQPENNYKTTPPMLDSDGSFFLYSKLTVDKSRWQQ GNVFSCSVMHGALHNHYTNESLSLSPGK |
| SEQ ID NO 90 | constant region human HC IgG2-E430G- S440K-Q438R | ASTKGPSVFPLAPCSRSTSESTAALGCLVKDYFPEPVTVSWNS GALTSGVHTFPAVLQSSGLYSLSSVVTVPSSNFGTQTYTCNVD HKPSNTKVDKTVERKCCVECPPCPAPPVAGPSVFLFPPKPKDT LMISRTPEVTCVVVDVSHEDPEVQFNWYVDGVEVHNAKTKPR EEQFNSTFRVVSVLTVVHQDWLNGKEYKCKVSNKGLPAPIEKT ISKTKGQPREPQVYTLPPSREEMTKNQVSLTCLVKGFYPSDIA VEWESNGQPENNYKTTPPMLDSDGSFFLYSKLTVDKSRWQQ GNVFSCSVMHGALHNHYTRKKLSLSPGK |
| SEQ ID NO 91 | constant region human HC IgG2-E430G- S440K-Y436K | ASTKGPSVFPLAPCSRSTSESTAALGCLVKDYFPEPVTVSWNS GALTSGVHTFPAVLQSSGLYSLSSVVTVPSSNFGTQTYTCNVD HKPSNTKVDKTVERKCCVECPPCPAPPVAGPSVFLFPPKPKDT LMISRTPEVTCVVVDVSHEDPEVQFNWYVDGVEVHNAKTKPR EEQFNSTFRVVSVLTVVHQDWLNGKEYKCKVSNKGLPAPIEKT ISKTKGQPREPQVYTLPPSREEMTKNQVSLTCLVKGFYPSDIA VEWESNGQPENNYKTTPPMLDSDGSFFLYSKLTVDKSRWQQ GNVFSCSVMHGALHNHKTQKKLSLSPGK |
| SEQ ID NO 92 | constant region human HC IgG2-E430G- K439E-Y436N | ASTKGPSVFPLAPCSRSTSESTAALGCLVKDYFPEPVTVSWNS GALTSGVHTFPAVLQSSGLYSLSSVVTVPSSNFGTQTYTCNVD HKPSNTKVDKTVERKCCVECPPCPAPPVAGPSVFLFPPKPKDT LMISRTPEVTCVVVDVSHEDPEVQFNWYVDGVEVHNAKTKPR EEQFNSTFRVVSVLTVVHQDWLNGKEYKCKVSNKGLPAPIEKT ISKTKGQPREPQVYTLPPSREEMTKNQVSLTCLVKGFYPSDIA VEWESNGQPENNYKTTPPMLDSDGSFFLYSKLTVDKSRWQQ GNVFSCSVMHGALHNHNTQESLSLSPGK |
| SEQ ID NO 93 | constant region human HC IgG4-S228P- E430G-K439E- Q438N | ASTKGPSVFPLAPCSRSTSESTAALGCLVKDYFPEPVTVSWNS GALTSGVHTFPAVLQSSGLYSLSSVVTVPSSSLGTKTYTCNVD HKPSNTKVDKRVESKYGPPCPPCPAPEFLGGPSVFLFPPKPK DTLMISRTPEVTCVVVDVSQEDPEVQFNWYVDGVEVHNAKTK PREEQFNSTYRVVSVLTVLHQDWLNGKEYKCKVSNKGLPSSIE KTISKAKGQPREPQVYTLPPSQEEMTKNQVSLTCLVKGFYPSD IAVEWESNGQPENNYKTTPPVLDSDGSFFLYSRLTVDKSRWQ EGNVFSCSVMHGALHNHYTNESLSLSLGK |
| SEQ ID NO 94 | constant region human HC IgG4-S228P- E430G-S440K- Q438R | ASTKGPSVFPLAPCSRSTSESTAALGCLVKDYFPEPVTVSWNS GALTSGVHTFPAVLQSSGLYSLSSVVTVPSSSLGTKTYTCNVD HKPSNTKVDKRVESKYGPPCPPCPAPEFLGGPSVFLFPPKPK DTLMISRTPEVTCVVVDVSQEDPEVQFNWYVDGVEVHNAKTK PREEQFNSTYRVVSVLTVLHQDWLNGKEYKCKVSNKGLPSSIE KTISKAKGQPREPQVYTLPPSQEEMTKNQVSLTCLVKGFYPSD IAVEWESNGQPENNYKTTPPVLDSDGSFFLYSRLTVDKSRWQ EGNVFSCSVMHGALHNHYTRKKLSLSLGK |

TABLE 1-continued

| SEQUENCE LIST | | |
|---|---|---|
| SEQ ID NO | Name | Sequence |

SEQ ID NO 95    constant region human HC IgG4-S228P-E430G-S440K-Y436K

ASTKGPSVFPLAPCSRSTSESTAALGCLVKDYFPEPVTVSWNS
GALTSGVHTFPAVLQSSGLYSLSSVVTVPSSSLGTKTYTCNVD
HKPSNTKVDKRVESKYGPPCPPCPAPEFLGGPSVFLFPPKPK
DTLMISRTPEVTCVVVDVSQEDPEVQFNWYVDGVEVHNAKTK
PREEQFNSTYRVVSVLTVLHQDWLNGKEYKCKVSNKGLPSSIE
KTISKAKGQPREPQVYTLPPSQEEMTKNQVSLTCLVKGFYPSD
IAVEWESNGQPENNYKTTPPVLDSDGSFFLYSRLTVDKSRWQ
EGNVFSCSVMHGALHNHKTQKKLSLSLGK

SEQ ID NO 96    constant region human HC IgG4-S228P-E430G-K439E-Y436N

ASTKGPSVFPLAPCSRSTSESTAALGCLVKDYFPEPVTVSWNS
GALTSGVHTFPAVLQSSGLYSLSSVVTVPSSSLGTKTYTCNVD
HKPSNTKVDKRVESKYGPPCPPCPAPEFLGGPSVFLFPPKPK
DTLMISRTPEVTCVVVDVSQEDPEVQFNWYVDGVEVHNAKTK
PREEQFNSTYRVVSVLTVLHQDWLNGKEYKCKVSNKGLPSSIE
KTISKAKGQPREPQVYTLPPSQEEMTKNQVSLTCLVKGFYPSD
IAVEWESNGQPENNYKTTPPVLDSDGSFFLYSRLTVDKSRWQ
EGNVFSCSVMHGALHNHNTQESLSLSLGK

SEQ ID NO 97    constant region human HC IgG1m(f)-I253G-E430G

ASTKGPSVFPLAPSSKSTSGGTAALGCLVKDYFPEPVTVSWNS
GALTSGVHTFPAVLQSSGLYSLSSVVTVPSSSLGTQTYICNVN
HKPSNTKVDKRVEPKSCDKTHTCPPCPAPELLGGPSVFLFPPK
PKDTLMGSRTPEVTCVVVDVSHEDPEVKFNWYVDGVEVHNAK
TKPREEQYNSTYRVVSVLTVLHQDWLNGKEYKCKVSNKALPA
PIEKTISKAKGQPREPQVYTLPPSREEMTKNQVSLTCLVKGFYP
SDIAVEWESNGQPENNYKTTPPVLDSDGSFFLYSKLTVDKSR
WQQGNVFSCSVMHGALHNHYTQKSLSLSPGK

SEQ ID NO 98    constant region human HC IgG1m(f)-I253K-E430G

ASTKGPSVFPLAPSSKSTSGGTAALGCLVKDYFPEPVTVSWNS
GALTSGVHTFPAVLQSSGLYSLSSVVTVPSSSLGTQTYICNVN
HKPSNTKVDKRVEPKSCDKTHTCPPCPAPELLGGPSVFLFPPK
PKDTLMKSRTPEVTCVVVDVSHEDPEVKFNWYVDGVEVHNAK
TKPREEQYNSTYRVVSVLTVLHQDWLNGKEYKCKVSNKALPA
PIEKTISKAKGQPREPQVYTLPPSREEMTKNQVSLTCLVKGFYP
SDIAVEWESNGQPENNYKTTPPVLDSDGSFFLYSKLTVDKSR
WQQGNVFSCSVMHGALHNHYTQKSLSLSPGK

SEQ ID NO 99    constant region human HC IgG1m(f)-I253R-E430G

ASTKGPSVFPLAPSSKSTSGGTAALGCLVKDYFPEPVTVSWNS
GALTSGVHTFPAVLQSSGLYSLSSVVTVPSSSLGTQTYICNVN
HKPSNTKVDKRVEPKSCDKTHTCPPCPAPELLGGPSVFLFPPK
PKDTLMRSRTPEVTCVVVDVSHEDPEVKFNWYVDGVEVHNAK
TKPREEQYNSTYRVVSVLTVLHQDWLNGKEYKCKVSNKALPA
PIEKTISKAKGQPREPQVYTLPPSREEMTKNQVSLTCLVKGFYP
SDIAVEWESNGQPENNYKTTPPVLDSDGSFFLYSKLTVDKSR
WQQGNVFSCSVMHGALHNHYTQKSLSLSPGK

SEQ ID NO 100    constant region human HC IgG1m(f)-H310D-E430G

ASTKGPSVFPLAPSSKSTSGGTAALGCLVKDYFPEPVTVSWNS
GALTSGVHTFPAVLQSSGLYSLSSVVTVPSSSLGTQTYICNVN
HKPSNTKVDKRVEPKSCDKTHTCPPCPAPELLGGPSVFLFPPK
PKDTLMISRTPEVTCVVVDVSHEDPEVKFNWYVDGVEVHNAK
TKPREEQYNSTYRVVSVLTVLDQDWLNGKEYKCKVSNKALPA
PIEKTISKAKGQPREPQVYTLPPSREEMTKNQVSLTCLVKGFYP
SDIAVEWESNGQPENNYKTTPPVLDSDGSFFLYSKLTVDKSR
WQQGNVFSCSVMHGALHNHYTQKSLSLSPGK

SEQ ID NO 101    constant region human HC IgG1m(f)-H310R-E430G

ASTKGPSVFPLAPSSKSTSGGTAALGCLVKDYFPEPVTVSWNS
GALTSGVHTFPAVLQSSGLYSLSSVVTVPSSSLGTQTYICNVN
HKPSNTKVDKRVEPKSCDKTHTCPPCPAPELLGGPSVFLFPPK
PKDTLMISRTPEVTCVVVDVSHEDPEVKFNWYVDGVEVHNAK
TKPREEQYNSTYRVVSVLTVLRQDWLNGKEYKCKVSNKALPA
PIEKTISKAKGQPREPQVYTLPPSREEMTKNQVSLTCLVKGFYP
SDIAVEWESNGQPENNYKTTPPVLDSDGSFFLYSKLTVDKSR
WQQGNVFSCSVMHGALHNHYTQKSLSLSPGK

SEQ ID NO 102    constant region human HC IgG1m(f)-I253G-E430G-K439E

ASTKGPSVFPLAPSSKSTSGGTAALGCLVKDYFPEPVTVSWNS
GALTSGVHTFPAVLQSSGLYSLSSVVTVPSSSLGTQTYICNVN
HKPSNTKVDKRVEPKSCDKTHTCPPCPAPELLGGPSVFLFPPK
PKDTLMGSRTPEVTCVVVDVSHEDPEVKFNWYVDGVEVHNAK
TKPREEQYNSTYRVVSVLTVLHQDWLNGKEYKCKVSNKALPA
PIEKTISKAKGQPREPQVYTLPPSREEMTKNQVSLTCLVKGFYP
SDIAVEWESNGQPENNYKTTPPVLDSDGSFFLYSKLTVDKSR
WQQGNVFSCSVMHGALHNHYTQESLSLSPGK

TABLE 1-continued

| SEQUENCE LIST | | |
|---|---|---|
| SEQ ID NO | Name | Sequence |

| SEQ ID NO 103 | constant region human HC IgG1m(f)-I253K-E430G-S440K | ASTKGPSVFPLAPSSKSTSGGTAALGCLVKDYFPEPVTVSWNS GALTSGVHTFPAVLQSSGLYSLSSVVTVPSSSLGTQTYICNVN HKPSNTKVDKRVEPKSCDKTHTCPPCPAPELLGGPSVFLFPPK PKDTLMKSRTPEVTCVVVDVSHEDPEVKFNWYVDGVEVHNAK TKPREEQYNSTYRVVSVLTVLHQDWLNGKEYKCKVSNKALPA PIEKTISKAKGQPREPQVYTLPPSREEMTKNQVSLTCLVKGFYP SDIAVEWESNGQPENNYKTTPPVLDSDGSFFLYSKLTVDKSR WQQGNVFSCSVMHGALHNHYTQKKLSLSPGK |
| SEQ ID NO 104 | constant region human HC IgG1m(f)-I253R-E430G-S440K | ASTKGPSVFPLAPSSKSTSGGTAALGCLVKDYFPEPVTVSWNS GALTSGVHTFPAVLQSSGLYSLSSVVTVPSSSLGTQTYICNVN HKPSNTKVDKRVEPKSCDKTHTCPPCPAPELLGGPSVFLFPPK PKDTLMRSRTPEVTCVVVDVSHEDPEVKFNWYVDGVEVHNAK TKPREEQYNSTYRVVSVLTVLHQDWLNGKEYKCKVSNKALPA PIEKTISKAKGQPREPQVYTLPPSREEMTKNQVSLTCLVKGFYP SDIAVEWESNGQPENNYKTTPPVLDSDGSFFLYSKLTVDKSR WQQGNVFSCSVMHGALHNHYTQKKLSLSPGK |
| SEQ ID NO 105 | constant region human HC IgG1m(f)-H310D-E430G-K439E | ASTKGPSVFPLAPSSKSTSGGTAALGCLVKDYFPEPVTVSWNS GALTSGVHTFPAVLQSSGLYSLSSVVTVPSSSLGTQTYICNVN HKPSNTKVDKRVEPKSCDKTHTCPPCPAPELLGGPSVFLFPPK PKDTLMISRTPEVTCVVVDVSHEDPEVKFNWYVDGVEVHNAK TKPREEQYNSTYRVVSVLTVLDQDWLNGKEYKCKVSNKALPA PIEKTISKAKGQPREPQVYTLPPSREEMTKNQVSLTCLVKGFYP SDIAVEWESNGQPENNYKTTPPVLDSDGSFFLYSKLTVDKSR WQQGNVFSCSVMHGALHNHYTQESLSLSPGK |
| SEQ ID NO 106 | constant region human HC IgG1m(f)-H310R-E430G-S440K | ASTKGPSVFPLAPSSKSTSGGTAALGCLVKDYFPEPVTVSWNS GALTSGVHTFPAVLQSSGLYSLSSVVTVPSSSLGTQTYICNVN HKPSNTKVDKRVEPKSCDKTHTCPPCPAPELLGGPSVFLFPPK PKDTLMISRTPEVTCVVVDVSHEDPEVKFNWYVDGVEVHNAK TKPREEQYNSTYRVVSVLTVLRQDWLNGKEYKCKVSNKALPA PIEKTISKAKGQPREPQVYTLPPSREEMTKNQVSLTCLVKGFYP SDIAVEWESNGQPENNYKTTPPVLDSDGSFFLYSKLTVDKSR WQQGNVFSCSVMHGALHNHYTQKKLSLSPGK |
| SEQ ID NO 107 | constant region human HC IgG1m(f)-K248E-T437R-K439E-Y436N | ASTKGPSVFPLAPSSKSTSGGTAALGCLVKDYFPEPVTVSWNS GALTSGVHTFPAVLQSSGLYSLSSVVTVPSSSLGTQTYICNVN HKPSNTKVDKRVEPKSCDKTHTCPPCPAPELLGGPSVFLFPPK PEDTLMISRTPEVTCVVVDVSHEDPEVKFNWYVDGVEVHNAK TKPREEQYNSTYRVVSVLTVLHQDWLNGKEYKCKVSNKALPA PIEKTISKAKGQPREPQVYTLPPSREEMTKNQVSLTCLVKGFYP SDIAVEWESNGQPENNYKTTPPVLDSDGSFFLYSKLTVDKSR WQQGNVFSCSVMHEALHNHNRQ ESLSLSPGK |
| SEQ ID NO 108 | constant region human HC IgG1m(f)-K248E-T437R-K439E-Q438N | ASTKGPSVFPLAPSSKSTSGGTAALGCLVKDYFPEPVTVSWNS GALTSGVHTFPAVLQSSGLYSLSSVVTVPSSSLGTQTYICNVN HKPSNTKVDKRVEPKSCDKTHTCPPCPAPELLGGPSVFLFPPK PEDTLMISRTPEVTCVVVDVSHEDPEVKFNWYVDGVEVHNAK TKPREEQYNSTYRVVSVLTVLHQDWLNGKEYKCKVSNKALPA PIEKTISKAKGQPREPQVYTLPPSREEMTKNQVSLTCLVKGFYP SDIAVEWESNGQPENNYKTTPPVLDSDGSFFLYSKLTVDKSR WQQGNVFSCSVMHEALHNHYRNESLSLSPGK |
| SEQ ID NO 109 | constant region human HC IgG1m(f)-K248E-T437R-S440K-Y436K | ASTKGPSVFPLAPSSKSTSGGTAALGCLVKDYFPEPVTVSWNS GALTSGVHTFPAVLQSSGLYSLSSVVTVPSSSLGTQTYICNVN HKPSNTKVDKRVEPKSCDKTHTCPPCPAPELLGGPSVFLFPPK PEDTLMISRTPEVTCVVVDVSHEDPEVKFNWYVDGVEVHNAK TKPREEQYNSTYRVVSVLTVLHQDWLNGKEYKCKVSNKALPA PIEKTISKAKGQPREPQVYTLPPSREEMTKNQVSLTCLVKGFYP SDIAVEWESNGQPENNYKTTPPVLDSDGSFFLYSKLTVDKSR WQQGNVFSCSVMHEALHNHKRQKKLSLSPGK |
| SEQ ID NO 110 | constant region human HC IgG1m(f)-K248E-T437R-S440K-Q438R | ASTKGPSVFPLAPSSKSTSGGTAALGCLVKDYFPEPVTVSWNS GALTSGVHTFPAVLQSSGLYSLSSVVTVPSSSLGTQTYICNVN HKPSNTKVDKRVEPKSCDKTHTCPPCPAPELLGGPSVFLFPPK PEDTLMISRTPEVTCVVVDVSHEDPEVKFNWYVDGVEVHNAK TKPREEQYNSTYRVVSVLTVLHQDWLNGKEYKCKVSNKALPA PIEKTISKAKGQPREPQVYTLPPSREEMTKNQVSLTCLVKGFYP SDIAVEWESNGQPENNYKTTPPVLDSDGSFFLYSKLTVDKSR WQQGNVFSCSVMHEALHNHYRRKKLSLSPGK |

TABLE 1-continued

| | | | |
|---|---|---|---|

SEQUENCE LIST

| SEQ ID NO | Name | Sequence |
|---|---|---|
| SEQ ID NO 111 | FcRnhsECDHis | AESHLSLLYHLTAVSSPAPGTPAFWVSGWLGPQQYLSYNSLR<br>GEAEPCGAWVWENQVSWYWEKETTDLRIKEKLFLEAFKALGG<br>KGPYTLQGLLGCELGPDNTSVPTAKFALNGEEFMNFDLKQGT<br>WGGDWPEALAISQRWQQQDKAANKELTFLLFSCPHRLREHLE<br>RGRGNLEWKEPPSMRLKARPSSPGFSVLTCSAFSFYPPELQL<br>RFLRNGLAAGTGQGDFGPNSDGSFHASSSLTVKSGDEHHYC<br>CIVQHAGLAQPLRVELESPAKSSHHHHHH |
| SEQ ID NO 112 | B2M | IQRTPKIQVYSRHPAENGKSNFLNCYVSGFHPSDIEVDLLKNGE<br>RIEKVEHSDLSFSKDWSFYLLYYTEFTPTEKDEYACRVNHVTLS<br>QPKIVKWDRDM |
| SEQ ID NO 113 | diFCGR2A-131H-HisBAP | METQMSQNVCPRNLWLLQPLTVLLLLASADSQAAAPPKAVLKL<br>EPPWINVLQEDSVTLTCQGARSPESDSIQWFHNGNLIPTHTQP<br>SYRFKANNNDSGEYTCQTGQTSLSDPVHLTVLSEWLVLQTPH<br>LEFQEGETIMLRCHSWKDKPLVKVTFFQNGKSQKFSHLDPTFS<br>IPQANHSHSGDYHCIGNIGYTLFSSKPVTITVQVPSMGSSSPV<br>APPKAVLKLEPPWINVLQEDSVTLTCQGARSPESDSIQWFHNG<br>NLIPTHTQPSYRFKANNNDSGEYTCQTGQTSLSDPVHLTVLSE<br>WLVLQTPHLEFQEGETIMLRCHSWKDKPLVKVTFFQNGKSQK<br>FSHLDPIFSIPQANHSHSGDYHCIGNIGYTLFSSKPVTITVQVP<br>SMGPGSSSHHHHHHPGGGLNDIFEAQKIEWHE |
| SEQ ID NO 114 | diFCGR2A-131R-HisBAP | MVLSLLYLLTALPGILSAAPPKAVLKLEPPWINVLQEDSVTLTCQ<br>GARSPESDSIQWFHNGNLIPTHTQPSYRFKANNNDSGEYTCQ<br>TGQTSLSDPVHLTVLSEWLVLQTPHLEFQEGETIMLRCHSWKD<br>KPLVKVIFFQNGKSQKFSRLDPIFSIPQANHSHSGDYHCIGNI<br>GYTLFSSKPVTITVQVPSMGSSSPAAPPKAVLKLEPPWINVLQE<br>DSVTLTCQGARSPESDSIQWFHNGNLIPTHTQPSYRFKANNND<br>SGEYTCQTGQTSLSDPVHLTVLSEWLVLQTPHLEFQEGETIML<br>RCHSWKDKPLVKVTFFQNGKSQKFSRLDPTFSIPQANHSHSG<br>DYHCIGNIGYTLFSSKPVTITVQVPSMGSSSPGSSSHHHHHHP<br>GGGLNDIFEAQKIEWHE |
| SEQ ID NO 115 | diFCGR2B-HisBAP | MVLSLLYLLTALPGILSAAPPKAVLKLEPQWINVLQEDSVTLTCR<br>GTHSPESDSIQWFHNGNLIPTHTQPSYRFKANNNDSGEYTCQ<br>TGQTSLSDPVHLTVLSEWLVLQTPHLEFQEGETIVLRCHSWKD<br>KPLVKVIFFQNGKSKKFSRSDPNFSIPQANHSHSGDYHCIGNI<br>GYTLYSSKPVTITVQAPSSSPMGPAAPPKAVLKLEPQWINVLQ<br>EDSVTLTCRGTHSPESDSIQWFHNGNLIPTHTQPSYRFKANNN<br>DSGEYTCQTGQTSLSDPVHLTVLSEWLVLQTPHLEFQEGETIV<br>LRCHSWKDKPLVKVTFFQNGKSKKFSRSDPNFSIPQANHSHS<br>GDYHCIGNIGYTLYSSKPVTITVQAPSSSPMGPGSSSHHHHH<br>HPGGGLNDIFEAQKIEWHE |
| SEQ ID NO 116 | diFCGR3A-158F-HisBAP | MVLSLLYLLTALPGISTEDLPKAVVFLEPQWYRVLEKDSVTLKC<br>QGAYSPEDNSTQWFHNESLISSQASSYFIDAATVDDSGEYRC<br>QTNLSTLSDPVQLEVHIGWLLLQAPRWVFKEEDPIHLRCHSWK<br>NTALHKVTYLQNGKGRKYFHHNSDFYIPKATLKDSGSYFCRGL<br>FGSKNVSSETVNITITQGPSMGSSSPSEDLPKAVVFLEPQVVYR<br>VLEKDSVTLKCQGAYSPEDNSTQWFHNESLISSQASSYFIDAA<br>TVDDSGEYRCQTNLSTLSDPVQLEVHIGWLLLQAPRWVFKEE<br>DPIHLRCHSWKNTALHKVTYLQNGKGRKYFHHNSDFYIPKATL<br>KDSGSYFCRGLFGSKNVSSETVNITITQGPSMGSSSPGPGSSS<br>HHHHHHPGGGLNDIFEAQKIEWHE |
| SEQ ID NO 117 | diFCGR3A-158V-HisBAP | MVLSLLYLLTALPGISTEDLPKAVVFLEPQWYRVLEKDSVTLKC<br>QGAYSPEDNSTQWFHNESLISSQASSYFIDAATVDDSGEYRC<br>QTNLSTLSDPVQLEVHIGWLLLQAPRWVFKEEDPIHLRCHSWK<br>NTALHKVTYLQNGKGRKYFHHNSDFYIPKATLKDSGSYFCRGL<br>VGSKNVSSETVNITITQGPSMGSSSPSEDLPKAVVFLEPQWYR<br>VLEKDSVTLKCQGAYSPEDNSTQWFHNESLISSQASSYFIDAA<br>TVDDSGEYRCQTNLSTLSDPVQLEVHIGWLLLQAPRWVFKEE<br>DPIHLRCHSWKNTALHKVTYLQNGKGRKYFHHNSDFYIPKATL<br>KDSGSYFCRGLVGSKNVSSETVNITITQGPSMGSSSPGPGSSS<br>HHHHHHPGGGLNDIFEAQKIEWHE |

TABLE 1-continued

| SEQUENCE LIST | | |
|---|---|---|
| SEQ ID NO | Name | Sequence |
| SEQ ID NO 118 | FCGR1A-ECDHis | MWWRLWWLLLLLLLLWPMVWAQVDTTKAVITLQPPWVSVFQ EETVTLHCEVLHLPGSSSTQWFLNGTATQTSTPSYRITSASVN DSGEYRCQRGLSGRSDPIQLEIHRGWLLLQVSSRVFTEGEPLA LRCHAWKDKLVYNVLYYRNGKAFKFFHWNSNLTILKTNISHNG TYHCSGMGKHRYTSAGISVTVKELFPAPVLNASVTSPLLEGNL VTLSCETKLLLQRPGLQLYFSFYMGSKTLRGRNTSSEYQILTAR REDSGLYWCEAATEDGNVLKRSPELELQVLGLQLPTPVHHHH HHHH |

TABLE 2 self-oligomerization inhibiting substitutions*

| First Fc-region containing polypeptide | Second Fc-region containing polypeptide |
|---|---|
| K439E | S440K |
| S440K | K439E |
| I253G | H310R |
| I253K | H310D |
| I253R | H310D |
| H310R | I253G |
| H310D | I253K |
| H310D | I253R |
| Y436N | Y436K |
| Y436N | Q438N |
| Y436N | Q438R |
| Y436K | Y436N |
| Y436K | Q438N |
| Y436K | Q438R |
| Q438N | Y436N |
| Q438N | Y436K |
| Q438N | Q438R |
| Q438R | Y436N |
| Q438R | Y436K |
| Q438R | Q438N |
| I253G-K439E | H310R-S440K |
| H310D-K439E | I253R-S440K |
| H310D-K439E | I253K-S440K |
| Y436N-K439E | Y436K-S440K |
| Y436N-K439E | Q438N-S440K |
| Y436N-K439E | Q438R-S440K |
| Y436K-K439E | Y436N-S440K |
| Y436K-K439E | Q438N-S440K |
| Y436K-K439E | Q438R-S440K |
| Q438N-K439E | Y436N-S440K |
| Q438N-K439E | Y436K-S440K |
| Q438N-K439E | Q438R-S440K |
| Q438R-K439E | Y436N-S440K |
| Q438R-K439E | Y436K-S440K |
| Q438R-K439E | Q438N-S440K |

Table 2*each column show self-oligomerization inhibiting substitutions, each row show Complementary self- self-oligomerization inhibiting

TABLE 3

Substitutions that were tested in examples 5-23.

| Substitution | Purpose |
|---|---|
| G237A | Inhibition of FcGammaR binding |
| K248E | Stimulation of self-oligomerization |
| I253G | Inhibition of self-oligomerization |
| I253K | Inhibition of self-oligomerization |
| I253R | Inhibition of self-oligomerization |
| H310D | Inhibition of self-oligomerization |
| H310R | Inhibition of self-oligomerization |
| K326W | Stimulation of C1q binding |
| E333S | Stimulation of C1q binding |
| E345K | Stimulation of self-oligomerization |

TABLE 3-continued

Substitutions that were tested in examples 5-23.

| Substitution | Purpose |
|---|---|
| E345R | Stimulation of self-oligomerization |
| E430G | Stimulation of self-oligomerization |
| Y436N | Inhibition of self-oligomerization |
| Y436K | Inhibition of self-oligomerization |
| T437R | Stimulation of self-oligomerization |
| Q438N | Inhibition of self-oligomerization |
| Q438R | Inhibition of self-oligomerization |
| K439E | Inhibition of self-oligomerization |
| S440K | Inhibition of self-oligomerization |

EXAMPLES

Example 1: Antibody Generation, Production and Purification

Expression Constructs for Antibodies

For the expression of human and humanized antibodies used herein, variable heavy (VH) chain and variable light (VL) chain sequences were prepared by gene synthesis (GeneArt Gene Synthesis; ThermoFisher Scientific, Germany) and cloned in pcDNA3.3 expression vectors (ThermoFisher Scientific, US) containing a constant region of a human IgG heavy chain (HC) (constant region human IgG1m(f) HC: SEQ ID NO 22; constant region human IgG2 HC: SEQ ID NO 31; constant region human IgG3 HC: SEQ ID NO 32; or constant region human IgG4 HC: SEQ ID NO 33) and or the constant region of the human kappa light chain (LC): SEQ ID NO 34. Desired mutations were introduced by gene synthesis. CD20 antibody variants in this application have VH and VL sequences derived from previously described CD20 antibodies (WO2004/035607) IgG1-CD20-7D8 (VH: SEQ ID NO 35; VL: SEQ ID NO 39) and IgG1-CD20-11B8 (VH: SEQ ID NO 8; VL: SEQ ID NO 12). CD52 antibody variants in this application have VH and VL sequences derived from previously described CD52 antibody CAMPATH-1H (alemtuzumab; Crowe et al., 1992 Clin Exp Immunol. 87(1):105-110; VH: SEQ ID NO 1; VL: SEQ ID NO 5) CD37 antibody variants in this application have VH and VL sequences derived from previously described CD37 antibody IgG1-CD37-37.3 (WO2011/112978; VH: SEQ ID NO 42; VL: SEQ ID NO 46). DR5 antibody variants in this application have VH and VL sequences derived from previously described DR5 antibody DR5-01-G56T (WO 2017/093447; VH: SEQ ID NO 49; VL: SEQ ID NO 53) and DR5-05 (WO2014/009358; VH: SEQ ID NO 56; VL: SEQ ID NO 60). The human IgG1 antibody b12, an HIV gp120-specific antibody was used as a negative control in some experiments (Barbas et al., J Mol Biol. 1993 Apr. 5; 230(3):812-23; VH: SEQ ID NO 15; VL: SEQ ID NO 19).

Transient Expression

Antibodies were expressed as IgG1K. Plasmid DNA mixtures encoding both heavy and light chains of antibodies were transiently transfected in Expi293F cells (Gibco, Cat #A14635) using 293fectin (Life Technologies) essentially as described by Vink et al. (Vink et al., Methods, 65 (1), 5-10 2014). Antibody concentrations in the supernatants were measured by absorbance at 280 nm. Antibodies were either directly used in in vitro assays, or purified as described below.

Purification and Analysis of Proteins

Antibodies were purified by protein A affinity chromatography. Culture supernatants were filtered over a 0.20 µM dead-end filter and loaded on 5 mL MabSelect SuRe columns (GE Healthcare), washed and eluted with 0.02 M sodium citrate-NaOH, pH 3. The eluates were loaded on a HiPrep Desalting column (GE Healthcare) immediately after purification and the antibodies were buffer exchanged into 12.6 mM $NaH_2PO_4$, 140 mM NaCl, pH 7.4 buffer (B.Braun or Thermo Fisher). After buffer exchange, samples were sterile filtered over 0.2 µm dead-end filters. Purified proteins were analyzed by a number of bioanalytical assays including capillary electrophoresis on sodium dodecyl sulfate-polyacrylamide gels (CE-SDS) and high-performance size exclusion chromatography (HP-SEC). Concentration was measured by absorbance at 280 nm. Purified antibodies were stored at 2-8° C.

Example 2: CDC Activity of IgG1-Campath-E430G Variants with Mutations at Positions I253 or H310

We searched the Fc-Fc interface in the crystal structure of IgG1 antibody b12 (Protein Data Bank 1HZH; Ollman Sapphire et al, Science 2001, 293(5532):1155-1159) for intermolecular amino acid pairs that showed sterical proximity and side-chain orientations at opposite sides of the Fc-Fc interface. Mutation pairs were tested for complementarity in controlling intermolecular Fc-Fc interactions between cell-surface-target-bound antibodies, by interfering with the Fc-Fc interactions between the antibodies that have the same mutation, and rescuing Fc-Fc interactions by mixtures of two antibodies, each harboring one and the other mutation. The amino acid pair I253+H310 was selected for extensive mutagenesis and functional characterization. An antibody mutant library was generated based on the positions I253 and H310 by substituting isoleucine at position 253 and histidine at position 310 by any other amino acid except cysteine or proline, and introducing the mutations in IgG1-Campath-E430G (i.e. antibody Campath-1H containing heavy chain constant domain SEQ ID: 26, comprising the Fc-Fc interaction-enhancing Glu to Gly mutation at position 430 (WO2013004842)). The effects of the individual mutations on positions 253 and 310 and of all possible I253 and H310 mutation pairs on the CDC efficacy of the respective IgG1-Campath-E430G variants and mixtures thereof were subsequently tested in an in vitro CDC assay using Wien 133 cells (kindly provided by Dr. Geoff Hale, BioAnaLab Limited, Oxford, UK). Cells were harvested and resuspended in medium [RPMI (Lonza, Cat #BE12-115F) with 0.2% bovine serum albumin (BSA; Roche Cat #10735086001)]. 5,000 cells per well were incubated with concentration series of the single antibodies and antibody combinations (15.6-2000 ng/mL final antibody concentrations in 2-fold dilutions; dilutions of supernatants of transient transfections as described in Example 1) in the presence of 5% normal human serum (NHS; Sanquin, Ref #M0008) as a source of human complement. Simultaneously, TO-PRO-3 iodide (ThermoFischer Scientific, CAT #T3605, 1 µM final concentration) was added as a cell viability marker and SYBR Green I (ThermoFischer Scientific, Cat #S7563; 12,500×diluted from original stock concentrate) was added to detect the presence of cells. Assay plates were incubated for one hour at room temperature and killing was calculated as the fraction of TO-PRO-3 iodide-positive cells (%) as determined by flow cytometry using a Celigo Imaging Cytometer (Brooks Life Science Systems).

Introduction of several tested I253 and H310 amino acid substitutions resulted in inhibition of CDC efficacy of IgG1-Campath-E430G, as represented by an increased EC50 value (summarized in FIG. 2; EC50 value of IgG1-Campath-E430G was <15 ng/µL). Most mixtures of IgG1-Campath-E430G variants each containing a mutation at either position 253 or 310, did not overcome the inhibition of CDC efficacy mediated by the single antibodies. However, an exception was the mutation pair I253G (Ile253→Gly)+H310R (His310→Arg), which each showed CDC inhibition when introduced and tested as single IgG1-Campath-E430G variants (containing the I253G or H310R mutation), but complete rescue of CDC efficacy when tested as a mixture of the two IgG1-Campath-E430G variants, each containing either I253G or H310R. Furthermore, for the mutation pairs I253K (Ile253→Lys)+H310D (His310→Asp), and I253R (Ile253→Arg)+H310D, CDC inhibition was observed for the single IgG1-Campath-E430G variants (containing the I253K, I253R or H310D mutation), and partial rescue of CDC efficacy by the mixture of the two IgG1-Campath-E430G variants with one containing the I253K or I253R mutation and the other H310D (FIG. 2).

Based on these results, it can be concluded that it is unpredictable which Fc mutations at positions I253 and H310 in human IgG1 antibodies with an E430G Fc-Fc-enhancing mutation create complementary mutation pairs that show inhibition of Fc-Fc interactions and inhibition of CDC efficacy by the single variants containing either a I253 or a H310 mutation, and rescue thereof by mixing the two variants, each containing one of the two complementary I253 and H310 mutations. Using the CDC assay with IgG1-Campath-E430G antibody variants on positions I253 and H310 on Wien 133 cells, I253G+H310R, I253K+H310D and I253R+H310D were identified as complementary mutation pairs that showed control of CDC activity of the antibody with the E430G Fc-Fc-enhancing mutation, i.e. inhibition of CDC efficacy by the single variants (I253G, I253K, H310D or H310R) and rescue by the complementary mixtures (I253G+H310R, I253K+H310D or I253R+H310D) thereof.

Example 3: CDC Activity of IgG1-Campath-E430G Variants with Mutations at Positions Y436 or Q438

Similar to the amino acid pair I253+H310 described in Example 2, also the amino acid pair Y436+Q438 was selected for extensive mutagenesis and functional characterization. An antibody mutant library was generated based on the positions Y436 and Q438 by substituting tyrosine at position 436 and glutamine at position 438 by any other amino acid except cysteine or proline in IgG1-Campath-E430G. The effects of the individual mutations on positions 436 and 438 and of all possible Y436 and Q438 mutation pairs on the CDC efficacy of the respective IgG1-Campath- E430G variants and mixtures thereof were subsequently tested in an in vitro CDC assay using Wien 133 cells as described in Example 2.

Introduction of several tested Y436 and Q438 amino acid substitutions resulted in inhibition of CDC efficacy of IgG1-Campath-E430G, as represented by an increased EC50 value (summarized in FIG. 3; EC50 value of IgG1-Campath-E430G was <15 ng/mL). Many mixtures of IgG1-Campath-E430G variants each containing a mutation at either position 436 or 438 did not overcome the inhibition of CDC efficacy mediated by the single antibodies. However, partial rescue of CDC efficacy was observed for mixtures of IgG1-Campath-E430G variants that brought together the mutation pairs Y436K+Q438G, Y436K+Q438H, Y436K+Q438K, Y436K+Q438N, Y436K+Q438R, Y436N+Q438G, Y436N+Q438H, Y436N+Q438K, Y436N+Q438N, Y436N+Q438R, Y436Q+Q438G, Y436Q+Q438H, Y436Q+Q438K, Y436Q+Q438N, Y436Q+Q438R, Y436R+Q438G, Y436R+Q438H, Y436R+Q438K, Y436R+Q438N, or Y436R+Q438R (FIG. 3).

Based on these results, it can be concluded that it is unpredictable which Fc mutations at positions Y436 and Q438 in human IgG1 antibodies with an E430G Fc-Fc-enhancing mutation will show inhibition of Fc-Fc interactions by the single mutants and whether a specific mixture of two variants could rescue it. Using the CDC assay with IgG1-Campath-E430G antibody variants on positions Y436 and Q438 on Wien 133 cells, the Y436K, Y436N, Y436Q, Y436R, Q438G, Q438H, Q438K, Q438N and Q438R mutations were identified that can inhibit Fc-Fc interactions and CDC activity of the antibody with the E430G Fc-Fc-enhancing mutation, and any mixture of one of these mutations at position 436 with one of these mutations at position 438 was identified as a complementary Y436;Q438 mutation pair that can rescue the inhibition of Fc-Fc interactions and CDC efficacy of the single mutants.

Example 4: CDC Activity of IgG1-Campath-E430G Variants with Mutations at Positions K439 or S440

Similar to the amino acid pairs I253+H310 (described in Example 2) and Y436+Q438 (described in Example 3), also the amino-acid pair K439+S440 was selected for extensive mutagenesis and functional characterization. An antibody mutant library was generated based on the positions K439 and S440 by substituting lysine at position 439 and serine at position 440 by any other amino acid except cysteine or proline in IgG1-Campath-E430G. The effects of the individual mutations on positions 439 and 440 and of all possible K439 and S440 mutation pairs on the CDC efficacy of the respective IgG1-Campath-E430G variants and mixtures thereof were subsequently tested in an in vitro CDC assay using Wien 133 cells as described in Example 2.

Introduction of several tested K439 and S440 amino acid substitutions resulted in inhibition of CDC efficacy of IgG1-Campath-E430G, as represented by an increased EC50 value (summarized in FIG. 4; EC50 value of IgG1-Campath-E430G was <15 ng/mL). Many mixtures of IgG1-Campath-E430G variants, each containing a mutation at either position 439 or 440, did not overcome the inhibition of CDC efficacy mediated by the single antibodies. Only for the mutation pairs in which S440K was combined with K439E, K439F K439I, K439Y, K439T, K439V or K439W, CDC inhibition was observed when introduced and tested as single IgG1-Campath-E430G variants, and rescue of CDC efficacy when tested as a mixture of the two IgG1-Campath- E430G variants, each containing either the S440K mutation or one of these K439 mutations (FIG. 4).

Based on these results, it can be concluded that it is unpredictable which Fc mutations at positions K439 and S440 in human IgG1 antibodies with an E430G Fc-Fc-enhancing mutation create complementary mutation pairs that show inhibition of Fc-Fc interactions and inhibition of CDC efficacy by the single variants containing one or the other K439 or S440 mutation, and rescue thereof by the mixture of the two, each containing one of the two complementary K439 and S440 mutations. Using the CDC assay with IgG1-Campath-E430G antibody variants on positions K439 and S440 on Wien 133 cells, K439E+S440K, K439F+S440K, K439I+S440K, K439Y+S440K, K439T+S440K, K439V+S440K and K439W+S440K were identified as complementary mutation pairs that showed control of CDC activity of the antibody with the E430G Fc-Fc-enhancing mutation, i.e. inhibition of CDC efficacy by the single variants and rescue by the complementary mixtures thereof.

Example 5: Validation of Complementary Mutation Pairs at Positions I253 and H310 of a Human IgG1-E430G Antibody The control of Fc-Fc interactions and CDC efficacy by the complementary I253+H310 mutation pairs, identified in the CDC assay described in Example 2, was validated in in vitro CDC assays with further concentration titration series of purified antibodies. $0.1 \times 10^6$ Wien 133 cells were pre-incubated in polystyrene round-bottom 96-well plates (Greiner bio-one Cat #650101) with concentration series of purified samples of IgG1-Campath-E430G variants (final concentration range 0.03-10.0 µg/mL in 3-fold dilution steps) in 80 µL culture medium (RPMI with 0.2% BSA) for 15 min on a shaker at room temperature. Next, 20 µL NHS was added as a source of complement (20% final NHS concentration) and incubated for 45 minutes at 37° C. The reaction was stopped by putting the plates on ice before pelleting the cells by centrifugation and replacing the supernatant by 30 µL of 1.67 µg/mL propidium iodide solution (PI; Sigma Aldrich, Zwijnaarde, The Netherlands). CDC efficacy was determined by the percentage PI-positive cells measured by flow cytometry using an Intellicyt iQue™ screener (Westburg). The data were analyzed using best-fit values of a non-linear dose-response fit using log-transformed concentrations in GraphPad PRISM 7.02 (GraphPad Software, San Diego, CA, USA). The percentage lysis was calculated as (number of PI-positive cells/total number of cells)×100%.

Introduction of I253G or H310R resulted in CDC inhibition for the single IgG1-Campath-E430G antibody variants containing either the I253G or H310R mutation, and complete rescue of CDC efficacy in the mixture thereof (FIG. 5A).

Figure 5B:
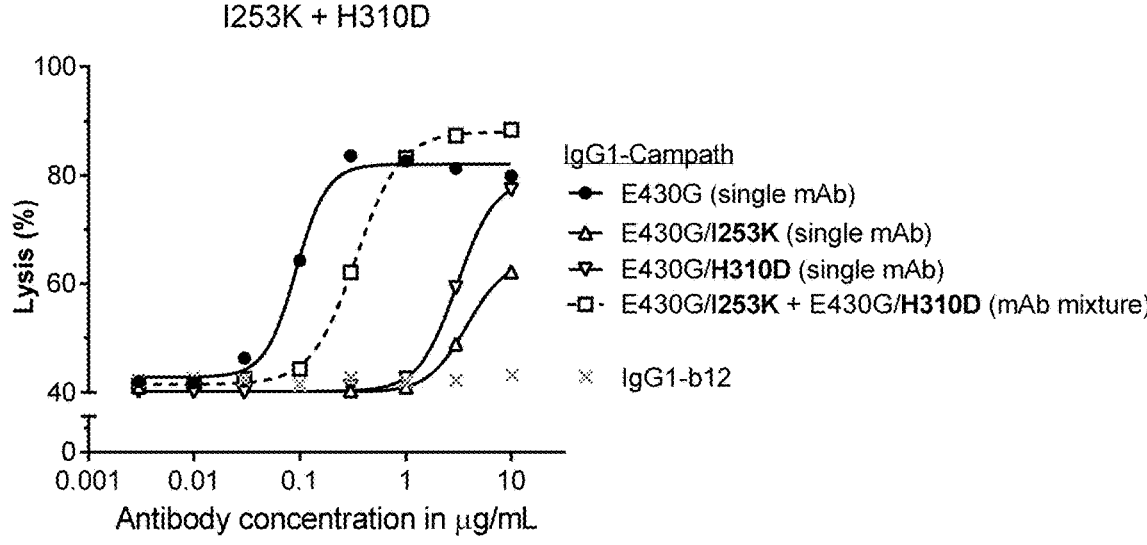
Figure 5C:
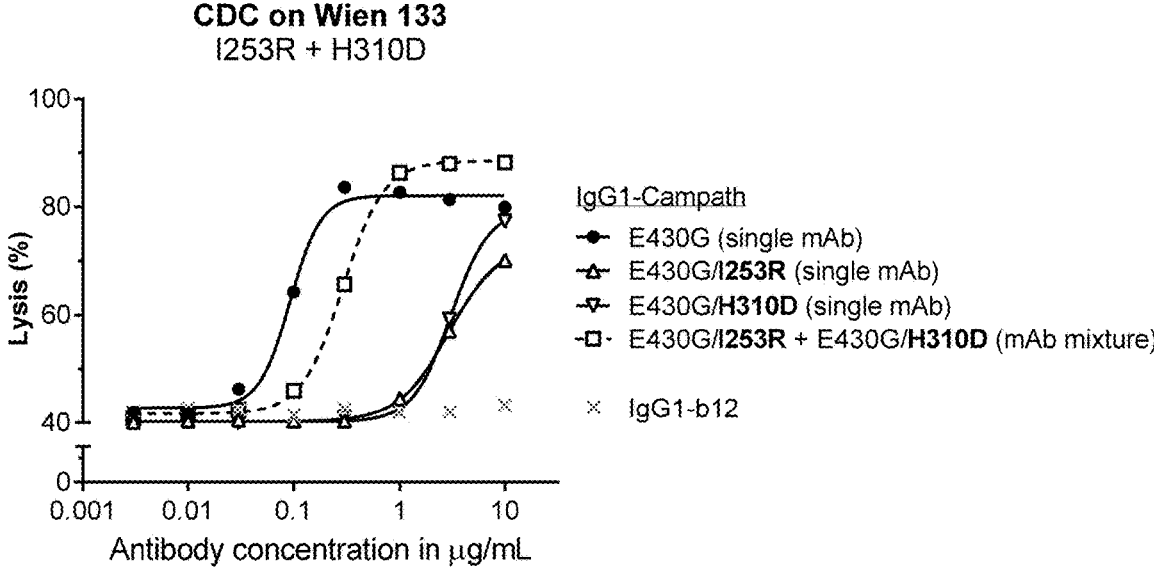

Introduction of I253K, I253R or H310D resulted in CDC inhibition for the single IgG1-Campath-E430G antibody variants containing either the I253K, I253R or H310D mutation, and partial rescue of CDC efficacy by the mixtures of two antibody variants that brought together the mutation pairs I253K+H310D (FIG. 5B) or I253R+H310D (FIG. 5C).

Together, these results confirmed that the introduction of the complementary mutation pairs I253G+H310R, I253K+H310D, or I253R+H310D identified in Example 2, can be used to control Fc-Fc interactions and CDC efficacy in mixtures of two human IgG1 antibodies with an Fc-Fc-enhancing background mutation, such as E430G.

Example 6: Combinations of Complementary Fc-Fc Inhibiting Mutation Pairs in Human IgG1

With the aim to further suppress the CDC activity of single antibody-agents while retaining high potency of the mixed antibody pairs, some of the Fc mutations that resulted in efficient inhibition of CDC efficacy in the CDC assays described in Example 2 and Example 3 were combined with the self-oligomerization inhibiting mutations K439E or S440K (Example 4; WO2013004842) in IgG1-Campath-E430G. The effect of these mutation combinations was tested in an in vitro CDC assay using Wien 133 cells as described in Example 5. The complementary mutation pairs I253G+H310R, I253K+H310D, I253R+H310D (identified in Example 2), Y436N+Q438R, and Q438N+Y436K (identified in Example 3) were pairwise combined with K439E and S440K, resulting in the Fc-Fc self-oligomerization inhibition double mutant pairs I253G/K439E+H310R/S440K, H310D/K439E+I253K/S440K, H310D/K439E+I253R/S440K, Y436N/K439E+Q438R/S440K, and Q438N/K439E+Y436K/S440K. Furthermore, also the following combinations of K439E+S440K with different Y436 or Q438 mutations (identified in Example 3) were tested in IgG1-Campath-E430G: Y436N/K439E (containing SEQ ID NO:81)+Y436K/S440K (containing SEQ ID NO: 80) and Q438N/K439E (containing SEQ ID NO: 74)+Q438R/S440K (containing SEQ ID NO: 77).

Introduction of all tested self-oligomerization inhibiting double mutations resulted in stronger inhibition of CDC than the IgG1-Campath-E430G antibody variants with only one self-oligomerization inhibiting mutation, K439E or S440K (FIG. 6). For the tested combinations of mutation pairs, complete rescue of CDC efficacy was observed for the I253G/K439E+H310R/S440K (FIG. 6A), H310D/K439E+I253K/S440K (FIG. 6B), H310D/K439E+I253R/S440K (FIG. 6C) and the Y436N/K439E+Q438R/S440K mutation pairs (FIG. 6D), which are thus complementary mutation pairs showing a large window to control CDC efficacy (difference between inhibited and rescued CDC efficacy of the single antibodies and combination thereof, respectively).

Figure 6E:
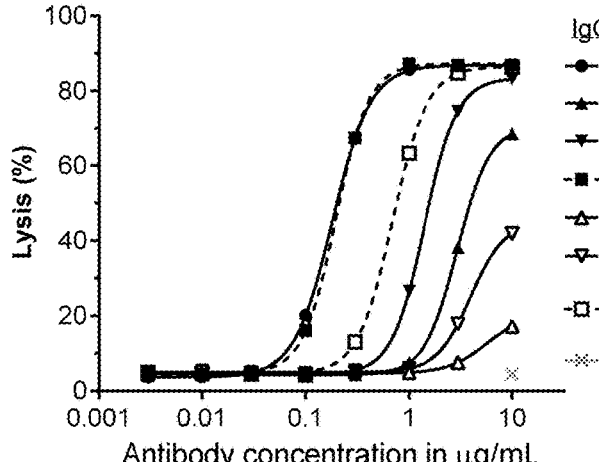
Figure 6F:
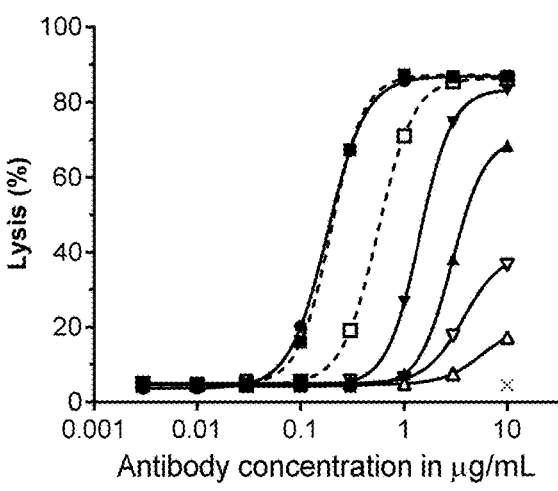

Partial recovery of CDC activity was observed for the mixture of IgG1-Campath-E430G antibody variants with the mixture of Q438N/K439E and Y436K/S440K (FIG. 6E) and, unexpectedly because not identified in previous examples, also the mixture Q438N/K439E+Q438R/S440K (FIG. 6F). These mixtures showed higher CDC efficacy than the individual antibodies, but lower CDC efficacy than the parental antibody IgG1-Campath-E430G without a self-oligomerization inhibiting mutation or the antibody combination of two IgG1-Campath-E430G variants with only one self-oligomerization inhibiting mutation pair, K439E+S440K (FIG. 6E/F).

Figure 6G:
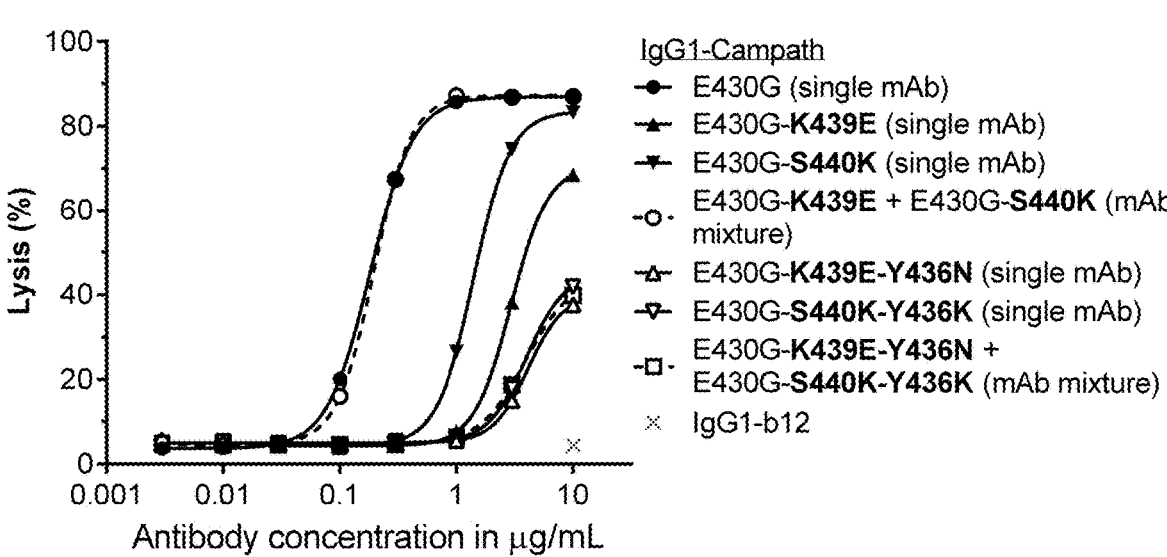

No rescue of CDC efficacy was observed for the combination of IgG1-Campath-E430G antibody variants with the Fc-Fc inhibiting double mutation pair Y436N/K439E+Y436K/S440K (FIG. 6G).

Taken together, it was shown for antibodies with an Fc-Fc interaction enhancing mutation, such as E430G, that the "window" between inhibited and rescued CDC efficacy by self-oligomerization inhibiting mutation pairs can be tuned by combining more than one self-oligomerization inhibiting mutation in each antibody, although the breadth of the window that was reached by the different combinations of IgG1-Campath-E430G variants was unpredictable.

Example 7: FcRn Binding of Anti-CD52 IgG1-CAMPATH-1H Antibody Variants

The neonatal Fc receptor (FcRn) is responsible for the long plasma half-life of IgG by protecting IgG from degradation. After internalization of the antibody, FcRn binds to antibody Fc regions in endosomes, where the interaction is stable in the mildly acidic environment (pH 6.0). Upon recycling to the plasma membrane, where the environment is neutral (pH 7.4), the interaction is lost and the antibody is released back into the circulation. This influences the plasma half-life of IgG.

An FcRn binding enzyme-linked immunosorbent assay (ELISA) was performed to evaluate binding of human FcRn to anti-CD52 IgG1-CAMPATH-1H containing the hexamerization enhancing mutation E430G, one of the self-oligomerization inhibiting mutations K439E or S440K, and one of the self-oligomerization inhibiting mutations I253G, I253K, I253R, H310D, or H310R identified in Example 2, or Y436K, Y436N, Q438N, or Q438R identified in Example 3. Streptawell 96 well plates (Roche, Cat No. 1734776001) were coated with 5 µg/mL (100 µL/well) recombinantly produced biotinylated extracellular domain of human FcRn [FcRnECDHis-B2M-BIO, i.e. the extracellular domain of human FcRn with a C-terminal His tag (FcRnECDHis; SEQ ID NO: 111) as dimer with beta2microglobulin (B2M; SEQ ID NO:112), diluted in PBS supplemented with 0.05% Tween 20 (PBST) plus 0.2% BSA for 2 hours while shaking at room temperature (RT). Plates were washed three times with PBST. Serially diluted antibody samples (range 0.003-40 µg/mL final concentrations in 5-fold dilutions in PBST/0.2% BSA, pH 6.0 or pH 7.4) were added and incubated for 1 hour at RT while shaking. Plates were washed with PBST/0.2% BSA, pH 6.0 or pH 7.4. Horseradish Peroxidase (HRP)-conjugated polyclonal Goat-anti-Human kappa light chain (1:5,000; Sigma, Cat No. A-7164) diluted in PBST/0.2% BSA, pH 6.0 or pH 7.4 was added, and plates were incubated for 1 hour at RT while shaking. After washing with PBST/0.2% BSA, pH 6.0 or pH 7.4., 100 µL 2,2'-Azino-bis(3-ethylbenzthiazoline-6-sulfonic acid (ABTS; 1 mg/mL; Roche Cat No. 11112422001 and 11112597001) was added as substrate and plates were incubated for 10 minutes at RT protected from light. The reaction was stopped using 100 µL 2% oxalic acid (Riedel de Haen, Cat No. 33506), incubated for 10 minutes at RT and absorbance was measured at 405 nm using an ELISA reader. Log-transformed data were analyzed by fitting sigmoidal dose-response curves with variable slope using GraphPad Prism software.

Figure 7:
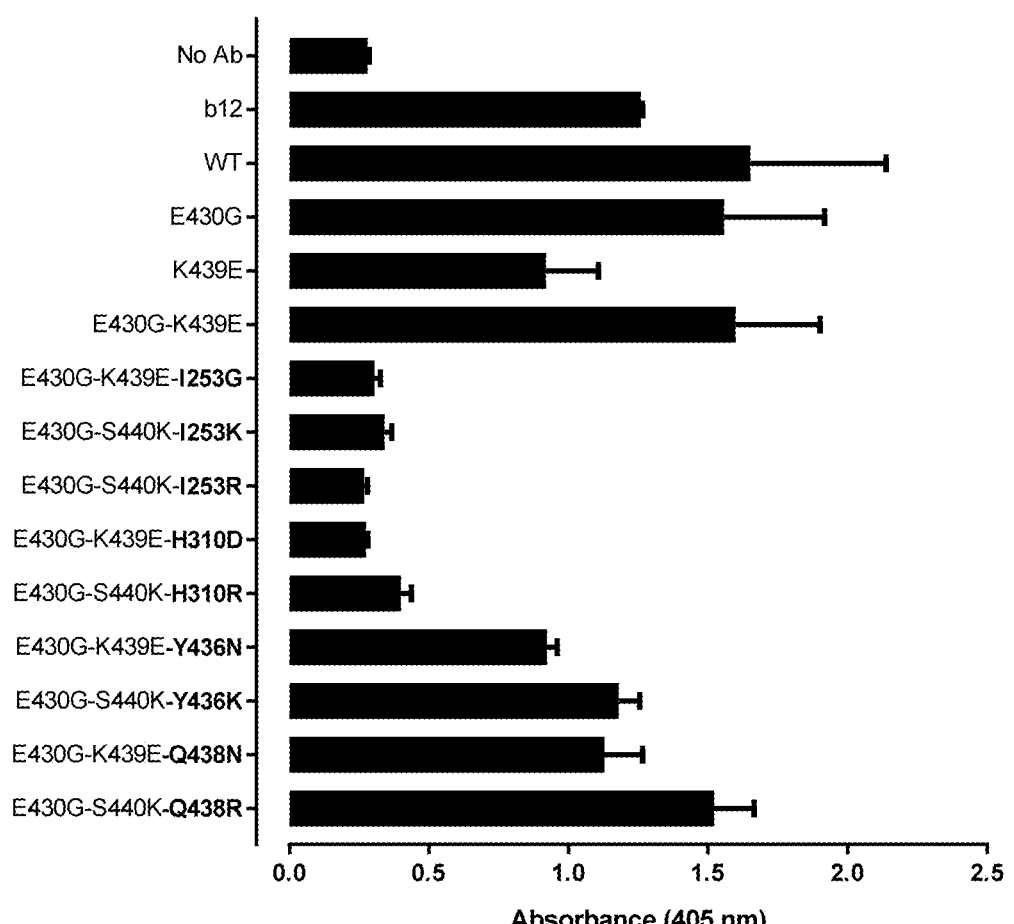
FIG. 7 shows FcRn binding of anti-CD52 IgG1-CAMPATH-1H antibodies with self-oligomerization inhibiting substitutions. Binding to human FcRn is shown of antibody variants of anti-CD52 IgG1-CAMPATH-1H-E430G-K439E and anti-CD52 IgG1-CAMPATH-1H-E430G-S440K with the self-oligomerization inhibiting substitutions I253G, I253K, I253R, H310D, H310R, Y436N, Y436K, Q438N and/or Q438R using a 40 µg/ml antibody concentration at (A) pH 7.4 and (B) pH 6.0. An FcRn ELISA was performed with 5 µg/mL coated recombinant extracellular domain of human FcRn (FcRnECDHis-B2M-BIO) and antibody dilution series. The amount of bound antibodies was determined with an HRP-conjugated goat anti-human IgG1 antibody and the chemiluminescent substrate ABTS. Absorbance was measured at 405 nm.
Figure 8A:
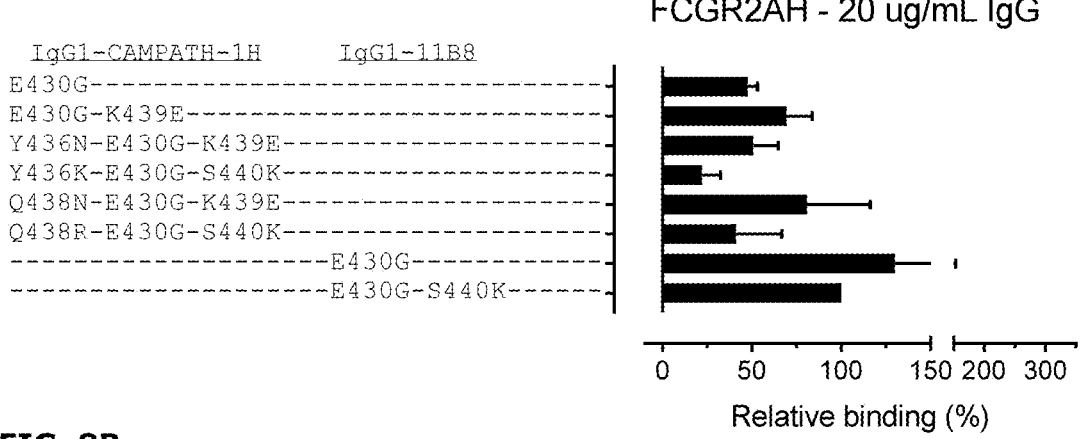
Figure 8B:
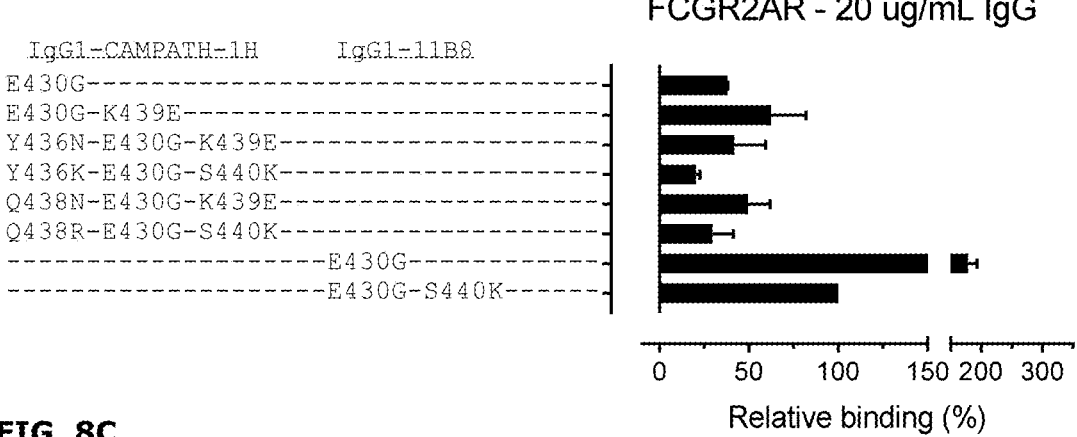
Figure 8C:
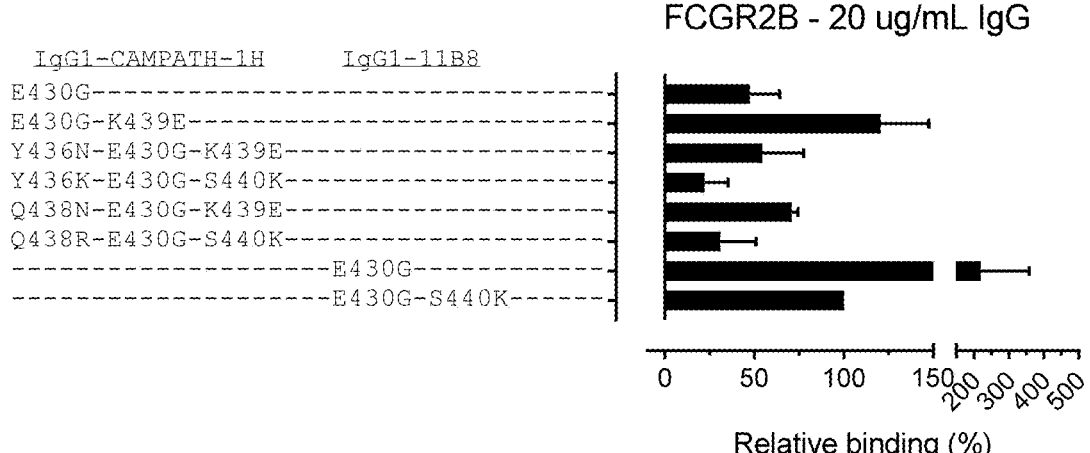

All tested IgG1-CAMPATH-1H antibody variants showed no binding to human FcRn at pH 7.4. At pH 6.0, antibodies IgG1-b12, wild-type anti-CD52 IgG1-CAMPATH-1H and anti-CD52 IgG1-CAMPATH-1H variants E430G, K439E did show binding, as well as the antibody variants of anti-CD52 IgG1-CAMPATH-1H with mutations at amino acid position Y436 and Q438 (FIG. 7). In addition, the S440K mutation did not inhibit FcRn binding. In contrast, no binding to FcRn at pH 6.0 was observed by antibody variants of anti-CD52 IgG1-CAMPATH-1H with mutations at amino acid position I253 and H310. Taken together, these results show that anti-CD52 IgG1-CAMPATH-1H with hexamerization enhancing mutation E430G and self-oligomerization inhibiting mutations K439E, S440K, Y436K, Y436N, Q438N and/or Q438R showed normal binding to human FcRn, while the ability to bind FcRn was lost by introduction of self-oligomerization inhibiting mutations H310D, H310R, I253G, I253K or I253R.

Example 8: The Effect of Y436K, Y436N, Q438N and Q438R Mutations on the In Vitro FcγR Binding of Anti-CD52 Antibodies with a Hexamerization Enhancing Mutation and K439E or S440K Using purified antibodies, binding of IgG1-CAMPATH-1H to dimeric ECDs of FcγRIIA allotype 131H (SEQ ID NO: 113), FcγRIIA allotype 131R (SEQ ID NO: 114), FcγRIIB (SEQ ID NO: 115), FcγRIIIA allotype 158F (SEQ ID NO: 116), and FcγRIIIA allotype 158V (SEQ ID NO: 117) was tested in ELISA assays. To detect binding to dimeric FcγR variants, 96-well Microlon ELISA plates (Greiner, Germany) were coated overnight at 4° C. with goat F(ab')₂-anti-human-IgG-F(ab')₂ (Jackson Laboratory, 109-006-097, 1 μg/mL) in PBS, washed and blocked with 200 μL/well PBS/0.2% BSA for 1 h at room temperature (RT). With washings in between incubations, plates were sequentially incubated with 100 μL/well of a dilution series of IgG1-CAMPATH-1H antibody variants (0.0013-20 μg/mL in five-fold steps) in PBST/0.2% BSA for 1 h at RT while shaking, 100 μL/well of dimeric, His-tagged, C-terminally biotinylated FcγR ECD variants (1 μg/mL) in PBST/0.2% BSA for 1 h at RT while shaking, and with 100 μL/well Streptavidin-polyHRP (CLB, M2032, 1:10.000) in PBST/0.2% BSA as detecting antibody for 30 min at RT while shaking. Development was performed for circa 24 (IIB) or 30 (IIA-131H, IIA-131R, IIIA-158V, IIIA-158F) min with 1 mg/mL ABTS (Roche, Mannheim, Germany). To stop the reactions, 100 μL/well of 2% oxalic acid was added. Absorbances were measured at 405 nm in a microplate reader (BioTek, Winooski, VT). FcγR binding at 20 μg/mL antibody concentration was plotted. Data is based on three independent replicates, normalized per experiment relative to background signal in ELISA (no antibody control, 0%) and an internal standard, IgG1-CAMPATH-1H-E430G, set to 100%.

Certain applications of co-dependent antibody mixtures with regulated Fc-Fc interaction properties may require the presence of intact FcγR-mediated effector functions. Assessment of binding of IgG1-CAMPATH-1H variants with Fc-Fc interaction enhancing mutation E430G and self-oligomerization inhibiting mutations K439E, S440K, Y436K, Y436N, Q438N and Q438R to FcγRIIa, FcγRIIb and FcγRIIIa by ELISA revealed that all tested antibodies retained FcγR binding at an antibody concentration of 20 μg/ml (FIG. 8A-E). A relatively lower FcγR-binding was observed for variants IgG1-CAMPATH-1H-E430G-S440K-Y436K and IgG1-CAMPATH-1H-E430G-S440K-Q438R.

In conclusion, IgG1-CAMPATH-1H antibody variants with Fc-Fc interaction enhancing mutation E430G and self-oligomerization inhibiting mutations K439E, S440K, Y436K, Y436N, Q438N and Q438R retained FcγR binding.

Example 9: Selectivity of CDC Activity by Mixed Antibody Variants by Introduction of Fc-Fc Self-Oligomerization Inhibiting Mutations in Anti-CD52 IgG1-CAMPATH-1H with an E430G Fc-Fc Interaction Enhancing Mutation The effect of self-oligomerization inhibiting mutations Y436K, Y436N, Q438N, Q438R, K439E, and S440K on in vitro CDC efficacy was tested using mixtures of variants of anti-CD52 antibody IgG1-CAMPATH-1H with an E430G Fc-Fc interaction enhancing mutation. Different concentrations of purified antibodies (range 0.01-40.0 μg/mL final concentrations) were tested in an in vitro CDC assay on Wien 133 cells with 20% NHS. Different mutations were introduced in antibody IgG1-CAMPATH-1H: E430G, which induces enhanced Fc-Fc interactions; and one or more of the self-oligomerization inhibiting mutations Y436K, Y436N, Q438N, Q438R, K439E, or S440K. As controls, single antibodies were also mixed 1:1 with non-binding isotype control antibody IgG1-b12 to enable direct comparison of the concentrations of individual components and mixtures composed thereof; these conditions will be referred to as single agent activity hereafter. For the CDC assay, 0.1×10⁶ Wien 133 cells (kindly provided by Dr. Geoff Hale, Bio-AnaLab Limited, Oxford, UK) in RPMI (Sigma, Cat No. R5886-500 mL) with 0.2% bovine serum albumin (BSA; Roche, Cat No. 10735086001) were pre-incubated in poly-styrene round-bottom 96-well plates (Greiner bio-one Cat No. 650180) with a concentration series of purified antibodies in a total volume of 80 μL for 15 min on a shaker at RT. Next, 20 μL normal human serum (NHS; Sanquin) was added as a source of complement and the mixture was incubated in a 37° C. incubator for 45 min (20% final NHS concentration; 40 to 0.01 μg/mL final IgG concentration in 3.3-fold dilutions). The reaction was stopped by putting the plates on ice before pelleting the cells by centrifugation and replacing the supernatant by 30 μL of 2 μg/mL propidium iodide solution (PI; Sigma Aldrich, Cat No. 1002570846). The number of PI-positive cells was determined by flow cytometry on an Intellicyt iQue screener (Westburg) and the percentage of lysis was calculated as (number of PI-positive cells/total number of cells)×100%. The area under the dose-response curves with log-transformed concentrations of two experimental replicates was calculated and averaged using GraphPad Prism 7. Relative areas under the curve (AUC) values represent values normalized relative to lysis induced by non-binding control IgG1-b12 (0%) and maximal lysis by anti-CD52 IgG1-CAMPATH-1H-E430G (100%).

Figure 9A:
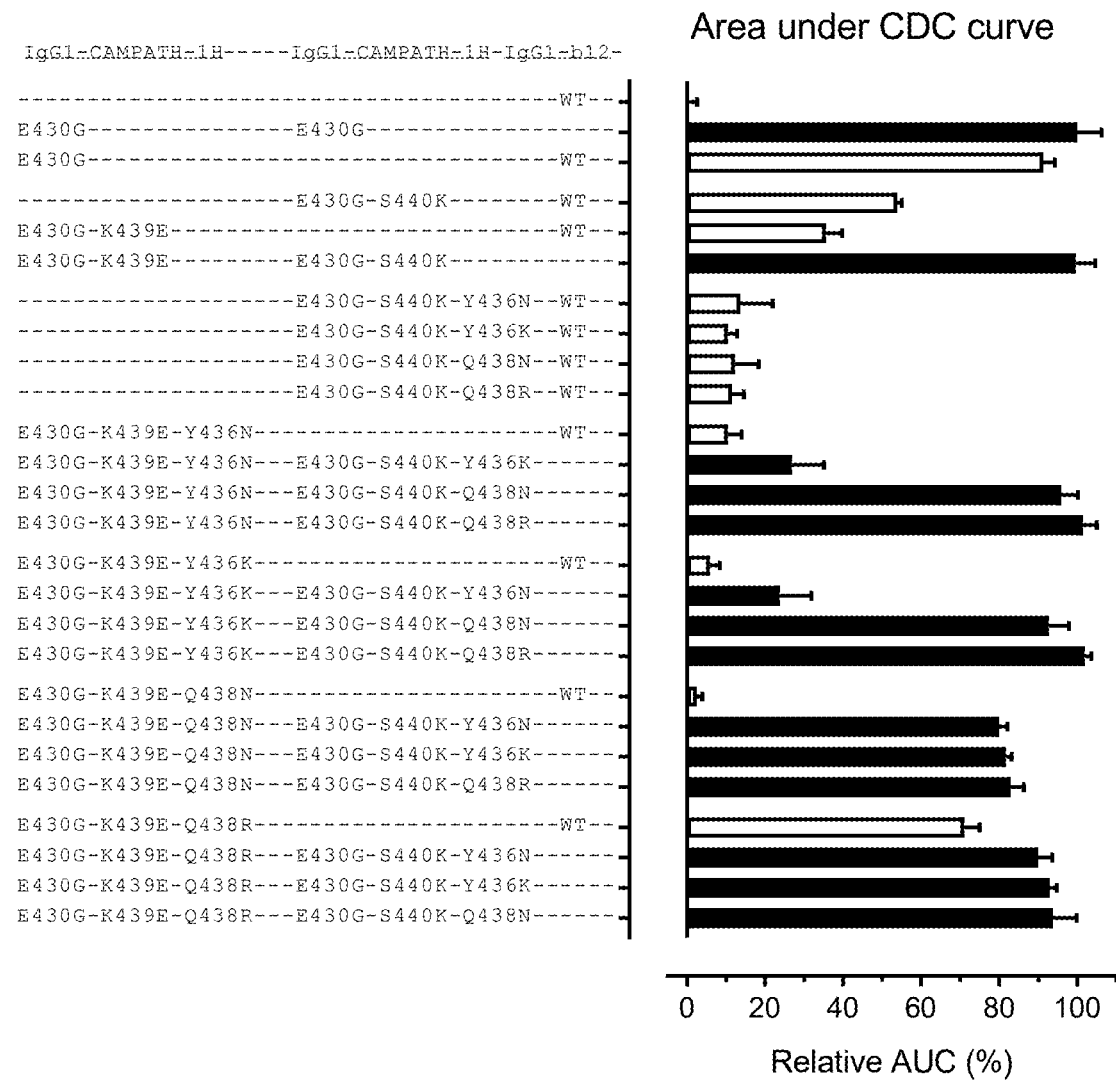
FIGS. 9A and 9B show CDC efficacy of single agent and combined anti-CD52 IgG1-CAMPATH-1H-E430G-K439E and anti-CD52 IgG1-CAMPATH-1H-E430G-S440K antibodies harboring self-oligomerization inhibiting mutations. Wien 133 cells were incubated with antibody concentration series in the presence of 20% NHS. CDC efficacy is presented as (FIG. 9A) the AUC normalized to non-binding control antibody IgG1-b12 (0%) and IgG1-CAMPATH-1H-E430G (100%) and (FIG. 9B) percentage lysis determined by the percentage PI-positive cells at an antibody concentration of 40 μg/ml.
Figure 9B:
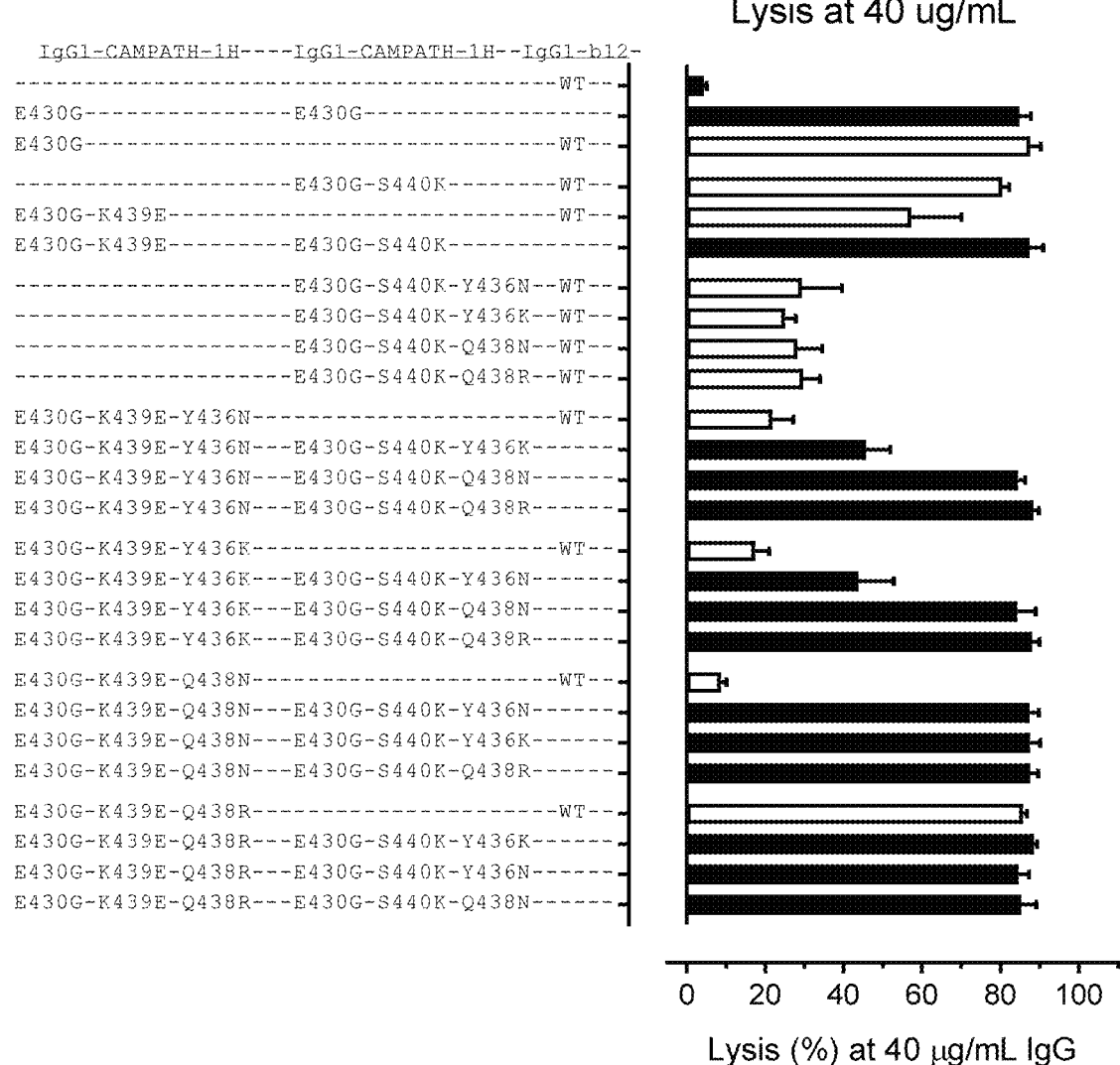

Anti-CD52 antibody IgG1-CAMPATH-1H-E430G induced efficient lysis of Wien 133 cells (represented as Area Under the Curve (AUC); FIG. 9A; set to 100%) compared to non-binding control IgG-b12 (set to 0%). All other antibody samples contained total IgG concentrations equal to these control reactions, but were composed of two different antibodies mixed at 1:1 ratio. Introduction of the K439E or S440K mutation in IgG1-CAMPATH-1H-E430G creating variants E430G-K439E and E430G-S440K resulted in decreased CDC efficacy when tested as a single agent in combination with IgG1-b12 (FIG. 9A), but both variants retained substantial single agent activity, particularly at 40 μg/mL IgG concentration (FIG. 9B). When IgG1-CAM-PATH-1H-E430G-K439E and IgG1-CAMPATH-1H-E430G-S440K were mixed, CDC efficacy was recovered. The residual CDC efficacy of IgG1-Campath-1H-E430G-S440K when tested as single agent in combination with IgG1-b12 was strongly decreased by introduction of either of the mutations Y436K, Y436N, Q438N or Q438R, including at 40 μg/mL IgG concentration (FIG. 9B). A strong decrease in CDC efficacy was also observed when either of the mutations Y436K, Y436N or Q438N was introduced in IgG1-CAMPATH-1H-E430G-K439E when tested as a single agent with IgG1-b12. In stark contrast, introduction of mutation Q438R in IgG1-CAMPATH-1H-E430G-K439E increased CDC efficacy as a single agent in combination with IgG1-b12 (FIG. 9A, 9B).

When variants of IgG1-CAMPATH-1H-E430G-K439E and IgG1-CAMPATH-1H-E430G-S440K with self-oligomerization inhibiting mutations Y436K, Y436N, Q438N or Q438R were combined, substantial recovery of CDC efficacy (represented as AUC; FIG. 9A) and maximal percentage of cell lysis (FIG. 9B) was observed for all combinations, except when one antibody harboring the Y436K mutation and one antibody harboring the Y436N mutation were combined. The latter occurred both when combining IgG1-CAMPATH-1H-E430G-K439E-Y436N with IgG1-CAMPATH-1H-E430G-S440K-Y436K and when combining IgG1-CAMPATH-1H-E430G-K439E-Y436K with IgG1-CAMPATH-1H-E430G-S440K-Y436N. Collectively, these data demonstrate that the introduction of self-oligomerization inhibiting mutations Y436K, Y436N, Q438N or Q438R in IgG1-CAMPATH-1H-E430G-S440K and Y436K, Y436N and Q438N mutations in IgG1-CAMPATH-1H-E430G-K439E results in a further reduction of CDC efficacy of the single agents. CDC efficacy was recovered by mixing complementary IgG1-CAMPATH-1H-E430G-K493E and IgG1-CAMPATH-1H-E430G-S440K variants harboring self-oligomerization inhibiting mutations, with the exception of combinations of IgG1-CAMPATH-1H-E430G-K439E-Y436N with IgG1-CAMPATH-1H-E430G-S440K-Y436K and IgG1-CAMPATH-1H-E430G-K439E-Y436K with IgG1-CAMPATH-1H-E430G-S440K-Y436N.

Example 10: Selectivity of CDC Activity by Mixed Antibody Variants by Introduction of Fc-Fc Self-Oligomerization Inhibiting Mutations in Anti-CD20 IgG1-11B8 with an E430G Fc-Fc Interaction Enhancing Mutation The effect of self-oligomerization inhibiting mutations Y436K, Y436N, Q438N, Q438R, K439E, or S440K on in vitro CDC efficacy was tested using mixtures of variants of anti-CD20 antibody IgG1-11B8 with an E430G Fc-Fc interaction enhancing mutation essentially as described in Example 9. Here, different mutations were introduced in CD20-directed antibody IgG1-11B8 instead: E430G, which induces enhanced Fc-Fc interactions; and one or more of the self-oligomerization inhibitory mutations Y436K, Y436N, Q438N, Q438R, K439E, or S440K. The area under the dose-response curves (AUC) with log-transformed concentrations of two experimental replicates was calculated using GraphPad Prism 7. The AUC was normalized per plate relative to lysis induced by non-binding control IgG1-b12 (0%) and maximal lysis by the mixture of anti-CD52 IgG1-CAMPATH-1H-E430G+anti-CD20 IgG1-11B8-E430G (100%), and subsequently averaged over multiple experiments.

Figure 10:
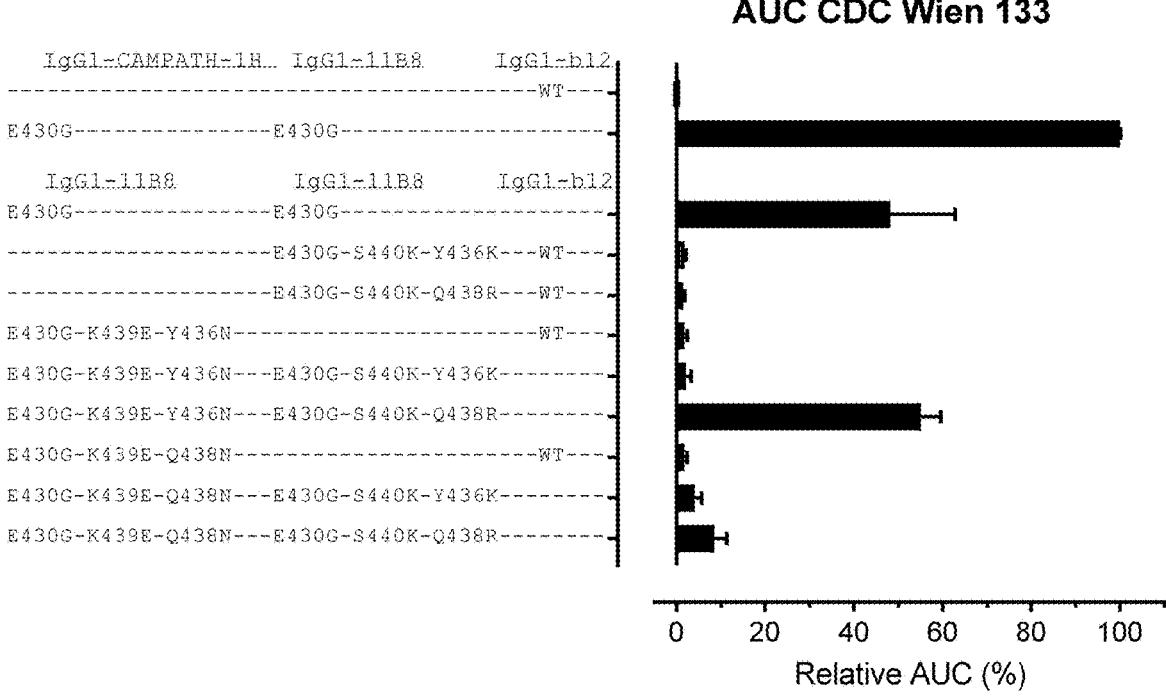
FIG. 10 shows CDC efficacy of single agent and combined anti-CD20 IgG1-11B8-E430G-K439E and anti-CD20 IgG1-11B8-E430G-S440K antibodies harboring additional self-oligomerization inhibiting mutations. Wien 133 cells were incubated with antibody concentration series in the presence of 20% NHS. CDC efficacy is presented as the AUC normalized to non-binding control antibody IgG1-b12 (0%) and the mixture of IgG1-CAMPATH-1H-E430G (CAMP-E430G)+IgG1-11B8-E430G (100%).

A mixture of anti-CD52 IgG1-CAMPATH-1H-E430G and anti-CD20 IgG1-11B8-E430G induced efficient lysis of Wien 133 cells (represented as Area Under the Curve (AUC); FIG. 10; set to 100%) compared to non-binding control IgG-b12 (set to 0%). Likewise, IgG1-11B8-E430G induced lysis of Wien 133 cells. No single agent activity was observed by the IgG1-11B8-E430G-S440K variants with self-oligomerization inhibiting mutations Y436K or Q438R, nor by the IgG1-11B8-E430G-K439E variants with self-oligomerization inhibiting mutations Y436N or Q438N. By mixing IgG1-11B8-E430G-K439E-Y436N and IgG1-11B8-E430G-S440K-Q438R, CDC efficacy could be recovered to a level similar to that induced by IgG1-11B8-E430G. However, no recovery was observed for mixtures of IgG1-11B8-E430G-K439E-Y436N+IgG1-11B8-E430G-S440K-Y436K or IgG1-11B8-E430G-K439E-Q438N+IgG1-11B8-E430G-S440K-Y436K, while low CDC efficacy was recovered after mixing IgG1-11B8-E430G-K439E-Q438N+IgG1-11B8-E430G-S440K-Q438R (FIG. 10).

Taken together, these results demonstrate that introduction of self-oligomerization inhibiting mutations Y436K, Y436N, Q438N or Q438R in IgG1-11B8-E430G that contain either of the self-oligomerization inhibiting mutations K439E or S440K results in loss of single agent CDC efficacy in the Wien 133 cell in vitro CDC model. In this model of antibody-mediated CD20-targeting, CDC efficacy could only be recovered by mixing IgG1-11B8-E430G-K439E-Y436N and IgG1-11B8-E430G-S440K-Q438R.

Example 11: Selectivity of CDC Activity by Mixed Antibody Variants by Introduction of Self-Oligomerization Inhibiting Mutations in Anti-CD52 IgG1-CAMPATH-1H and Anti-CD20 IgG1-11B8 with an E430G Fc-Fc Interaction Enhancing Mutation It was described in Examples 9 and 10 that introduction of self-oligomerization inhibiting mutations in either IgG1-CAMPATH-1H (Example 9) or IgG1-11B8 (Example 10) with the Fc-Fc interaction enhancing mutation E430G and either of the self-oligomerization inhibiting mutations K439E or S440K resulted in reduced single agent activity in an in vitro CDC model, while recovery of CDC efficacy was observed when mixing complementary antibody variants with said mutations targeting the same antigen. Here, the effect of introducing self-oligomerization inhibiting mutations in two antibodies targeting different antigens was tested, namely anti-CD20 IgG1-11B8 and anti-CD52 IgG1-CAMPATH-1H. CDC activity was tested essentially as described in Example 9. Different mutations were introduced in antibodies IgG1-11B8 and IgG1-CAMPATH-1H: E430G, which induces enhanced Fc-Fc interactions; and one or more of the self-oligomerization inhibiting mutations Y436K, Y436N, Q438N, Q438R, K439E, or S440K, which inhibit the formation of homo-hexameric antibody complexes and promote the formation of hetero-hexameric antibody complexes. The area under the dose-response curves (AUC) with log-transformed concentrations of two experimental replicates was calculated using GraphPad Prism 7. The AUC was normalized per plate relative to lysis induced by non-binding control IgG1-b12 (0%) and maximal lysis by the mixture of anti-CD52 IgG1-CAMPATH-1H-E430G+anti-CD20 IgG1-11B8-E430G (100%), and subsequently averaged over multiple experiments.

Figure 11:
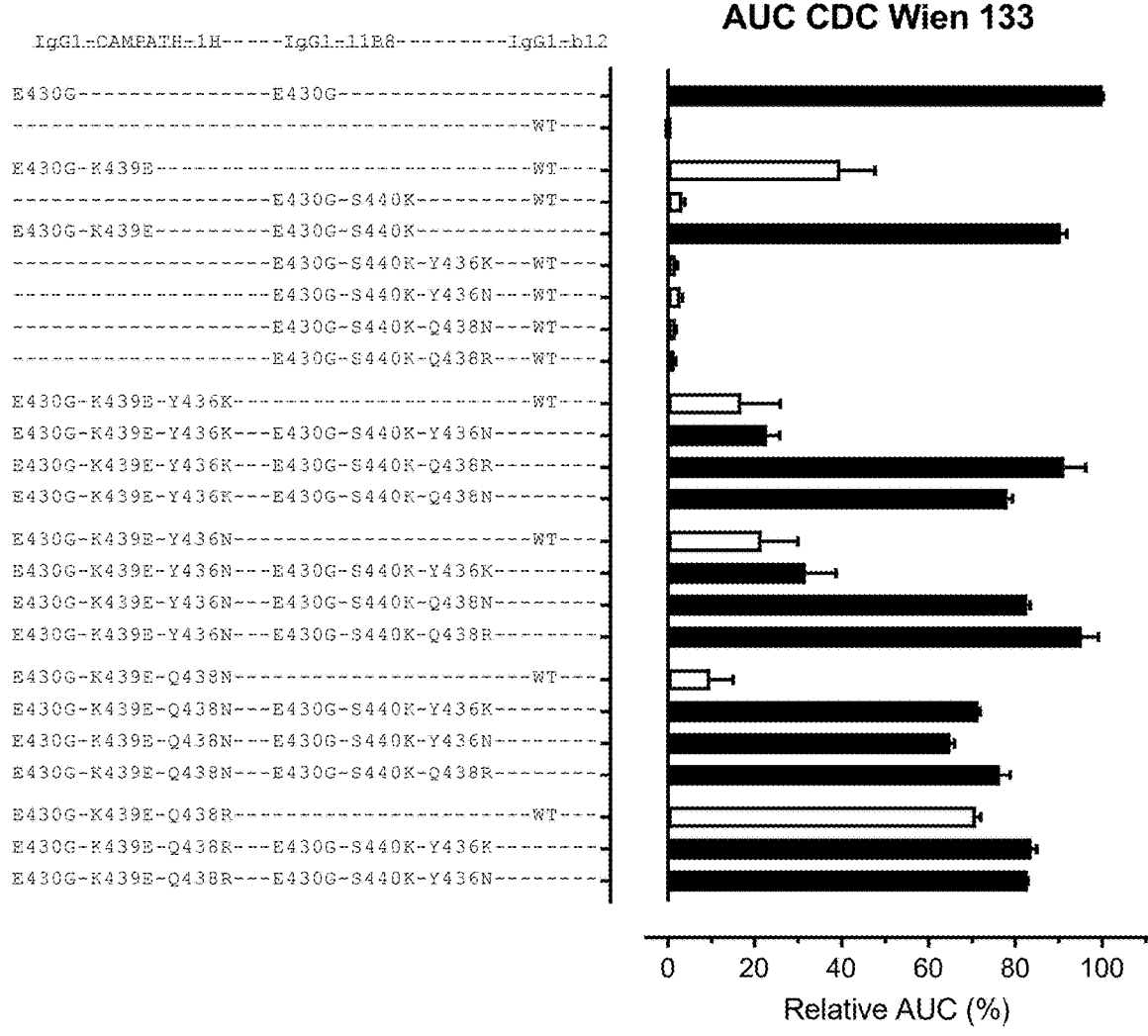
FIG. 11 shows CDC efficacy of single agent and combined anti-CD52 IgG1-CAMPATH-1H-E430G-K439E and anti-CD20 IgG1-11B8-E430G-S440K antibodies harboring self-oligomerization inhibiting mutations. Wien 133 cells were incubated with antibody concentration series in the presence of 20% NHS. CDC efficacy is presented as the AUC normalized to non-binding control antibody IgG1-b12 (0%) and the mixture of IgG1-CAMPATH-1H-E430G+IgG1-11B8-E430G (100%).

A mixture of anti-CD52 IgG1-CAMPATH-1H-E430G and anti-CD20 IgG1-11B8-E430G induced efficient lysis of Wien 133 cells (represented as Area Under the Curve (AUC); FIG. 11; set to 100%) compared to non-binding control IgG-b12 (set to 0%). While CDC efficacy was fully abrogated by the introduction of mutation S440K in IgG1-11B8-E430G, introduction of mutation K439E in IgG1-CAMPATH-1H-E430G only reduced the single agent activity. CDC efficacy was recovered by mixing of antibodies IgG1-CAMPATH-1H-E430G-K439E and IgG1-11B8-E430G-S440K, hereafter referred to as the prior art mixture.

Introduction of the self-oligomerization inhibiting mutations Y436K, Y436N, Q438N or Q438R in IgG1-11B8-E430G-S440K resulted in complete loss of single agent CDC activity. Similar to the data presented in Example 9, introduction of mutations Y436K, Y436N or Q436N, but not Q438R, in IgG1-CAMPATH-1H-E430G-K439E resulted in low single agent activity as compared with IgG1-CAMPATH-1H-E430G-K439E.

Approximately 80 to 90% of the CDC efficacy induced by the prior art mixture could be restored by a mixture of IgG1-CAMPATH-1H-E430G-K439E-Y436K with IgG1-11B8-E430G-S440K-Q438N or with IgG1-11B8-E430G-S440K-Q438R (but not IgG1-11B8-E430G-S440K-Y438N). Approximately 80 to 90% of the CDC efficacy induced by the prior art mixture was also recovered by a mixture of IgG1-CAMPATH-1H-E430G-K439E-Y436N with IgG1-11B8-E430G-S440K-Q438N or with IgG1-11B8-E430G-S440K-Q438R (but not IgG1-11B8-E430G-

S440K-Y436K). Mixtures of IgG1-CAMPATH-1H-E430G-K439E-Q438N with IgG1-11B8-E430G-S440K-Y436K, IgG1-11B8-E430G-S440K-Y436N or IgG1-11B8-E430G-S440K-Q438R recovered up to 84% of the efficacy of the prior art mixture. Although single agent activity of IgG1-CAMPATH-1H-E430G-K439E-Q438N was relatively high, CDC efficacy was slightly further increased by mixing IgG1-CAMPATH-1H-E430G-K439E-Q438R with IgG1-11B8-E430G-S440K-Y436K or IgG1-11B8-E430G-S440K-Y436N.

Collectively, these data demonstrate that the introduction of self-oligomerization inhibiting mutations Y436K, Y436N, Q438N or Q438R in IgG1-11B8-E430G-S440K and Y436K, Y436N and Q438N mutations in IgG1-CAMPATH-1H-E430G-K439E results in a further reduction of CDC efficacy of the single agents, confirming results described in Example 9 and 10. CDC efficacy was restored after mixing complementary antibodies targeting different antigens, demonstrated by the observation that CDC efficacy was restored by mixtures of IgG1-CAMPATH-1H-E430G-K493E and IgG1-11B8-E430G-S440K variants harboring said self-oligomerization inhibiting mutations, with the exception of combinations of IgG1-CAMPATH-1H-E430G-K439E-Y436N with IgG1-11B8-E430G-S440K-Y436K and IgG1-CAMPATH-1H-E430G-K439E-Y436K with IgG1-11B8-E430G-S440K-Y436N.

Example 12: Selectivity of CDC Activity by Mixed Antibody Variants of Anti-CD52 IgG1-CAMPATH-1H+Anti-CD20 IgG1-11B8 with Different Fc-Fc Interaction Enhancing Mutations It was shown in Example 11 that the introduction of self-oligomerization inhibiting mutations could enhance CDC selectivity of two antibodies targeting different antigens. Here, we test the selectivity of CDC activity of antibody variants with different Fc-Fc interaction enhancing mutations, E430G, E345K, E345R and K248E/T437R.

An in vitro CDC assay using Wien 133 cells was performed with 20% NHS and antibody concentration series (final concentration range 0.01-40.0 µg/mL in 3.3-fold dilutions), essentially as described in Example 9. Cell lysis and relative AUC values were calculated from the number of PI-positive cells as described in Example 9, from two experimental replicates. AUC was normalized to the values for negative control antibody IgG1-b12 (0%) and for positive control IgG1-CAMPATH-1H-E430G+IgG1-11B8-E430G (100%).

Figure 12A:
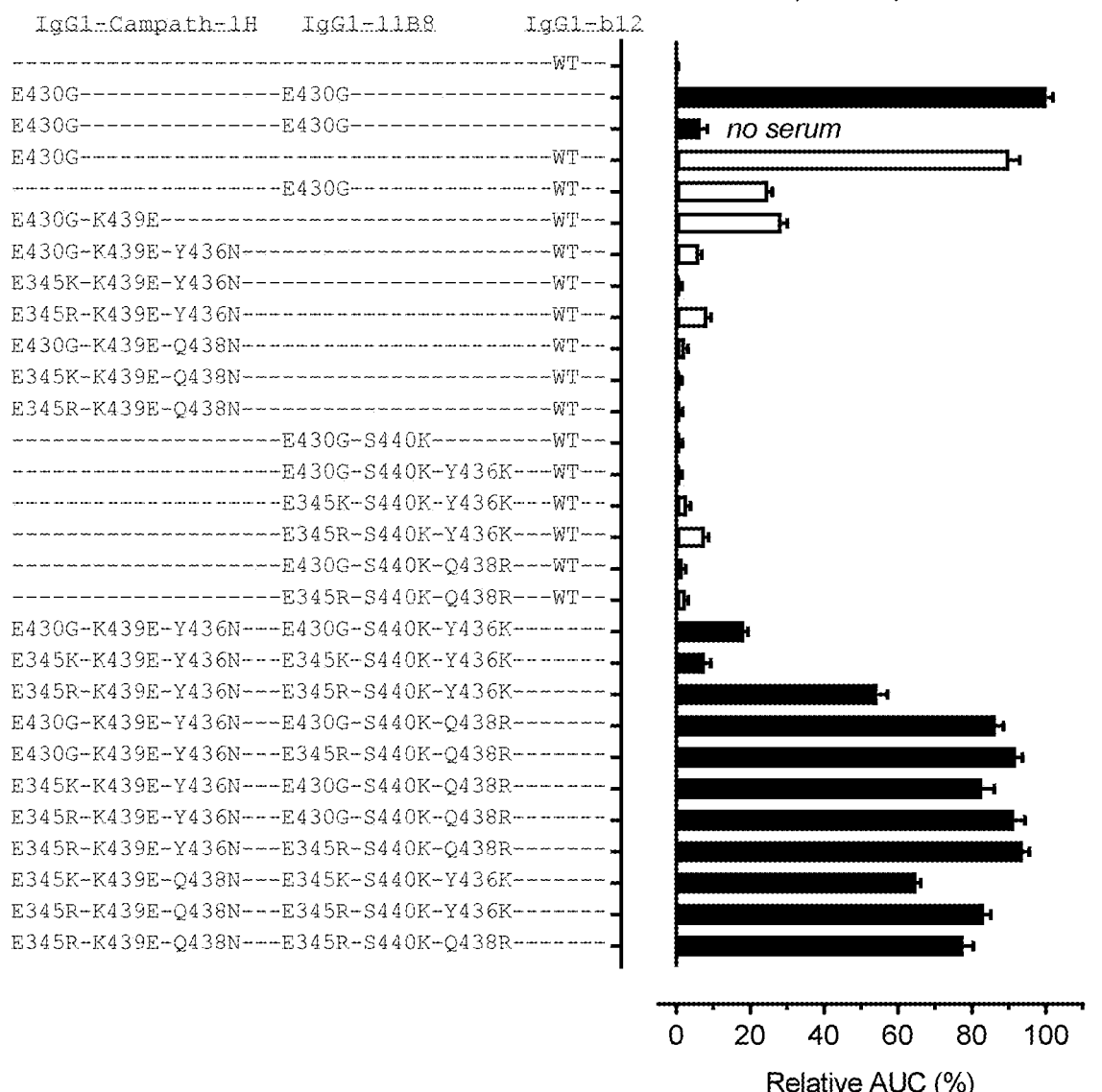
FIGS. 12A and 12B show CDC efficacy of single agent and combined variants of anti-CD52 IgG1-CAMPATH-1H and anti-CD20 IgG1-11B8 antibodies harboring different Fc-Fc interaction enhancing mutations.

No cell lysis was observed by IgG1-b12 (FIG. 12A, B; set to 0%), while a 1:1 mixture of anti-CD52 IgG1-CAMPATH-1H-E430G+anti-CD20 IgG1-11B8-E430G induced efficient cell lysis of Wien 133 cells (FIG. 12A, B; set to 100%). The latter activity was not observed in the absence of serum, indicating cell lysis was C1q-dependent.

The single agent activity of IgG1-CAMPATH-1H-E430G was close to the activity of the mixture of IgG1-CAMPATH-1H-E430G+IgG1-11B8-E430G (FIG. 12A). Introduction of self-oligomerization inhibiting mutation K439E into IgG1-CAMPATH-1H-E430G resulted in strongly reduced cell lysis. An even further reduction of single agent activity was accomplished by introduction of mutations Y436N or Q438N in IgG1-CAMPATH-1H-E430G-K439E. Single agent activity was similarly suppressed after substitution of the Fc-Fc interaction enhancing mutation E430G by either E345K or E345R in IgG1-CAMPATH-1H-E430G-K439E-Y436N or IgG1-CAMPATH-1H-E430G-K439E-Q438N. In summary, single agent activity of IgG1-CAMPATH-1H with either of the Fc-Fc interaction enhancing mutations E430G, E345K or E345R can be abrogated by introduction of self-oligomerization inhibiting mutation K439E in combination with either Y436N or Q438N.

Antibody anti-CD20 IgG1-11B8-E430G shows intermediate single agent activity (FIG. 12A). Introduction of self-oligomerization inhibiting mutation S440K abrogated the single agent activity of IgG1-11B8-E430G. Complete abrogation of single agent activity was also observed after introduction of self-oligomerization inhibiting mutation Y436K or Q438R in IgG1-11B8-E430G-S440K. Similar to the results described for IgG1-CAMPATH-1H, antibody variants with either of the Fc-Fc interaction enhancing mutations E345K or E345R instead of E430G resulted in similar abrogation of cell lysis as observed with antibody variants containing the E430G mutation. In summary, single agent activity of IgG1-11B8 with either of the Fc-Fc interaction enhancing mutations E430G, E345K or E345R can be abrogated by introduction of self-oligomerization inhibiting mutation S440K in combination with either Y436K or Q438R.

While only marginal single agent activity was observed by IgG1-CAMPATH-1H-E430G-K439E-Y436N and no single agent activity was observed by IgG1-11B8-E430G-S440K-Q438R, a mixture of these antibodies recovered CDC efficacy close to the level of a mixture of IgG1-CAMPATH-1H-E430G+IgG1-11B8-E430G (FIG. 12A). Similar restoration of cell lysis was accomplished by mixing antibody variants in which the E430G mutation was replaced by the E345K or E345R mutation. As previously described in Example 11, only partial recovery of CDC efficacy was obtained by mixing IgG1-CAMPATH-1H-E430G-K439E-Y436N with IgG1-11B8-E430G-S440K-Y436K (FIG. 12A). Similar results were obtained when the E430G mutation in the latter antibodies was replaced by the E345K mutation. A stronger recovery of CDC efficacy as compared with the variants harboring the E345K mutation was accomplished by mixing the same antibody variants in which the E430G mutation was replaced by E345R, which may be interesting when maximal potency is desired. While limited single agent activity was observed by IgG1-CAMPATH-1H-E345K-K439E-Q438N and by IgG1-11B8-E345K-S440K-Y436K, a mixture of these antibodies recovered ~65% of the CDC efficacy of positive control mixture of IgG1-CAMPATH-1H-E430G+IgG1-11B8-E430G (FIG. 12A). Substituting E345K with E345R in both antibody variants in the mixture recovered ~80% CDC potency. Similar efficacy was observed for a mixture of IgG1-CAMPATH-1H-E345R-K439E-Q438N and IgG1-11B8-E345R-S440K-Q438R.

Figure 12B:
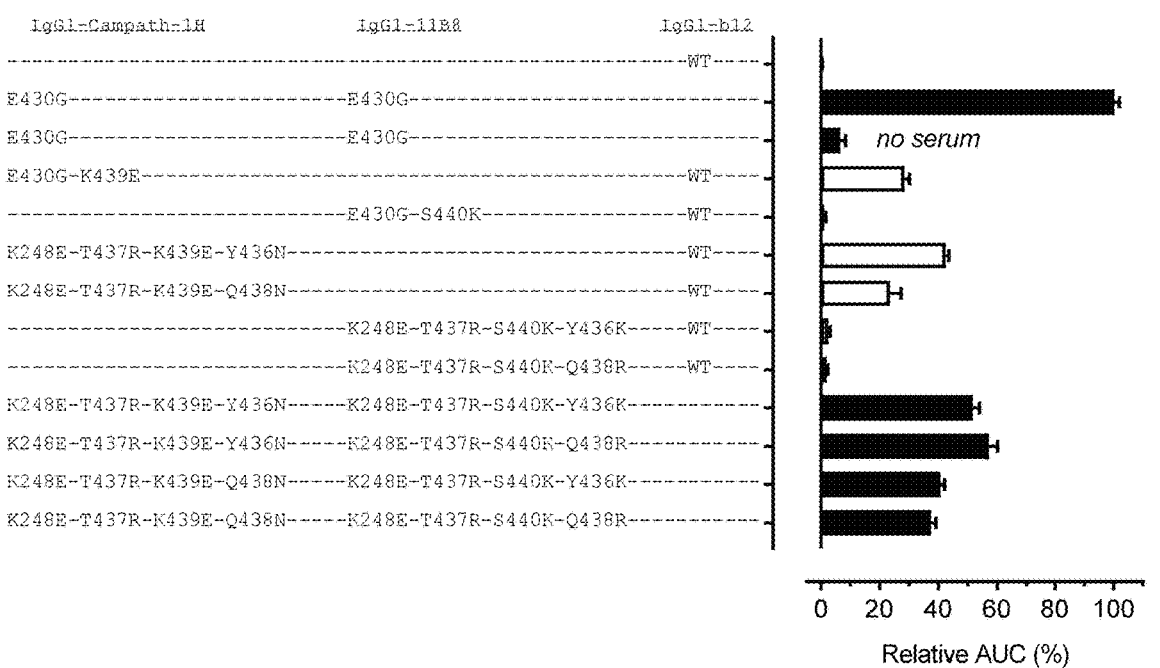

As described above, single agent activity could be reduced by introduction of mutation K439E in IgG1-CAMPATH-1H-E430G while single agent activity was completely abrogated by introduction of mutation S440K in IgG1-11B8 (FIG. 12A, B). When the Fc-Fc interaction enhancing mutations K248E and T437R were introduced in IgG1-CAMPATH-1H instead of E430G, substantial single agent activity was observed, also when combined with the self-oligomerization inhibiting mutation K439E in combination with Y436N or Q438N (FIG. 12B). No single agent activity was observed by IgG1-11B8 variants in which the K248E and T437R mutations were introduced together with S440K and either Y436K or Q438R. Although CDC efficacy could be enhanced by mixing antibodies containing the K248E and T437R mutations, this enhancement did not result in CDC efficacy as efficient as mixtures of antibodies containing any of the Fc-Fc interaction enhancing mutations E430G, E345K or E345R. Overall, these results show that recovery of CDC efficacy can be accomplished by mixing antibody variants harboring complementary self-oligomerization inhibiting mutations K439E, S440K, Y436K, Y436N, Q438N and/or Q438R, regardless of which of the largely functionally equivalent Fc-Fc interaction enhancing mutations E430G, E345K or E345R is included. Mixtures of two antibodies containing the Y436K and Y436N mutations only partially restored CDC efficacy. However, mixing variants of such antibodies containing the E345R mutation induced stronger recovery of CDC efficacy than antibody variants containing either the E345K or E430G mutation. Furthermore, a partial recovery of CDC efficacy could be accomplished by mixing antibody variants containing the K248E and T437R Fc-Fc interaction enhancing mutations, which was less efficient than mixtures of antibodies containing either of the E430G, E345K or E345R mutations.

Example 13: Analysis of Selective CDC Activity for Mixtures of Anti-CD52 and Anti-CD20 Antibody Variants in Different Human IgG Subclass Backbones In the previous Examples, it was described that the introduction of self-oligomerization inhibiting mutations in anti-CD20 and anti-CD52 IgG1 antibodies resulted in selective co-dependent induction of target cell lysis. Here, we tested whether these principles also apply to other IgG subclasses and combinations of different IgG subclasses.

The VH sequences of anti-CD52 CAMPATH-1H were cloned in human IgG1, IgG2 and hinge-stabilized IgG4 (S228P) Fc backbones containing the E430G-K439E mutations, and the VH sequences of anti-CD20 11B8 were cloned in human IgG1, IgG2 and hinge-stabilized IgG4 (S228P) Fc backbones containing the E430G-S440K mutations. Different combinations of these anti-CD52 and anti-CD20 subclass variants with additional self-oligomerization inhibiting mutations Y436N, Y436K, Q438N, or Q438R were tested for selective CDC activity. An in vitro CDC assay using Wien 133 cells was performed with 20% NHS and antibody concentration series (final total IgG concentration range 0.01-40.0 μg/mL in 3.3-fold dilutions), essentially as described in Example 9. Cell lysis and relative AUC values were calculated from the number of PI-positive cells as described in Example 9, from two experimental replicates. AUC was normalized to the values for negative control antibody IgG1-b12 (0%) and for positive control IgG1-CAMPATH-1H-E430G+IgG1-11B8-E430G (100%).

Figure 13:
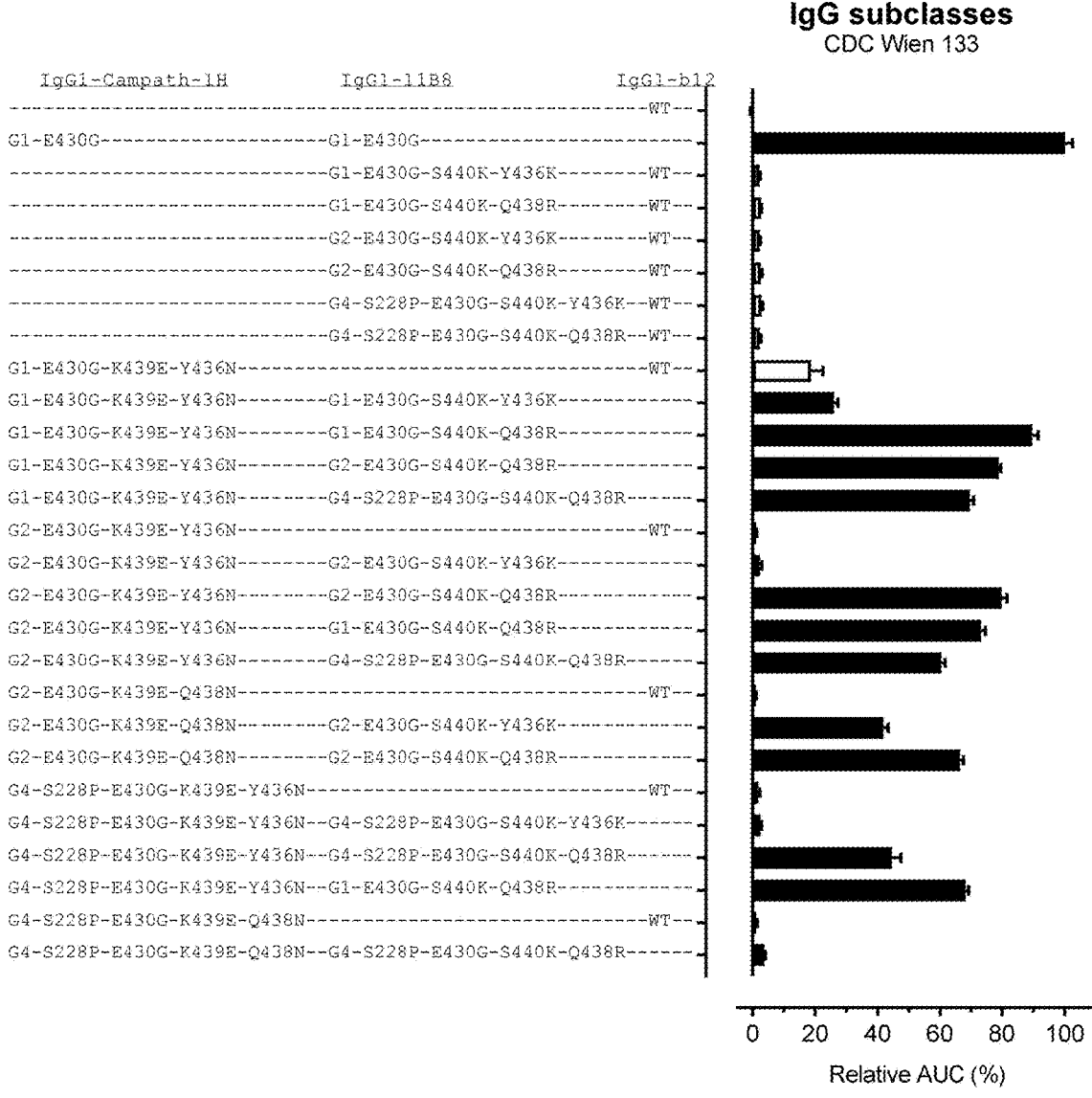
FIG. 13 shows selectivity of CDC activity by mixed antibody subclass variants (IgG1, IgG2 and hinge-stabilized IgG4) of anti-CD52 CAMPATH-1H-E430G-K439E with additional self-oligomerization inhibiting mutations+anti-CD20 11B8-E430G-S440K with additional self-oligomerization inhibiting mutations. Wien 133 cells were incubated with antibody concentration series in the presence of 20% NHS. CDC efficacy is presented as the normalized AUC of the percentage PI-positive cells. Normalization was performed to non-binding control antibody IgG1-b12 (0%) and the mixture of IgG1-CAMPATH-1H-E430G+IgG1-11B8-E430G (100%).

As described in Examples 9, 10 and 11, the single agent activity of anti-CD20 IgG1-11B8-E430G could be abrogated by introduction of self-oligomerization inhibiting mutation S440K in combination with either the Y436K or Q438R mutation. Introduction of the S440K, Y436K and Q438R mutations in IgG2 or IgG4 subclass backbones likewise resulted in abrogation of CDC efficacy. The CD52-targeting antibody variant IgG1-CAMPATH-1H-E430G-K439E-Y436N showed residual single agent activity, though much lower than the mixture of IgG1-CAMPATH-1H-E430G+IgG1-11B8-E430G. No CDC efficacy was observed for the IgG2 or IgG4 subclass backbone variants of this antibody (FIG. 13) when used as a single agent, which is highly interesting if maximal selectivity for cells or tissues bound by both components is desired. A similar observation was made for IgG1-CAMPATH-1H-E430G-K439E-Q438N: while low single agent activity was observed for the IgG1 subclass variant (FIG. 11, Example 11) no single agent activity could be detected for the IgG2 or IgG4 subclass variants (FIG. 13). Without being limited by theory, this may be explained by reduced C1q binding affinity of the IgG2 and IgG4 subclasses compared to IgG1.

Recovery of CDC efficacy could be attained by mixing IgG1-CAMPATH-1H-E430G-K439E-Y436N with IgG1-11B8-E430G-S440K-Q438R, IgG2-11B8-E430G-S440K-Q438R or IgG4-11B8-S228P-E430G-S440K-Q438R. CDC potency of the IgG2 and IgG4 combinations was lower compared to the mixture of the corresponding IgG1 antibody variants (FIG. 13). CDC efficacy could also be recovered by mixing IgG2-CAMPATH-1H-E430G-K439E-Y436N with IgG1-11B8-E430G-S440K-Q438R, IgG2-11B8-E430G-S440K-Q438R or IgG4-11B8-S228P-E430G-S440K-Q438R, however with reduced CDC potency compared to the mixture of the corresponding IgG1 antibody variants. Partial recovery of CDC efficacy could be accomplished by mixing IgG2-CAMPATH-1H-E430G-K439E-Q438N with IgG2-11B8-E430G-S440K-Y436K or IgG2-11B8-E430G-S440K-Q438R with the latter combination showing more activity than the former combination. Partial recovery of CDC efficacy could also be attained by mixing IgG4-CAMPATH-1H-S228P-E430G-K439E-Y436N with IgG4-11B8-S228P-E430G-S440K-Q438R or IgG1-11B8-S440K-Q438R (FIG. 13). No substantial recovery of CDC efficacy was observed by a mixture of IgG4-CAMPATH-1H-S228P-E430G-K439E-Q438N and IgG4-11B8-S228P-E430G-S440K-Q438R.

Consistent with the observations in Example 9, mixing IgG1-CAMPATH-1H-E430G-K439E-Y436N with IgG1-11B8-E430G-S440K-Y436K did not result in recovery of CDC efficacy. Similarly, IgG2 subclass variants IgG2-CAMPATH-1H-E430G-K439E-Y436N+IgG2-11B8-E430G-S440K-Y436K and IgG4 subclass variants IgG4-CAMPATH-1H-S228P-E430G-K439E-Y436N+IgG4-11B8-S228P-E430G-S440K-Y436K failed to recover substantial CDC activity.

When comparing IgG subclass combinations per individual subclass class, combinations of IgG1 antibodies induced stronger co-dependent CDC efficacy than combinations of IgG2 antibodies, which in turn performed stronger than combinations of IgG4 antibodies. In addition, combinations of different IgG subclasses showed that combinations of an IgG1 and an IgG2 antibody induced stronger co-dependent CDC efficacy than combinations of an IgG1 and an IgG4 antibody, which in turn performed stronger than combinations of an IgG2 and IgG4 antibody. In conclusion, co-dependent CDC activity could be induced by antibodies derived from all tested IgG subclasses, both when using combinations of two antibodies derived from the same IgG subclass, as well as when derived from two different IgG subclasses.

Example 14: Analysis of Selective CDC Activity for Mixtures of Anti-CD52 and Anti-CD20 Antibody Variants with FcγR-Binding Inhibiting Mutation G237A In Example 11 and subsequent Examples, it was described that the introduction of self-oligomerization inhibiting mutations in anti-CD20 and anti-CD52 IgG1 antibodies resulted in selective co-dependent induction of target cell lysis. As an example of mutations that strongly suppress FcγR-binding and FcγR-mediated effector functions while having limited effect on C1q-binding or CDC by co-dependent antibodies, we tested the effect of further introducing mutation G237A. Only the effector functions sensitive to co-dependent hexamerization of the two components could be expected to recover after mixing, while both the single agents and the mixture would be expected to show severely inhibited FcγR-mediated effector functions.

Figure 14A:
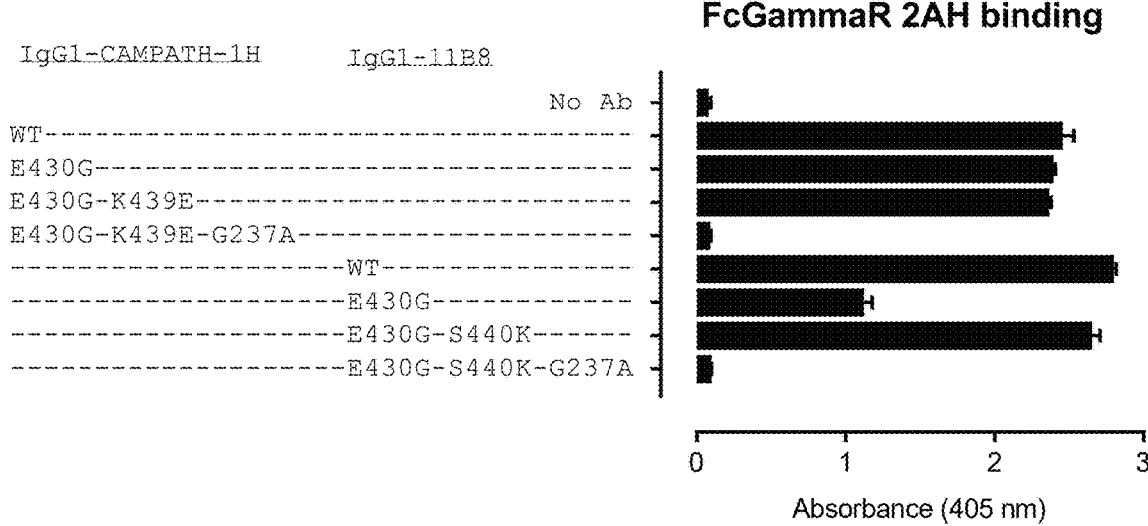
FIGS. 14A-14G show the effect of introducing FcγR-binding inhibiting mutation G237A in IgG1-CAMPATH-1H and IgG1-11B8 variants with Fc-Fc interaction enhancing and self-oligomerization inhibiting mutations on FcγR binding and CDC activity. Binding of immobilized IgG1-CAMPATH-1H and IgG1-11B8 variants with self-oligomerization inhibiting mutations K439E or S440K to dimeric His-tagged biotinylated ECDs of (FIG. 14A) FcγRIIA allotype 131H, (FIG. 14B) FcγRIIA allotype 131R, (FIG. 14C) FcγRIIB, (FIG. 14D) FcγRIIIA allotype 158F and (FIG. 14E) FcγRIIIA allotype 158V as tested in ELISA assays. Binding is presented as the absorbance at 405 nm wavelength for 20 μg/mL antibody samples. Detection was performed using Streptavidin-polyHRP and ABTS.
Figure 14B:
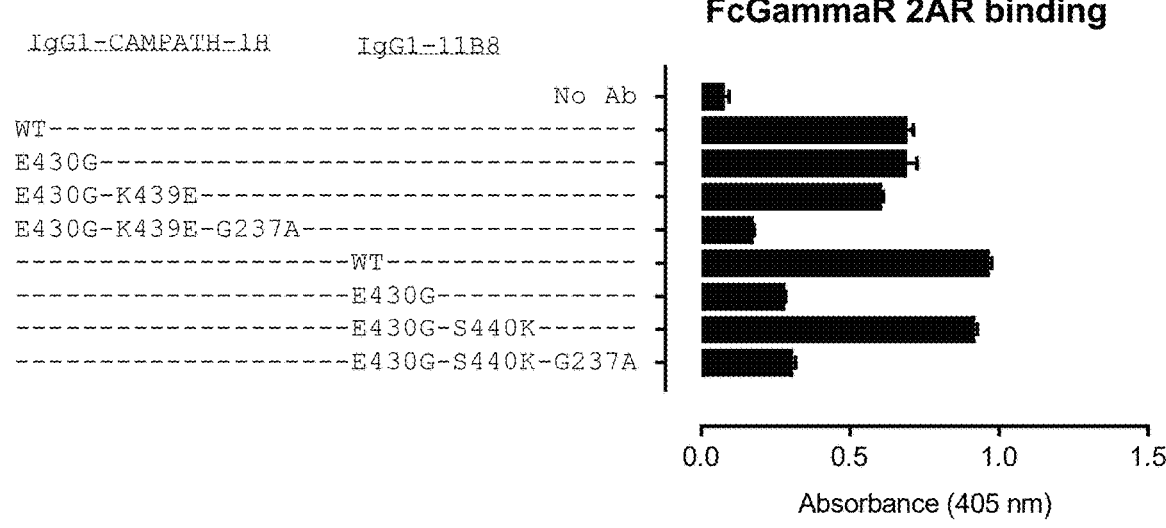
Figure 14C:
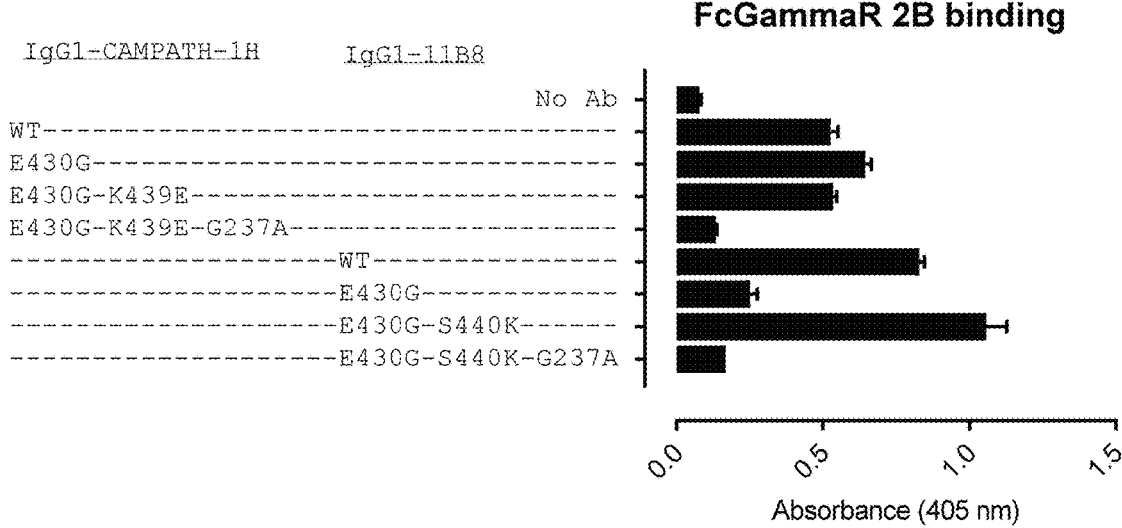
Figure 14D:
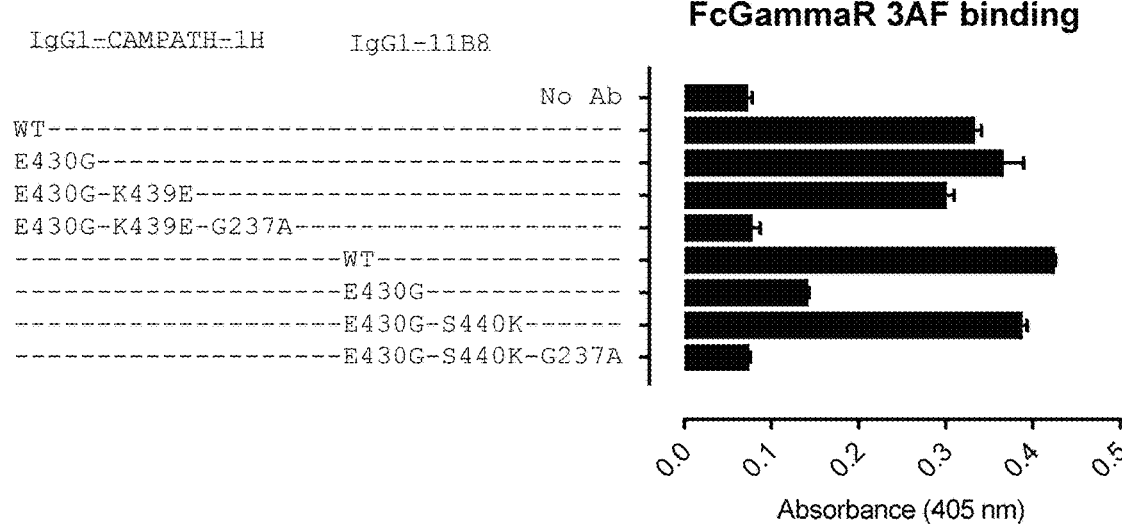
Figure 14E:
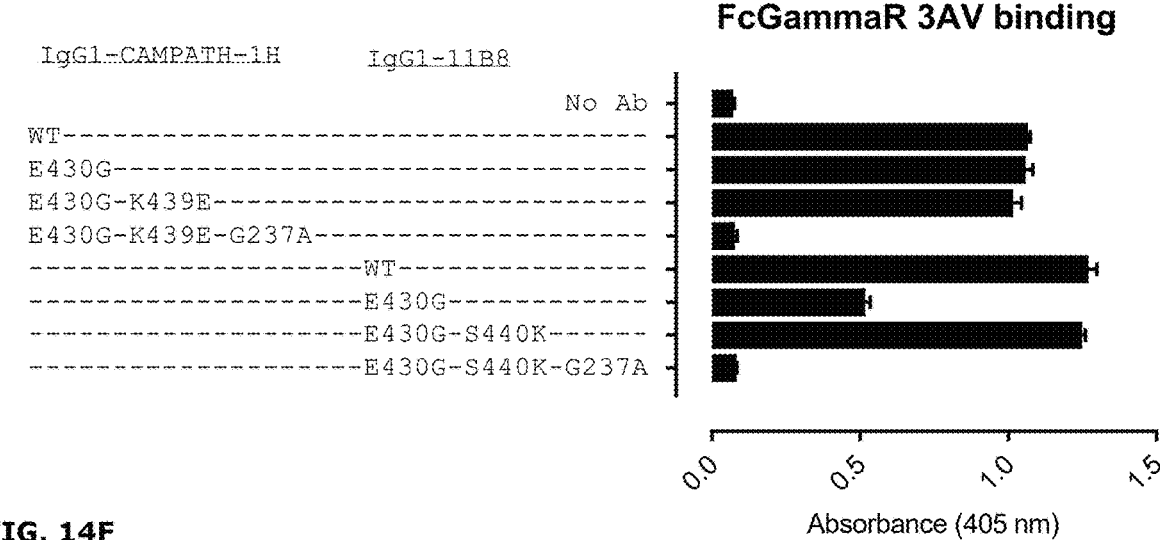
Figure 14F:
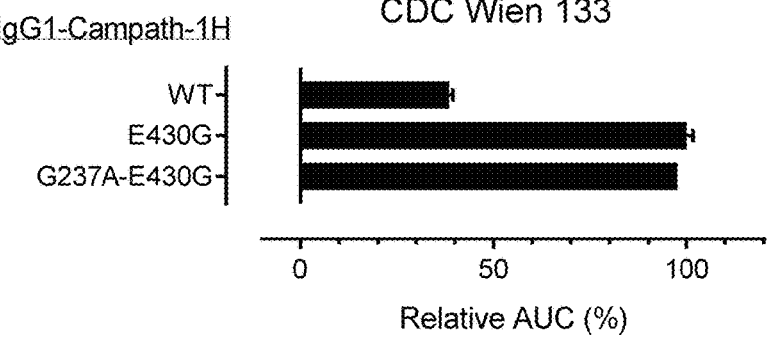
Figure 14G:
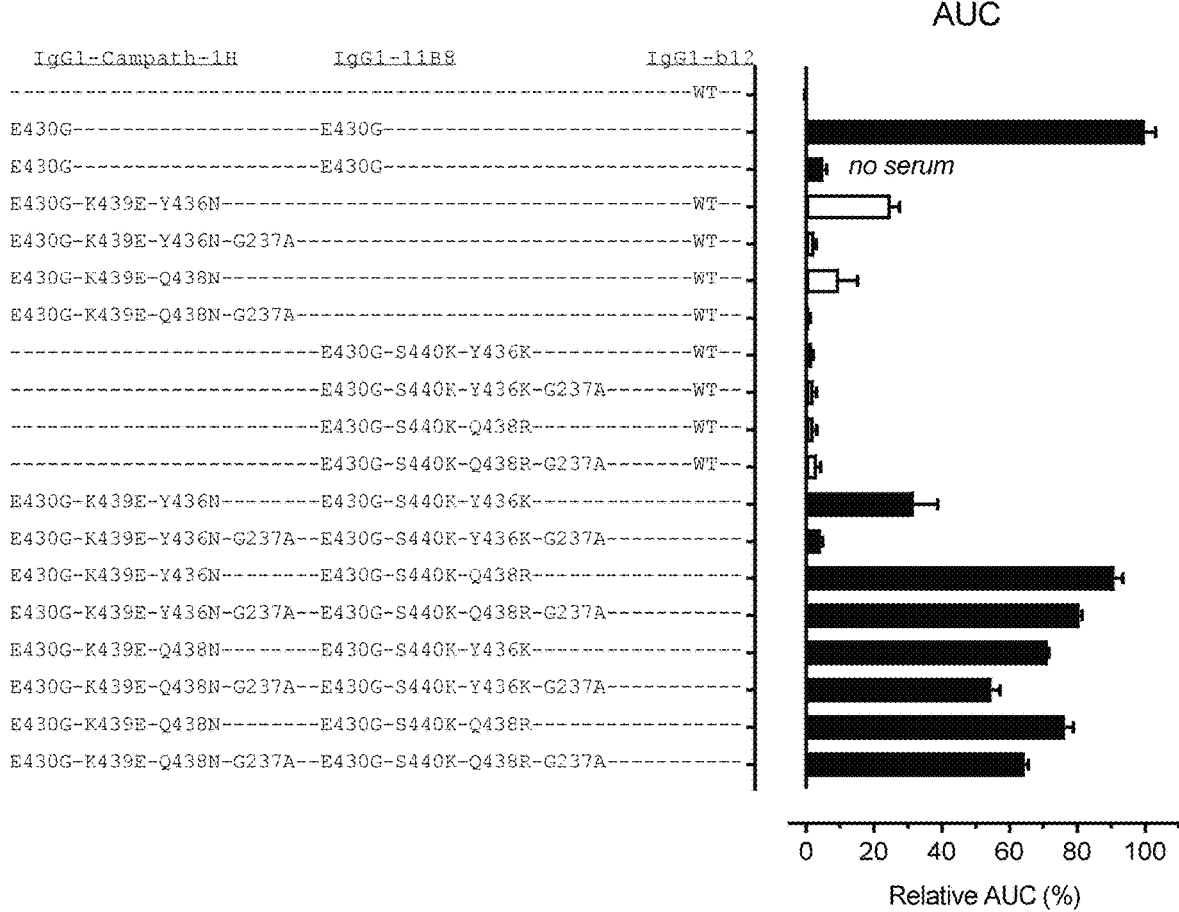

To detect binding of IgG1-CAMPATH-1H and IgG1-11B8 antibody variants to dimeric FcγR variants, an FcγR binding assay was performed essentially as described in Example 8. Furthermore, In vitro CDC assays using Wien 133 cells were performed with 20% NHS and antibody concentration series, final concentration range 0.002-40.0 μg/mL in 4-fold dilutions (FIG. 14F) or 0.01-40.0 μg/mL in 3.3-fold dilutions (FIG. 14G), essentially as described in Example 9. Cell lysis and relative AUC values were calculated from the number of PI-positive cells as described in Example 9, from two experimental replicates. AUC was normalized to the values for negative control antibody IgG1-b12 (0%) and for positive control IgG1-CAMPATH-1H-E430G (FIG. 14F) or a mixture of IgG1-CAMPATH-1H-E430G+IgG1-11B8-E430G (100%; FIG. 14G). No CDC activity was observed after exposure of Wien 133 cells to the latter mixture in the absence of serum, indicating cell lysis was C1q-dependent (FIG. 14G).

The wild-type IgG1-CAMPATH-1H antibody and variants thereof with introduced mutations E430G or E430G-K439E bound FcγRIIA allotype 131H, FcγRIIA allotype 131R, FcγRIIB, FcγRIIIA allotype 158F and FcγRIIIA allotype 158V (FIG. 14A-E). The wild-type antibody IgG1-11B8 and the variant with introduced mutations E430G-S440K also showed binding to the tested FcγR variants. Antibody variant IgG1-11B8-E430G showed less efficient FcγR variant binding for reasons that were unclear, but retained substantial binding to high affinity variants FcγRIIA allotype 131H and FcγRIIIA allotype 158V. Binding to FcγR was completely abrogated by introduction of mutation G237A in all of the aforementioned antibody variants.

Efficient cell lysis was observed after exposing Wien 133 cells to IgG1-CAMPATH-No single agent activity was observed of IgG1-11B8-E430G-S440K-Q438R or IgG1-11B8-E430G-S440K-Y436K, and the introduction of mutation G237A in these antibody variants did not affect this (FIG. 14G). The residual single agent activity observed for IgG1-CAMPATH-1H-E430G-K439E-Y436N was efficiently abrogated by introduction of mutation G237A, which is highly interesting if maximal selectivity for cells or tissues bound by both components is desired. The mixture of IgG1-CAMPATH-1H-E430G-K439E-Y436N and IgG1-11B8-E430G-S440K-Q438R did induce efficient CDC, approaching the level of the mixture of IgG1-CAMPATH-1H-E430G and IgG1-11B8-E430G. Recovery of cell lysis was also observed after mixing IgG1-CAMPATH-1H-E430G-K439E-Y436N-G237A with IgG1-11B8-E430G-S440K-Q438R-G237A, but not after mixing with IgG1-11B8-E430G-S440K-Y436K-G237A, in line with results described in previous Examples.

The low single agent activity of IgG1-CAMPATH-1H-E430G-K439E-Q438N was eliminated upon introduction of mutation G237A (FIG. 14). CDC efficacy could be restored to intermediate levels by mixing IgG1-CAMPATH-1H-E430G-K439E-Q438N-G237A with either IgG1-11B8-E430G-S440K-Y436K-G237A or IgG1-11B8-E430G-S440K-Q438R-G237A, but at antigen-saturating antibody concentrations approximately 80% lysis was observed. Overall, mixtures of antibody variants containing the G237A mutation show a relatively lower restoration of CDC efficacy than antibody variants without this mutation. Without being limited by theory, this may be explained by a modest inhibitory effect of mutation G237A on C1q binding.

In summary, these data demonstrate that the introduction of FcγR-binding inhibiting mutation G237A eliminates the residual single agent activity of antibody variants with self-oligomerization inhibiting mutations Y436N and Q438N. Recovery of CDC efficacy could be attained by mixing antibody variants with complementary self-oligomerization inhibiting mutations and the G237A mutation, albeit with lower efficiency than mixtures of complementary antibody variants without the G237A mutation.

Example 15: Analysis of C1q Binding by Mixtures of Anti-CD52 and Anti-CD20 Antibody Variants with an FcγR-Binding Inhibiting Mutation and Enhanced C1q Binding Mutations It was demonstrated in Example 14 that the introduction of FcγR-binding inhibiting mutation G237A resulted in elimination of single agent activity of anti-CD52 and anti-CD20 IgG1 antibody variants with self-oligomerization inhibiting mutations. However, as compared to antibody variants without the G237A mutation, mixtures of complementary antibody variants containing the G237A mutation did not fully restore selective co-dependent CDC efficacy. Here, we tested whether the introduction of C1q binding enhancing mutations E333S or K326W-E333S in one antibody component of a mixture of two antibodies could compensate for the possibly reduced C1q binding of a G237A-containing antibody component.

An in vitro CDC assay using Wien 133 cells was performed with 20% NHS and antibody concentration series (final concentration range 0.01-40.0 μg/mL in 3.3-fold dilutions), essentially as described in Example 9. Cell lysis and relative AUC values were calculated from the number of PI-positive cells as described in Example 9, from two experimental replicates. AUC was normalized to the values for negative control antibody IgG1-b12 (0%) and for positive control IgG1-CAMPATH-1H-E430G+IgG1-11B8-E430G (100%). The latter activity was not observed in the absence of serum, indicating cell lysis was C1q-dependent.

Figure 15:
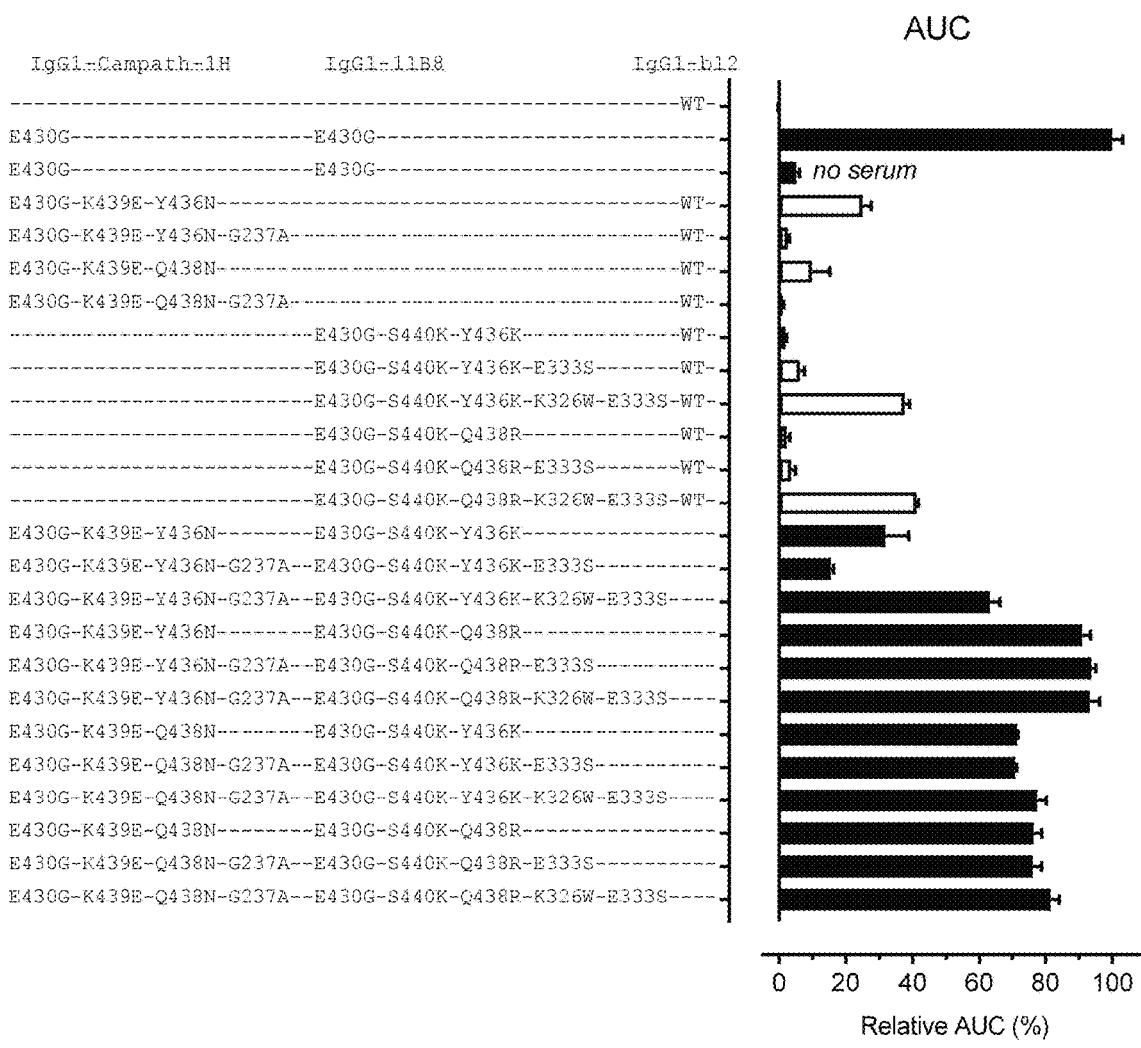
FIG. 15 shows the selectivity of CDC activity by mixed antibody variants of anti-CD52 CAMPATH-1H-E430G-K439E and anti-CD20 11B8-E430G-S440K with or without self-oligomerization inhibiting mutations, FcγR-binding inhibiting mutation G237A, and/or C1q-binding-enhancing mutations E333S or K326W-E333S. Wien 133 cells were incubated with antibody concentration series in the presence of 20% NHS. CDC efficacy is presented as the normalized AUC of the percentage PI-positive cells. Normalization was performed to non-binding control antibody IgG1-b12 (0%) and the mixture of IgG1-CAMPATH-1H-E430G+IgG1-11B8-E430G (100%).

As described in Example 14, introduction of mutation G237A in IgG1-CAMPATH-1H-E430G-K439E variants with either the Y436N or Q438N mutation abrogated single agent activity (FIG. 14, 15). The C1q-binding enhancing mutations E333S or K326W-E333S were introduced in anti-CD20 IgG1-11B8-E430G antibody variants to investigate the effects of this mutation on single agent CDC efficacy (FIG. 15). While the introduction of E333S in IgG1-11B8-E430G-S440K-Q438R or IgG1-11B8-E430G-S440K-Y436K resulted in low CDC efficacy close to background levels, the introduction of the K326W-E333S mutations in the same antibodies resulted in intermediate single agent CDC efficacy.

Full recovery of CDC efficacy was observed after mixing IgG1-CAMPATH-1H-E430G-K439E-Y436N-G237A with IgG1-11B8-E430G-S440K-Q438R antibody variants containing either the E333S or K326W-E333S mutations (FIG. 15). Partial recovery of CDC efficacy was attained by mixing IgG1-CAMPATH-1H-E430G-K439E-Y436N-G237A with IgG1-11B8-E430G-S440-Y436K-K326W-E333S and to a lesser extent with IgG1-11B8-E430G-S440-Y436K-E333S, in line with the results described in Example 9 and 11.

As described in both Example 14 and here, antibody variant IgG1-CAMPATH-1H-E430G-K439E-Q438N with mutation G237A did not show any single agent activity. Furthermore, mixtures of this antibody with IgG1-11B8-E430G-S440K variants containing either Y436K or Q438R and G237A did not fully restore CDC efficacy (FIG. 14). However, CDC efficacy could be restored to levels closer to that of the positive control mixture by mixing IgG1-CAM-PATH-1H-E430G-K439E-Q438N-G237A with variants of IgG1-11B8-E430G-S440K-Q438R or IgG1-11B8-E430G-S440K-Y436K containing either the E333S or K326W-E333S mutations (FIG. 15), reaching absolute lysis levels of approximately 90% upon antigen saturation.

Taken together, the largest window of selectivity was attained by mixing one antibody harboring self-oligomer-ization inhibiting mutations and FcγR-binding inhibiting mutation G237A with an antibody harboring self-oligomer-ization inhibiting mutations and enhanced C1q-binding mutation E333S.

Example 16: Selectivity of CDC Activity on Raji Cells by Mixed Anti-CD37 IgG1-37-37-3 Antibody Variants with an E430G Fc-Fc Interaction Enhancing Mutation and Fc-Fc Self-Oligomerization Inhibiting Mutations The effect of self-oligomerization inhibiting mutations Y436K, Y436N, Q438N and Q438R on in vitro CDC efficacy on Raji cells was tested using mixtures of variants of anti-CD37 antibody IgG1-CD37-37-3 with an E430G Fc-Fc interaction enhancing mutation.

An in vitro CDC assay using Raji cells was performed with 20% NHS and antibody concentration series (final concentration range 0.01-40.0 µg/mL in 3.3-fold dilutions), essentially as described in Example 9. Burkitt's lymphoma cell line Raji was purchased from ATCC (Cat No. CCL-86). Cell lysis and relative AUC values were calculated from the number of PI-positive cells as described in Example 9, from two experimental replicates. AUC was normalized to the values for negative control antibody IgG1-b12 (0%) and for positive control IgG1-CAMPATH-1H-E430G+IgG1-CD37-37-3-E430G (100%).

Figure 16:
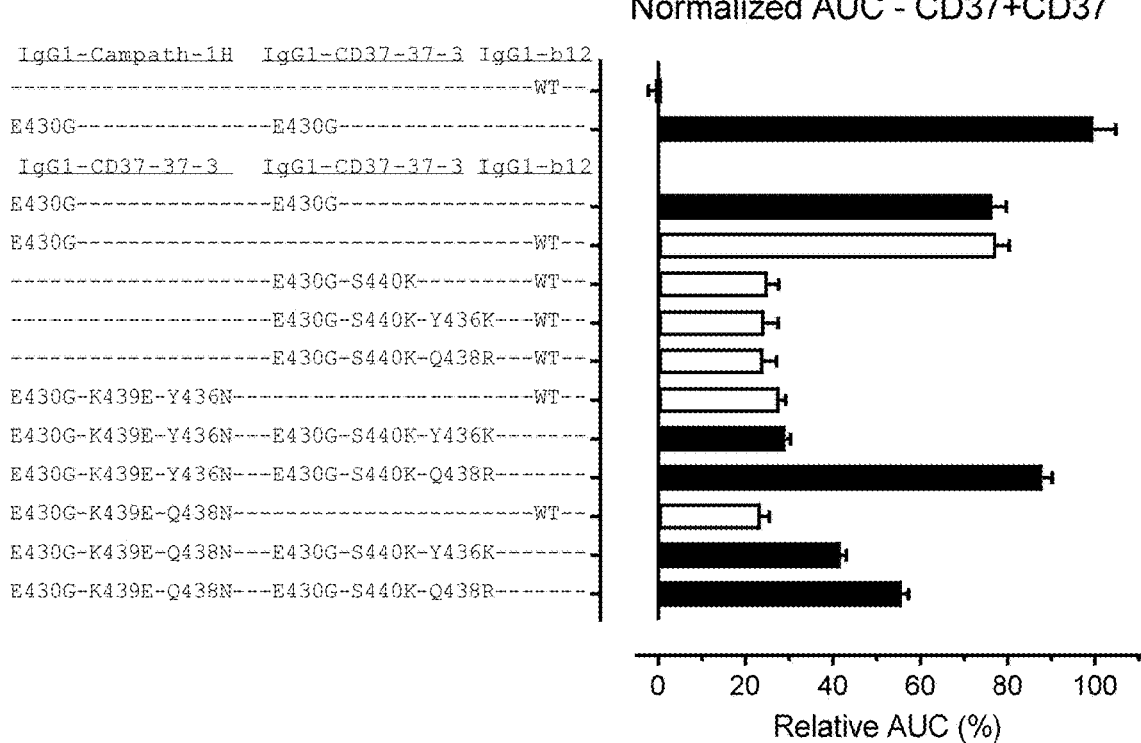
FIG. 16 shows CDC efficacy of single agent and combined anti-CD37 IgG1-CD37-37-3-E430G antibody variants harboring self-oligomerization inhibiting mutations. Raji cells were incubated with antibody concentration series in the presence of 20% NHS. CDC efficacy is presented as the AUC normalized to non-binding control antibody IgG1-b12 (0%) and IgG1-CAMPATH-1H-E430G+IgG1-CD37-37-3-E430G (100%).

Antibody IgG1-CD37-37-3-E430G on itself induced potent CDC efficacy on Raji cells, regardless of whether it was mixed with non-antigen binding antibody IgG1-b12 or not (FIG. 16). Although considerably reduced as compared with IgG1-CD37-37-3-E430G itself, residual single agent activity was observed upon introduction of self-oligomer-ization inhibiting mutations S440K, S440K-Y436K, S440K-Q438R, K439E-Y436N or K439E-Q438N in IgG1-CD37-37-3-E430G. CDC efficacy could be fully restored to the level of IgG1-CD37-37-3-E430G by mixing IgG1-CD37-37-3-E430G-K439E-Y436N with IgG1-CD37-37-3-E430G-S440K-Q438R, but not with IgG1-CD37-37-3-E430G-S440K-Y436K, consistent with the results presented in Examples 9-15. Likewise, the reduced CDC efficacy of IgG1-CD37-37-3-E430G-K439E-Q438N could be partially restored by mixing with IgG1-CD37-37-3-E430G-S440K-Y436K or IgG1-CD37-37-3-E430G-S440K-Q438R.

Overall, these data show that CDC efficacy of IgG1-CD37-37-3-E430G on Raji cells could be partially abro-gated by introduction of self-oligomerization inhibiting mutations K439E-Y436N, K439E-Q438N, S440K-Y436K or S440K-Q438R. Recovery of CDC efficacy was attained to varying extent by mixing, in order of strong to weak recovery, IgG1-CD37-37-3-E430G-K439E-Y436N with IgG1-CD37-37-3-E430G-S440K-Q438R, IgG1-CD37-37-3-E430G-K439E-Q438N with IgG1-CD37-37-3-E430G-S440K-Q438R or IgG1-CD37-37-3-E430G-K439E-Q438N with IgG1-CD37-37-3-E430G-S440K-Y436K.

Example 17: Selectivity of CDC Activity on Raji Cells by Mixed Anti-CD37 IgG1-37-37-3 and Anti-CD20 IgG1-11B8 Antibody Variants with an E430G Fc-Fc Interaction Enhancing Mutation and Fc-Fc Self-Oligomerization Inhibiting Mutations The effect of self-oligomerization inhibiting mutations Y436K, Y436N, Q438N and Q438R on in vitro CDC efficacy on Raji cells was tested using mixtures of variants of anti-CD37 antibody IgG1-CD37-37-3 and anti-CD20 IgG1-11B8 with an E430G Fc-Fc interaction enhancing mutation.

An in vitro CDC assay using Raji cells was performed with 20% NHS and antibody concentration series (final concentration range 0.01-40.0 µg/mL in 3.3-fold dilutions), essentially as described in Example 9. Burkitt's lymphoma cell line Raji was purchased from ATCC (Cat No. CCL-86). Cell lysis and relative AUC values were calculated from the number of PI-positive cells as described in Example 9, from two experimental replicates. AUC was normalized to the values for negative control antibody IgG1-b12 (0%) and for positive control IgG1-CAMPATH-1H-E430G+IgG1-CD37-37-3-E430G (100%).

Figure 17:
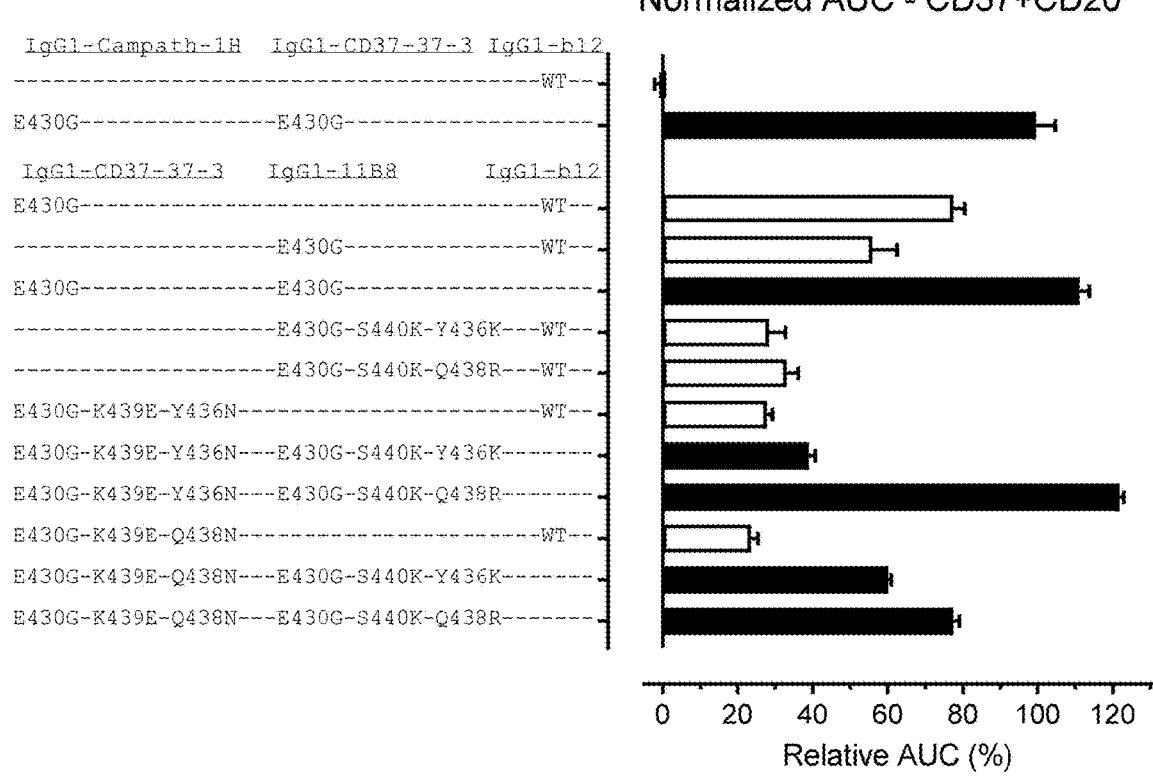
FIG. 17 shows CDC efficacy of single agent and combined anti-CD37 IgG1-CD37-37-3-E430G and IgG1-11B8-E430G antibody variants harboring self-oligomerization inhibiting mutations. Raji cells were incubated with antibody concentration series in the presence of 20% NHS. CDC efficacy is presented as the AUC normalized to non-binding control antibody IgG1-b12 (0%) and IgG1-CAMPATH-1H-E430G+IgG1-CD37-37-3-E430G (100%).

Both IgG1-CD37-37-3-E430G and IgG1-11B8-E430G demonstrated potent single agent CDC activity on Raji cells, albeit with lower efficiency than a mixture of said antibodies (FIG. 17). Low single agent CDC activity was observed upon introduction of self-oligomerization inhibiting muta-tions S440K-Y436K or S440K-Q438R in IgG1-11B8-E430G and by introduction of mutations K439E-Y436N or K439E-Q438N in IgG1-CD37-37-3-E430G. CDC efficacy could be fully restored to the level of a mixture of IgG1-CD37-37-3-E430G and IgG1-11B8-E430G by mixing IgG1-CD37-37-3-E430G-K439E-Y436N with IgG1-11B8-E430G-S440K-Q438R, but not with IgG1-11B8-E430G-S440K-Y436K, consistent with the results presented in Examples 9-16. The reduced CDC efficacy of IgG1-CD37-37-3-E430G-K439E-Q438N could be partially restored by mixing with IgG1-11B8-E430G-S440K-Y436K or IgG1-11B8-E430G-S440K-Q438R.

Overall, these data show that CDC efficacy of IgG1-CD37-37-3-E430G on Raji cells could be partially abro-gated by introduction of self-oligomerization inhibiting mutations K439E-Y436N or K439E-Q438N. Similarly, CDC efficacy of IgG1-11B8-E430G on Raji cells could be partially abrogated by introduction of self-oligomerization inhibiting mutations S440K-Y436K or S440K-Q438R. Recovery of CDC efficacy was attained to varying extent by mixing, in order of strong to weak recovery, IgG1-CD37-37-3-E430G-K439E-Y436N with IgG1-11B8-E430G-S440K-Q438R, IgG1-CD37-37-3-E430G-K439E-Q438N with IgG1-11B8-E430G-S440K-Q438R, or IgG1-CD37-37-3-E430G-K439E-Q438N with IgG1-11B8-E430G-S440K-Y436K.

Example 18: Selectivity of CDC Activity on Raji Cells by Mixed Anti-CD52 IgG1-CAMPATH-1H and Anti-CD37 IgG1-37-37-3 Antibody Variants with an E430G Fc-Fc Interaction Enhancing Mutation and Fc-Fc Self-Oligomerization Inhibiting Mutations The effect of self-oligomerization inhibiting mutations Y436K, Y436N, Q438N, Q438R, K439E and S440K on in vitro CDC efficacy on Raji cells was tested using mixtures of variants of anti-CD52 IgG1-CAMPATH-1H and anti-CD37 IgG1-37-37-3 with an E430G Fc-Fc interaction enhancing mutation.

An in vitro CDC assay using Raji cells was performed with 20% NHS and antibody concentration series (final concentration range 0.01-40.0 µg/mL in 3.3-fold dilutions), essentially as described in Example 9. Burkitt's lymphoma cell line Raji was purchased from ATCC (Cat No. CCL-86). Cell lysis and relative AUC values were calculated from the number of PI-positive cells as described in Example 9, from two experimental replicates. AUC was normalized to the values for negative control antibody IgG1-b12 (0%) and for positive control IgG1-CAMPATH-1H-E430G+IgG1-CD37-37-3-E430G (100%).

Figure 18:
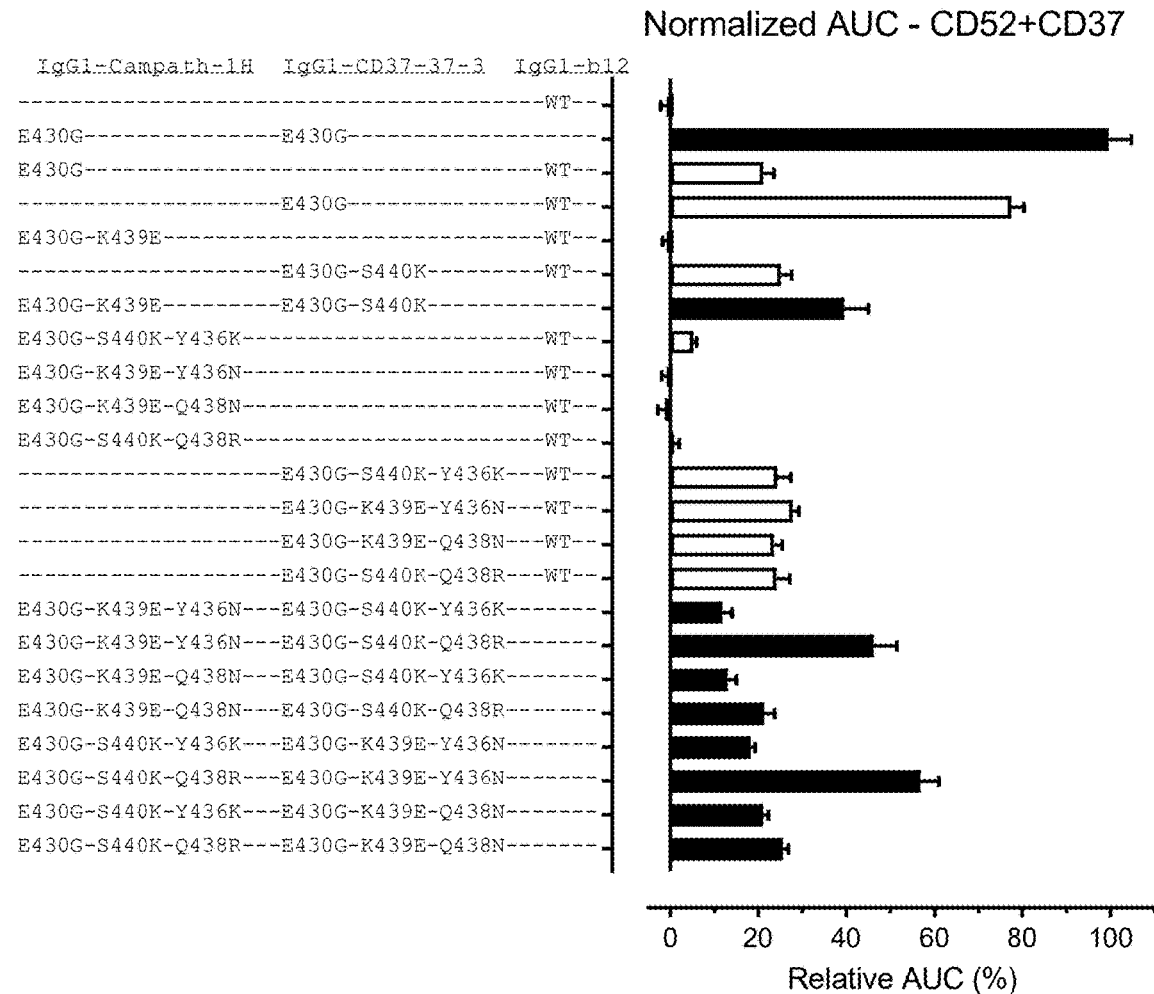
FIG. 18 shows CDC efficacy of single agent and combined anti-CD52 IgG1-CAMPATH-1H-E430G anti-CD37 IgG1-CD37-37-3-E430G antibody variants harboring self-oligomerization inhibiting mutations. Raji cells were incubated with antibody concentration series in the presence of 20% NHS. CDC efficacy is presented as the AUC normalized to non-binding control antibody IgG1-b12 (0%) and IgG1-CAMPATH-1H-E430G+IgG1-CD37-37-3-E430G (100%).

Antibody variant IgG1-CAMPATH-1H-E430G showed low to intermediate single agent CDC activity on Raji cells, while the single agent CDC activity of IgG1-CD37-37-3-E430G reached almost 80% of the activity induced by the mixture of IgG1-CAMPATH-1H-E430G and IgG1-CD37-37-3-E430G (FIG. 18). Introduction of self-oligomerization inhibiting mutation K439E in IgG1-CAMPATH-1H-E430G completely abrogated single agent CDC activity, while introduction of mutation S440K in IgG1-CD37-37-3-E430G reduced single agent CDC activity. By mixing IgG1-CAMPATH-1H-E430G-K439E and IgG1-CD37-37-3-E430G-S440K, a modest increase in CDC activity could be attained to approximately 40% of the level of the positive control mixture. Introduction of mutation Y436K, Y436N, Q438N or Q438R in either IgG1-CD37-37-3-E430G-S440K or IgG1-CAMPATH-1H-E430G-K439E did not significantly affect single agent CDC activity.

After mixing antibody variants of IgG1-CAMPATH-1H-E430G and IgG1CD37-37-3-E430G, CDC could only be partially recovered by a mixture of IgG1-CAMPATH-1H-E430G-K439E-Y436N and IgG1-CD37-37-3-E430G-S440K-Q438R, and not by mixing IgG1-CAMPATH-1H-E430G-K439E-Y436N with IgG1-CD37-37-3-E430G-S440K-Y436K, mixing IgG1-CAMPATH-1H-E430G-K439E-Q438N with IgG1-CD37-37-3-E430G-S440K-Y436K or mixing IgG1-CAMPATH-1H-E430G-K439E-Q438N with IgG1-CD37-37-3-E430G-S440K-Q438R.

Consistent with these observations, when an S440K and an additional self-oligomerization mutation were introduced in the IgG1-CAMPATH-1H-E430G antibody instead of the IgG1-CD37-37-3-E430G antibody, a partial recovery of CDC activity could only be attained by mixing IgG1-CAMPATH-1H-E430G-S440K-Q438R with IgG1-CD37-37-3-E430G-K439E-Y436N, and not by mixing IgG1-CAMPATH-1H-E430G-S440K-Y436K with IgG1-CD37-37-3-E430G-K439E-Y436N, mixing IgG1-CAMPATH-1H-E430G-S440K-Y436K with IgG1-CD37-37-3-E430G-K439E-Q438N or mixing IgG1-CAMPATH-1H-E430G-S440K-Q438R with IgG1-CD37-37-3-E430G-K439E-Q438N.

Overall, the results presented here indicate that mixtures of IgG1-CAMPATH-1H-E430G and IgG1-CD37-37-3-E430G antibody variants harboring self-oligomerization inhibiting mutations induced partial recovery of CDC efficacy in Raji cells, only when an antibody variant harboring the K439E-Y436N mutations was mixed with an antibody variant harboring the S440K-Q438R mutations. These effects were observed regardless of whether the aforementioned combinations of mutations were introduced in the IgG1-CAMPATH-1H-E430G or IgG1-CD37-37-3-E430G antibody variants.

Example 19: Selective DR5 Agonist Activity of a Mixture of Two Non-Crossblocking Anti-DR5 Antibodies with an E430G Fc-Fc Interaction Enhancing Mutation and Self-Oligomerization Inhibiting Mutations on BxPC-3 Cells The mixture of the two non-crossblocking anti-death receptor 5 (DR5) antibodies IgG1-DR5-01-G56T-E430G+ IgG1-DR5-05-E430G acts as a DR5 agonist inducing killing of DR5-positive cancer cells (WO17093447). Here, a viability assay was performed to study whether the introduction of self-oligomerization inhibiting mutations Y436K, Y436N, Q438N and Q438R in mixed DR5-targeting antibody variants results in co-dependent cytotoxicity on BxPC-3 pancreatic cancer cells (ATCC, Cat No. CRL-1687), which express low levels of DR5 (data not shown).

BxPC-3 cells were harvested by trypsinization and passed through a cell strainer. Cells were pelleted by centrifugation for 5 minutes at 1,200 rpm and resuspended in culture medium at a concentration of $1.1\times10^5$ cells/mL (RPMI 1640 medium (ATCC modification), Life Technologies Cat No. A10491-01+10% DBSI (Life Technologies Cat No. 20371). 45 µL of the single cell suspensions (5,000 cells/well) were seeded in polystyrene 96-well flat-bottom plates (Greiner Bio-One, Cat No. 655180) and allowed to adhere overnight at 37° C. The next day, 50 µL samples of an antibody dilution series (final concentration range 0.003-20 µg/mL in 3-fold dilutions) and 24 µL purified human C1q stock solution (Quidel, Cat No. A400, 2.9 µg/mL final concentration) were added and incubated for 3 days at 37° C. As a positive control, cells were incubated with 5 µM staurosporine (Sigma Aldrich, Cat No. S6942). The viability of the cell cultures was determined in a CellTiter-Glo luminescence cell viability assay (Promega, Cat No. G755A) that quantifies the ATP present, which is an indicator of metabolically active cells. From the kit, 12 µL Luciferin Solution Reagent was added per well. Next, plates were incubated for 1.5 hours at 37° C. 100 µL supernatant was transferred to a white OptiPlate-96 (Perkin Elmer, Cat No. 6005290) and luminescence was measured on an EnVision Multilabel Reader (PerkinElmer). Data were analyzed using GraphPad Prism 7 and plotted as cell viability at 20 µg/ml antibody concentration. The percentage viable cells was calculated using the following formula: % viable cells=[(luminescence antibody sample–luminescence staurosporine sample)/(luminescence no antibody sample–luminescence staurosporine sample)]*100.

Figure 19:
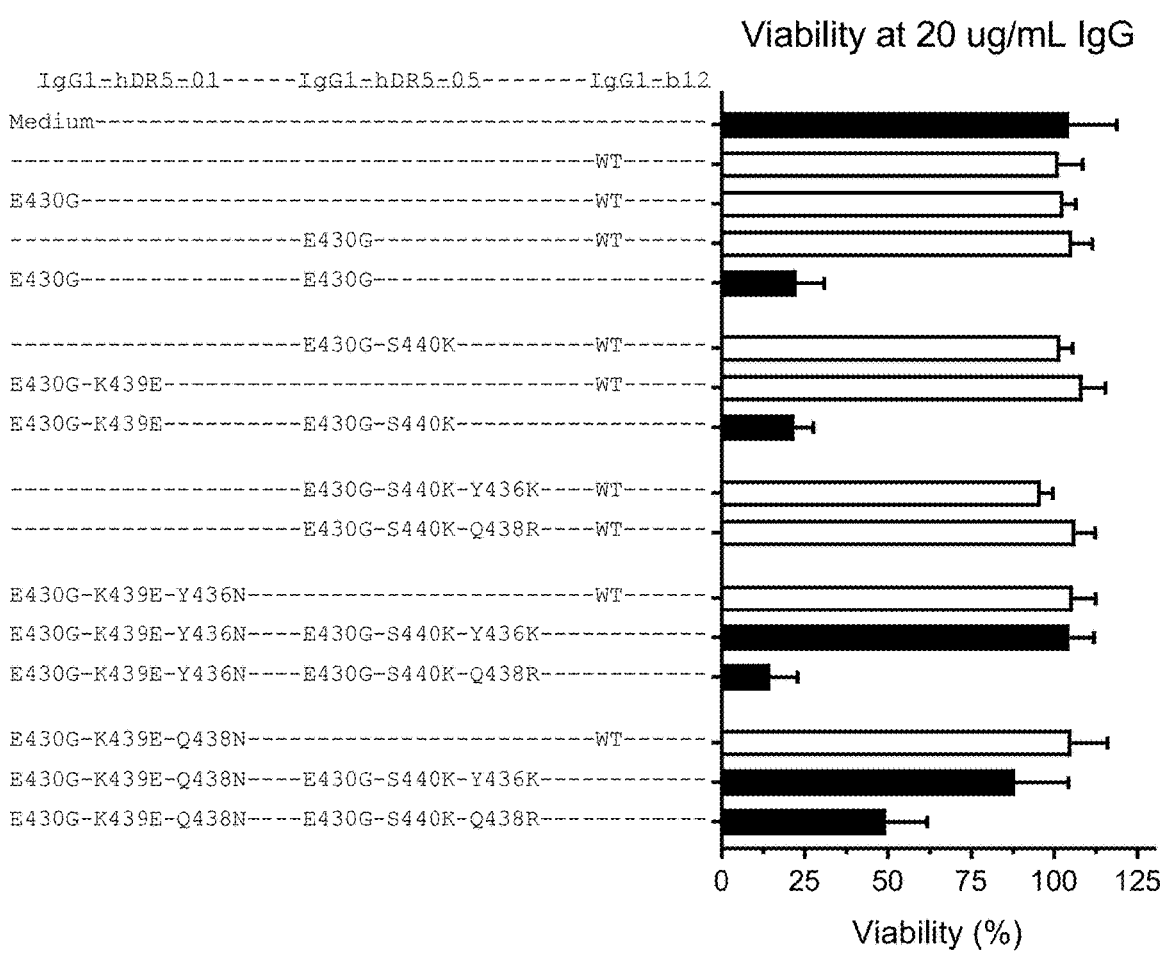
FIG. 19 shows cytotoxicity of anti-DR5 antibody variants of IgG1-DR5-01-G56T-E430G and IgG1-DR5-05-E430G harboring self-oligomerization inhibiting mutations. BxPC-3 cells were incubated with antibody concentration series in the presence of purified human C1q (2.9 μg/mL final concentration). Cytotoxicity is presented as the cell viability at 20 μg/ml antibody concentration. The percentage viable cells was calculated using the following formula: % viable cells=[(luminescence antibody sample–luminescence staurosporine sample)/(luminescence no antibody sample–luminescence staurosporine sample)]*100%.

No cytotoxicity was observed after exposure of BxPC-3 cells to negative controls medium or IgG1-b12 (FIG. 19). Also, no single agent activity was observed after exposing BxPC-3 cells to 20 µg/ml of either IgG1-DR5-01-G56T-E430G or IgG1-DR5-05-E430G. In contrast, strong cytotoxicity was induced by a mixture of 20 µg/ml IgG1-hDR5-01-G56T-E430G and IgG1-hDR5-05-E430G, resulting in a cell viability of approximately 22%. Similarly, strong cytotoxicity was induced by a mixture of the same antibodies in which either of the self-oligomerization inhibiting mutations K439E and S440K were introduced, while the single components did not induce any cytotoxicity.

No single agent cytotoxicity was observed by antibody variants of IgG1-DR5-01-G56T-E430G and IgG1-DR5-05-E430G in which either of the K439E or S440K mutations, in combination with either of the Y436K, Y436N, Q438N or Q438R mutations were introduced. However, the potency to induce cytotoxicity could be recovered by mixing, in order of strong to weak recovery, IgG1-DR5-01-G56T-E430G-K439E-Y436N with IgG1-DR5-05-E430G-S440K-Q438R, IgG1-DR5-01-G56T-E430G-K439E-Q438N with IgG1-DR5-05-E430G-S440K-Q438R, or IgG1-DR5-01-G56T-E430G-K439E-Q438N with IgG1-DR5-05-E430G-Y436K. In line with the results described in Examples 9-17, no recovery of cytotoxicity was observed by mixing IgG1-DR5-01-G56T-E430G-K439E-Y436N with IgG1-DR5-05-E430G-S440K-Y436K.

In summary, these data show that DR5-targeting antibody variants with introduced self-oligomerization inhibiting mutations K439E, S440K, Y436K, Y436N, Q438N and Q438R do not induce single agent cytotoxicity of BxPC-3 cells, while cytotoxicity is restored by mixing complementary DR5-targeting antibody variants. Notably, the data presented in this Example represent a different mechanism of action compared to the data the described in Examples 9-17.

Example 20: Selectivity of CDC Activity on Raji Cells by Mixed Anti-CD20 IgG1-7D8 Antibody Variants with an E430G Fc-Fc Interaction Enhancing Mutation and Fc-Fc Self-Oligomerization Inhibiting Mutations The effect of self-oligomerization inhibiting mutations Y436K, Y436N, Q438N, Q438R, K439E, and S440K on in vitro CDC efficacy on Raji cells was tested using mixtures of variants of anti-CD20 IgG1-7D8 with an E430G Fc-Fc interaction enhancing mutation, as opposed to Example 10 in which antibody variants of anti-CD20 IgG1-11B8 were tested.

An in vitro CDC assay using Raji cells was performed with 20% NHS and antibody concentration series (final concentration range 0.01-40.0 µg/mL in 3.3-fold dilutions), essentially as described in Example 9. Burkitt's lymphoma cell line Raji was purchased from ATCC (Cat No. CCL-86). Cell lysis and relative AUC values were calculated from the number of PI-positive cells as described in Example 9, from two experimental replicates. AUC was normalized to the values for negative control antibody IgG1-b12 (0%) and for positive control IgG1-CAMPATH-1H-E430G+IgG1-7D8-E430G (100%).

Figure 20:
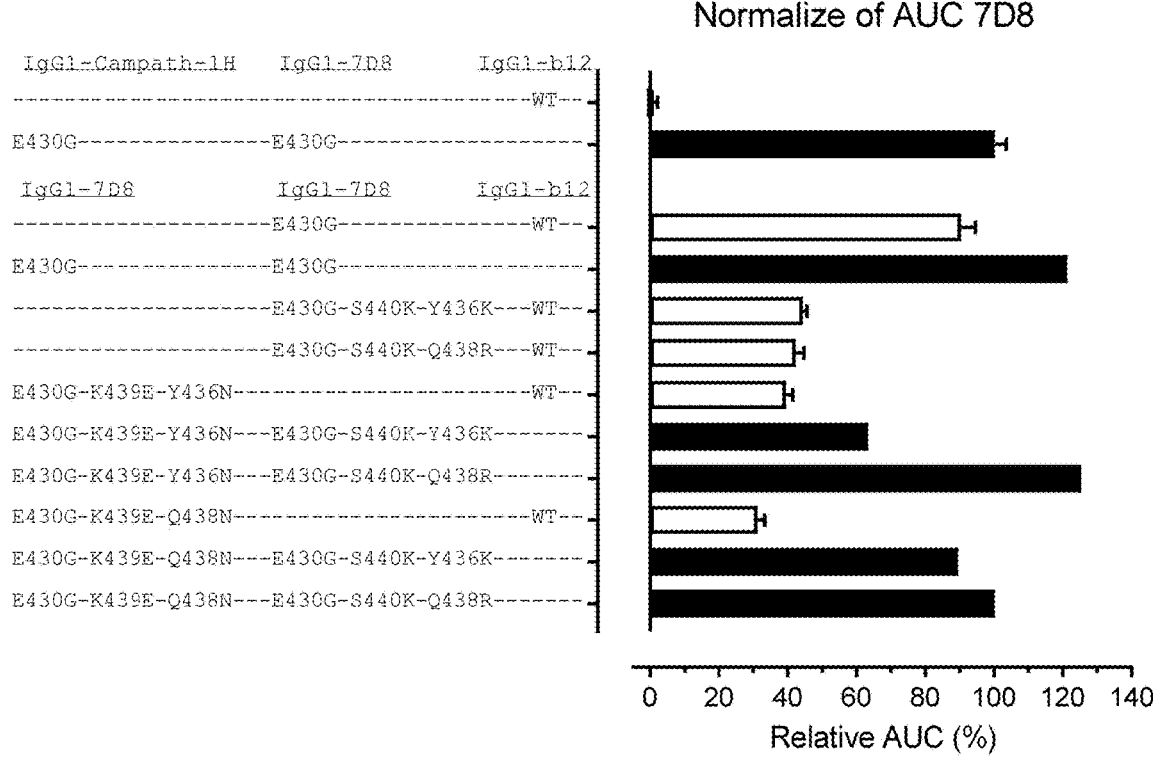
FIG. 20 shows CDC efficacy of single agent and combined anti-CD37 IgG1-7D8-E430G antibody variants harboring self-oligomerization inhibiting mutations. Raji cells were incubated with antibody concentration series in the presence of 20% NHS. CDC efficacy is presented as the AUC normalized to non-binding control antibody IgG1-b12 (0%) and IgG1-CAMPATH-1H-E430G+IgG1-7D8-E430G (100%).

Antibody IgG1-7D8-E430G on itself induced potent CDC efficacy on Raji cells, regardless of whether it was mixed with non-antigen binding antibody IgG1-b12 or not (FIG. 20). Antibody variants of IgG1-7D8-E430G in which the self-oligomerization inhibiting mutations K439E-Y436N, K439E-Q438N, S440K-Y436K or S440K-Q438R were introduced demonstrated substantial single agent activity. CDC efficacy could be fully restored to the level of IgG1-7D8-E430G by mixing IgG1-7D8-E430G-K439E-Y436N with IgG1-7D8-E430G-S440K-Q438R, but not with IgG1-7D8-E430G-S440K-Y436K, consistent with the results presented in Examples 9-17. The reduced CDC efficacy of IgG1-7D8-E430G-K439E-Q438N could be partially restored by mixing with IgG1-7D8-E430G-S440K-Y436K or IgG1-7D8-E430G-S440K-Q438R. Overall, these data show that CDC efficacy of IgG1-7D8-E430G on Raji cells could be partially abrogated by introduction of self-oligomerization inhibiting mutations K439E-Y436N or K439E-Q438N. Similarly, CDC efficacy of IgG1-7D8-E430G on Raji cells could be partially abrogated by introduction of self-oligomerization inhibiting mutations S440K-Y436K or S440K-Q438R. Recovery of CDC efficacy was attained to varying extent by mixing, in order of strong to weak recovery, IgG1-7D8-E430G-K439E-Y436N with IgG1-7D8-E430G-S440K-Q438R, IgG1-7D8-E430G-

K439E-Q438N with IgG1-7D8-E430G-S440K-Q438R, or IgG1-7D8-E430G-K439E-Q438N with IgG1-7D8-E430G-S440K-Y436K.

Example 21: Selectivity of CDC Activity on Wien 133 Cells after Titrating Components of a Mixture of Anti-CD52 IgG1-CAMPATH-1H and Anti-CD20 IgG1-11B8 Antibody Variants with an E430G Fc-Fc Interaction Enhancing Mutation and Self-Oligomerization Inhibiting Mutations In the previous Examples, antibody variants harboring an Fc-Fc interaction enhancing mutation in combination with one or more self-oligomerization inhibiting mutations were mixed in a 1:1 ratio. Here, we tested whether selective co-dependent CDC activity was also attained by mixing two antibody variants at different ratios.

An in vitro CDC assay using Wien 133 cells was performed with 20% NHS, essentially as described in Example 9. Single antibodies were titrated in 5-fold dilutions (final concentration range 0.0003-20.0 µg/mL). When antibody mixtures were applied, one component was titrated (final concentration range 0.0003-20.0 µg/mL in 5-fold dilutions) and the other component was used at a fixed concentration of 20 or 2 µg/mL. Cell lysis was calculated from the number of PI-positive cells as described in Example 9, from two experimental replicates.

Figure 21A:
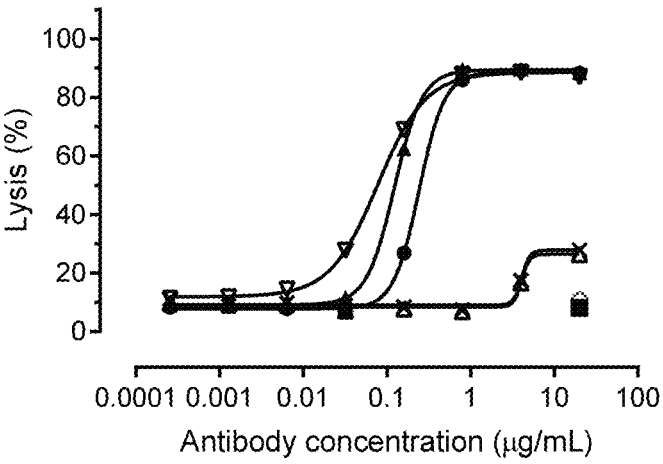
FIGS. 21A and 21B show CDC efficacy by anti-CD52 IgG1-CAMPATH-1H-E430G and anti-CD20 IgG1-11B8-E430G antibody variants harboring self-oligomerization inhibiting mutations, as single agents or mixed in different ratios. Wien 133 cells were incubated with antibody concentration series in the presence of 20% NHS. CDC efficacy is presented as the percentage of cell lysis calculated from the number of PI-positive cells.

Efficient CDC activity on Wien 133 cells was induced by a titrated mixture (1:1 ratio) of IgG1-CAMPATH-1H-E430G-K439E-Q438N and IgG1-11B8-E430G-S440K-Y436K (FIG. 21A), consistent with the results in Examples 11, 14, and 15. When CD20 was saturated with 20 µg/mL IgG1-11B8-E430G-S440K-Y436K, >60% lysis was already detected in the presence of 0.16 µg/mL IgG1-CAMPATH-1H-E430G-K439E-Q438N. Likewise, saturating CD52 with 2 µg/mL IgG1-CAMPATH-1H-E430G-K439E-Q438N yielded >60% lysis in the presence of 0.16 µg/mL IgG1-11B8-E430G-S440K-Y436K. In contrast, low CDC efficacy close to background levels was observed for a mixture of titrated IgG1-CAMPATH-1H-E430G-K439E-Q438N and either 20 µg/mL of non-antigen binding IgG1-b12-E430G-S440K-Y436K or IgG1-b12. Upon mixing 20 µg/mL IgG1-11B8-E430G-S440K-Y436K with 20 µg/mL of either IgG1-b12-E430G-K439E-Q438N or IgG1-b12, no CDC activity was observed.

Figure 21B:
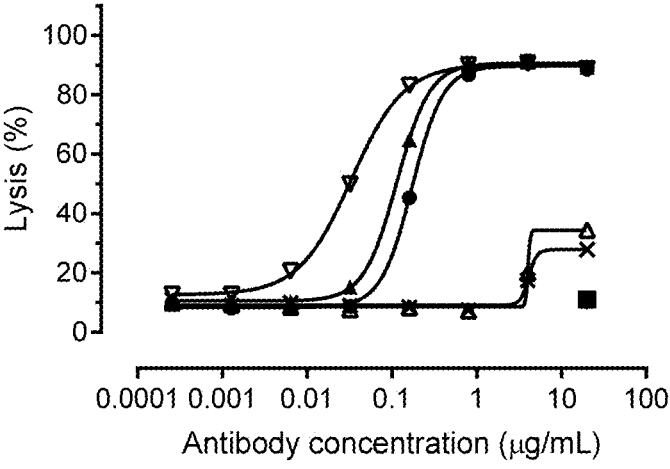

Similar patterns of CDC activity were observed for a titrated mixture (1:1 ratio) of IgG1-CAMPATH-1H-E430G-K439E-Q438N and IgG1-11B8-E430G-S440K-Q438R (FIG. 21B), consistent with Examples 11, 14, and 15. When saturating CD20 using 20 µg/mL IgG1-11B8-E430G-S440K-Q438R, 0.16 µg/mL IgG1-CAMPATH-1H-E430G-K439E-Q438N sufficed to induce >60% lysis. When CD52 was saturated with a fixed concentration of 2 µg/mL of IgG1-CAMPATH-1H-E430G-K439E-Q438N, 0.04 µg/mL IgG1-11B8-E430G-S440K-Q438R already sufficed to induce >50% lysis. Low CDC efficacy, close to background levels, was observed for a mixture of titrated IgG1-CAMPATH-1H-E430G-K439E-Q438N and either 20 µg/mL of non-antigen binding IgG1-b12-E430G-S440K-Q438R or IgG1-b12. Upon mixing 20 µg/mL IgG1-11B8-E430G-S440K-Q438R with 20 µg/mL of either IgG1-b12-E430G-K439E-Q438N or IgG1-b12, no CDC activity was observed.

From these data, it can be concluded that efficient CDC activity could still be induced by complementary antibody variants harboring an Fc-Fc interaction enhancing mutation and self-oligomerization inhibiting mutations when mixed at different antibody ratios in which either of the components was present at >50-fold excess relative to the other component.

Example 22: Selectivity of CDC Activity on Wien 133 Cells Through Antigen-Binding Independent Hexamerization of Mixed Antibody Variants with an E430G Fc-Fc Interaction Enhancing Mutation and Fc-Fc Self-Oligomerization Inhibiting Mutations In the previous Examples, it was demonstrated that single agent CDC activity of antigen-binding antibody variants harboring an Fc-Fc interaction enhancing mutation could be reduced or abrogated by introducing self-oligomerization inhibiting mutations. Recovery of CDC efficacy was observed after mixing complementary antigen-binding antibody variants harboring self-oligomerization inhibiting mutations. Here, we tested whether co-dependent hexamerization could also be induced by mixtures of antigen-binding and non-antigen-binding antibody variants harboring said mutations.

An in vitro CDC assay using Wien 133 cells was performed with 20% NHS and antibody concentration series (final concentration range 0.01-40.0 µg/mL in 3.3-fold dilutions), essentially as described in Example 9. Cell lysis and relative area under the curve (AUC) values were calculated from the number of PI-positive cells as described in Example 9, from two experimental replicates. AUC was normalized to the values for negative control antibody IgG1-b12 (0%) and for positive control IgG1-CAMPATH-1H-E430G (100%).

Figure 22A:
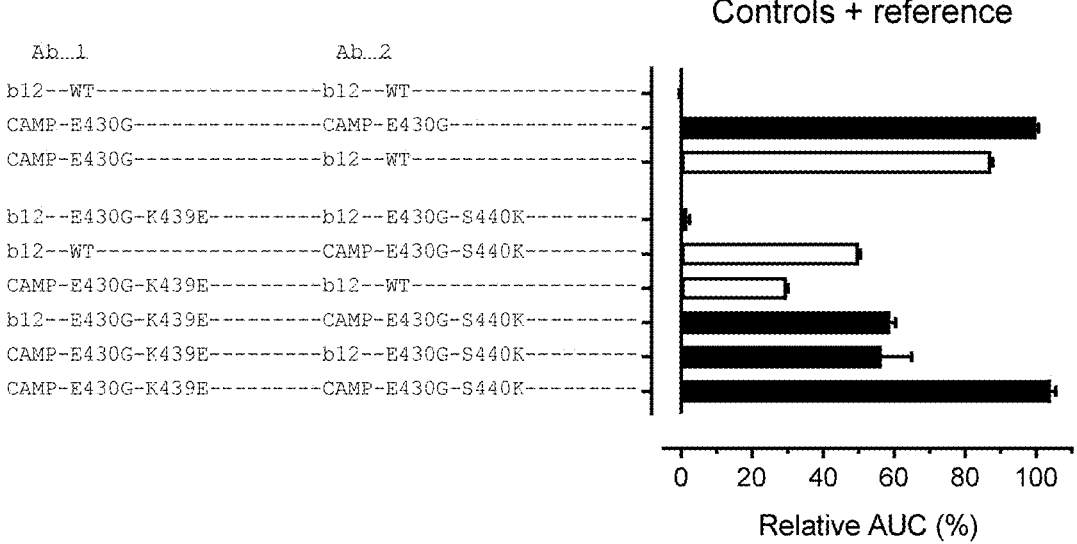
FIGS. 22A-22F show CDC efficacy of single agent and combined anti-CD52 IgG1-CAMPATH-1H-E430G and non-antigen-binding IgG1-b12-E430G antibody variants harboring self-oligomerization inhibiting mutations. Wien 133 cells were incubated with antibody concentration series in the presence of 20% NHS. CDC efficacy is presented as the AUC normalized to non-binding control antibody IgG1-b12 (0%) and IgG1-CAMPATH-1H-E430G (100%).
Figure 22B:
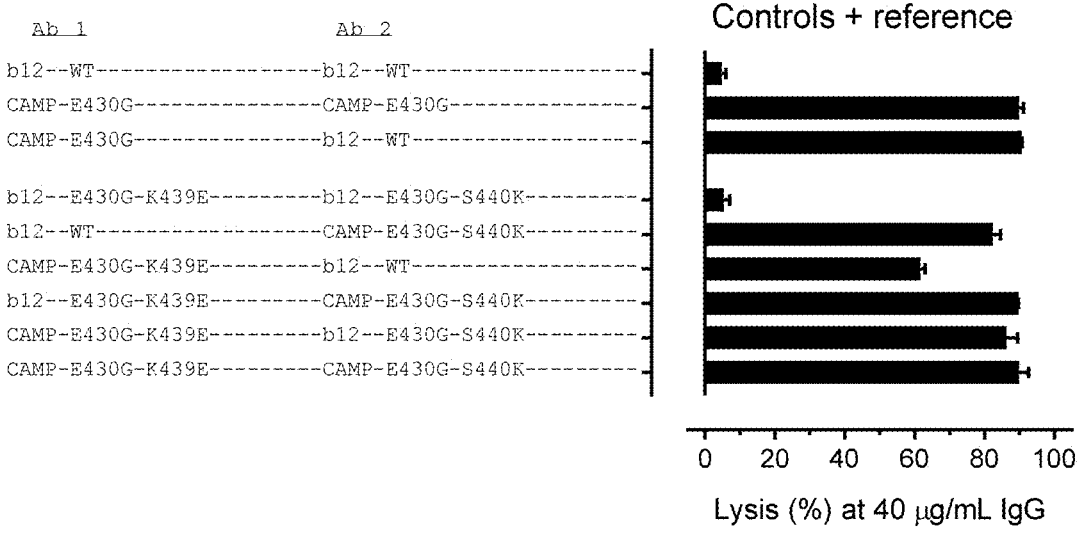

Efficient CDC activity was observed after exposing Wien 133 cells to IgG1-CAMPATH-1H-E430G as a single agent (FIG. 22A). The introduction of additional self-oligomerization inhibiting mutations K439E or S440K reduced the single agent CDC efficacy, while CDC efficacy was fully restored by mixing IgG1-CAMPATH-1H-E430G-K439E and IgG1-CAMPATH-1H-E430G-S440K. A slight increase in CDC activity was observed when IgG1-CAMPATH-1H-E430G-K439E was mixed with non-antigen binding antibody variant IgG1-b12-E430G-S440K, while similar activity was observed for a mixture of IgG1-b12-E430G-K439E and IgG1-CAMPATH-1H-E430G-S440K. Apparently, upon binding to an antigen by at least one of the components in a mixture, non-antigen binding antibody variants harboring complementary mutations could be recruited from solution. At the highest antibody concentration tested (40 µg/ml), CDC by mixtures of one antigen-binding and one non-antigen binding antibody variant harboring the E430G mutation and self-oligomerization inhibiting mutations K439E or S440K was as efficient as a mixture of IgG1-CAMPATH- 1H-E430G-K439E and IgG1-CAMPATH-1H-E430G-S440K (FIG. 22B) although the latter mixture was superior at lower concentrations as shown by its higher AUC value in FIG. 22A.

Figure 22C:
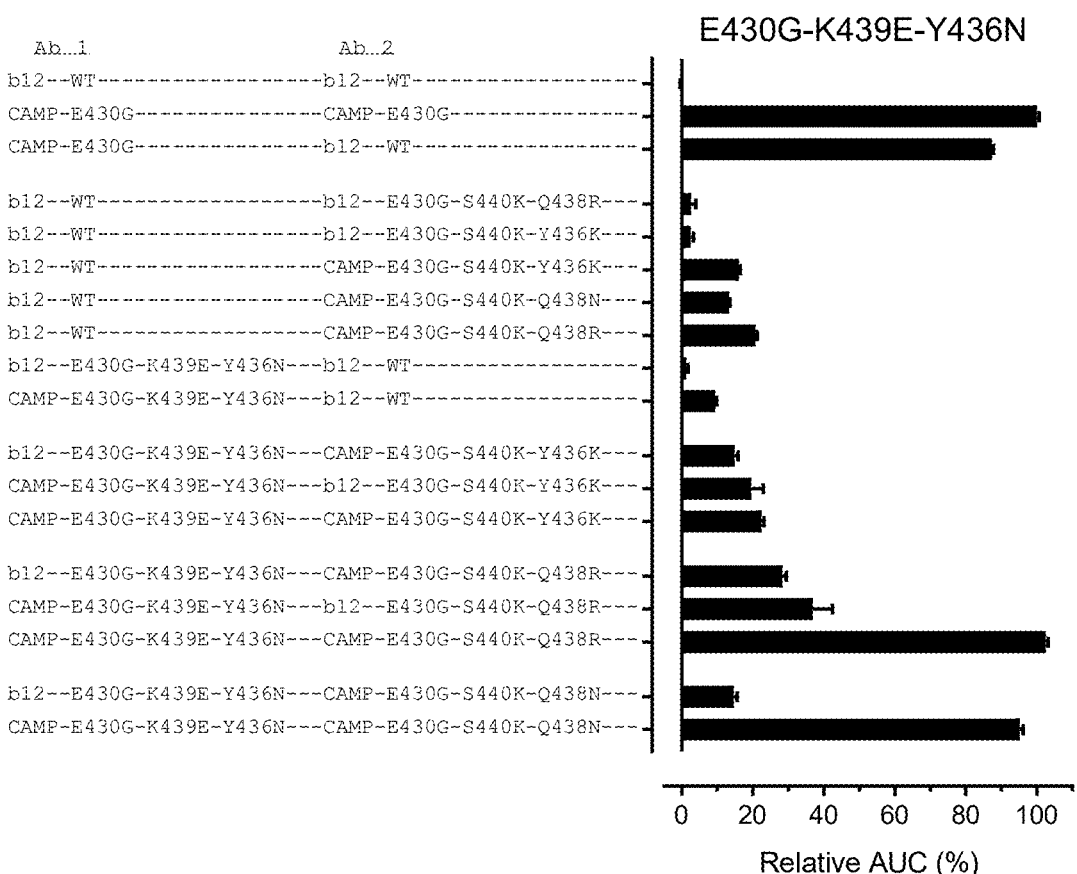
Figure 22D:
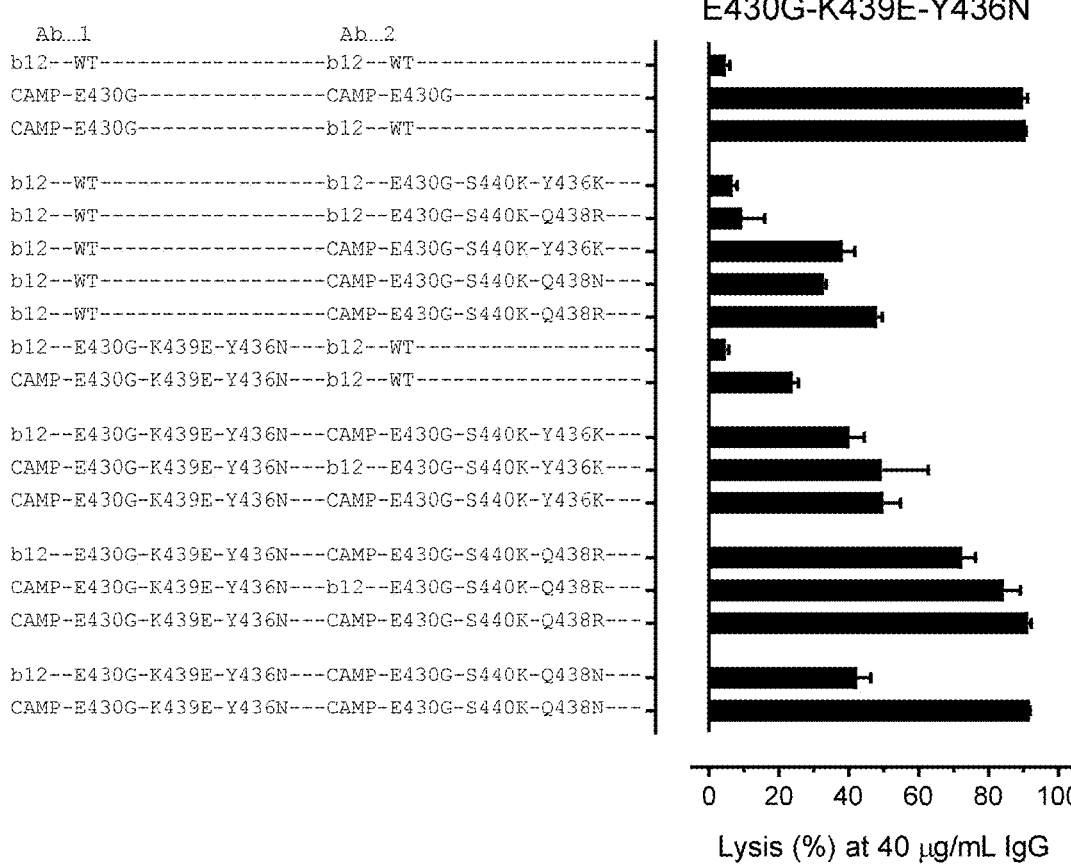

Introduction of additional self-oligomerization inhibiting mutations Y436K, Y436N, Q438N or Q438R in IgG1-CAMPATH-1H-E430G resulted in a reduction of single agent CDC activity (FIG. 22C). CDC efficacy was increased to variable extent by mixing IgG1-CAMPATH-1H-E430G-K439E-Y436N with IgG1-b12-E430G-S440K antibody variants harboring complementary mutations or by mixing IgG1-b12-E430G-K439E-Y436N with IgG1-CAMPATH-1H-E430G-S440K antibody variants harboring complementary mutations (FIG. 22C). Especially the mixture of IgG1-CAMPATH-1H-E430G-K439E-Y436N+IgG1-CAMPATH-1H-E430G-S440K-Q438R showed potent maximal lysis when the CD52-binding specificity of either component was replaced with b12 (FIG. 22D), indicating that the selectivity of this mixture for only cells bound by both antibodies may be compromised at 40 µg/ml antibody concentration. In contrast, mixture IgG1-CAMPATH-1H-E430G-K439E-Y436N+IgG1-CAMPATH-1H-E430G-S440K-Q438N showed similar maximal activity and relative potency, but remained largely dependent on antigen binding by IgG1-CAMPATH-1H-E430G-K439E-Y436N even at 40 µg/ml antibody concentration.

Figure 22E:
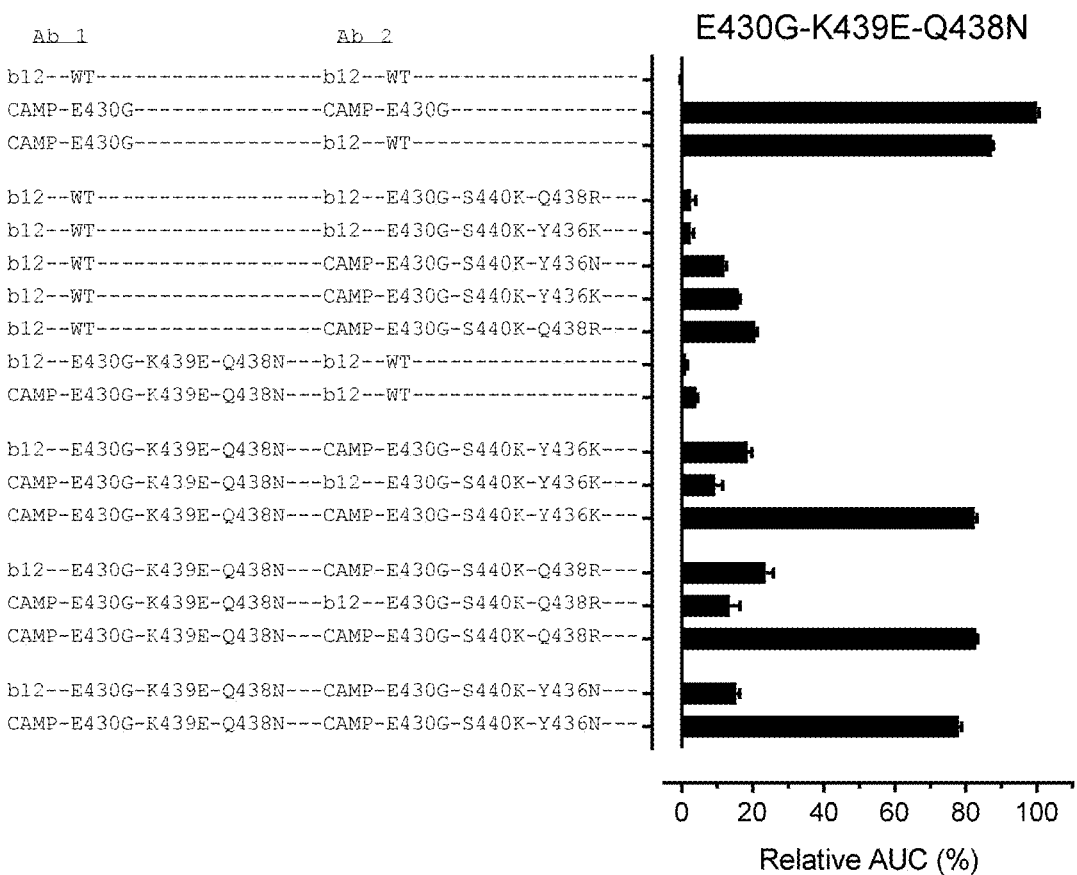
Figure 22F:
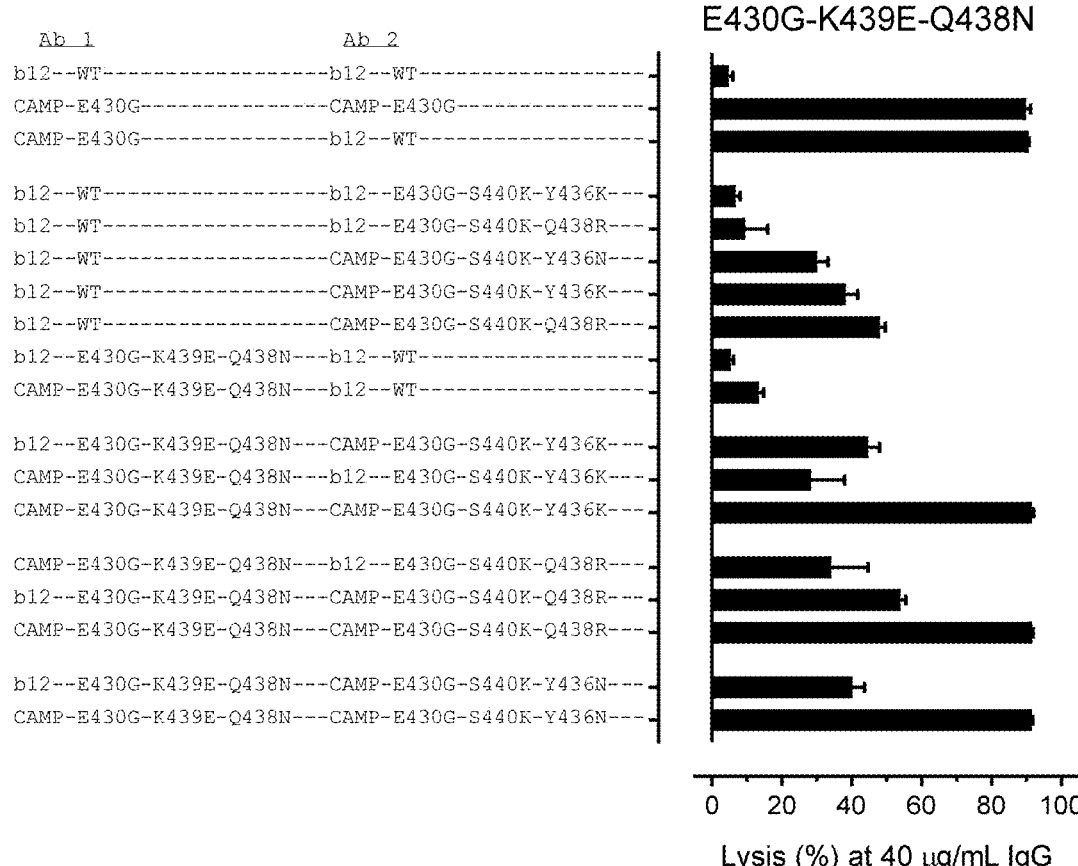

CDC efficacy was increased to a limited extent by mixing IgG1-CAMPATH-1H-E430G-K439E-Q438N with IgG1-b12-E430G-S440K antibody variants harboring complementary mutations or by mixing IgG1-b12-E430G-K439E-Q438N with IgG1-CAMPATH-1H-E430G-S440K antibody variants harboring complementary mutations (FIG. 22E). Both when considering CDC efficacy (22E) and maximally induced cell lysis (at 40 µg/ml antibody concentration; FIG. 22F), mixtures with two antigen-bound components remained substantially more active than mixtures with only one antigen-bound component.

These data indicate that introduction of self-oligomerization inhibiting mutations K439E or S440K in combination with Y436K, Y436N, Q438N or Q438R in IgG1 antibody variants harboring the Fc-Fc interaction enhancing mutation E430G could result in residual CDC efficacy on Wien 133 cells when one of the antibody components did not bind the Wien 133 cells. In these experiments, the antibody mixtures displaying the largest difference in CDC activity between that induced by two antigen-bound components compared to that induced by one antigen-bound component were: antibodies harboring E430G-K439E-Q438N mutations mixed with antibodies harboring mutations E430G-S440K-Y436K, E430G-S440K-Q438R, or E430G-S440K-Y436N; and antibodies harboring E430G-K439E-Y436N mutations mixed with antibodies harboring mutations E430G-S440K-Q438N.

The invention claimed is:

1. A polypeptide comprising a Fc region of a human IgG and an antigen-binding region capable of binding to an antigen, wherein said polypeptide comprises a Y436N, Y436K, Y436Q or Y436R mutation of an amino acid position corresponding to Y436 in human IgG1, and a K439F, K439I, K439Y, K439T, K439V, K439W, or K439E mutation of an amino acid position corresponding to K439 in human IgG1.

2. A polypeptide comprising a Fc region of a human IgG and an antigen-binding region capable of binding to an antigen, wherein said polypeptide comprises a Q438R, Q438H, Q438G or Q438N mutation of an amino acid position corresponding to Q438 in human IgG1, and an S440K mutation of an amino acid position corresponding to S440 in human IgG1.

3. The polypeptide according to claim 1, wherein said polypeptide further comprises an E430G mutation of an amino acid position corresponding to E430 in human IgG1.

4. The polypeptide according to claim 2, wherein said polypeptide further comprises an E430G mutation of an amino acid position corresponding to E430 in human IgG1.

5. The polypeptide according to claim 1, wherein said polypeptide is an antibody.

6. The polypeptide according to claim 1, wherein said polypeptide is an IgG1 antibody.

7. The polypeptide according to claim 5, wherein said antibody is human, humanized or chimeric.

8. The polypeptide according to claim 5, wherein said antibody is bispecific.

9. The polypeptide according to claim 1, wherein said antigen is a cell surface-exposed molecule.

10. The polypeptide according to claim 1, wherein said antigen is not a death receptor.

11. A pharmaceutical composition comprising the polypeptide as defined in claim 1 and a pharmaceutically-acceptable carrier.

12. The polypeptide according to claim 1, wherein said polypeptide is a full-length antibody.

13. The polypeptide according to claim 2, wherein said polypeptide is an antibody.

14. The polypeptide according to claim 2, wherein said polypeptide is a full-length antibody.

15. The polypeptide according to claim 2, wherein said polypeptide is an IgG1 antibody.

16. The polypeptide according to claim 14, wherein said antibody is human, humanized or chimeric.

17. The polypeptide according to claim 14, wherein said antibody is bispecific.

18. A pharmaceutical composition comprising the polypeptide as defined in claim 2 and a pharmaceutically-acceptable carrier.

19. A mixture of antibodies comprising:
(a) a first antibody comprising an Fc region of a human IgG, wherein the Fc region comprises a Y436N, Y436K, Y436Q or Y436R mutation of an amino acid position corresponding to Y436 in human IgG1, and a K439F, K439I, K439Y, K439T, K439V, K439W, or K439E mutation of an amino acid position corresponding to K439 in human IgG1, and
(b) a second antibody comprising an Fc region of a human IgG, wherein the Fc region comprises a Q438R, Q438K, Q438H, Q438G or Q438N mutation of an amino acid position corresponding to Q438 in human IgG1, and an S440K mutation of an amino acid position corresponding to S440 in human IgG1.

20. The mixture of antibodies according to claim 19, wherein the Fc regions of the first and second antibodies further comprise an E430G mutation of an amino acid position corresponding to E430 in human IgG1.

21. The mixture of antibodies according to claim 19, wherein:
(a) the Fc region of the first antibody comprises a Y436N mutation and a K439E mutation of amino acid positions corresponding to Y436 and K439 in human IgG1, respectively, and
(b) the Fc region of the second antibody comprises a Q438R mutation and a S440K mutation of amino acid positions corresponding to Q438 and S440 in human IgG1, respectively.

22. The mixture of antibodies according to claim 21, wherein the Fc regions of the first and second antibodies further comprise an E430G mutation of an amino acid position corresponding to E430 in human IgG1.

23. The mixture of antibodies according to claim 19, wherein:
(a) the Fc region of the first antibody comprises Y436N, K439E, and E430G mutations of amino acid positions corresponding to Y436, K439, and E430 in human IgG1, respectively, and
(b) the Fc region of the second antibody comprises Q438R, S440K, and E430G mutations of amino acid positions corresponding to Q438, S440, and E430 in human IgG1, respectively.

24. The mixture of antibodies according to claim 23, wherein the first antibody and/or second antibody is an IgG1 antibody.

25. The mixture of antibodies according to claim 23, wherein the first antibody and/or second antibody is human, humanized, or chimeric.

26. A pharmaceutical composition comprising the mixture of antibodies according to claim 23 and a pharmaceutically-acceptable carrier.

27. A kit comprising a first container comprising a first antibody and a second container comprising a second antibody, wherein both the first and second antibodies are as defined in claim 23.

28. A dual chamber syringe comprising a first compartment comprising a first antibody and a second compartment comprising a second antibody, wherein the first and second antibodies are as defined in claim 23.

* * * * *

SEQUENCE LISTING

<160> NUMBER OF SEQ ID NOS: 118

<210> SEQ ID NO 1
<211> LENGTH: 121
<212> TYPE: PRT
<213> ORGANISM: Artificial sequence
<220> FEATURE:
<223> OTHER INFORMATION: Humanized antibody variable region

<400> SEQUENCE: 1

Gln Val Gln Leu Gln Glu Ser Gly Pro Gly Leu Val Arg Pro Ser Gln

```
1               5               10              15

Thr Leu Ser Leu Thr Cys Thr Val Ser Gly Phe Thr Phe Thr Asp Phe
                20              25              30

Tyr Met Asn Trp Val Arg Gln Pro Pro Gly Arg Gly Leu Glu Trp Ile
        35              40              45

Gly Phe Ile Arg Asp Lys Ala Lys Gly Tyr Thr Thr Glu Tyr Asn Pro
    50              55              60

Ser Val Lys Gly Arg Val Thr Met Leu Val Asp Thr Ser Lys Asn Gln
65              70              75              80

Phe Ser Leu Arg Leu Ser Ser Val Thr Ala Ala Asp Thr Ala Val Tyr
                85              90              95

Tyr Cys Ala Arg Glu Gly His Thr Ala Ala Pro Phe Asp Tyr Trp Gly
            100             105             110

Gln Gly Ser Leu Val Thr Val Ser Ser
        115             120
```

```
<210> SEQ ID NO 2
<211> LENGTH: 8
<212> TYPE: PRT
<213> ORGANISM: Rattus norvegicus

<400> SEQUENCE: 2

Gly Phe Thr Phe Thr Asp Phe Tyr
1               5
```

```
<210> SEQ ID NO 3
<211> LENGTH: 10
<212> TYPE: PRT
<213> ORGANISM: Rattus norvegicus

<400> SEQUENCE: 3

Ile Arg Asp Lys Ala Lys Gly Tyr Thr Thr
1               5               10
```

```
<210> SEQ ID NO 4
<211> LENGTH: 12
<212> TYPE: PRT
<213> ORGANISM: Rattus norvegicus

<400> SEQUENCE: 4

Ala Arg Glu Gly His Thr Ala Ala Pro Phe Asp Tyr
1               5               10
```

```
<210> SEQ ID NO 5
<211> LENGTH: 107
<212> TYPE: PRT
<213> ORGANISM: Artificial sequence
<220> FEATURE:
<223> OTHER INFORMATION: Humanized antibody variable region

<400> SEQUENCE: 5

Asp Ile Gln Met Thr Gln Ser Pro Ser Ser Leu Ser Ala Ser Val Gly
1               5               10              15

Asp Arg Val Thr Ile Thr Cys Lys Ala Ser Gln Asn Ile Asp Lys Tyr
                20              25              30

Leu Asn Trp Tyr Gln Gln Lys Pro Gly Lys Ala Pro Lys Leu Leu Ile
        35              40              45

Tyr Asn Thr Asn Asn Leu Gln Thr Gly Val Pro Ser Arg Phe Ser Gly
    50              55              60

Ser Gly Ser Gly Thr Asp Phe Thr Phe Thr Ile Ser Ser Leu Gln Pro
```

-continued

```
65              70              75              80

Glu Asp Ile Ala Thr Tyr Tyr Cys Leu Gln His Ile Ser Arg Pro Arg
                85              90              95

Thr Phe Gly Gln Gly Thr Lys Val Glu Ile Lys
            100             105

<210> SEQ ID NO 6
<211> LENGTH: 6
<212> TYPE: PRT
<213> ORGANISM: Rattus norvegicus

<400> SEQUENCE: 6

Gln Asn Ile Asp Lys Tyr
1               5

<210> SEQ ID NO 7
<211> LENGTH: 9
<212> TYPE: PRT
<213> ORGANISM: Rattus norvegicus

<400> SEQUENCE: 7

Leu Gln His Ile Ser Arg Pro Arg Thr
1               5

<210> SEQ ID NO 8
<211> LENGTH: 125
<212> TYPE: PRT
<213> ORGANISM: Homo sapiens

<400> SEQUENCE: 8

Glu Val Gln Leu Val Gln Ser Gly Gly Gly Leu Val His Pro Gly Gly
1               5               10              15

Ser Leu Arg Leu Ser Cys Thr Gly Ser Gly Phe Thr Phe Ser Tyr His
                20              25              30

Ala Met His Trp Val Arg Gln Ala Pro Gly Lys Gly Leu Glu Trp Val
            35              40              45

Ser Ile Ile Gly Thr Gly Gly Val Thr Tyr Tyr Ala Asp Ser Val Lys
        50              55              60

Gly Arg Phe Thr Ile Ser Arg Asp Asn Val Lys Asn Ser Leu Tyr Leu
65              70              75              80

Gln Met Asn Ser Leu Arg Ala Glu Asp Met Ala Val Tyr Tyr Cys Ala
                85              90              95

Arg Asp Tyr Tyr Gly Ala Gly Ser Phe Tyr Asp Gly Leu Tyr Gly Met
            100             105             110

Asp Val Trp Gly Gln Gly Thr Thr Val Thr Val Ser Ser
        115             120             125

<210> SEQ ID NO 9
<211> LENGTH: 8
<212> TYPE: PRT
<213> ORGANISM: Homo Sapiens

<400> SEQUENCE: 9

Gly Phe Thr Phe Ser Tyr His Ala
1               5

<210> SEQ ID NO 10
<211> LENGTH: 7
<212> TYPE: PRT
<213> ORGANISM: Homo Sapiens
```

```
<400> SEQUENCE: 10

Ile Gly Thr Gly Gly Val Thr
1               5

<210> SEQ ID NO 11
<211> LENGTH: 19
<212> TYPE: PRT
<213> ORGANISM: Homo Sapiens

<400> SEQUENCE: 11

Ala Arg Asp Tyr Tyr Gly Ala Gly Ser Phe Tyr Asp Gly Leu Tyr Gly
1               5                   10                  15

Met Asp Val

<210> SEQ ID NO 12
<211> LENGTH: 107
<212> TYPE: PRT
<213> ORGANISM: Homo Sapiens

<400> SEQUENCE: 12

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asp Trp Pro Leu
                85                  90                  95

Thr Phe Gly Gly Gly Thr Lys Val Glu Ile Lys
            100                 105

<210> SEQ ID NO 13
<211> LENGTH: 6
<212> TYPE: PRT
<213> ORGANISM: Homo Sapiens

<400> SEQUENCE: 13

Gln Ser Val Ser Ser Tyr
1               5

<210> SEQ ID NO 14
<211> LENGTH: 9
<212> TYPE: PRT
<213> ORGANISM: Homo Sapiens

<400> SEQUENCE: 14

Gln Gln Arg Ser Asp Trp Pro Leu Thr
1               5

<210> SEQ ID NO 15
<211> LENGTH: 127
<212> TYPE: PRT
<213> ORGANISM: Homo Sapiens

<400> SEQUENCE: 15

Gln Val Gln Leu Val Gln Ser Gly Ala Glu Val Lys Lys Pro Gly Ala
1               5                   10                  15
```

-continued

```
Ser Val Lys Val Ser Cys Gln Ala Ser Gly Tyr Arg Phe Ser Asn Phe
            20              25              30

Val Ile His Trp Val Arg Gln Ala Pro Gly Gln Arg Phe Glu Trp Met
            35              40              45

Gly Trp Ile Asn Pro Tyr Asn Gly Asn Lys Glu Phe Ser Ala Lys Phe
        50              55              60

Gln Asp Arg Val Thr Phe Thr Ala Asp Thr Ser Ala Asn Thr Ala Tyr
65              70              75              80

Met Glu Leu Arg Ser Leu Arg Ser Ala Asp Thr Ala Val Tyr Tyr Cys
                85              90              95

Ala Arg Val Gly Pro Tyr Ser Trp Asp Asp Ser Pro Gln Asp Asn Tyr
            100             105             110

Tyr Met Asp Val Trp Gly Lys Gly Thr Thr Val Ile Val Ser Ser
        115             120             125
```

```
<210> SEQ ID NO 16
<211> LENGTH: 8
<212> TYPE: PRT
<213> ORGANISM: Homo Sapiens

<400> SEQUENCE: 16

Gly Tyr Arg Phe Ser Asn Phe Val
1               5
```

```
<210> SEQ ID NO 17
<211> LENGTH: 8
<212> TYPE: PRT
<213> ORGANISM: Homo Sapiens

<400> SEQUENCE: 17

Ile Asn Pro Tyr Asn Gly Asn Lys
1               5
```

```
<210> SEQ ID NO 18
<211> LENGTH: 20
<212> TYPE: PRT
<213> ORGANISM: Homo Sapiens

<400> SEQUENCE: 18

Ala Arg Val Gly Pro Tyr Ser Trp Asp Asp Ser Pro Gln Asp Asn Tyr
1               5               10              15

Tyr Met Asp Val
            20
```

```
<210> SEQ ID NO 19
<211> LENGTH: 108
<212> TYPE: PRT
<213> ORGANISM: Homo Sapiens

<400> SEQUENCE: 19

Glu Ile Val Leu Thr Gln Ser Pro Gly Thr Leu Ser Leu Ser Pro Gly
1               5               10              15

Glu Arg Ala Thr Phe Ser Cys Arg Ser Ser His Ser Ile Arg Ser Arg
            20              25              30

Arg Val Ala Trp Tyr Gln His Lys Pro Gly Gln Ala Pro Arg Leu Val
            35              40              45

Ile His Gly Val Ser Asn Arg Ala Ser Gly Ile Ser Asp Arg Phe Ser
        50              55              60

Gly Ser Gly Ser Gly Thr Asp Phe Thr Leu Thr Ile Thr Arg Val Glu
```

-continued

```
      65                  70                  75                  80

Pro Glu Asp Phe Ala Leu Tyr Tyr Cys Gln Val Tyr Gly Ala Ser Ser
                85                  90                  95

Tyr Thr Phe Gly Gln Gly Thr Lys Leu Glu Arg Lys
            100                 105

<210> SEQ ID NO 20
<211> LENGTH: 7
<212> TYPE: PRT
<213> ORGANISM: Homo Sapiens

<400> SEQUENCE: 20

His Ser Ile Arg Ser Arg Arg
1               5

<210> SEQ ID NO 21
<211> LENGTH: 9
<212> TYPE: PRT
<213> ORGANISM: Homo Sapiens

<400> SEQUENCE: 21

Gln Val Tyr Gly Ala Ser Ser Tyr Thr
1               5

<210> SEQ ID NO 22
<211> LENGTH: 330
<212> TYPE: PRT
<213> ORGANISM: Homo Sapiens

<400> SEQUENCE: 22

Ala Ser Thr Lys Gly Pro Ser Val Phe Pro Leu Ala Pro Ser Ser Lys
1               5                  10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220
```

-continued

```
Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 23
<211> LENGTH: 330
<212> TYPE: PRT
<213> ORGANISM: Homo Sapiens

<400> SEQUENCE: 23

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65              70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
            165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
```

-continued

```
                    260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 24
<211> LENGTH: 330
<212> TYPE: PRT
<213> ORGANISM: Homo Sapiens

<400> SEQUENCE: 24

Ala Ser Thr Lys Gly Pro Ser Val Phe Pro Leu Ala Pro Ser Ser Lys
1                   5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Pro Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
        290                 295                 300
```

-continued

```
Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 25
<211> LENGTH: 330
<212> TYPE: PRT
<213> ORGANISM: Homo Sapiens

<400> SEQUENCE: 25

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
                35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                    85                  90                  95

Pro Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
                115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
                275                 280                 285

Leu Tyr Ser Lys Leu Thr Val Asp Lys Ser Arg Trp Gln Gln Gly Asn
        290                 295                 300

Val Phe Ser Cys Ser Val Met His Glu Gly Leu His Asn His Tyr Thr
305                 310                 315                 320

Gln Lys Ser Leu Ser Leu Ser Pro Gly Lys
                325                 330

<210> SEQ ID NO 26
```

<211> LENGTH: 330
<212> TYPE: PRT
<213> ORGANISM: Artificial sequence
<220> FEATURE:
<223> OTHER INFORMATION: Modified antibody constant region

<400> SEQUENCE: 26

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Gly Ala Leu His Asn His Tyr Thr
305                 310                 315                 320

Gln Lys Ser Leu Ser Leu Ser Pro Gly Lys
                325                 330
```

<210> SEQ ID NO 27
<211> LENGTH: 330
<212> TYPE: PRT
<213> ORGANISM: Artificial sequence
<220> FEATURE:
<223> OTHER INFORMATION: Modified antibody constant region -continued

<400> SEQUENCE: 27

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
    210                 215                 220

Gln Pro Arg Lys Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 28
<211> LENGTH: 330
<212> TYPE: PRT
<213> ORGANISM: Artificial sequence
<220> FEATURE:
<223> OTHER INFORMATION: Modified antibody constant region

<400> SEQUENCE: 28

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
```

-continued

```
                20              25                  30

Phe Pro Glu Pro Val Thr Val Ser Trp Asn Ser Gly Ala Leu Thr Ser
            35              40                  45

Gly Val His Thr Phe Pro Ala Val Leu Gln Ser Ser Gly Leu Tyr Ser
        50              55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100             105                 110

Pro Ala Pro Glu Leu Leu Gly Gly Pro Ser Val Phe Leu Phe Pro Pro
            115             120                 125

Lys Pro Lys Asp Thr Leu Met Ile Ser Arg Thr Pro Glu Val Thr Cys
        130             135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180             185                 190

His Gln Asp Trp Leu Asn Gly Lys Glu Tyr Lys Cys Lys Val Ser Asn
            195             200                 205

Lys Ala Leu Pro Ala Pro Ile Glu Lys Thr Ile Ser Lys Ala Lys Gly
        210             215                 220

Gln Pro Arg Arg Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275             280                 285

Leu Tyr Ser Lys Leu Thr Val Asp Lys Ser Arg Trp Gln Gln Gly Asn
        290             295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325             330
```

<210> SEQ ID NO 29
<211> LENGTH: 330
<212> TYPE: PRT
<213> ORGANISM: Artificial sequence
<220> FEATURE:
<223> OTHER INFORMATION: Modified antibody constant region

<400> SEQUENCE: 29

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20              25                  30

Phe Pro Glu Pro Val Thr Val Ser Trp Asn Ser Gly Ala Leu Thr Ser
        35              40                  45

Gly Val His Thr Phe Pro Ala Val Leu Gln Ser Ser Gly Leu Tyr Ser
```

```
            50                    55                    60
Leu Ser Ser Val Val Thr Val Pro Ser Ser Leu Gly Thr Gln Thr
65                    70                    75                    80

Tyr Ile Cys Asn Val Asn His Lys Pro Ser Asn Thr Lys Val Asp Lys
                    85                    90                    95

Arg Val Glu Pro Lys Ser Cys Asp Lys Thr His Thr Cys Pro Pro Cys
                    100                   105                   110

Pro Ala Pro Glu Leu Leu Gly Gly Pro Ser Val Phe Leu Phe Pro Pro
                    115                   120                   125

Lys Pro Lys Asp Thr Leu Met Ile Ser Arg Thr Pro Glu Val Thr Cys
        130                   135                   140

Val Val Val Asp Val Ser His Glu Asp Pro Glu Val Lys Phe Asn Trp
145                   150                   155                   160

Tyr Val Asp Gly Val Glu Val His Asn Ala Lys Thr Lys Pro Arg Glu
                    165                   170                   175

Glu Gln Tyr Asn Ser Thr Tyr Arg Val Val Ser Val Leu Thr Val Leu
                    180                   185                   190

His Gln Asp Trp Leu Asn Gly Lys Glu Tyr Lys Cys Lys Val Ser Asn
                    195                   200                   205

Lys Ala Leu Pro Ala Pro Ile Glu Lys Thr Ile Ser Lys Ala Lys Gly
        210                   215                   220

Gln Pro Arg Glu Pro Gln Val Tyr Thr Leu Pro Pro Ser Arg Glu Glu
225                   230                   235                   240

Met Thr Lys Asn Gln Val Ser Leu Thr Cys Leu Val Lys Gly Phe Tyr
                    245                   250                   255

Pro Ser Asp Ile Ala Val Glu Trp Glu Ser Asn Gly Gln Pro Glu Asn
                    260                   265                   270

Asn Tyr Lys Thr Thr Pro Pro Val Leu Asp Ser Asp Gly Ser Phe Phe
                    275                   280                   285

Leu Tyr Ser Lys Leu Thr Val Asp Lys Ser Arg Trp Gln Gln Gly Asn
        290                   295                   300

Val Phe Ser Cys Ser Val Met His Glu Ala Leu His Asn His Tyr Thr
305                   310                   315                   320

Gln Glu Ser Leu Ser Leu Ser Pro Gly Lys
                    325                   330
```

<210> SEQ ID NO 30
<211> LENGTH: 330
<212> TYPE: PRT
<213> ORGANISM: Artificial sequence
<220> FEATURE:
<223> OTHER INFORMATION: Modified antibody constant region

<400> SEQUENCE: 30

```
Ala Ser Thr Lys Gly Pro Ser Val Phe Pro Leu Ala Pro Ser Ser Lys
1                    5                     10                    15

Ser Thr Ser Gly Gly Thr Ala Ala Leu Gly Cys Leu Val Lys Asp Tyr
                    20                    25                    30

Phe Pro Glu Pro Val Thr Val Ser Trp Asn Ser Gly Ala Leu Thr Ser
        35                    40                    45

Gly Val His Thr Phe Pro Ala Val Leu Gln Ser Ser Gly Leu Tyr Ser
        50                    55                    60

Leu Ser Ser Val Val Thr Val Pro Ser Ser Leu Gly Thr Gln Thr
65                    70                    75                    80

Tyr Ile Cys Asn Val Asn His Lys Pro Ser Asn Thr Lys Val Asp Lys
```

-continued

```
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
            130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Lys Leu Ser Leu Ser Pro Gly Lys
                325                 330
```

<210> SEQ ID NO 31
<211> LENGTH: 326
<212> TYPE: PRT
<213> ORGANISM: Homo Sapiens

<400> SEQUENCE: 31

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
            115                 120                 125
```

-continued

```
Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
            195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
            275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325
```

```
<210> SEQ ID NO 32
<211> LENGTH: 377
<212> TYPE: PRT
<213> ORGANISM: Homo Sapiens

<400> SEQUENCE: 32
```

```
Ala Ser Thr Lys Gly Pro Ser Val Phe Pro Leu Ala Pro Cys Ser Arg
1                   5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
                100                 105                 110

Arg Cys Pro Glu Pro Lys Ser Cys Asp Thr Pro Pro Pro Cys Pro Arg
            115                 120                 125

Cys Pro Glu Pro Lys Ser Cys Asp Thr Pro Pro Pro Cys Pro Arg Cys
    130                 135                 140

Pro Glu Pro Lys Ser Cys Asp Thr Pro Pro Pro Cys Pro Arg Cys Pro
145                 150                 155                 160

Ala Pro Glu Leu Leu Gly Gly Pro Ser Val Phe Leu Phe Pro Pro Lys
                165                 170                 175
```

-continued

```
Pro Lys Asp Thr Leu Met Ile Ser Arg Thr Pro Glu Val Thr Cys Val
        180                     185                 190

Val Val Asp Val Ser His Glu Asp Pro Glu Val Gln Phe Lys Trp Tyr
        195                     200                 205

Val Asp Gly Val Glu Val His Asn Ala Lys Thr Lys Pro Arg Glu Glu
        210                     215                 220

Gln Tyr Asn Ser Thr Phe Arg Val Val Ser Val Leu Thr Val Leu His
225                     230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
                260                 265                 270

Pro Arg Glu Pro Gln Val Tyr Thr Leu Pro Pro Ser Arg Glu Glu Met
        275                     280                 285

Thr Lys Asn Gln Val Ser Leu Thr Cys Leu Val Lys Gly Phe Tyr Pro
        290                     295                 300

Ser Asp Ile Ala Val Glu Trp Glu Ser Ser Gly Gln Pro Glu Asn Asn
305                     310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
                340                 345                 350

Phe Ser Cys Ser Val Met His Glu Ala Leu His Asn Arg Phe Thr Gln
        355                     360                 365

Lys Ser Leu Ser Leu Ser Pro Gly Lys
        370                     375

<210> SEQ ID NO 33
<211> LENGTH: 327
<212> TYPE: PRT
<213> ORGANISM: Homo Sapiens

<400> SEQUENCE: 33

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
                100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
        130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
```

```
                        165                 170                 175
Asn Ser Thr Tyr Arg Val Val Ser Val Leu Thr Val Leu His Gln Asp
                180                 185                 190

Trp Leu Asn Gly Lys Glu Tyr Lys Cys Lys Val Ser Asn Lys Gly Leu
                195                 200                 205

Pro Ser Ser Ile Glu Lys Thr Ile Ser Lys Ala Lys Gly Gln Pro Arg
                210                 215                 220

Glu Pro Gln Val Tyr Thr Leu Pro Pro Ser Gln Glu Glu Met Thr Lys
    225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
                260                 265                 270

Thr Thr Pro Pro Val Leu Asp Ser Asp Gly Ser Phe Phe Leu Tyr Ser
                275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
    305                 310                 315                 320

Leu Ser Leu Ser Leu Gly Lys
                325

<210> SEQ ID NO 34
<211> LENGTH: 107
<212> TYPE: PRT
<213> ORGANISM: Homo Sapiens

<400> SEQUENCE: 34

Arg Thr Val Ala Ala Pro Ser Val Phe Ile Phe Pro Pro Ser Asp Glu
1                   5                   10                  15

Gln Leu Lys Ser Gly Thr Ala Ser Val Val Cys Leu Leu Asn Asn Phe
                20                  25                  30

Tyr Pro Arg Glu Ala Lys Val Gln Trp Lys Val Asp Asn Ala Leu Gln
                35                  40                  45

Ser Gly Asn Ser Gln Glu Ser Val Thr Glu Gln Asp Ser Lys Asp Ser
                50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
                100                 105

<210> SEQ ID NO 35
<211> LENGTH: 122
<212> TYPE: PRT
<213> ORGANISM: Homo Sapiens

<400> SEQUENCE: 35

Glu Val Gln Leu Val Glu Ser Gly Gly Gly Leu Val Gln Pro Asp Arg
1                   5                   10                  15

Ser Leu Arg Leu Ser Cys Ala Ala Ser Gly Phe Thr Phe His Asp Tyr
                20                  25                  30

Ala Met His Trp Val Arg Gln Ala Pro Gly Lys Gly Leu Glu Trp Val
                35                  40                  45

Ser Thr Ile Ser Trp Asn Ser Gly Thr Ile Gly Tyr Ala Asp Ser Val
```

```
       50                    55                    60

Lys Gly Arg Phe Thr Ile Ser Arg Asp Asn Ala Lys Asn Ser Leu Tyr
65                    70                    75                    80

Leu Gln Met Asn Ser Leu Arg Ala Glu Asp Thr Ala Leu Tyr Tyr Cys
                  85                    90                    95

Ala Lys Asp Ile Gln Tyr Gly Asn Tyr Tyr Tyr Gly Met Asp Val Trp
              100                   105                   110

Gly Gln Gly Thr Thr Val Thr Val Ser Ser
          115                   120

<210> SEQ ID NO 36
<211> LENGTH: 8
<212> TYPE: PRT
<213> ORGANISM: Homo Sapiens

<400> SEQUENCE: 36

Gly Phe Thr Phe His Asp Tyr Ala
1               5

<210> SEQ ID NO 37
<211> LENGTH: 8
<212> TYPE: PRT
<213> ORGANISM: Homo Sapiens

<400> SEQUENCE: 37

Ile Ser Trp Asn Ser Gly Thr Ile
1               5

<210> SEQ ID NO 38
<211> LENGTH: 15
<212> TYPE: PRT
<213> ORGANISM: Homo Sapiens

<400> SEQUENCE: 38

Ala Lys Asp Ile Gln Tyr Gly Asn Tyr Tyr Tyr Gly Met Asp Val
1               5                   10                  15

<210> SEQ ID NO 39
<211> LENGTH: 107
<212> TYPE: PRT
<213> ORGANISM: Homo Sapiens

<400> SEQUENCE: 39

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                  20                    25                    30

Leu Ala Trp Tyr Gln Gln Lys Pro Gly Gln Ala Pro Arg Leu Leu Ile
              35                    40                    45

Tyr Asp Ala Ser Asn Arg Ala Thr Gly Ile Pro Ala Arg Phe Ser Gly
          50                    55                    60

Ser Gly Ser Gly Thr Asp Phe Thr Leu Thr Ile Ser Ser Leu Glu Pro
65                    70                    75                    80

Glu Asp Phe Ala Val Tyr Tyr Cys Gln Gln Arg Ser Asn Trp Pro Ile
                  85                    90                    95

Thr Phe Gly Gln Gly Thr Arg Leu Glu Ile Lys
              100                   105

<210> SEQ ID NO 40
<211> LENGTH: 6
```

-continued

```
<212> TYPE: PRT
<213> ORGANISM: Homo Sapiens

<400> SEQUENCE: 40

Gln Ser Val Ser Ser Tyr
1               5

<210> SEQ ID NO 41
<211> LENGTH: 9
<212> TYPE: PRT
<213> ORGANISM: Homo Sapiens

<400> SEQUENCE: 41

Gln Gln Arg Ser Asn Trp Pro Ile Thr
1               5

<210> SEQ ID NO 42
<211> LENGTH: 115
<212> TYPE: PRT
<213> ORGANISM: Mus musculus

<400> SEQUENCE: 42

Gln Val Gln Val Lys Glu Ser Gly Pro Gly Leu Val Ala Pro Ser Gln
1               5                   10                  15

Ser Leu Ser Ile Thr Cys Thr Val Ser Gly Phe Ser Leu Thr Thr Ser
                20                  25                  30

Gly Val Ser Trp Val Arg Gln Pro Pro Gly Lys Gly Leu Glu Trp Leu
            35                  40                  45

Gly Val Ile Trp Gly Asp Gly Ser Thr Asn Tyr His Ser Ala Leu Lys
        50                  55                  60

Ser Arg Leu Ser Ile Lys Lys Asp His Ser Lys Ser Gln Val Phe Leu
65                  70                  75                  80

Lys Leu Asn Ser Leu Gln Thr Asp Asp Thr Ala Thr Tyr Tyr Cys Ala
                85                  90                  95

Lys Gly Gly Tyr Ser Leu Ala His Trp Gly Gln Gly Thr Leu Val Thr
            100                 105                 110

Val Ser Ala
        115

<210> SEQ ID NO 43
<211> LENGTH: 8
<212> TYPE: PRT
<213> ORGANISM: Mus musculus

<400> SEQUENCE: 43

Gly Phe Ser Leu Thr Thr Ser Gly
1               5

<210> SEQ ID NO 44
<211> LENGTH: 7
<212> TYPE: PRT
<213> ORGANISM: Mus musculus

<400> SEQUENCE: 44

Ile Trp Gly Asp Gly Ser Thr
1               5

<210> SEQ ID NO 45
<211> LENGTH: 9
<212> TYPE: PRT
<213> ORGANISM: Mus musculus
```

-continued

```
<400> SEQUENCE: 45

Ala Lys Gly Gly Tyr Ser Leu Ala His
1               5

<210> SEQ ID NO 46
<211> LENGTH: 107
<212> TYPE: PRT
<213> ORGANISM: Mus musculus

<400> SEQUENCE: 46

Asp Ile Gln Met Thr Gln Ser Pro Ala Ser Leu Ser Val Ser Val Gly
1               5                   10                  15

Glu Thr Val Thr Ile Thr Cys Arg Ala Ser Glu Asn Ile Arg Ser Asn
                20                  25                  30

Leu Ala Trp Tyr Gln Gln Lys Gln Gly Lys Ser Pro Gln Leu Leu Val
            35                  40                  45

Asn Val Ala Thr Asn Leu Ala Asp Gly Val Pro Ser Arg Phe Ser Gly
        50                  55                  60

Ser Gly Ser Gly Thr Gln Tyr Ser Leu Lys Ile Asn Ser Leu Gln Ser
65                  70                  75                  80

Glu Asp Phe Gly Thr Tyr Tyr Cys Gln His Tyr Trp Gly Thr Thr Trp
                85                  90                  95

Thr Phe Gly Gly Gly Thr Lys Leu Glu Ile Lys
            100                 105

<210> SEQ ID NO 47
<211> LENGTH: 6
<212> TYPE: PRT
<213> ORGANISM: Mus musculus

<400> SEQUENCE: 47

Glu Asn Ile Arg Ser Asn
1               5

<210> SEQ ID NO 48
<211> LENGTH: 9
<212> TYPE: PRT
<213> ORGANISM: Mus musculus

<400> SEQUENCE: 48

Gln His Tyr Trp Gly Thr Thr Trp Thr
1               5

<210> SEQ ID NO 49
<211> LENGTH: 118
<212> TYPE: PRT
<213> ORGANISM: Artificial sequence
<220> FEATURE:
<223> OTHER INFORMATION: Humanized antibody variable region

<400> SEQUENCE: 49

Glu Val Gln Leu Gln Gln Ser Gly Ala Glu Val Val Lys Pro Gly Ala
1               5                   10                  15

Ser Val Lys Leu Ser Cys Lys Ala Ser Gly Phe Asn Ile Lys Asp Thr
                20                  25                  30

Phe Ile His Trp Val Lys Gln Ala Pro Gly Gln Gly Leu Glu Trp Ile
            35                  40                  45

Gly Arg Ile Asp Pro Ala Asn Thr Asn Thr Lys Tyr Asp Pro Lys Phe
        50                  55                  60

Gln Gly Lys Ala Thr Ile Thr Thr Asp Thr Ser Ser Asn Thr Ala Tyr
```

-continued

```
65                    70                    75                    80

Met Glu Leu Ser Ser Leu Arg Ser Glu Asp Thr Ala Val Tyr Tyr Cys
                85                    90                    95

Val Arg Gly Leu Tyr Thr Tyr Tyr Phe Asp Tyr Trp Gly Gln Gly Thr
                100                   105                   110

Leu Val Thr Val Ser Ser
        115
```

```
<210> SEQ ID NO 50
<211> LENGTH: 8
<212> TYPE: PRT
<213> ORGANISM: Artificial sequence
<220> FEATURE:
<223> OTHER INFORMATION: CDR sequence

<400> SEQUENCE: 50

Gly Phe Asn Ile Lys Asp Thr Phe
1               5
```

```
<210> SEQ ID NO 51
<211> LENGTH: 8
<212> TYPE: PRT
<213> ORGANISM: Mus musculus

<400> SEQUENCE: 51

Ile Asp Pro Ala Asn Thr Asn Thr
1               5
```

```
<210> SEQ ID NO 52
<211> LENGTH: 11
<212> TYPE: PRT
<213> ORGANISM: Mus musculus

<400> SEQUENCE: 52

Val Arg Gly Leu Tyr Thr Tyr Tyr Phe Asp Tyr
1               5                   10
```

```
<210> SEQ ID NO 53
<211> LENGTH: 107
<212> TYPE: PRT
<213> ORGANISM: Artificial sequence
<220> FEATURE:
<223> OTHER INFORMATION: Humanized antibody variable region

<400> SEQUENCE: 53

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Ile Ser Asn Asn
                20                  25                  30

Leu His Trp Tyr Gln Gln Lys Pro Gly Gln Ala Pro Arg Leu Leu Ile
        35                  40                  45

Lys Phe Ala Ser Gln Ser Ile Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Gly Asn Ser Trp Pro Tyr
                85                  90                  95

Thr Phe Gly Gln Gly Thr Lys Leu Glu Ile Lys
            100                 105
```

```
<210> SEQ ID NO 54
```

```
<211> LENGTH: 6
<212> TYPE: PRT
<213> ORGANISM: Mus musculus

<400> SEQUENCE: 54

Gln Ser Ile Ser Asn Asn
1               5

<210> SEQ ID NO 55
<211> LENGTH: 9
<212> TYPE: PRT
<213> ORGANISM: Mus musculus

<400> SEQUENCE: 55

Gln Gln Gly Asn Ser Trp Pro Tyr Thr
1               5

<210> SEQ ID NO 56
<211> LENGTH: 118
<212> TYPE: PRT
<213> ORGANISM: Artificial sequence
<220> FEATURE:
<223> OTHER INFORMATION: Humanized antibody variable region

<400> SEQUENCE: 56

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
                20                  25                  30

His Met His Trp Val Arg Gln Ala Pro Gly Gln Arg Leu Glu Trp Ile
            35                  40                  45

Gly Arg Ile Asp Pro Ala Asn Gly Asn Thr Glu Tyr Asp Gln Lys Phe
        50                  55                  60

Gln Gly Arg Val Thr Ile Thr Val Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Gly Thr Asn Val Tyr Phe Ala Tyr Trp Gly Gln Gly Thr
            100                 105                 110

Leu Val Thr Val Ser Ser
        115

<210> SEQ ID NO 57
<211> LENGTH: 8
<212> TYPE: PRT
<213> ORGANISM: Mus musculus

<400> SEQUENCE: 57

Gly Phe Asn Ile Lys Asp Thr His
1               5

<210> SEQ ID NO 58
<211> LENGTH: 8
<212> TYPE: PRT
<213> ORGANISM: Mus musculus

<400> SEQUENCE: 58

Ile Asp Pro Ala Asn Gly Asn Thr
1               5

<210> SEQ ID NO 59
<211> LENGTH: 11
```

<212> TYPE: PRT
<213> ORGANISM: Mus musculus

<400> SEQUENCE: 59

Ala Arg Trp Gly Thr Asn Val Tyr Phe Ala Tyr
1               5                   10

<210> SEQ ID NO 60
<211> LENGTH: 106
<212> TYPE: PRT
<213> ORGANISM: Artificial sequence
<220> FEATURE:
<223> OTHER INFORMATION: Humanized antibody variable region

<400> SEQUENCE: 60

Asp Ile Gln Leu Thr Gln Ser Pro Ser Ser Leu Ser Ala Ser Val Gly
1               5                   10                  15

Asp Arg Val Thr Ile Thr Cys Ser Ala Ser Ser Ser Val Ser Tyr Met
            20                  25                  30

Tyr Trp Tyr Gln Gln Lys Pro Gly Lys Ala Pro Lys Pro Trp Ile Tyr
        35                  40                  45

Arg Thr Ser Asn Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Tyr His Ser Tyr Pro Pro Thr
                85                  90                  95

Phe Gly Gly Gly Thr Lys Val Glu Ile Lys
            100                 105

<210> SEQ ID NO 61
<211> LENGTH: 5
<212> TYPE: PRT
<213> ORGANISM: Mus musculus

<400> SEQUENCE: 61

Ser Ser Val Ser Tyr
1               5

<210> SEQ ID NO 62
<211> LENGTH: 9
<212> TYPE: PRT
<213> ORGANISM: Mus musculus

<400> SEQUENCE: 62

Gln Gln Tyr His Ser Tyr Pro Pro Thr
1               5

<210> SEQ ID NO 63
<211> LENGTH: 330
<212> TYPE: PRT
<213> ORGANISM: Artificial sequence
<220> FEATURE:
<223> OTHER INFORMATION: Modified antibody constant region

<400> SEQUENCE: 63

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

-continued

```
Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
                115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
    195                 200                 205

Lys Ala Leu Pro Ala Pro Ile Ser Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
                275                 280                 285

Leu Tyr Ser Lys Leu Thr Val Asp Lys Ser Arg Trp Gln Gln Gly Asn
    290                 295                 300

Val Phe Ser Cys Ser Val Met His Gly Ala Leu His Asn His Tyr Thr
305                 310                 315                 320

Arg Lys Lys Leu Ser Leu Ser Pro Gly Lys
                325                 330
```

```
<210> SEQ ID NO 64
<211> LENGTH: 330
<212> TYPE: PRT
<213> ORGANISM: Artificial sequence
<220> FEATURE:
<223> OTHER INFORMATION: Modified antibody constant region

<400> SEQUENCE: 64

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80
```

-continued

```
Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Ser Lys Thr Ile Ser Lys Ala Lys Gly
        210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Gly Ala Leu His Asn His Lys Thr
305                 310                 315                 320

Gln Lys Lys Leu Ser Leu Ser Pro Gly Lys
                325                 330
```

```
<210> SEQ ID NO 65
<211> LENGTH: 330
<212> TYPE: PRT
<213> ORGANISM: Artificial sequence
<220> FEATURE:
<223> OTHER INFORMATION: Modified antibody constant region

<400> SEQUENCE: 65
```

```
Ala Ser Thr Lys Gly Pro Ser Val Phe Pro Leu Ala Pro Ser Ser Lys
1                   5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110
```

-continued

```
Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
        210                 215                 220

Gln Pro Arg Lys Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
                275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Asn Glu Ser Leu Ser Leu Ser Pro Gly Lys
                325                 330
```

```
<210> SEQ ID NO 66
<211> LENGTH: 330
<212> TYPE: PRT
<213> ORGANISM: Artificial sequence
<220> FEATURE:
<223> OTHER INFORMATION: Modified antibody constant region

<400> SEQUENCE: 66
```

```
Ala Ser Thr Lys Gly Pro Ser Val Phe Pro Leu Ala Pro Ser Ser Lys
1                 5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
        130                 135                 140
```

```
Val Val Val Asp Val Ser His Glu Asp Pro Glu Val Lys Phe Asn Trp
145             150             155             160

Tyr Val Asp Gly Val Glu Val His Asn Ala Lys Thr Lys Pro Arg Glu
            165             170             175

Glu Gln Tyr Asn Ser Thr Tyr Arg Val Val Ser Val Leu Thr Val Leu
            180             185             190

His Gln Asp Trp Leu Asn Gly Lys Glu Tyr Lys Cys Lys Val Ser Asn
            195             200             205

Lys Ala Leu Pro Ala Pro Ile Glu Lys Thr Ile Ser Lys Ala Lys Gly
    210             215             220

Gln Pro Arg Lys Pro Gln Val Tyr Thr Leu Pro Pro Ser Arg Glu Glu
225             230             235             240

Met Thr Lys Asn Gln Val Ser Leu Thr Cys Leu Val Lys Gly Phe Tyr
            245             250             255

Pro Ser Asp Ile Ala Val Glu Trp Glu Ser Asn Gly Gln Pro Glu Asn
            260             265             270

Asn Tyr Lys Thr Thr Pro Pro Val Leu Asp Ser Asp Gly Ser Phe Phe
            275             280             285

Leu Tyr Ser Lys Leu Thr Val Asp Lys Ser Arg Trp Gln Gln Gly Asn
    290             295             300

Val Phe Ser Cys Ser Val Met His Glu Ala Leu His Asn His Tyr Thr
305             310             315             320

Arg Lys Lys Leu Ser Leu Ser Pro Gly Lys
            325             330
```

<210> SEQ ID NO 67
<211> LENGTH: 330
<212> TYPE: PRT
<213> ORGANISM: Artificial sequence
<220> FEATURE:
<223> OTHER INFORMATION: Modified antibody constant region

<400> SEQUENCE: 67

```
Ala Ser Thr Lys Gly Pro Ser Val Phe Pro Leu Ala Pro Ser Ser Lys
1               5               10              15

Ser Thr Ser Gly Gly Thr Ala Ala Leu Gly Cys Leu Val Lys Asp Tyr
            20              25              30

Phe Pro Glu Pro Val Thr Val Ser Trp Asn Ser Gly Ala Leu Thr Ser
            35              40              45

Gly Val His Thr Phe Pro Ala Val Leu Gln Ser Ser Gly Leu Tyr Ser
    50              55              60

Leu Ser Ser Val Val Thr Val Pro Ser Ser Ser Leu Gly Thr Gln Thr
65              70              75              80

Tyr Ile Cys Asn Val Asn His Lys Pro Ser Asn Thr Lys Val Asp Lys
            85              90              95

Arg Val Glu Pro Lys Ser Cys Asp Lys Thr His Thr Cys Pro Pro Cys
            100             105             110

Pro Ala Pro Glu Leu Leu Gly Gly Pro Ser Val Phe Leu Phe Pro Pro
            115             120             125

Lys Pro Lys Asp Thr Leu Met Ile Ser Arg Thr Pro Glu Val Thr Cys
    130             135             140

Val Val Val Asp Val Ser His Glu Asp Pro Glu Val Lys Phe Asn Trp
145             150             155             160

Tyr Val Asp Gly Val Glu Val His Asn Ala Lys Thr Lys Pro Arg Glu
            165             170             175
```

-continued

```
Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Lys Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                    245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Lys Thr
305                 310                 315                 320

Gln Lys Lys Leu Ser Leu Ser Pro Gly Lys
                    325                 330
```

```
<210> SEQ ID NO 68
<211> LENGTH: 330
<212> TYPE: PRT
<213> ORGANISM: Artificial sequence
<220> FEATURE:
<223> OTHER INFORMATION: Modified antibody constant region

<400> SEQUENCE: 68
```

```
Ala Ser Thr Lys Gly Pro Ser Val Phe Pro Leu Ala Pro Ser Ser Lys
1                   5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
            50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                    85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
            130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                    165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205
```

```
Lys Ala Leu Pro Ala Pro Ile Glu Lys Thr Ile Ser Lys Ala Lys Gly
    210             215             220

Gln Pro Arg Lys Pro Gln Val Tyr Thr Leu Pro Pro Ser Arg Glu Glu
225             230             235             240

Met Thr Lys Asn Gln Val Ser Leu Thr Cys Leu Val Lys Gly Phe Tyr
            245             250             255

Pro Ser Asp Ile Ala Val Glu Trp Glu Ser Asn Gly Gln Pro Glu Asn
            260             265             270

Asn Tyr Lys Thr Thr Pro Pro Val Leu Asp Ser Asp Gly Ser Phe Phe
            275             280             285

Leu Tyr Ser Lys Leu Thr Val Asp Lys Ser Arg Trp Gln Gln Gly Asn
    290             295             300

Val Phe Ser Cys Ser Val Met His Glu Ala Leu His Asn His Asn Thr
305             310             315             320

Gln Glu Ser Leu Ser Leu Ser Pro Gly Lys
            325             330
```

<210> SEQ ID NO 69
<211> LENGTH: 330
<212> TYPE: PRT
<213> ORGANISM: Artificial sequence
<220> FEATURE:
<223> OTHER INFORMATION: Modified antibody constant region

<400> SEQUENCE: 69

```
Ala Ser Thr Lys Gly Pro Ser Val Phe Pro Leu Ala Pro Ser Ser Lys
1               5               10              15

Ser Thr Ser Gly Gly Thr Ala Ala Leu Gly Cys Leu Val Lys Asp Tyr
            20              25              30

Phe Pro Glu Pro Val Thr Val Ser Trp Asn Ser Gly Ala Leu Thr Ser
            35              40              45

Gly Val His Thr Phe Pro Ala Val Leu Gln Ser Ser Gly Leu Tyr Ser
    50              55              60

Leu Ser Ser Val Val Thr Val Pro Ser Ser Ser Leu Gly Thr Gln Thr
65              70              75              80

Tyr Ile Cys Asn Val Asn His Lys Pro Ser Asn Thr Lys Val Asp Lys
            85              90              95

Arg Val Glu Pro Lys Ser Cys Asp Lys Thr His Thr Cys Pro Pro Cys
            100             105             110

Pro Ala Pro Glu Leu Leu Gly Gly Pro Ser Val Phe Leu Phe Pro Pro
            115             120             125

Lys Pro Lys Asp Thr Leu Met Ile Ser Arg Thr Pro Glu Val Thr Cys
    130             135             140

Val Val Val Asp Val Ser His Glu Asp Pro Glu Val Lys Phe Asn Trp
145             150             155             160

Tyr Val Asp Gly Val Glu Val His Asn Ala Lys Thr Lys Pro Arg Glu
            165             170             175

Glu Gln Tyr Asn Ser Thr Tyr Arg Val Val Ser Val Leu Thr Val Leu
            180             185             190

His Gln Asp Trp Leu Asn Gly Lys Glu Tyr Lys Cys Lys Val Ser Asn
            195             200             205

Lys Ala Leu Pro Ala Pro Ile Glu Lys Thr Ile Ser Lys Ala Lys Gly
    210             215             220

Gln Pro Arg Arg Pro Gln Val Tyr Thr Leu Pro Pro Ser Arg Glu Glu
225             230             235             240
```

-continued

```
Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
                275                 280                 285

Leu Tyr Ser Lys Leu Thr Val Asp Lys Ser Arg Trp Gln Gln Gly Asn
                290                 295                 300

Val Phe Ser Cys Ser Val Met His Glu Ala Leu His Asn His Tyr Thr
305                 310                 315                 320

Asn Glu Ser Leu Ser Leu Ser Pro Gly Lys
                325                 330

<210> SEQ ID NO 70
<211> LENGTH: 330
<212> TYPE: PRT
<213> ORGANISM: Artificial sequence
<220> FEATURE:
<223> OTHER INFORMATION: Modified antibody constant region

<400> SEQUENCE: 70

Ala Ser Thr Lys Gly Pro Ser Val Phe Pro Leu Ala Pro Ser Ser Lys
1                 5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
                35                  40                  45

Gly Val His Thr Phe Pro Ala Val Leu Gln Ser Ser Gly Leu Tyr Ser
                50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
                115                 120                 125

Lys Pro Lys Asp Thr Leu Met Ile Ser Arg Thr Pro Glu Val Thr Cys
                130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
                195                 200                 205

Lys Ala Leu Pro Ala Pro Ile Glu Lys Thr Ile Ser Lys Ala Lys Gly
                210                 215                 220

Gln Pro Arg Arg Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270
```

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Arg Lys Lys Leu Ser Leu Ser Pro Gly Lys
                325                 330

<210> SEQ ID NO 71
<211> LENGTH: 330
<212> TYPE: PRT
<213> ORGANISM: Artificial sequence
<220> FEATURE:
<223> OTHER INFORMATION: Modified antibody constant region

<400> SEQUENCE: 71

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
        20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
        100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
        210                 215                 220

Gln Pro Arg Arg Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
        245                 250                 255

Pro Ser Asp Ile Ala Val Glu Trp Glu Ser Asn Gly Gln Pro Glu Asn
        260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
        290                 295                 300

```
Val Phe Ser Cys Ser Val Met His Glu Ala Leu His Asn His Lys Thr
305                 310                 315                 320

Gln Lys Lys Leu Ser Leu Ser Pro Gly Lys
                325                 330

<210> SEQ ID NO 72
<211> LENGTH: 330
<212> TYPE: PRT
<213> ORGANISM: Artificial sequence
<220> FEATURE:
<223> OTHER INFORMATION: Modified antibody constant region

<400> SEQUENCE: 72

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Arg Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Asn Thr
305                 310                 315                 320

Gln Glu Ser Leu Ser Leu Ser Pro Gly Lys
                325                 330
```

<210> SEQ ID NO 73
<211> LENGTH: 330
<212> TYPE: PRT
<213> ORGANISM: Artificial sequence
<220> FEATURE:
<223> OTHER INFORMATION: Modified antibody constant region

<400> SEQUENCE: 73

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
                195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
                275                 280                 285

Leu Tyr Ser Lys Leu Thr Val Asp Lys Ser Arg Trp Gln Gln Gly Asn
        290                 295                 300

Val Phe Ser Cys Ser Val Met His Gly Ala Leu His Asn His Tyr Thr
305                 310                 315                 320

Gln Glu Ser Leu Ser Leu Ser Pro Gly Lys
                325                 330

<210> SEQ ID NO 74
<211> LENGTH: 330
<212> TYPE: PRT
<213> ORGANISM: Artificial sequence
<220> FEATURE:
<223> OTHER INFORMATION: Modified antibody constant region

<400> SEQUENCE: 74

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Gly Ala Leu His Asn His Tyr Thr
305                 310                 315                 320

Asn Glu Ser Leu Ser Leu Ser Pro Gly Lys
                325                 330
```

<210> SEQ ID NO 75
<211> LENGTH: 330
<212> TYPE: PRT
<213> ORGANISM: Artificial sequence
<220> FEATURE:
<223> OTHER INFORMATION: Modified antibody constant region

<400> SEQUENCE: 75

```
Ala Ser Thr Lys Gly Pro Ser Val Phe Pro Leu Ala Pro Ser Ser Lys
```

-continued

```
1                    5                        10                       15

Ser Thr Ser Gly Gly Thr Ala Ala Leu Gly Cys Leu Val Lys Asp Tyr
                20                      25                      30

Phe Pro Glu Pro Val Thr Val Ser Trp Asn Ser Gly Ala Leu Thr Ser
                35                      40                      45

Gly Val His Thr Phe Pro Ala Val Leu Gln Ser Ser Gly Leu Tyr Ser
        50                      55                      60

Leu Ser Ser Val Val Thr Val Pro Ser Ser Ser Leu Gly Thr Gln Thr
65                      70                      75                      80

Tyr Ile Cys Asn Val Asn His Lys Pro Ser Asn Thr Lys Val Asp Lys
                85                      90                      95

Arg Val Glu Pro Lys Ser Cys Asp Lys Thr His Thr Cys Pro Pro Cys
                100                     105                     110

Pro Ala Pro Glu Leu Leu Gly Gly Pro Ser Val Phe Leu Phe Pro Pro
                115                     120                     125

Lys Pro Lys Asp Thr Leu Met Ile Ser Arg Thr Pro Glu Val Thr Cys
        130                     135                     140

Val Val Val Asp Val Ser His Glu Asp Pro Glu Val Lys Phe Asn Trp
145                     150                     155                     160

Tyr Val Asp Gly Val Glu Val His Asn Ala Lys Thr Lys Pro Arg Glu
                165                     170                     175

Glu Gln Tyr Asn Ser Thr Tyr Arg Val Val Ser Val Leu Thr Val Leu
                180                     185                     190

His Gln Asp Trp Leu Asn Gly Lys Glu Tyr Lys Cys Lys Val Ser Asn
                195                     200                     205

Lys Ala Leu Pro Ala Pro Ile Glu Lys Thr Ile Ser Lys Ala Lys Gly
        210                     215                     220

Gln Pro Arg Glu Pro Gln Val Tyr Thr Leu Pro Pro Ser Arg Glu Glu
225                     230                     235                     240

Met Thr Lys Asn Gln Val Ser Leu Thr Cys Leu Val Lys Gly Phe Tyr
                245                     250                     255

Pro Ser Asp Ile Ala Val Glu Trp Glu Ser Asn Gly Gln Pro Glu Asn
                260                     265                     270

Asn Tyr Lys Thr Thr Pro Pro Val Leu Asp Ser Asp Gly Ser Phe Phe
                275                     280                     285

Leu Tyr Ser Lys Leu Thr Val Asp Lys Ser Arg Trp Gln Gln Gly Asn
        290                     295                     300

Val Phe Ser Cys Ser Val Met His Gly Ala Leu His Asn His Tyr Thr
305                     310                     315                     320

Asn Lys Lys Leu Ser Leu Ser Pro Gly Lys
                325                     330
```

```
<210> SEQ ID NO 76
<211> LENGTH: 330
<212> TYPE: PRT
<213> ORGANISM: Artificial sequence
<220> FEATURE:
<223> OTHER INFORMATION: Modified antibody constant region

<400> SEQUENCE: 76

Ala Ser Thr Lys Gly Pro Ser Val Phe Pro Leu Ala Pro Ser Ser Lys
1                    5                        10                       15

Ser Thr Ser Gly Gly Thr Ala Ala Leu Gly Cys Leu Val Lys Asp Tyr
                20                      25                      30

Phe Pro Glu Pro Val Thr Val Ser Trp Asn Ser Gly Ala Leu Thr Ser
```

```
              35                    40                    45

Gly Val His Thr Phe Pro Ala Val Leu Gln Ser Ser Gly Leu Tyr Ser
    50                    55                    60

Leu Ser Ser Val Val Thr Val Pro Ser Ser Ser Leu Gly Thr Gln Thr
65                    70                    75                    80

Tyr Ile Cys Asn Val Asn His Lys Pro Ser Asn Thr Lys Val Asp Lys
                  85                    90                    95

Arg Val Glu Pro Lys Ser Cys Asp Lys Thr His Thr Cys Pro Pro Cys
                 100                   105                   110

Pro Ala Pro Glu Leu Leu Gly Gly Pro Ser Val Phe Leu Phe Pro Pro
                 115                   120                   125

Lys Pro Lys Asp Thr Leu Met Ile Ser Arg Thr Pro Glu Val Thr Cys
    130                   135                   140

Val Val Val Asp Val Ser His Glu Asp Pro Glu Val Lys Phe Asn Trp
145                   150                   155                   160

Tyr Val Asp Gly Val Glu Val His Asn Ala Lys Thr Lys Pro Arg Glu
                 165                   170                   175

Glu Gln Tyr Asn Ser Thr Tyr Arg Val Val Ser Val Leu Thr Val Leu
                 180                   185                   190

His Gln Asp Trp Leu Asn Gly Lys Glu Tyr Lys Cys Lys Val Ser Asn
             195                   200                   205

Lys Ala Leu Pro Ala Pro Ile Glu Lys Thr Ile Ser Lys Ala Lys Gly
    210                   215                   220

Gln Pro Arg Glu Pro Gln Val Tyr Thr Leu Pro Pro Ser Arg Glu Glu
225                   230                   235                   240

Met Thr Lys Asn Gln Val Ser Leu Thr Cys Leu Val Lys Gly Phe Tyr
                 245                   250                   255

Pro Ser Asp Ile Ala Val Glu Trp Glu Ser Asn Gly Gln Pro Glu Asn
                 260                   265                   270

Asn Tyr Lys Thr Thr Pro Pro Val Leu Asp Ser Asp Gly Ser Phe Phe
                 275                   280                   285

Leu Tyr Ser Lys Leu Thr Val Asp Lys Ser Arg Trp Gln Gln Gly Asn
    290                   295                   300

Val Phe Ser Cys Ser Val Met His Gly Ala Leu His Asn His Tyr Thr
305                   310                   315                   320

Arg Glu Ser Leu Ser Leu Ser Pro Gly Lys
                 325                   330

<210> SEQ ID NO 77
<211> LENGTH: 330
<212> TYPE: PRT
<213> ORGANISM: Artificial sequence
<220> FEATURE:
<223> OTHER INFORMATION: Modified antibody constant region

<400> SEQUENCE: 77

Ala Ser Thr Lys Gly Pro Ser Val Phe Pro Leu Ala Pro Ser Ser Lys
1                    5                    10                    15

Ser Thr Ser Gly Gly Thr Ala Ala Leu Gly Cys Leu Val Lys Asp Tyr
                  20                    25                    30

Phe Pro Glu Pro Val Thr Val Ser Trp Asn Ser Gly Ala Leu Thr Ser
             35                    40                    45

Gly Val His Thr Phe Pro Ala Val Leu Gln Ser Ser Gly Leu Tyr Ser
    50                    55                    60

Leu Ser Ser Val Val Thr Val Pro Ser Ser Ser Leu Gly Thr Gln Thr
```

```
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
    290                 295                 300

Val Phe Ser Cys Ser Val Met His Gly Ala Leu His Asn His Tyr Thr
305                 310                 315                 320

Arg Lys Lys Leu Ser Leu Ser Pro Gly Lys
                325                 330
```

```
<210> SEQ ID NO 78
<211> LENGTH: 330
<212> TYPE: PRT
<213> ORGANISM: Artificial sequence
<220> FEATURE:
<223> OTHER INFORMATION: Modified antibody constant region

<400> SEQUENCE: 78
```

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
```

-continued

```
                100                 105                 110

Pro Ala Pro Glu Leu Leu Gly Gly Pro Ser Val Phe Leu Phe Pro Pro
                115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
                275                 280                 285

Leu Tyr Ser Lys Leu Thr Val Asp Lys Ser Arg Trp Gln Gln Gly Asn
        290                 295                 300

Val Phe Ser Cys Ser Val Met His Gly Ala Leu His Asn His Tyr Thr
305                 310                 315                 320

Gln Lys Lys Leu Ser Leu Ser Pro Gly Lys
                325                 330

<210> SEQ ID NO 79
<211> LENGTH: 330
<212> TYPE: PRT
<213> ORGANISM: Artificial sequence
<220> FEATURE:
<223> OTHER INFORMATION: Modified antibody constant region

<400> SEQUENCE: 79

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
                115                 120                 125

Lys Pro Lys Asp Thr Leu Met Ile Ser Arg Thr Pro Glu Val Thr Cys
```

-continued

```
        130                135                140

Val Val Val Asp Val Ser His Glu Asp Pro Glu Val Lys Phe Asn Trp
145                150                155                160

Tyr Val Asp Gly Val Glu Val His Asn Ala Lys Thr Lys Pro Arg Glu
                165                170                175

Glu Gln Tyr Asn Ser Thr Tyr Arg Val Val Ser Val Leu Thr Val Leu
                180                185                190

His Gln Asp Trp Leu Asn Gly Lys Glu Tyr Lys Cys Lys Val Ser Asn
                195                200                205

Lys Ala Leu Pro Ala Pro Ile Glu Lys Thr Ile Ser Lys Ala Lys Gly
                210                215                220

Gln Pro Arg Glu Pro Gln Val Tyr Thr Leu Pro Pro Ser Arg Glu Glu
225                230                235                240

Met Thr Lys Asn Gln Val Ser Leu Thr Cys Leu Val Lys Gly Phe Tyr
                245                250                255

Pro Ser Asp Ile Ala Val Glu Trp Glu Ser Asn Gly Gln Pro Glu Asn
                260                265                270

Asn Tyr Lys Thr Thr Pro Pro Val Leu Asp Ser Asp Gly Ser Phe Phe
                275                280                285

Leu Tyr Ser Lys Leu Thr Val Asp Lys Ser Arg Trp Gln Gln Gly Asn
                290                295                300

Val Phe Ser Cys Ser Val Met His Gly Ala Leu His Asn His Lys Thr
305                310                315                320

Gln Glu Ser Leu Ser Leu Ser Pro Gly Lys
                325                330
```

```
<210> SEQ ID NO 80
<211> LENGTH: 330
<212> TYPE: PRT
<213> ORGANISM: Artificial sequence
<220> FEATURE:
<223> OTHER INFORMATION: Modified antibody constant region

<400> SEQUENCE: 80

Ala Ser Thr Lys Gly Pro Ser Val Phe Pro Leu Ala Pro Ser Ser Lys
1                5                10                15

Ser Thr Ser Gly Gly Thr Ala Ala Leu Gly Cys Leu Val Lys Asp Tyr
                20                25                30

Phe Pro Glu Pro Val Thr Val Ser Trp Asn Ser Gly Ala Leu Thr Ser
                35                40                45

Gly Val His Thr Phe Pro Ala Val Leu Gln Ser Ser Gly Leu Tyr Ser
                50                55                60

Leu Ser Ser Val Val Thr Val Pro Ser Ser Ser Leu Gly Thr Gln Thr
65                70                75                80

Tyr Ile Cys Asn Val Asn His Lys Pro Ser Asn Thr Lys Val Asp Lys
                85                90                95

Arg Val Glu Pro Lys Ser Cys Asp Lys Thr His Thr Cys Pro Pro Cys
                100                105                110

Pro Ala Pro Glu Leu Leu Gly Gly Pro Ser Val Phe Leu Phe Pro Pro
                115                120                125

Lys Pro Lys Asp Thr Leu Met Ile Ser Arg Thr Pro Glu Val Thr Cys
                130                135                140

Val Val Val Asp Val Ser His Glu Asp Pro Glu Val Lys Phe Asn Trp
145                150                155                160

Tyr Val Asp Gly Val Glu Val His Asn Ala Lys Thr Lys Pro Arg Glu
```

-continued

```
                    165                    170                    175
Glu Gln Tyr Asn Ser Thr Tyr Arg Val Val Ser Val Leu Thr Val Leu
                180                    185                    190

His Gln Asp Trp Leu Asn Gly Lys Glu Tyr Lys Cys Lys Val Ser Asn
                195                    200                    205

Lys Ala Leu Pro Ala Pro Ile Glu Lys Thr Ile Ser Lys Ala Lys Gly
                210                    215                    220

Gln Pro Arg Glu Pro Gln Val Tyr Thr Leu Pro Pro Ser Arg Glu Glu
225                    230                    235                    240

Met Thr Lys Asn Gln Val Ser Leu Thr Cys Leu Val Lys Gly Phe Tyr
                    245                    250                    255

Pro Ser Asp Ile Ala Val Glu Trp Glu Ser Asn Gly Gln Pro Glu Asn
                    260                    265                    270

Asn Tyr Lys Thr Thr Pro Pro Val Leu Asp Ser Asp Gly Ser Phe Phe
                    275                    280                    285

Leu Tyr Ser Lys Leu Thr Val Asp Lys Ser Arg Trp Gln Gln Gly Asn
                290                    295                    300

Val Phe Ser Cys Ser Val Met His Gly Ala Leu His Asn His Lys Thr
305                    310                    315                    320

Gln Lys Lys Leu Ser Leu Ser Pro Gly Lys
                    325                    330
```

```
<210> SEQ ID NO 81
<211> LENGTH: 330
<212> TYPE: PRT
<213> ORGANISM: Artificial sequence
<220> FEATURE:
<223> OTHER INFORMATION: Modified antibody constant region

<400> SEQUENCE: 81
```

```
Ala Ser Thr Lys Gly Pro Ser Val Phe Pro Leu Ala Pro Ser Ser Lys
1                    5                     10                    15

Ser Thr Ser Gly Gly Thr Ala Ala Leu Gly Cys Leu Val Lys Asp Tyr
                20                    25                    30

Phe Pro Glu Pro Val Thr Val Ser Trp Asn Ser Gly Ala Leu Thr Ser
                35                    40                    45

Gly Val His Thr Phe Pro Ala Val Leu Gln Ser Ser Gly Leu Tyr Ser
                50                    55                    60

Leu Ser Ser Val Val Thr Val Pro Ser Ser Ser Leu Gly Thr Gln Thr
65                    70                    75                    80

Tyr Ile Cys Asn Val Asn His Lys Pro Ser Asn Thr Lys Val Asp Lys
                    85                    90                    95

Arg Val Glu Pro Lys Ser Cys Asp Lys Thr His Thr Cys Pro Pro Cys
                100                    105                    110

Pro Ala Pro Glu Leu Leu Gly Gly Pro Ser Val Phe Leu Phe Pro Pro
                115                    120                    125

Lys Pro Lys Asp Thr Leu Met Ile Ser Arg Thr Pro Glu Val Thr Cys
                130                    135                    140

Val Val Val Asp Val Ser His Glu Asp Pro Glu Val Lys Phe Asn Trp
145                    150                    155                    160

Tyr Val Asp Gly Val Glu Val His Asn Ala Lys Thr Lys Pro Arg Glu
                165                    170                    175

Glu Gln Tyr Asn Ser Thr Tyr Arg Val Val Ser Val Leu Thr Val Leu
                180                    185                    190

His Gln Asp Trp Leu Asn Gly Lys Glu Tyr Lys Cys Lys Val Ser Asn
```

```
              195                200                205

Lys Ala Leu Pro Ala Pro Ile Glu Lys Thr Ile Ser Lys Ala Lys Gly
    210                215                220

Gln Pro Arg Glu Pro Gln Val Tyr Thr Leu Pro Pro Ser Arg Glu Glu
225                230                235                240

Met Thr Lys Asn Gln Val Ser Leu Thr Cys Leu Val Lys Gly Phe Tyr
            245                250                255

Pro Ser Asp Ile Ala Val Glu Trp Glu Ser Asn Gly Gln Pro Glu Asn
            260                265                270

Asn Tyr Lys Thr Thr Pro Pro Val Leu Asp Ser Asp Gly Ser Phe Phe
            275                280                285

Leu Tyr Ser Lys Leu Thr Val Asp Lys Ser Arg Trp Gln Gln Gly Asn
    290                295                300

Val Phe Ser Cys Ser Val Met His Gly Ala Leu His Asn His Asn Thr
305                310                315                320

Gln Glu Ser Leu Ser Leu Ser Pro Gly Lys
            325                330
```

```
<210> SEQ ID NO 82
<211> LENGTH: 330
<212> TYPE: PRT
<213> ORGANISM: Artificial sequence
<220> FEATURE:
<223> OTHER INFORMATION: Modified antibody constant region

<400> SEQUENCE: 82

Ala Ser Thr Lys Gly Pro Ser Val Phe Pro Leu Ala Pro Ser Ser Lys
1               5                10                15

Ser Thr Ser Gly Gly Thr Ala Ala Leu Gly Cys Leu Val Lys Asp Tyr
            20                25                30

Phe Pro Glu Pro Val Thr Val Ser Trp Asn Ser Gly Ala Leu Thr Ser
        35                40                45

Gly Val His Thr Phe Pro Ala Val Leu Gln Ser Ser Gly Leu Tyr Ser
    50                55                60

Leu Ser Ser Val Val Thr Val Pro Ser Ser Ser Leu Gly Thr Gln Thr
65                70                75                80

Tyr Ile Cys Asn Val Asn His Lys Pro Ser Asn Thr Lys Val Asp Lys
                85                90                95

Arg Val Glu Pro Lys Ser Cys Asp Lys Thr His Thr Cys Pro Pro Cys
            100                105                110

Pro Ala Pro Glu Leu Leu Gly Gly Pro Ser Val Phe Leu Phe Pro Pro
            115                120                125

Lys Pro Lys Asp Thr Leu Met Ile Ser Arg Thr Pro Glu Val Thr Cys
    130                135                140

Val Val Val Asp Val Ser His Glu Asp Pro Glu Val Lys Phe Asn Trp
145                150                155                160

Tyr Val Asp Gly Val Glu Val His Asn Ala Lys Thr Lys Pro Arg Glu
            165                170                175

Glu Gln Tyr Asn Ser Thr Tyr Arg Val Val Ser Val Leu Thr Val Leu
            180                185                190

His Gln Asp Trp Leu Asn Gly Lys Glu Tyr Lys Cys Lys Val Ser Asn
            195                200                205

Lys Ala Leu Pro Ala Pro Ile Glu Lys Thr Ile Ser Lys Ala Lys Gly
    210                215                220

Gln Pro Arg Glu Pro Gln Val Tyr Thr Leu Pro Pro Ser Arg Glu Glu
```

-continued 225                230                235                240

Met Thr Lys Asn Gln Val Ser Leu Thr Cys Leu Val Lys Gly Phe Tyr
                245                250                255

Pro Ser Asp Ile Ala Val Glu Trp Glu Ser Asn Gly Gln Pro Glu Asn
                260                265                270

Asn Tyr Lys Thr Thr Pro Pro Val Leu Asp Ser Asp Gly Ser Phe Phe
                275                280                285

Leu Tyr Ser Lys Leu Thr Val Asp Lys Ser Arg Trp Gln Gln Gly Asn
        290                295                300

Val Phe Ser Cys Ser Val Met His Gly Ala Leu His Asn His Asn Thr
305                310                315                320

Gln Lys Lys Leu Ser Leu Ser Pro Gly Lys
                325                330

<210> SEQ ID NO 83
<211> LENGTH: 330
<212> TYPE: PRT
<213> ORGANISM: Artificial sequence
<220> FEATURE:
<223> OTHER INFORMATION: Modified antibody constant region

<400> SEQUENCE: 83

Ala Ser Thr Lys Gly Pro Ser Val Phe Pro Leu Ala Pro Ser Ser Lys
1                5                10                15

Ser Thr Ser Gly Gly Thr Ala Ala Leu Gly Cys Leu Val Lys Asp Tyr
                20                25                30

Phe Pro Glu Pro Val Thr Val Ser Trp Asn Ser Gly Ala Leu Thr Ser
                35                40                45

Gly Val His Thr Phe Pro Ala Val Leu Gln Ser Ser Gly Leu Tyr Ser
        50                55                60

Leu Ser Ser Val Val Thr Val Pro Ser Ser Ser Leu Gly Thr Gln Thr
65                70                75                80

Tyr Ile Cys Asn Val Asn His Lys Pro Ser Asn Thr Lys Val Asp Lys
                85                90                95

Arg Val Glu Pro Lys Ser Cys Asp Lys Thr His Thr Cys Pro Pro Cys
                100                105                110

Pro Ala Pro Glu Leu Leu Gly Ala Pro Ser Val Phe Leu Phe Pro Pro
                115                120                125

Lys Pro Lys Asp Thr Leu Met Ile Ser Arg Thr Pro Glu Val Thr Cys
        130                135                140

Val Val Val Asp Val Ser His Glu Asp Pro Glu Val Lys Phe Asn Trp
145                150                155                160

Tyr Val Asp Gly Val Glu Val His Asn Ala Lys Thr Lys Pro Arg Glu
                165                170                175

Glu Gln Tyr Asn Ser Thr Tyr Arg Val Val Ser Val Leu Thr Val Leu
                180                185                190

His Gln Asp Trp Leu Asn Gly Lys Glu Tyr Lys Cys Lys Val Ser Asn
                195                200                205

Lys Ala Leu Pro Ala Pro Ile Glu Lys Thr Ile Ser Lys Ala Lys Gly
        210                215                220

Gln Pro Arg Glu Pro Gln Val Tyr Thr Leu Pro Pro Ser Arg Glu Glu
225                230                235                240

Met Thr Lys Asn Gln Val Ser Leu Thr Cys Leu Val Lys Gly Phe Tyr
                245                250                255

Pro Ser Asp Ile Ala Val Glu Trp Glu Ser Asn Gly Gln Pro Glu Asn

-continued

```
                260               265               270

Asn Tyr Lys Thr Thr Pro Pro Val Leu Asp Ser Asp Gly Ser Phe Phe
        275               280               285

Leu Tyr Ser Lys Leu Thr Val Asp Lys Ser Arg Trp Gln Gln Gly Asn
        290               295               300

Val Phe Ser Cys Ser Val Met His Gly Ala Leu His Asn His Tyr Thr
305               310               315               320

Asn Glu Ser Leu Ser Leu Ser Pro Gly Lys
                325               330

<210> SEQ ID NO 84
<211> LENGTH: 330
<212> TYPE: PRT
<213> ORGANISM: Artificial sequence
<220> FEATURE:
<223> OTHER INFORMATION: Modified antibody constant region

<400> SEQUENCE: 84

Ala Ser Thr Lys Gly Pro Ser Val Phe Pro Leu Ala Pro Ser Ser Lys
1               5                 10                15

Ser Thr Ser Gly Gly Thr Ala Ala Leu Gly Cys Leu Val Lys Asp Tyr
                20                25                30

Phe Pro Glu Pro Val Thr Val Ser Trp Asn Ser Gly Ala Leu Thr Ser
        35                40                45

Gly Val His Thr Phe Pro Ala Val Leu Gln Ser Ser Gly Leu Tyr Ser
        50                55                60

Leu Ser Ser Val Val Thr Val Pro Ser Ser Ser Leu Gly Thr Gln Thr
65                70                75                80

Tyr Ile Cys Asn Val Asn His Lys Pro Ser Asn Thr Lys Val Asp Lys
                85                90                95

Arg Val Glu Pro Lys Ser Cys Asp Lys Thr His Thr Cys Pro Pro Cys
                100               105               110

Pro Ala Pro Glu Leu Leu Gly Ala Pro Ser Val Phe Leu Phe Pro Pro
        115               120               125

Lys Pro Lys Asp Thr Leu Met Ile Ser Arg Thr Pro Glu Val Thr Cys
        130               135               140

Val Val Val Asp Val Ser His Glu Asp Pro Glu Val Lys Phe Asn Trp
145               150               155               160

Tyr Val Asp Gly Val Glu Val His Asn Ala Lys Thr Lys Pro Arg Glu
                165               170               175

Glu Gln Tyr Asn Ser Thr Tyr Arg Val Val Ser Val Leu Thr Val Leu
                180               185               190

His Gln Asp Trp Leu Asn Gly Lys Glu Tyr Lys Cys Lys Val Ser Asn
                195               200               205

Lys Ala Leu Pro Ala Pro Ile Glu Lys Thr Ile Ser Lys Ala Lys Gly
        210               215               220

Gln Pro Arg Glu Pro Gln Val Tyr Thr Leu Pro Pro Ser Arg Glu Glu
225               230               235               240

Met Thr Lys Asn Gln Val Ser Leu Thr Cys Leu Val Lys Gly Phe Tyr
                245               250               255

Pro Ser Asp Ile Ala Val Glu Trp Glu Ser Asn Gly Gln Pro Glu Asn
                260               265               270

Asn Tyr Lys Thr Thr Pro Pro Val Leu Asp Ser Asp Gly Ser Phe Phe
        275               280               285

Leu Tyr Ser Lys Leu Thr Val Asp Lys Ser Arg Trp Gln Gln Gly Asn
```

-continued

```
        290              295              300

Val Phe Ser Cys Ser Val Met His Gly Ala Leu His Asn His Tyr Thr
305                310                315                320

Arg Lys Lys Leu Ser Leu Ser Pro Gly Lys
                325                330

<210> SEQ ID NO 85
<211> LENGTH: 330
<212> TYPE: PRT
<213> ORGANISM: Artificial sequence
<220> FEATURE:
<223> OTHER INFORMATION: Modified antibody constant region

<400> SEQUENCE: 85

Ala Ser Thr Lys Gly Pro Ser Val Phe Pro Leu Ala Pro Ser Ser Lys
1                5                10                15

Ser Thr Ser Gly Gly Thr Ala Ala Leu Gly Cys Leu Val Lys Asp Tyr
                20                25                30

Phe Pro Glu Pro Val Thr Val Ser Trp Asn Ser Gly Ala Leu Thr Ser
            35                40                45

Gly Val His Thr Phe Pro Ala Val Leu Gln Ser Ser Gly Leu Tyr Ser
        50                55                60

Leu Ser Ser Val Val Thr Val Pro Ser Ser Ser Leu Gly Thr Gln Thr
65                70                75                80

Tyr Ile Cys Asn Val Asn His Lys Pro Ser Asn Thr Lys Val Asp Lys
                85                90                95

Arg Val Glu Pro Lys Ser Cys Asp Lys Thr His Thr Cys Pro Pro Cys
            100                105                110

Pro Ala Pro Glu Leu Leu Gly Ala Pro Ser Val Phe Leu Phe Pro Pro
        115                120                125

Lys Pro Lys Asp Thr Leu Met Ile Ser Arg Thr Pro Glu Val Thr Cys
    130                135                140

Val Val Val Asp Val Ser His Glu Asp Pro Glu Val Lys Phe Asn Trp
145                150                155                160

Tyr Val Asp Gly Val Glu Val His Asn Ala Lys Thr Lys Pro Arg Glu
                165                170                175

Glu Gln Tyr Asn Ser Thr Tyr Arg Val Val Ser Val Leu Thr Val Leu
            180                185                190

His Gln Asp Trp Leu Asn Gly Lys Glu Tyr Lys Cys Lys Val Ser Asn
        195                200                205

Lys Ala Leu Pro Ala Pro Ile Glu Lys Thr Ile Ser Lys Ala Lys Gly
    210                215                220

Gln Pro Arg Glu Pro Gln Val Tyr Thr Leu Pro Pro Ser Arg Glu Glu
225                230                235                240

Met Thr Lys Asn Gln Val Ser Leu Thr Cys Leu Val Lys Gly Phe Tyr
                245                250                255

Pro Ser Asp Ile Ala Val Glu Trp Glu Ser Asn Gly Gln Pro Glu Asn
            260                265                270

Asn Tyr Lys Thr Thr Pro Pro Val Leu Asp Ser Asp Gly Ser Phe Phe
        275                280                285

Leu Tyr Ser Lys Leu Thr Val Asp Lys Ser Arg Trp Gln Gln Gly Asn
    290                295                300

Val Phe Ser Cys Ser Val Met His Gly Ala Leu His Asn His Lys Thr
305                310                315                320

Gln Lys Lys Leu Ser Leu Ser Pro Gly Lys
```

-continued

```
                    325                    330

<210> SEQ ID NO 86
<211> LENGTH: 330
<212> TYPE: PRT
<213> ORGANISM: Artificial sequence
<220> FEATURE:
<223> OTHER INFORMATION: Modified antibody constant region

<400> SEQUENCE: 86

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Ala Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
    290                 295                 300

Val Phe Ser Cys Ser Val Met His Gly Ala Leu His Asn His Asn Thr
305                 310                 315                 320

Gln Glu Ser Leu Ser Leu Ser Pro Gly Lys
                325                 330

<210> SEQ ID NO 87
<211> LENGTH: 330
<212> TYPE: PRT
```

-continued

<213> ORGANISM: Artificial sequence
<220> FEATURE:
<223> OTHER INFORMATION: Modified antibody constant region

<400> SEQUENCE: 87

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Trp Ala Leu Pro Ala Pro Ile Ser Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
    290                 295                 300

Val Phe Ser Cys Ser Val Met His Gly Ala Leu His Asn His Tyr Thr
305                 310                 315                 320

Arg Lys Lys Leu Ser Leu Ser Pro Gly Lys
                325                 330
```

<210> SEQ ID NO 88
<211> LENGTH: 330
<212> TYPE: PRT
<213> ORGANISM: Artificial sequence
<220> FEATURE:
<223> OTHER INFORMATION: Modified antibody constant region

<400> SEQUENCE: 88

-continued

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Trp Ala Leu Pro Ala Pro Ile Ser Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Gly Ala Leu His Asn His Lys Thr
305                 310                 315                 320

Gln Lys Lys Leu Ser Leu Ser Pro Gly Lys
            325                 330
```

```
<210> SEQ ID NO 89
<211> LENGTH: 326
<212> TYPE: PRT
<213> ORGANISM: Artificial sequence
<220> FEATURE:
<223> OTHER INFORMATION: Modified antibody constant region

<400> SEQUENCE: 89

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30
```

```
Phe Pro Glu Pro Val Thr Val Ser Trp Asn Ser Gly Ala Leu Thr Ser
        35              40              45

Gly Val His Thr Phe Pro Ala Val Leu Gln Ser Ser Gly Leu Tyr Ser
        50              55              60

Leu Ser Ser Val Val Thr Val Pro Ser Ser Asn Phe Gly Thr Gln Thr
65              70              75              80

Tyr Thr Cys Asn Val Asp His Lys Pro Ser Asn Thr Lys Val Asp Lys
                85              90              95

Thr Val Glu Arg Lys Cys Cys Val Glu Cys Pro Pro Cys Pro Ala Pro
            100             105             110

Pro Val Ala Gly Pro Ser Val Phe Leu Phe Pro Pro Lys Pro Lys Asp
            115             120             125

Thr Leu Met Ile Ser Arg Thr Pro Glu Val Thr Cys Val Val Val Asp
        130             135             140

Val Ser His Glu Asp Pro Glu Val Gln Phe Asn Trp Tyr Val Asp Gly
145             150             155             160

Val Glu Val His Asn Ala Lys Thr Lys Pro Arg Glu Glu Gln Phe Asn
                165             170             175

Ser Thr Phe Arg Val Val Ser Val Leu Thr Val Val His Gln Asp Trp
            180             185             190

Leu Asn Gly Lys Glu Tyr Lys Cys Lys Val Ser Asn Lys Gly Leu Pro
            195             200             205

Ala Pro Ile Glu Lys Thr Ile Ser Lys Thr Lys Gly Gln Pro Arg Glu
        210             215             220

Pro Gln Val Tyr Thr Leu Pro Pro Ser Arg Glu Glu Met Thr Lys Asn
225             230             235             240

Gln Val Ser Leu Thr Cys Leu Val Lys Gly Phe Tyr Pro Ser Asp Ile
                245             250             255

Ala Val Glu Trp Glu Ser Asn Gly Gln Pro Glu Asn Asn Tyr Lys Thr
            260             265             270

Thr Pro Pro Met Leu Asp Ser Asp Gly Ser Phe Phe Leu Tyr Ser Lys
            275             280             285

Leu Thr Val Asp Lys Ser Arg Trp Gln Gln Gly Asn Val Phe Ser Cys
        290             295             300

Ser Val Met His Gly Ala Leu His Asn His Tyr Thr Asn Glu Ser Leu
305             310             315             320

Ser Leu Ser Pro Gly Lys
                325
```

<210> SEQ ID NO 90
<211> LENGTH: 326
<212> TYPE: PRT
<213> ORGANISM: Artificial sequence
<220> FEATURE:
<223> OTHER INFORMATION: Modified antibody constant region

<400> SEQUENCE: 90

```
Ala Ser Thr Lys Gly Pro Ser Val Phe Pro Leu Ala Pro Cys Ser Arg
1               5               10              15

Ser Thr Ser Glu Ser Thr Ala Ala Leu Gly Cys Leu Val Lys Asp Tyr
                20              25              30

Phe Pro Glu Pro Val Thr Val Ser Trp Asn Ser Gly Ala Leu Thr Ser
        35              40              45

Gly Val His Thr Phe Pro Ala Val Leu Gln Ser Ser Gly Leu Tyr Ser
        50              55              60
```

-continued

```
Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
            115                 120                 125

Thr Leu Met Ile Ser Arg Thr Pro Glu Val Thr Cys Val Val Val Asp
        130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
            195                 200                 205

Ala Pro Ile Glu Lys Thr Ile Ser Lys Thr Lys Gly Gln Pro Arg Glu
        210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
            275                 280                 285

Leu Thr Val Asp Lys Ser Arg Trp Gln Gln Gly Asn Val Phe Ser Cys
        290                 295                 300

Ser Val Met His Gly Ala Leu His Asn His Tyr Thr Arg Lys Lys Leu
305                 310                 315                 320

Ser Leu Ser Pro Gly Lys
                325
```

```
<210> SEQ ID NO 91
<211> LENGTH: 326
<212> TYPE: PRT
<213> ORGANISM: Artificial sequence
<220> FEATURE:
<223> OTHER INFORMATION: Modified antibody constant region

<400> SEQUENCE: 91
```

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95
```

```
Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
            115                 120                 125

Thr Leu Met Ile Ser Arg Thr Pro Glu Val Thr Cys Val Val Val Asp
            130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
                180                 185                 190

Leu Asn Gly Lys Glu Tyr Lys Cys Lys Val Ser Asn Lys Gly Leu Pro
            195                 200                 205

Ala Pro Ile Glu Lys Thr Ile Ser Lys Thr Lys Gly Gln Pro Arg Glu
            210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
                260                 265                 270

Thr Pro Pro Met Leu Asp Ser Asp Gly Ser Phe Phe Leu Tyr Ser Lys
            275                 280                 285

Leu Thr Val Asp Lys Ser Arg Trp Gln Gln Gly Asn Val Phe Ser Cys
            290                 295                 300

Ser Val Met His Gly Ala Leu His Asn His Lys Thr Gln Lys Lys Leu
305                 310                 315                 320

Ser Leu Ser Pro Gly Lys
                325

<210> SEQ ID NO 92
<211> LENGTH: 326
<212> TYPE: PRT
<213> ORGANISM: Artificial sequence
<220> FEATURE:
<223> OTHER INFORMATION: Modified antibody constant region

<400> SEQUENCE: 92

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
            50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
            115                 120                 125
```

-continued

```
Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
                180                 185                 190

Leu Asn Gly Lys Glu Tyr Lys Cys Lys Val Ser Asn Lys Gly Leu Pro
                195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
                260                 265                 270

Thr Pro Pro Met Leu Asp Ser Asp Gly Ser Phe Phe Leu Tyr Ser Lys
                275                 280                 285

Leu Thr Val Asp Lys Ser Arg Trp Gln Gln Gly Asn Val Phe Ser Cys
    290                 295                 300

Ser Val Met His Gly Ala Leu His Asn His Asn Thr Gln Glu Ser Leu
305                 310                 315                 320

Ser Leu Ser Pro Gly Lys
                325
```

```
<210> SEQ ID NO 93
<211> LENGTH: 327
<212> TYPE: PRT
<213> ORGANISM: Artificial sequence
<220> FEATURE:
<223> OTHER INFORMATION: Modified antibody constant region

<400> SEQUENCE: 93
```

```
Ala Ser Thr Lys Gly Pro Ser Val Phe Pro Leu Ala Pro Cys Ser Arg
1                   5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
                100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160
```

-continued

```
Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
                180                 185                 190

Trp Leu Asn Gly Lys Glu Tyr Lys Cys Lys Val Ser Asn Lys Gly Leu
                195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
                260                 265                 270

Thr Thr Pro Pro Val Leu Asp Ser Asp Gly Ser Phe Phe Leu Tyr Ser
                275                 280                 285

Arg Leu Thr Val Asp Lys Ser Arg Trp Gln Glu Gly Asn Val Phe Ser
    290                 295                 300

Cys Ser Val Met His Gly Ala Leu His Asn His Tyr Thr Asn Glu Ser
305                 310                 315                 320

Leu Ser Leu Ser Leu Gly Lys
                325
```

```
<210> SEQ ID NO 94
<211> LENGTH: 327
<212> TYPE: PRT
<213> ORGANISM: Artificial sequence
<220> FEATURE:
<223> OTHER INFORMATION: Modified antibody constant region

<400> SEQUENCE: 94
```

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
                35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
                100                 105                 110

Glu Phe Leu Gly Gly Pro Ser Val Phe Leu Phe Pro Pro Lys Pro Lys
                115                 120                 125

Asp Thr Leu Met Ile Ser Arg Thr Pro Glu Val Thr Cys Val Val Val
                130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
                180                 185                 190
```

-continued

```
Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
        210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
                260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
        290                 295                 300

Cys Ser Val Met His Gly Ala Leu His Asn His Tyr Thr Arg Lys Lys
305                 310                 315                 320

Leu Ser Leu Ser Leu Gly Lys
                325
```

<210> SEQ ID NO 95
<211> LENGTH: 327
<212> TYPE: PRT
<213> ORGANISM: Artificial sequence
<220> FEATURE:
<223> OTHER INFORMATION: Modified antibody constant region

<400> SEQUENCE: 95

```
Ala Ser Thr Lys Gly Pro Ser Val Phe Pro Leu Ala Pro Cys Ser Arg
1                   5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
                100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
        130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
                180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
        210                 215                 220
```

```
Glu Pro Gln Val Tyr Thr Leu Pro Pro Ser Gln Glu Glu Met Thr Lys
225             230             235             240

Asn Gln Val Ser Leu Thr Cys Leu Val Lys Gly Phe Tyr Pro Ser Asp
            245             250             255

Ile Ala Val Glu Trp Glu Ser Asn Gly Gln Pro Glu Asn Asn Tyr Lys
            260             265             270

Thr Thr Pro Pro Val Leu Asp Ser Asp Gly Ser Phe Phe Leu Tyr Ser
            275             280             285

Arg Leu Thr Val Asp Lys Ser Arg Trp Gln Glu Gly Asn Val Phe Ser
            290             295             300

Cys Ser Val Met His Gly Ala Leu His Asn His Lys Thr Gln Lys Lys
305             310             315             320

Leu Ser Leu Ser Leu Gly Lys
            325
```

```
<210> SEQ ID NO 96
<211> LENGTH: 327
<212> TYPE: PRT
<213> ORGANISM: Artificial sequence
<220> FEATURE:
<223> OTHER INFORMATION: Modified antibody constant region

<400> SEQUENCE: 96

Ala Ser Thr Lys Gly Pro Ser Val Phe Pro Leu Ala Pro Cys Ser Arg
1               5               10              15

Ser Thr Ser Glu Ser Thr Ala Ala Leu Gly Cys Leu Val Lys Asp Tyr
            20              25              30

Phe Pro Glu Pro Val Thr Val Ser Trp Asn Ser Gly Ala Leu Thr Ser
            35              40              45

Gly Val His Thr Phe Pro Ala Val Leu Gln Ser Ser Gly Leu Tyr Ser
            50              55              60

Leu Ser Ser Val Val Thr Val Pro Ser Ser Ser Leu Gly Thr Lys Thr
65              70              75              80

Tyr Thr Cys Asn Val Asp His Lys Pro Ser Asn Thr Lys Val Asp Lys
            85              90              95

Arg Val Glu Ser Lys Tyr Gly Pro Pro Cys Pro Pro Cys Pro Ala Pro
            100             105             110

Glu Phe Leu Gly Gly Pro Ser Val Phe Leu Phe Pro Pro Lys Pro Lys
            115             120             125

Asp Thr Leu Met Ile Ser Arg Thr Pro Glu Val Thr Cys Val Val Val
            130             135             140

Asp Val Ser Gln Glu Asp Pro Glu Val Gln Phe Asn Trp Tyr Val Asp
145             150             155             160

Gly Val Glu Val His Asn Ala Lys Thr Lys Pro Arg Glu Glu Gln Phe
            165             170             175

Asn Ser Thr Tyr Arg Val Val Ser Val Leu Thr Val Leu His Gln Asp
            180             185             190

Trp Leu Asn Gly Lys Glu Tyr Lys Cys Lys Val Ser Asn Lys Gly Leu
            195             200             205

Pro Ser Ser Ile Glu Lys Thr Ile Ser Lys Ala Lys Gly Gln Pro Arg
            210             215             220

Glu Pro Gln Val Tyr Thr Leu Pro Pro Ser Gln Glu Glu Met Thr Lys
225             230             235             240

Asn Gln Val Ser Leu Thr Cys Leu Val Lys Gly Phe Tyr Pro Ser Asp
            245             250             255
```

-continued

```
Ile Ala Val Glu Trp Glu Ser Asn Gly Gln Pro Glu Asn Asn Tyr Lys
            260             265             270

Thr Thr Pro Pro Val Leu Asp Ser Asp Gly Ser Phe Phe Leu Tyr Ser
            275             280             285

Arg Leu Thr Val Asp Lys Ser Arg Trp Gln Glu Gly Asn Val Phe Ser
            290             295             300

Cys Ser Val Met His Gly Ala Leu His Asn His Asn Thr Gln Glu Ser
305             310             315             320

Leu Ser Leu Ser Leu Gly Lys
            325

<210> SEQ ID NO 97
<211> LENGTH: 330
<212> TYPE: PRT
<213> ORGANISM: Artificial sequence
<220> FEATURE:
<223> OTHER INFORMATION: Modified antibody constant region

<400> SEQUENCE: 97

Ala Ser Thr Lys Gly Pro Ser Val Phe Pro Leu Ala Pro Ser Ser Lys
1               5               10              15

Ser Thr Ser Gly Gly Thr Ala Ala Leu Gly Cys Leu Val Lys Asp Tyr
            20              25              30

Phe Pro Glu Pro Val Thr Val Ser Trp Asn Ser Gly Ala Leu Thr Ser
            35              40              45

Gly Val His Thr Phe Pro Ala Val Leu Gln Ser Ser Gly Leu Tyr Ser
            50              55              60

Leu Ser Ser Val Val Thr Val Pro Ser Ser Ser Leu Gly Thr Gln Thr
65              70              75              80

Tyr Ile Cys Asn Val Asn His Lys Pro Ser Asn Thr Lys Val Asp Lys
                85              90              95

Arg Val Glu Pro Lys Ser Cys Asp Lys Thr His Thr Cys Pro Pro Cys
            100             105             110

Pro Ala Pro Glu Leu Leu Gly Gly Pro Ser Val Phe Leu Phe Pro Pro
            115             120             125

Lys Pro Lys Asp Thr Leu Met Gly Ser Arg Thr Pro Glu Val Thr Cys
            130             135             140

Val Val Val Asp Val Ser His Glu Asp Pro Glu Val Lys Phe Asn Trp
145             150             155             160

Tyr Val Asp Gly Val Glu Val His Asn Ala Lys Thr Lys Pro Arg Glu
                165             170             175

Glu Gln Tyr Asn Ser Thr Tyr Arg Val Val Ser Val Leu Thr Val Leu
            180             185             190

His Gln Asp Trp Leu Asn Gly Lys Glu Tyr Lys Cys Lys Val Ser Asn
            195             200             205

Lys Ala Leu Pro Ala Pro Ile Glu Lys Thr Ile Ser Lys Ala Lys Gly
            210             215             220

Gln Pro Arg Glu Pro Gln Val Tyr Thr Leu Pro Pro Ser Arg Glu Glu
225             230             235             240

Met Thr Lys Asn Gln Val Ser Leu Thr Cys Leu Val Lys Gly Phe Tyr
                245             250             255

Pro Ser Asp Ile Ala Val Glu Trp Glu Ser Asn Gly Gln Pro Glu Asn
                260             265             270

Asn Tyr Lys Thr Thr Pro Pro Val Leu Asp Ser Asp Gly Ser Phe Phe
            275             280             285
```

-continued

Leu Tyr Ser Lys Leu Thr Val Asp Lys Ser Arg Trp Gln Gln Gly Asn
    290                 295                 300

Val Phe Ser Cys Ser Val Met His Gly Ala Leu His Asn His Tyr Thr
305                 310                 315                 320

Gln Lys Ser Leu Ser Leu Ser Pro Gly Lys
                325                 330

<210> SEQ ID NO 98
<211> LENGTH: 330
<212> TYPE: PRT
<213> ORGANISM: Artificial sequence
<220> FEATURE:
<223> OTHER INFORMATION: Modified antibody constant region

<400> SEQUENCE: 98

Ala Ser Thr Lys Gly Pro Ser Val Phe Pro Leu Ala Pro Ser Ser Lys
1                   5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
        115                 120                 125

Lys Pro Lys Asp Thr Leu Met Lys Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Gly Ala Leu His Asn His Tyr Thr
305                 310                 315                 320

-continued

```
Gln Lys Ser Leu Ser Leu Ser Pro Gly Lys
            325                 330

<210> SEQ ID NO 99
<211> LENGTH: 330
<212> TYPE: PRT
<213> ORGANISM: Artificial sequence
<220> FEATURE:
<223> OTHER INFORMATION: Modified antibody constant region

<400> SEQUENCE: 99

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Arg Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
    290                 295                 300

Val Phe Ser Cys Ser Val Met His Gly Ala Leu His Asn His Tyr Thr
305                 310                 315                 320

Gln Lys Ser Leu Ser Leu Ser Pro Gly Lys
            325                 330

<210> SEQ ID NO 100
<211> LENGTH: 330
```

<212> TYPE: PRT
<213> ORGANISM: Artificial sequence
<220> FEATURE:
<223> OTHER INFORMATION: Modified antibody constant region

<400> SEQUENCE: 100

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

Asp Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
    290                 295                 300

Val Phe Ser Cys Ser Val Met His Gly Ala Leu His Asn His Tyr Thr
305                 310                 315                 320

Gln Lys Ser Leu Ser Leu Ser Pro Gly Lys
                325                 330
```

<210> SEQ ID NO 101
<211> LENGTH: 330
<212> TYPE: PRT
<213> ORGANISM: Artificial sequence
<220> FEATURE:
<223> OTHER INFORMATION: Modified antibody constant region

<400> SEQUENCE: 101

-continued

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

Arg Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Gly Ala Leu His Asn His Tyr Thr
305                 310                 315                 320

Gln Lys Ser Leu Ser Leu Ser Pro Gly Lys
                325                 330
```

```
<210> SEQ ID NO 102
<211> LENGTH: 330
<212> TYPE: PRT
<213> ORGANISM: Artificial sequence
<220> FEATURE:
<223> OTHER INFORMATION: Modified antibody constant region

<400> SEQUENCE: 102
```

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30
```

```
Phe Pro Glu Pro Val Thr Val Ser Trp Asn Ser Gly Ala Leu Thr Ser
        35              40              45

Gly Val His Thr Phe Pro Ala Val Leu Gln Ser Ser Gly Leu Tyr Ser
    50              55              60

Leu Ser Ser Val Val Thr Val Pro Ser Ser Ser Leu Gly Thr Gln Thr
65              70              75              80

Tyr Ile Cys Asn Val Asn His Lys Pro Ser Asn Thr Lys Val Asp Lys
                85              90              95

Arg Val Glu Pro Lys Ser Cys Asp Lys Thr His Thr Cys Pro Pro Cys
            100             105             110

Pro Ala Pro Glu Leu Leu Gly Gly Pro Ser Val Phe Leu Phe Pro Pro
        115             120             125

Lys Pro Lys Asp Thr Leu Met Gly Ser Arg Thr Pro Glu Val Thr Cys
    130             135             140

Val Val Val Asp Val Ser His Glu Asp Pro Glu Val Lys Phe Asn Trp
145             150             155             160

Tyr Val Asp Gly Val Glu Val His Asn Ala Lys Thr Lys Pro Arg Glu
            165             170             175

Glu Gln Tyr Asn Ser Thr Tyr Arg Val Val Ser Val Leu Thr Val Leu
            180             185             190

His Gln Asp Trp Leu Asn Gly Lys Glu Tyr Lys Cys Lys Val Ser Asn
        195             200             205

Lys Ala Leu Pro Ala Pro Ile Glu Lys Thr Ile Ser Lys Ala Lys Gly
    210             215             220

Gln Pro Arg Glu Pro Gln Val Tyr Thr Leu Pro Pro Ser Arg Glu Glu
225             230             235             240

Met Thr Lys Asn Gln Val Ser Leu Thr Cys Leu Val Lys Gly Phe Tyr
            245             250             255

Pro Ser Asp Ile Ala Val Glu Trp Glu Ser Asn Gly Gln Pro Glu Asn
            260             265             270

Asn Tyr Lys Thr Thr Pro Pro Val Leu Asp Ser Asp Gly Ser Phe Phe
        275             280             285

Leu Tyr Ser Lys Leu Thr Val Asp Lys Ser Arg Trp Gln Gln Gly Asn
    290             295             300

Val Phe Ser Cys Ser Val Met His Gly Ala Leu His Asn His Tyr Thr
305             310             315             320

Gln Glu Ser Leu Ser Leu Ser Pro Gly Lys
            325             330
```

<210> SEQ ID NO 103
<211> LENGTH: 330
<212> TYPE: PRT
<213> ORGANISM: Artificial sequence
<220> FEATURE:
<223> OTHER INFORMATION: Modified antibody constant region

<400> SEQUENCE: 103

```
Ala Ser Thr Lys Gly Pro Ser Val Phe Pro Leu Ala Pro Ser Ser Lys
1               5               10              15

Ser Thr Ser Gly Gly Thr Ala Ala Leu Gly Cys Leu Val Lys Asp Tyr
            20              25              30

Phe Pro Glu Pro Val Thr Val Ser Trp Asn Ser Gly Ala Leu Thr Ser
        35              40              45

Gly Val His Thr Phe Pro Ala Val Leu Gln Ser Ser Gly Leu Tyr Ser
    50              55              60
```

```
Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Lys Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Gly Ala Leu His Asn His Tyr Thr
305                 310                 315                 320

Gln Lys Lys Leu Ser Leu Ser Pro Gly Lys
                325                 330

<210> SEQ ID NO 104
<211> LENGTH: 330
<212> TYPE: PRT
<213> ORGANISM: Artificial sequence
<220> FEATURE:
<223> OTHER INFORMATION: Modified antibody constant region

<400> SEQUENCE: 104

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95
```

```
Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Arg Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Gly Ala Leu His Asn His Tyr Thr
305                 310                 315                 320

Gln Lys Lys Leu Ser Leu Ser Pro Gly Lys
                325                 330
```

```
<210> SEQ ID NO 105
<211> LENGTH: 330
<212> TYPE: PRT
<213> ORGANISM: Artificial sequence
<220> FEATURE:
<223> OTHER INFORMATION: Modified antibody constant region

<400> SEQUENCE: 105
```

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125
```

```
Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

Asp Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
    290                 295                 300

Val Phe Ser Cys Ser Val Met His Gly Ala Leu His Asn His Tyr Thr
305                 310                 315                 320

Gln Glu Ser Leu Ser Leu Ser Pro Gly Lys
                325                 330
```

```
<210> SEQ ID NO 106
<211> LENGTH: 330
<212> TYPE: PRT
<213> ORGANISM: Artificial seqeunce
<220> FEATURE:
<223> OTHER INFORMATION: Modified antibody constant region

<400> SEQUENCE: 106

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160
```

-continued

```
Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

Arg Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Gly Ala Leu His Asn His Tyr Thr
305                 310                 315                 320

Gln Lys Lys Leu Ser Leu Ser Pro Gly Lys
                325                 330
```

```
<210> SEQ ID NO 107
<211> LENGTH: 330
<212> TYPE: PRT
<213> ORGANISM: Artificial sequence
<220> FEATURE:
<223> OTHER INFORMATION: Modified antibody constant region

<400> SEQUENCE: 107
```

```
Ala Ser Thr Lys Gly Pro Ser Val Phe Pro Leu Ala Pro Ser Ser Lys
1                 5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Glu Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190
```

-continued

```
His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Asn Arg
305                 310                 315                 320

Gln Glu Ser Leu Ser Leu Ser Pro Gly Lys
                325                 330
```

```
<210> SEQ ID NO 108
<211> LENGTH: 330
<212> TYPE: PRT
<213> ORGANISM: Artificial sequence
<220> FEATURE:
<223> OTHER INFORMATION: Modified antibody constant region

<400> SEQUENCE: 108
```

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Glu Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220
```

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
                275                 280                 285

Leu Tyr Ser Lys Leu Thr Val Asp Lys Ser Arg Trp Gln Gln Gly Asn
                290                 295                 300

Val Phe Ser Cys Ser Val Met His Glu Ala Leu His Asn His Tyr Arg
305                 310                 315                 320

Asn Glu Ser Leu Ser Leu Ser Pro Gly Lys
                325                 330

<210> SEQ ID NO 109
<211> LENGTH: 330
<212> TYPE: PRT
<213> ORGANISM: Artificial sequence
<220> FEATURE:
<223> OTHER INFORMATION: Modified antibody constant region

<400> SEQUENCE: 109

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
                35                  40                  45

Gly Val His Thr Phe Pro Ala Val Leu Gln Ser Ser Gly Leu Tyr Ser
                50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
                115                 120                 125

Lys Pro Glu Asp Thr Leu Met Ile Ser Arg Thr Pro Glu Val Thr Cys
                130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
                195                 200                 205

Lys Ala Leu Pro Ala Pro Ile Glu Lys Thr Ile Ser Lys Ala Lys Gly
                210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

-continued

```
Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Lys Arg
305                 310                 315                 320

Gln Lys Lys Leu Ser Leu Ser Pro Gly Lys
                325                 330

<210> SEQ ID NO 110
<211> LENGTH: 330
<212> TYPE: PRT
<213> ORGANISM: Artificial sequence
<220> FEATURE:
<223> OTHER INFORMATION: Modified antibody constant region

<400> SEQUENCE: 110

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Glu Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285
```

```
Leu Tyr Ser Lys Leu Thr Val Asp Lys Ser Arg Trp Gln Gln Gly Asn
    290             295             300

Val Phe Ser Cys Ser Val Met His Glu Ala Leu His Asn His Tyr Arg
305             310             315             320

Arg Lys Lys Leu Ser Leu Ser Pro Gly Lys
            325             330
```

```
<210> SEQ ID NO 111
<211> LENGTH: 280
<212> TYPE: PRT
<213> ORGANISM: Artificial sequence
<220> FEATURE:
<223> OTHER INFORMATION: Modified Fc receptor

<400> SEQUENCE: 111

Ala Glu Ser His Leu Ser Leu Leu Tyr His Leu Thr Ala Val Ser Ser
1               5               10              15

Pro Ala Pro Gly Thr Pro Ala Phe Trp Val Ser Gly Trp Leu Gly Pro
            20              25              30

Gln Gln Tyr Leu Ser Tyr Asn Ser Leu Arg Gly Glu Ala Glu Pro Cys
        35              40              45

Gly Ala Trp Val Trp Glu Asn Gln Val Ser Trp Tyr Trp Glu Lys Glu
    50              55              60

Thr Thr Asp Leu Arg Ile Lys Glu Lys Leu Phe Leu Glu Ala Phe Lys
65              70              75              80

Ala Leu Gly Gly Lys Gly Pro Tyr Thr Leu Gln Gly Leu Leu Gly Cys
            85              90              95

Glu Leu Gly Pro Asp Asn Thr Ser Val Pro Thr Ala Lys Phe Ala Leu
            100             105             110

Asn Gly Glu Glu Phe Met Asn Phe Asp Leu Lys Gln Gly Thr Trp Gly
            115             120             125

Gly Asp Trp Pro Glu Ala Leu Ala Ile Ser Gln Arg Trp Gln Gln Gln
    130             135             140

Asp Lys Ala Ala Asn Lys Glu Leu Thr Phe Leu Leu Phe Ser Cys Pro
145             150             155             160

His Arg Leu Arg Glu His Leu Glu Arg Gly Arg Gly Asn Leu Glu Trp
            165             170             175

Lys Glu Pro Pro Ser Met Arg Leu Lys Ala Arg Pro Ser Ser Pro Gly
            180             185             190

Phe Ser Val Leu Thr Cys Ser Ala Phe Ser Phe Tyr Pro Pro Glu Leu
            195             200             205

Gln Leu Arg Phe Leu Arg Asn Gly Leu Ala Ala Gly Thr Gly Gln Gly
    210             215             220

Asp Phe Gly Pro Asn Ser Asp Gly Ser Phe His Ala Ser Ser Ser Leu
225             230             235             240

Thr Val Lys Ser Gly Asp Glu His His Tyr Cys Cys Ile Val Gln His
            245             250             255

Ala Gly Leu Ala Gln Pro Leu Arg Val Glu Leu Glu Ser Pro Ala Lys
            260             265             270

Ser Ser His His His His His His
        275             280
```

```
<210> SEQ ID NO 112
<211> LENGTH: 99
<212> TYPE: PRT
<213> ORGANISM: Homo sapiens
```

<400> SEQUENCE: 112

Ile Gln Arg Thr Pro Lys Ile Gln Val Tyr Ser Arg His Pro Ala Glu
1               5                   10                  15

Asn Gly Lys Ser Asn Phe Leu Asn Cys Tyr Val Ser Gly Phe His Pro
                20                  25                  30

Ser Asp Ile Glu Val Asp Leu Leu Lys Asn Gly Glu Arg Ile Glu Lys
        35                  40                  45

Val Glu His Ser Asp Leu Ser Phe Ser Lys Asp Trp Ser Phe Tyr Leu
    50                  55                  60

Leu Tyr Tyr Thr Glu Phe Thr Pro Thr Glu Lys Asp Glu Tyr Ala Cys
65                  70                  75                  80

Arg Val Asn His Val Thr Leu Ser Gln Pro Lys Ile Val Lys Trp Asp
                85                  90                  95

Arg Asp Met

<210> SEQ ID NO 113
<211> LENGTH: 417
<212> TYPE: PRT
<213> ORGANISM: Artificial sequence
<220> FEATURE:
<223> OTHER INFORMATION: Modified Fc receptor

<400> SEQUENCE: 113

Met Glu Thr Gln Met Ser Gln Asn Val Cys Pro Arg Asn Leu Trp Leu
1               5                   10                  15

Leu Gln Pro Leu Thr Val Leu Leu Leu Leu Ala Ser Ala Asp Ser Gln
                20                  25                  30

Ala Ala Ala Pro Pro Lys Ala Val Leu Lys Leu Glu Pro Pro Trp Ile
        35                  40                  45

Asn Val Leu Gln Glu Asp Ser Val Thr Leu Thr Cys Gln Gly Ala Arg
    50                  55                  60

Ser Pro Glu Ser Asp Ser Ile Gln Trp Phe His Asn Gly Asn Leu Ile
65                  70                  75                  80

Pro Thr His Thr Gln Pro Ser Tyr Arg Phe Lys Ala Asn Asn Asn Asp
                85                  90                  95

Ser Gly Glu Tyr Thr Cys Gln Thr Gly Gln Thr Ser Leu Ser Asp Pro
                100                 105                 110

Val His Leu Thr Val Leu Ser Glu Trp Leu Val Leu Gln Thr Pro His
        115                 120                 125

Leu Glu Phe Gln Glu Gly Glu Thr Ile Met Leu Arg Cys His Ser Trp
        130                 135                 140

Lys Asp Lys Pro Leu Val Lys Val Thr Phe Phe Gln Asn Gly Lys Ser
145                 150                 155                 160

Gln Lys Phe Ser His Leu Asp Pro Thr Phe Ser Ile Pro Gln Ala Asn
                165                 170                 175

His Ser His Ser Gly Asp Tyr His Cys Thr Gly Asn Ile Gly Tyr Thr
                180                 185                 190

Leu Phe Ser Ser Lys Pro Val Thr Ile Thr Val Gln Val Pro Ser Met
        195                 200                 205

Gly Ser Ser Ser Pro Val Ala Pro Pro Lys Ala Val Leu Lys Leu Glu
        210                 215                 220

Pro Pro Trp Ile Asn Val Leu Gln Glu Asp Ser Val Thr Leu Thr Cys
225                 230                 235                 240

Gln Gly Ala Arg Ser Pro Glu Ser Asp Ser Ile Gln Trp Phe His Asn

-continued

```
              245                    250                    255

Gly Asn Leu Ile Pro Thr His Thr Gln Pro Ser Tyr Arg Phe Lys Ala
              260                    265                    270

Asn Asn Asn Asp Ser Gly Glu Tyr Thr Cys Gln Thr Gly Gln Thr Ser
              275                    280                    285

Leu Ser Asp Pro Val His Leu Thr Val Leu Ser Glu Trp Leu Val Leu
              290                    295                    300

Gln Thr Pro His Leu Glu Phe Gln Glu Gly Glu Thr Ile Met Leu Arg
305                    310                    315                    320

Cys His Ser Trp Lys Asp Lys Pro Leu Val Lys Val Thr Phe Phe Gln
              325                    330                    335

Asn Gly Lys Ser Gln Lys Phe Ser His Leu Asp Pro Thr Phe Ser Ile
              340                    345                    350

Pro Gln Ala Asn His Ser His Ser Gly Asp Tyr His Cys Thr Gly Asn
              355                    360                    365

Ile Gly Tyr Thr Leu Phe Ser Ser Lys Pro Val Thr Ile Thr Val Gln
              370                    375                    380

Val Pro Ser Met Gly Gly Ser Ser Ser His His His His His His Pro
385                    390                    395                    400

Gly Gly Gly Leu Asn Asp Ile Phe Glu Ala Gln Lys Ile Glu Trp His
              405                    410                    415

Glu

<210> SEQ ID NO 114
<211> LENGTH: 405
<212> TYPE: PRT
<213> ORGANISM: Artificial sequence
<220> FEATURE:
<223> OTHER INFORMATION: Modified Fc receptor

<400> SEQUENCE: 114

Met Val Leu Ser Leu Leu Tyr Leu Leu Thr Ala Leu Pro Gly Ile Leu
1               5                     10                     15

Ser Ala Ala Pro Pro Lys Ala Val Leu Lys Leu Glu Pro Pro Trp Ile
              20                     25                     30

Asn Val Leu Gln Glu Asp Ser Val Thr Leu Thr Cys Gln Gly Ala Arg
              35                     40                     45

Ser Pro Glu Ser Asp Ser Ile Gln Trp Phe His Asn Gly Asn Leu Ile
              50                     55                     60

Pro Thr His Thr Gln Pro Ser Tyr Arg Phe Lys Ala Asn Asn Asn Asp
65                     70                     75                     80

Ser Gly Glu Tyr Thr Cys Gln Thr Gly Gln Thr Ser Leu Ser Asp Pro
              85                     90                     95

Val His Leu Thr Val Leu Ser Glu Trp Leu Val Leu Gln Thr Pro His
              100                    105                    110

Leu Glu Phe Gln Glu Gly Glu Thr Ile Met Leu Arg Cys His Ser Trp
              115                    120                    125

Lys Asp Lys Pro Leu Val Lys Val Thr Phe Phe Gln Asn Gly Lys Ser
              130                    135                    140

Gln Lys Phe Ser Arg Leu Asp Pro Thr Phe Ser Ile Pro Gln Ala Asn
145                    150                    155                    160

His Ser His Ser Gly Asp Tyr His Cys Thr Gly Asn Ile Gly Tyr Thr
              165                    170                    175

Leu Phe Ser Ser Lys Pro Val Thr Ile Thr Val Gln Val Pro Ser Met
              180                    185                    190
```

-continued

```
Gly Ser Ser Ser Pro Ala Ala Pro Pro Lys Ala Val Leu Lys Leu Glu
        195             200             205

Pro Pro Trp Ile Asn Val Leu Gln Glu Asp Ser Val Thr Leu Thr Cys
    210             215             220

Gln Gly Ala Arg Ser Pro Glu Ser Asp Ser Ile Gln Trp Phe His Asn
225             230             235             240

Gly Asn Leu Ile Pro Thr His Thr Gln Pro Ser Tyr Arg Phe Lys Ala
            245             250             255

Asn Asn Asn Asp Ser Gly Glu Tyr Thr Cys Gln Thr Gly Gln Thr Ser
            260             265             270

Leu Ser Asp Pro Val His Leu Thr Val Leu Ser Glu Trp Leu Val Leu
            275             280             285

Gln Thr Pro His Leu Glu Phe Gln Glu Gly Glu Thr Ile Met Leu Arg
    290             295             300

Cys His Ser Trp Lys Asp Lys Pro Leu Val Lys Val Thr Phe Phe Gln
305             310             315             320

Asn Gly Lys Ser Gln Lys Phe Ser Arg Leu Asp Pro Thr Phe Ser Ile
            325             330             335

Pro Gln Ala Asn His Ser His Ser Gly Asp Tyr His Cys Thr Gly Asn
            340             345             350

Ile Gly Tyr Thr Leu Phe Ser Ser Lys Pro Val Thr Ile Thr Val Gln
            355             360             365

Val Pro Ser Met Gly Ser Ser Ser Pro Gly Ser Ser Ser His His His
    370             375             380

His His His Pro Gly Gly Gly Leu Asn Asp Ile Phe Glu Ala Gln Lys
385             390             395             400

Ile Glu Trp His Glu
            405
```

```
<210> SEQ ID NO 115
<211> LENGTH: 405
<212> TYPE: PRT
<213> ORGANISM: Artificial sequence
<220> FEATURE:
<223> OTHER INFORMATION: Modified Fc receptor

<400> SEQUENCE: 115
```

```
Met Val Leu Ser Leu Leu Tyr Leu Leu Thr Ala Leu Pro Gly Ile Leu
1               5               10              15

Ser Ala Ala Pro Pro Lys Ala Val Leu Lys Leu Glu Pro Gln Trp Ile
            20              25              30

Asn Val Leu Gln Glu Asp Ser Val Thr Leu Thr Cys Arg Gly Thr His
        35              40              45

Ser Pro Glu Ser Asp Ser Ile Gln Trp Phe His Asn Gly Asn Leu Ile
    50              55              60

Pro Thr His Thr Gln Pro Ser Tyr Arg Phe Lys Ala Asn Asn Asn Asp
65              70              75              80

Ser Gly Glu Tyr Thr Cys Gln Thr Gly Gln Thr Ser Leu Ser Asp Pro
            85              90              95

Val His Leu Thr Val Leu Ser Glu Trp Leu Val Leu Gln Thr Pro His
            100             105             110

Leu Glu Phe Gln Glu Gly Glu Thr Ile Val Leu Arg Cys His Ser Trp
            115             120             125

Lys Asp Lys Pro Leu Val Lys Val Thr Phe Phe Gln Asn Gly Lys Ser
    130             135             140
```

```
Lys Lys Phe Ser Arg Ser Asp Pro Asn Phe Ser Ile Pro Gln Ala Asn
145                 150                 155                 160

His Ser His Ser Gly Asp Tyr His Cys Thr Gly Asn Ile Gly Tyr Thr
                165                 170                 175

Leu Tyr Ser Ser Lys Pro Val Thr Ile Thr Val Gln Ala Pro Ser Ser
                180                 185                 190

Ser Pro Met Gly Pro Ala Ala Pro Pro Lys Ala Val Leu Lys Leu Glu
            195                 200                 205

Pro Gln Trp Ile Asn Val Leu Gln Glu Asp Ser Val Thr Leu Thr Cys
        210                 215                 220

Arg Gly Thr His Ser Pro Glu Ser Asp Ser Ile Gln Trp Phe His Asn
225                 230                 235                 240

Gly Asn Leu Ile Pro Thr His Thr Gln Pro Ser Tyr Arg Phe Lys Ala
                245                 250                 255

Asn Asn Asn Asp Ser Gly Glu Tyr Thr Cys Gln Thr Gly Gln Thr Ser
                260                 265                 270

Leu Ser Asp Pro Val His Leu Thr Val Leu Ser Glu Trp Leu Val Leu
            275                 280                 285

Gln Thr Pro His Leu Glu Phe Gln Glu Gly Glu Thr Ile Val Leu Arg
        290                 295                 300

Cys His Ser Trp Lys Asp Lys Pro Leu Val Lys Val Thr Phe Phe Gln
305                 310                 315                 320

Asn Gly Lys Ser Lys Lys Phe Ser Arg Ser Asp Pro Asn Phe Ser Ile
                325                 330                 335

Pro Gln Ala Asn His Ser His Ser Gly Asp Tyr His Cys Thr Gly Asn
            340                 345                 350

Ile Gly Tyr Thr Leu Tyr Ser Ser Lys Pro Val Thr Ile Thr Val Gln
            355                 360                 365

Ala Pro Ser Ser Ser Pro Met Gly Pro Gly Ser Ser Ser His His His
        370                 375                 380

His His His Pro Gly Gly Gly Leu Asn Asp Ile Phe Glu Ala Gln Lys
385                 390                 395                 400

Ile Glu Trp His Glu
                405
```

<210> SEQ ID NO 116
<211> LENGTH: 410
<212> TYPE: PRT
<213> ORGANISM: Artificial sequence
<220> FEATURE:
<223> OTHER INFORMATION: Modified Fc receptor

<400> SEQUENCE: 116

```
Met Val Leu Ser Leu Leu Tyr Leu Leu Thr Ala Leu Pro Gly Ile Ser
1               5                   10                  15

Thr Glu Asp Leu Pro Lys Ala Val Val Phe Leu Glu Pro Gln Trp Tyr
                20                  25                  30

Arg Val Leu Glu Lys Asp Ser Val Thr Leu Lys Cys Gln Gly Ala Tyr
            35                  40                  45

Ser Pro Glu Asp Asn Ser Thr Gln Trp Phe His Asn Glu Ser Leu Ile
        50                  55                  60

Ser Ser Gln Ala Ser Ser Tyr Phe Ile Asp Ala Ala Thr Val Asp Asp
65                  70                  75                  80

Ser Gly Glu Tyr Arg Cys Gln Thr Asn Leu Ser Thr Leu Ser Asp Pro
                85                  90                  95
```

-continued

```
Val Gln Leu Glu Val His Ile Gly Trp Leu Leu Leu Gln Ala Pro Arg
              100                 105                 110

Trp Val Phe Lys Glu Glu Asp Pro Ile His Leu Arg Cys His Ser Trp
              115                 120                 125

Lys Asn Thr Ala Leu His Lys Val Thr Tyr Leu Gln Asn Gly Lys Gly
              130                 135                 140

Arg Lys Tyr Phe His His Asn Ser Asp Phe Tyr Ile Pro Lys Ala Thr
145                 150                 155                 160

Leu Lys Asp Ser Gly Ser Tyr Phe Cys Arg Gly Leu Phe Gly Ser Lys
                  165                 170                 175

Asn Val Ser Ser Glu Thr Val Asn Ile Thr Ile Thr Gln Gly Pro Ser
              180                 185                 190

Met Gly Ser Ser Ser Pro Ser Glu Asp Leu Pro Lys Ala Val Val Phe
              195                 200                 205

Leu Glu Pro Gln Trp Tyr Arg Val Leu Glu Lys Asp Ser Val Thr Leu
              210                 215                 220

Lys Cys Gln Gly Ala Tyr Ser Pro Glu Asp Asn Ser Thr Gln Trp Phe
225                 230                 235                 240

His Asn Glu Ser Leu Ile Ser Ser Gln Ala Ser Ser Tyr Phe Ile Asp
                  245                 250                 255

Ala Ala Thr Val Asp Asp Ser Gly Glu Tyr Arg Cys Gln Thr Asn Leu
                  260                 265                 270

Ser Thr Leu Ser Asp Pro Val Gln Leu Glu Val His Ile Gly Trp Leu
              275                 280                 285

Leu Leu Gln Ala Pro Arg Trp Val Phe Lys Glu Glu Asp Pro Ile His
              290                 295                 300

Leu Arg Cys His Ser Trp Lys Asn Thr Ala Leu His Lys Val Thr Tyr
305                 310                 315                 320

Leu Gln Asn Gly Lys Gly Arg Lys Tyr Phe His His Asn Ser Asp Phe
                  325                 330                 335

Tyr Ile Pro Lys Ala Thr Leu Lys Asp Ser Gly Ser Tyr Phe Cys Arg
              340                 345                 350

Gly Leu Phe Gly Ser Lys Asn Val Ser Ser Glu Thr Val Asn Ile Thr
              355                 360                 365

Ile Thr Gln Gly Pro Ser Met Gly Ser Ser Ser Pro Gly Pro Gly Ser
              370                 375                 380

Ser His His His His His His Pro Gly Gly Gly Leu Asn Asp Ile
385                 390                 395                 400

Phe Glu Ala Gln Lys Ile Glu Trp His Glu
                  405                 410

<210> SEQ ID NO 117
<211> LENGTH: 410
<212> TYPE: PRT
<213> ORGANISM: Artificial sequence
<220> FEATURE:
<223> OTHER INFORMATION: Modified Fc receptor

<400> SEQUENCE: 117

Met Val Leu Ser Leu Leu Tyr Leu Leu Thr Ala Leu Pro Gly Ile Ser
1                 5                   10                  15

Thr Glu Asp Leu Pro Lys Ala Val Val Phe Leu Glu Pro Gln Trp Tyr
              20                  25                  30

Arg Val Leu Glu Lys Asp Ser Val Thr Leu Lys Cys Gln Gly Ala Tyr
              35                  40                  45
```

-continued

```
Ser Pro Glu Asp Asn Ser Thr Gln Trp Phe His Asn Glu Ser Leu Ile
    50              55              60

Ser Ser Gln Ala Ser Ser Tyr Phe Ile Asp Ala Ala Thr Val Asp Asp
65              70              75              80

Ser Gly Glu Tyr Arg Cys Gln Thr Asn Leu Ser Thr Leu Ser Asp Pro
                85              90              95

Val Gln Leu Glu Val His Ile Gly Trp Leu Leu Leu Gln Ala Pro Arg
            100             105             110

Trp Val Phe Lys Glu Glu Asp Pro Ile His Leu Arg Cys His Ser Trp
        115             120             125

Lys Asn Thr Ala Leu His Lys Val Thr Tyr Leu Gln Asn Gly Lys Gly
    130             135             140

Arg Lys Tyr Phe His His Asn Ser Asp Phe Tyr Ile Pro Lys Ala Thr
145             150             155             160

Leu Lys Asp Ser Gly Ser Tyr Phe Cys Arg Gly Leu Val Gly Ser Lys
                165             170             175

Asn Val Ser Ser Glu Thr Val Asn Ile Thr Ile Thr Gln Gly Pro Ser
            180             185             190

Met Gly Ser Ser Ser Pro Ser Glu Asp Leu Pro Lys Ala Val Val Phe
        195             200             205

Leu Glu Pro Gln Trp Tyr Arg Val Leu Glu Lys Asp Ser Val Thr Leu
    210             215             220

Lys Cys Gln Gly Ala Tyr Ser Pro Glu Asp Asn Ser Thr Gln Trp Phe
225             230             235             240

His Asn Glu Ser Leu Ile Ser Ser Gln Ala Ser Ser Tyr Phe Ile Asp
                245             250             255

Ala Ala Thr Val Asp Asp Ser Gly Glu Tyr Arg Cys Gln Thr Asn Leu
            260             265             270

Ser Thr Leu Ser Asp Pro Val Gln Leu Glu Val His Ile Gly Trp Leu
        275             280             285

Leu Leu Gln Ala Pro Arg Trp Val Phe Lys Glu Glu Asp Pro Ile His
    290             295             300

Leu Arg Cys His Ser Trp Lys Asn Thr Ala Leu His Lys Val Thr Tyr
305             310             315             320

Leu Gln Asn Gly Lys Gly Arg Lys Tyr Phe His His Asn Ser Asp Phe
                325             330             335

Tyr Ile Pro Lys Ala Thr Leu Lys Asp Ser Gly Ser Tyr Phe Cys Arg
            340             345             350

Gly Leu Val Gly Ser Lys Asn Val Ser Ser Glu Thr Val Asn Ile Thr
        355             360             365

Ile Thr Gln Gly Pro Ser Met Gly Ser Ser Ser Pro Gly Pro Gly Ser
    370             375             380

Ser Ser His His His His His His Pro Gly Gly Gly Leu Asn Asp Ile
385             390             395             400

Phe Glu Ala Gln Lys Ile Glu Trp His Glu
                405             410
```

<210> SEQ ID NO 118
<211> LENGTH: 303
<212> TYPE: PRT
<213> ORGANISM: Artificial sequence
<220> FEATURE:
<223> OTHER INFORMATION: Modified Fc receptor

<400> SEQUENCE: 118

-continued

```
Met Trp Trp Arg Leu Trp Trp Leu Leu Leu Leu Leu Leu Leu Leu Trp
1               5                   10                  15

Pro Met Val Trp Ala Gln Val Asp Thr Thr Lys Ala Val Ile Thr Leu
            20                  25                  30

Gln Pro Pro Trp Val Ser Val Phe Gln Glu Glu Thr Val Thr Leu His
        35                  40                  45

Cys Glu Val Leu His Leu Pro Gly Ser Ser Ser Thr Gln Trp Phe Leu
    50                  55                  60

Asn Gly Thr Ala Thr Gln Thr Ser Thr Pro Ser Tyr Arg Ile Thr Ser
65                  70                  75                  80

Ala Ser Val Asn Asp Ser Gly Glu Tyr Arg Cys Gln Arg Gly Leu Ser
                85                  90                  95

Gly Arg Ser Asp Pro Ile Gln Leu Glu Ile His Arg Gly Trp Leu Leu
            100                 105                 110

Leu Gln Val Ser Ser Arg Val Phe Thr Glu Gly Glu Pro Leu Ala Leu
        115                 120                 125

Arg Cys His Ala Trp Lys Asp Lys Leu Val Tyr Asn Val Leu Tyr Tyr
    130                 135                 140

Arg Asn Gly Lys Ala Phe Lys Phe Phe His Trp Asn Ser Asn Leu Thr
145                 150                 155                 160

Ile Leu Lys Thr Asn Ile Ser His Asn Gly Thr Tyr His Cys Ser Gly
            165                 170                 175

Met Gly Lys His Arg Tyr Thr Ser Ala Gly Ile Ser Val Thr Val Lys
            180                 185                 190

Glu Leu Phe Pro Ala Pro Val Leu Asn Ala Ser Val Thr Ser Pro Leu
            195                 200                 205

Leu Glu Gly Asn Leu Val Thr Leu Ser Cys Glu Thr Lys Leu Leu Leu
    210                 215                 220

Gln Arg Pro Gly Leu Gln Leu Tyr Phe Ser Phe Tyr Met Gly Ser Lys
225                 230                 235                 240

Thr Leu Arg Gly Arg Asn Thr Ser Ser Glu Tyr Gln Ile Leu Thr Ala
            245                 250                 255

Arg Arg Glu Asp Ser Gly Leu Tyr Trp Cys Glu Ala Ala Thr Glu Asp
            260                 265                 270

Gly Asn Val Leu Lys Arg Ser Pro Glu Leu Glu Leu Gln Val Leu Gly
            275                 280                 285

Leu Gln Leu Pro Thr Pro Val His His His His His His His His
    290                 295                 300
```